(12) United States Patent
Bannen et al.

(10) Patent No.: US 12,195,475 B2
(45) Date of Patent: Jan. 14, 2025

(54) COMPOUNDS FOR THE TREATMENT OF KINASE-DEPENDENT DISORDERS

(71) Applicant: Exelixis, Inc., Alameda, CA (US)

(72) Inventors: Lynne Canne Bannen, Novato, CA (US); Minna Bui, Oakland, CA (US); Faming Jiang, Castro Valley, CA (US); Yong Wang, South San Francisco, CA (US); Wei Xu, Danville, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 18/334,113

(22) Filed: Jun. 13, 2023

(65) Prior Publication Data

US 2023/0374024 A1 Nov. 23, 2023

Related U.S. Application Data

(63) Continuation of application No. 16/964,228, filed as application No. PCT/US2019/015289 on Jan. 25, 2019, now Pat. No. 11,708,367.

(60) Provisional application No. 62/622,626, filed on Jan. 26, 2018, provisional application No. 62/622,629, filed on Jan. 26, 2018.

(51) Int. Cl.
*C07D 487/04* (2006.01)
*C07D 239/88* (2006.01)
*C07D 403/04* (2006.01)
*C07D 403/12* (2006.01)
*C07D 405/12* (2006.01)

(52) U.S. Cl.
CPC ......... *C07D 487/04* (2013.01); *C07D 239/88* (2013.01); *C07D 403/04* (2013.01); *C07D 403/12* (2013.01); *C07D 405/12* (2013.01)

(58) Field of Classification Search
CPC .. C07D 487/04; C07D 239/88; C07D 403/04; C07D 403/12; C07D 405/12; A61K 31/517
See application file for complete search history.

(56) References Cited

U.S. PATENT DOCUMENTS

| 11,708,367 | B2 * | 7/2023 | Bannen | C07D 471/04 514/264.1 |
| 2007/0015746 | A1 | 1/2007 | Martin et al. | |
| 2007/0238726 | A1 | 10/2007 | Blake et al. | |
| 2013/0331359 | A1 | 12/2013 | Yun et al. | |
| 2014/0221425 | A1 | 8/2014 | Yun et al. | |
| 2017/0042880 | A1 | 2/2017 | Aftab et al. | |
| 2018/0009758 | A1 | 1/2018 | Horn | |
| 2018/0244667 | A1 * | 8/2018 | Long | A61K 31/444 |
| 2019/0248772 | A1 | 8/2019 | Sun et al. | |

FOREIGN PATENT DOCUMENTS

| CN | 104817497 A | 8/2015 |
| CN | 105797123 A | 7/2016 |
| CN | 106400155 A | 2/2017 |
| EP | 2769976 A1 | 8/2014 |
| WO | 2005030140 A2 | 4/2005 |
| WO | 2010045095 A1 | 4/2010 |
| WO | 2011017639 A1 | 2/2011 |
| WO | 2012006960 A1 | 1/2012 |
| WO | 2012034055 A2 | 3/2012 |
| WO | WO 2016/184434 A1 * | 11/2016 |
| WO | WO 2019/125798 A1 * | 6/2019 |

OTHER PUBLICATIONS

International Search Report for PCT/US2019/015289, mailed May 13, 2019.

* cited by examiner

*Primary Examiner* — Deepak R Rao
(74) *Attorney, Agent, or Firm* — Honigman LLP; Heidi M. Berven; Li Gao

(57) ABSTRACT

Disclosed herein are compounds of Formula (I'). Compounds of Formula (I') inhibit, regulate and/or modulate kinase receptor, particularly Axl and Mer signal transduction pathways related to the changes in cellular activities as mentioned above, compositions which contain these compounds, and methods of using them to treat kinase-dependent diseases and conditions. The present invention also provides methods for making compounds as mentioned above, and compositions which contain these compounds.

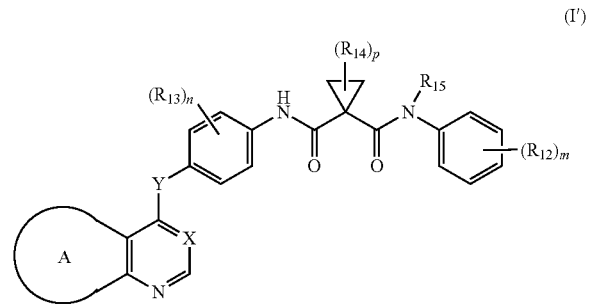

12 Claims, No Drawings
Specification includes a Sequence Listing.

SEQUENCE LISTING

```
Sequence total quantity: 45
SEQ ID NO: 1            moltype = AA  length = 587
FEATURE                 Location/Qualifiers
source                  1..587
                        mol_type = protein
                        organism = Homo sapiens
SEQUENCE: 1
MRPRGLPPLL VVLLGCWASV SAQTDATPAV TTEGLNSTEA ALATFGTFPS TRPPGTPRAP  60
GPSSGPRPTP VTDVAVLCVC DLSPAQCDIN CCCDPDCSSV DFSVFSACSV PVVTGDSQFC 120
SQKAVIYSLN FTANPPQRVF ELVDQINPSI FCIHITNYKP ALSFINPEVP DENNFDTLMK 180
TSDGFTLNAE SYVSFTTKLD IPTAAKYEYG VPLQTSDSFL RFPSSLTSSL CTDNNPAAFL 240
VNQAVKCTRK INLEQCEEIE ALSMAFYSSP EILRVPDSRK KVPITVQSIV IQSLNKTLTR 300
REDTDVLQPT LVNAGHFSLC VNVVLEVKYS LTYTDAGEVT KADLSFVLGT VSSVVVPLQQ 360
KFEIHFLQEN TQPVPLSGNP GYVVGLPLAA GFQPHKGSGI IQTTNRYGQL TILHSTTEQD 420
CLALEGVRTP VLFGYTMQSG CKLRLTGALP CQLVAQKVKS LLWGQGFPDY VAPFGNSQAQ 480
DMLDWVPIHF ITQSFNRKDS CQLPGALVIE VKWTKYGSLL NPQAKIVNVT ANLISSSFPE 540
ANSGNERTIL ISTAVTFVDV SAPAEAGFRA PPAINARLPF NFFFPFV              587

SEQ ID NO: 2            moltype = AA  length = 697
FEATURE                 Location/Qualifiers
source                  1..697
                        mol_type = protein
                        organism = Homo sapiens
SEQUENCE: 2
MGFQPPAALL LRLFLLQGIL RLLWGDLAFI PPFIRMSGPA VSASLVGDTE GVTVSLAVLQ  60
DEAGILPIPT CGVLNNETED WSVTVIPGAK VLEVTVRWKR GLDWCSSNET DSFSESPCIL 120
QTLLVSASHN SSCSAHLLIQ VEIYANSSLT HNASENVTVI PNQVYQPLGP CPCNLTAGAC 180
DVRCCCDQEC SSNLTTLFRR SCFTGVFGGD VNPPFDQLCS AGTTTRGVPD WFPFLCVQSP 240
LANTPFLGYF YHGAVSPKQD SSFEVYVDTD AKDFADFGVK QGDPIMTVKK AYFTIPQVSL 300
AGQCMQNAPV AFLHNFDVKC VTNLELYQER DGIINAKIKN VALGGIVTPK VIYEEATDLD 360
KFITNTETPL NNGSTPRIVN VEEHYIFKWN NNTISEINVK IFRAEINAHQ KGIMTQRFVV 420
KFLSYNSGNE EELSGNPGYQ LGKPVRALNI NRMNNVTTLH LWQSAGRGLC TSATFKPILF 480
GENVLSGCLL EVGINENCTQ LRENAVERLD SLIQATHVAM RGNSDYADLS DGWLEIIRVD 540
APDPGADPLA SSVNGMCLDI PAHLSIRILI SDAGAVEGIT QGEILGVETR FSSVNWQYQC 600
GLTCEHKADL LPISASVQFI KIPAQLPHPL TRFQINYTEY DCNRNEVCWP QLLYPWTQYY 660
QGELHSQCVA KGLLLLLFLT LALFLSNPWT RICKAYS                         697

SEQ ID NO: 3            moltype = AA  length = 607
FEATURE                 Location/Qualifiers
source                  1..607
                        mol_type = protein
                        organism = Homo sapiens
SEQUENCE: 3
MRTPQLALLQ VFFLVFPDGV RPQPSSSPSG AVPTSLELQR GTDGGTLQSP SEATATRPAV  60
PGLPTVVPTL VTPSAPGNRT VDLFPVLPIC VCDLTPGACD INCCCDRDCY LLHPRTVFSF 120
CLPGSVRSSS WVCVDNSVIF RSNSPFPSRV FMDSNGIRQF CVHVNNSNLN YFQKLQKVNA 180
TNFQALAAEF GGESFTSTFQ TQSPPSFYRA GDPILTYFPK WSVISLLRQP AGVGAGGLCA 240
ESNPAGFLES KSTTCTRFFK NLASSCTLDS ALNAASYYNF TVLKVPRSMT DPQNMEFQVP 300
VILTSQANAP LLAGNTCQNV VSQVTYEIET NGTFGIQKVS VSLGQTNLTV EPGASLQQHF 360
ILRFRAFQQS TAASLTSPRS GNPGYIVGKP LLALTDDISY SMTLLQSQGN GSCSVKRHEV 420
QFGVNAISGC KLRLKKADCS HLQQEIYQTL HGRPRPEYVA IFGNADPAQK GGWTRILNRH 480
CSISAINCTS CCLIPVSLEI QVLWAYVGLL SNPQAHVSGV RFLYQCQSIQ DSQQVTEVSL 540
TTLVNFVDIT QKPQPPRGQP KMDWKWPFDF FPPFKVAFSRG VFSQKCSVSP ILILCLLLLG 600
VLNLETM                                                          607

SEQ ID NO: 4            moltype = AA  length = 106
FEATURE                 Location/Qualifiers
source                  1..106
                        mol_type = protein
                        organism = Homo sapiens
SEQUENCE: 4
MATPGPVIPE VPFEPSKPPV IEGLSPTVYR NPESFKEKFV RKTRENPVVP IGCLATAAAL  60
```

```
TYGLYSFHRG NSQRSQLMMR TRIAAQGFTV AAILLGLAVT AMKSRP                      106

SEQ ID NO: 5            moltype = AA   length = 106
FEATURE                 Location/Qualifiers
source                  1..106
                        mol_type = protein
                        organism = Homo sapiens
SEQUENCE: 5
MATLGFVTPE APFESSKPPI FEGLSPTVYS NPEGFKEKFL RKTRENPVVP IGFLCTAAVL       60
TNGLYCFHQG NSQCSRLMMH TQIAAQGFTI AAILLGLAAT AMKSPP                      106

SEQ ID NO: 6            moltype = AA   length = 132
FEATURE                 Location/Qualifiers
source                  1..132
                        mol_type = protein
                        organism = Homo sapiens
SEQUENCE: 6
MCSAGELLRG GDGGERDEDG DALAEREAAG TGWDPGASPR RRGQRPKESE QDVEDSQNHT       60
GEPVGDDYKK MGTLFGELNK NLINMGFTRM YFGERIVEPV IVIFFWVMLW FLGLQALGLV       120
AVLCLVIIYV QQ                                                           132

SEQ ID NO: 7            moltype = AA   length = 1104
FEATURE                 Location/Qualifiers
source                  1..1104
                        mol_type = protein
                        organism = Homo sapiens
SEQUENCE: 7
MERSPGEGPS PSPMDQPSAP SDPTDQPPAA HAKPDPGSGG QPAGPGAAGE ALAVLTSFGR       60
RLLVLIPVYL AGAVGLSVGF VLFGLALYLG WRRVRDEKER SLRAARQLLD DEEQLTAKTL       120
YMSHRELPAW VSFPDVEKAE WLNKIVAQVW PFLGQYMEKL LAETVAPAVR GSNPHLQTFT       180
FTRVELGEKP LRIIGVKVHP GQRKEQILLD LNISYVGDVQ IDVEVKKYFC KAGVKGMQLH       240
GVLRVILEPL IGDLPFVGAV SMFFIRRPTL DINWTGMTNL LDIPGLSSLS DTMIMDSIAA       300
FLVLPNRLLV PLVPDLQDVA QLRSPLPRGI IRIHLLAARG LSSKDKYVKG LIEGKSDPYA       360
LVRLGTQTFC SRVIDEELNP QWGETYEVMV HEVPGQEIEV EVPDKDPDKD DFLGRMKLDV       420
GKVLQASVLD DWFPLQGGQG QVHLRLEWLS LLSDAEKLEQ VLQWNWGVSS RPDPPSAAIL       480
VVYLDRAQDL PLKKGNKEPN PMVQLSIQDV TQESKAVYST NCPVWEEAFR FFLQDPQSQE       540
LDVQVKDDSR ALTLGALTLP LARLLTAPEL ILDQWFQLSS SGPNSRLYMK LVMRILYLDS       600
SEICFPTVPG CPGAWDVDSE NPQRGSSVDA PPRPCHTTPD SQFGTEHVLR IHVLEAQDLI       660
AKDRFLGGLV KGKSDPYVKL KLAGRSFRSH VVREDLNPRW NEVFEVITVS VPGQELEVEV       720
FDKDLDKDDF LGRCKVRLTT VLNSGFLDEW LTLEDVPSGR LHLRLERLTP RPTAAELEEV       780
LQVNSLIQTQ KSAELAAALL SIYMERAEDL PLRKGTKHLS PYATLTVGDS SHKTKTISQT       840
SAPVWDESAS FLIRKPHTES LELQVRGEGT GVLGSLSLPL SELLVADQLC LDRWFTLSSG       900
QGQVLLRAQL GILVSQHSGV EAHSHSYSHS SSSLSEEPEL SGGPPHITSS APELRQRLTH       960
VDSPLEAPAG PLGQVKLTLW YYSEERKLVS IVHGCRSLRQ NGRDPPDPYV SLLLLPDKNR       1020
GTKRRTSQKK RTLSPEFNER FEWELPLDEA QRRKLDVSVK SNSSFMSRER ELLGKVQLDL       1080
AETDLSQGVA RWYDLMDNKD KGSS                                              1104

SEQ ID NO: 8            moltype = AA   length = 271
FEATURE                 Location/Qualifiers
source                  1..271
                        mol_type = protein
                        organism = Homo sapiens
SEQUENCE: 8
MRGNLALVGV LISLAFLSLL PSGHPQPAGD DACSVQILVP GLKGDAGEKG DKGAPGRPGR       60
VGPTGEKGDM GDKGQKSVG RHGKIGPIGS KGEKGDSGDI GPPGPNGEPG LPCECSQLRK        120
AIGEMDNQVS QLTSELKFIK NAVAGVRETE SKIYLLVKEE KRYADAQLSC QGRGGTLSMP       180
KDEAANGLMA AYLAQAGLAR VFIGINDLEK EGAFVYSDHS PMRTFNKWRS GEPNNAYDEE       240
DCVEMVASGG WNDVACHTTM YFMCEFDKEN M                                      271

SEQ ID NO: 9            moltype = AA   length = 847
FEATURE                 Location/Qualifiers
source                  1..847
                        mol_type = protein
                        organism = Homo sapiens
SEQUENCE: 9
MFKCWSVVLV LGFIFLESEG RPTKEGGYGL KSYQPLMRLR HKQEKNQESS RVKGFMIQDG       60
PFGSCENKYC GLGRHCVTSR ETGQAECACM DLCKRHYKPV CGSDGEFYEN HCEVHRAACL       120
KKQKITIVHN EDCFFKGDKC KTTEYSKMKN MLLDLQNQKY IMQENENPNG DDISRKKLLV       180
DQMFKYFDAD SNGLVDINEL TQVIKQEELG KDLFDCTLYV LLKYDDFNAD KHLALEEFYR       240
AFQVIQLSLP EDQKLSITAA TVGQSAVLSC AIQGTLRPPI IWKRNNIILN NLDLEDINDF       300
GDDGSLYITK VTTHVGNYT CYADGYEQVY QTHIFQVNVP PVIRVYPESQ AREPGVTASL        360
RCHAEGIPKP QLGWLKNGID ITPKLSKQLT LQANGSEVHI SNVRYEDTGA YTCIAKNEAG       420
VDEDISSLFV EDSARKTLAN ILWREEGLGI GNMFYVFYED GLKVIQPIEC EFQRHIKPSE       480
KLLGFQDEVC PKAEGDEVQR CVWASAVNVK DKFIYVAQPT LDRVLIVDVQ SQKVVQAVST       540
DPVPVKLHYD KSHDQVWVLS WGTLEKTSPT LQVITLASGN VPHHTIHTQP VGKQFDRVDD       600
FFIPTTTLII THMRFGFILH KDEAALQKID LETMSYIKTI NLKDYKCVPQ SLAYTHLGGY       660
YFIGCKPDST GAVSPQVMVD GVTDSVIGFN SDVTGTPYVS PDGHYLVSIN DVKGLVRVQY       720
ITIRGEIQEA FDIYTNLHIS DLAFQPSFTE AHQYNIYGSS STQDVLFVE LSSGKVKMIK        780
SLKEPLKAEE WPWNRKNRQI QDSGLFGQYL MTPSKDSLFI LDGRLNKLNC EITEVEKGNT       840
```

```
                                    -continued
VIWVGDA                                                                847

SEQ ID NO: 10          moltype = AA   length = 470
FEATURE                Location/Qualifiers
source                 1..470
                       mol_type = protein
                       organism = Homo sapiens
SEQUENCE: 10
MSRLGALGGA RAGLGLLLGT AAGLGFLCLL YSQRWKRTQR HGRSQSLPNS LDYTQTSDPG    60
RHVMLLRAVP GGAGDASVLP SLPREGQEKV LDRLDFVLTS LVALRREVEE LRSSLRGLAG   120
EIVGEVRCHM EENQRVARRR RFPFVRERSD STGSSSVYFT ASSGATFTDA ESEGGYTTAN   180
AESDNERDSD KESEDGEDEV SCETVKMGRK DSLDLEEEAA SGASSALEAG GSSGLEDVLP   240
LLQQADELHR GDEQGKREGF QLLLNNKLVY GSRQDFLWRL ARAYSDMCEL TEEVSEKKSY   300
ALDGKEEAEA ALEKGDESAD CHLWYAVLCG QLAEHESIQR RIQSGFSFKE HVDKAIALQP   360
ENPMAHFLLG RWCYQVSHLS WLEKKTATAL LESPLSATVE DALQSFLKAE ELQPGFSKAG   420
RVYISKCYRE LGKNSEARWW MKLALELPDV TKEDLAIQKD LEELEVILRD              470

SEQ ID NO: 11          moltype = AA   length = 495
FEATURE                Location/Qualifiers
source                 1..495
                       mol_type = protein
                       organism = Homo sapiens
SEQUENCE: 11
MENKAMYLHT VSDCDTSSIC EDSFDGRSLS KLNLCEDGPC HKRRASICCT QLGSLSALKH    60
AVLGLYLLVF LILVGIFILA VSRPRSSPDD LKALTRNVNR LNESFRDLQL RLLQAPLQAD   120
LTEQVWKVQD ALQNQSDSLL ALAGAVQRLE GALWGLQAQA VQTEQAVALL RDRTGQQSDT   180
AQLELYQLQV ESNSSQLLLR RHAGLLDGLA RRVGILGEEL ADVGGVLRGL NHSLSYDVAL   240
HRTRLQDLRV LVSNASEDTR RLRLAHVGME LQLKQELAML NAVTEDLRLK DWEHSIALRN   300
ISLAKGPPGP KGDQGDEGKE GRPGIPGLPG LRGLPGERGT PGLPGPKGDD GKLGATGPMG   360
MRGFKGDRGP KGEKGEKGDR AGDASGVEAP MMIRLVNGSG PHEGRVEVYH DRRWGTVCDD   420
GWDKKDGDVV CRMLGFRGVE EVYRTARFGQ GTGRIWMDDV ACKGTEETIF RCSFSKWGVT   480
NCGHAEDASV TCNRH                                                   495

SEQ ID NO: 12          moltype = AA   length = 236
FEATURE                Location/Qualifiers
source                 1..236
                       mol_type = protein
                       organism = Homo sapiens
SEQUENCE: 12
MTAEFLSLLC LGLCLGYEDE KKNEKPPKPS LHAWPSSVVE AESNVTLKCQ AHSQNVTFVL    60
RKVNDSGYKQ EQSSAENEAE FPFTDLKPKD AGRYFCAYKT TASHEWSESS EHLQLVVTDK   120
HDELEAPSMK TDTRTIFVAI FSCISILLLF LSVFIIYRCS QHSSSSEEST KRTSHSKLPE   180
QEAAEADLSN MERVSLSTAD PQGVTYAELS TSALSEAASD TTQEPPGSHE YAALKV       236

SEQ ID NO: 13          moltype = AA   length = 180
FEATURE                Location/Qualifiers
source                 1..180
                       mol_type = protein
                       organism = Homo sapiens
SEQUENCE: 13
MAAAEEEDGG PEGPNRERGG AGATFECNIC LETAREAVVS VCGHLYCWPC LHQWLETRPE    60
RQECPVCKAG ISREKVVPLY GRGSQKPQDP RLKTPPRPQG QRPAPESRGG FQPFGDTGGF   120
HFSFGVGAFP FGFFTTVFNA HEPFRRGTGV DLGQGHPASS WQDSLFLFLA IFFFFWLLSI   180

SEQ ID NO: 14          moltype = AA   length = 157
FEATURE                Location/Qualifiers
source                 1..157
                       mol_type = protein
                       organism = Homo sapiens
SEQUENCE: 14
MLPEQGPQPS TMPLWCLLAA CTSLPRQAAT MLEEAASPNE AVHASTSGSG ALTDQTFTDL    60
SAAEASSEEV PDFMEVPHSV HHKINCFFYL EKQLCQLPSP LCLSSLLTLK LKTTVPAPGR   120
WWSFQPHKAF PLLVGTPGSW QSTIDPAWAA PSQPSPG                            157

SEQ ID NO: 15          moltype = AA   length = 716
FEATURE                Location/Qualifiers
source                 1..716
                       mol_type = protein
                       organism = Homo sapiens
SEQUENCE: 15
MMSIRQRREI RATEVSEDFP AQEENVKLEN KLPSGCTSRR LWKILSLTIG GTIALCIGLL    60
TSVYLATHLE NDLWFSNIKE VEREISFRTE CGLYYSYYKQ MLQAPTLVQG FHGLIYDNKT   120
ESMKTINLLQ RMNIYQEVFL SILYRVLPIQ KYLEPVYFYI YTLFGLQAIY VTALYITSWL   180
LSGTWLSGLL AAFWYVTNRI DTTRVEFTIP LRENWALPAT AIQIAAITYF LRPNLQPLSE   240
RLTLLAIFIS TFLFSLTWQF NQFMMLMQAL VLFTLDSLDM LPAVKATWLY GIQITSLLLV   300
CILQFFNSMI LGSLLISFNL SVFIARKLQK NLKTGSFLNR LGKLLLHLFM VLCLTLFLNN   360
IIKKILNLKS DEHIFKFLKA KFGLGATRDF DANLYLCEEA FGLLPFNTFG RLSDTLLFYA   420
YIFVLSITVI VAFVVAFHNL SDSTNQQSVG KMEKGTVDLK PETAYNLIHT ILFGFLALST   480
MRMKYLWTSH MCVFASFGLC SPEIWELLLK SVHLYNPKRI CIMRYSVPIL ILLYLCYKFW   540
```

```
PGMMDELSEL REFYDPDTVE LMNWINSNTP RKAVFAGSMQ LLAGVKLCTG RTLTNHPHYE   600
DSSLRERTRA VYQIYAKRAP EEVHALLRSF GTDYVILEDS ICYERRHRRG CRLRDLLDIA   660
NGHMMDGPGE NDPDLKPADH PRFCEEIKRN LPPYVAYFTR VFQNKTFHVY KLSRNK       716

SEQ ID NO: 16              moltype = AA  length = 831
FEATURE                    Location/Qualifiers
source                     1..831
                           mol_type = protein
                           organism = Homo sapiens
SEQUENCE: 16
MKVHMHTKFC LICLLTFIFH HCNHCHEEHD HGPEALHRQH RGMTELEPSK FSKQAAENEK    60
KYYIEKLFER YGENGRLSFF GLEKLLTNLG LGERKVVEIN HEDLGHDHVS HLDILAVQEG   120
KHFHSHNHQH SHNHLNSENQ TVTSVSTKRN HKCDPEKETV EVSVKSDDKH MHDHNHRLRH   180
HHRLHHHLDH NNTHHFHNDS ITPSERGEPS NEPSTETNKT QEQSDVKLPK GKRKKKGRKS   240
NENSEVITPG FPPNHDQGEQ YEHNRVHKPD RVHNPGHSHV HLPERNGHDP GRGHQDLDPD   300
NEGELRHTRK REAPHVKNNA IISLRKDLNE DDHHHECLNV TQLLKYYGHG ANSPISTDLF   360
TYLCPALLYQ IDSRLCIEHF DKLLVEDINK DKNLVPEDEA NIGASAWICG IISITVISLL   420
SLLGVILVPI INQGCFKFLL TFLVALAVGT MSGDALLHLL PHSQGGHDHS HQHAHGHGHS   480
HGHESNKFLE EYDAVLKGLV ALGGIYLLFI IEHCIRMFKH YKQQRGKQKW FMKQNTEEST   540
IGRKLSDHKL NNTPDSDWLQ LKPLAGTDDS VVSEDRLNET ELTDLEGQQE SPPKNYLCIE   600
EEKIIDHSHS DGLHTIHEHD LHAAAHNHHG ENKTVLRKHN HQWHHKHSHH SHGPCHSGSD   660
LKETGIANIA WMVIMGDGIH NFSDGLAIGA AFSAGLTGGI STSIAVFCHE LPHELGDFAV   720
LLKAGMTVKQ AIVYNLLSAM MAYIGMLIGT AVGQYANNIT LWIFAVTAGM FLYVALVDML   780
PEMLHGDGDN EEHGFCPVGQ FILQNLGLLF GFAIMLVIAL YEDKIVFDIQ F            831

SEQ ID NO: 17              moltype = AA  length = 600
FEATURE                    Location/Qualifiers
source                     1..600
                           mol_type = protein
                           organism = Homo sapiens
SEQUENCE: 17
MAALAPVGSP ASRGPRLAAG LRLLPMLGLL QLLAEPGLGR VHHLALKDDV RHKVHLNTFG    60
FFKDGYMVVN VSSLSLNEPE DKDVTIGFSL DRTKNDGFSS YLDEDVNYCI LKKQSVSVTL   120
LILDISRSEV RVKSPPEAGT QLPKIIFSRD EKVLGQSAGN NVNPASAGNQ TQKTQDGGKS   180
KRSTVDSKAM GEKSFSVHNN GGAVSFQFFF NISTDDQEGL YSLYFHKCLG KELPSDKFTF   240
SLDIEITEKN PDSYLSAGEI PLPKLYISMA FFFFLSGTIW IHILRKRRND VFKIHWLMAA   300
LPFTKSLSLV FHAIDYHYIS SQGFPIEGWA VVYYITHLLK GALLFITIAL IGTGWAFIKH   360
ILSDKDKKIF MIVIPLQVLA NVAYIIIEST EEGTTEYGLW KDSLFLVDLL CCGAILFPVV   420
WSIRHLQEAS ATDGKGDSMG PLQQRANLRA GSRIESHHFA QADLELLASS CPPASVSQRA   480
GITAAINLAK LKLFRHYYVL IVCYIYFTRI IAFLLKLAVP FQWKWLYQLL DETATLVFFV   540
LTGYKFRPAS DNPYLQLSQE EEDLEMESVV TTSGVMESMK KVKKVTNGSV EPQGEWEGAV   600

SEQ ID NO: 18              moltype = AA  length = 1284
FEATURE                    Location/Qualifiers
source                     1..1284
                           mol_type = protein
                           organism = Homo sapiens
SEQUENCE: 18
MSSGDPAHLG LCLWLWLGAT LGREQVQASG LLRLAVLPED RLQMKWRESE GSGLGYLVQV    60
KPMAGDSEQE VILTTKTPKA TVGGLSPSKG YTLQIFELTG SGRFLLARRE FVIEDLKSSS   120
LDRSSQPRLG SGAPEPTPSH TGSPDPEQAS EPQVAFTPSQ DPRTPAGPQF RCLPPVPADM   180
VFLVDGSWSI GHSHFQQVKD FLASVIAPFE IGPDKVQVGL TQYSGDAQTE WDLNSLSTKE   240
QVLAAVRRLR YKGGNTFTGL ALTHVLGQNL QPAAGLRPEA AKVVILVTDG KSQDDVHTAA   300
RVLKDLGVNV FAVGVKNADE AELRLLASPP RDITVHSVLD FLQLGALAGL LSRLICQRLQ   360
GGSPRQGPAA APALDTLPAP TSLVLSQVTS SSIRLSWTPA PRHPLKYLIV WRASRGGTPR   420
EVVVEGPAAS TELHNLASRT EYLVSVFPIY EGGVGEGLRG LVTTAPLPPP RALTLAAVTP   480
RTVHLTWQPS AGATHYLVRC SPASPKGEEE EREVQVGRPE VLLDGLEPGR DYEVSVQSLR   540
GPEGSEARGI RARTPTLAPP RHLGFSDVSH DAARVFWEGA PRPVRLVRVT YVSSEGGHSG   600
QTEAPGNATS ATLGPLSSST TYTVRVTCLY PGGGSSTLTG RVTTKKAPSP SQLSMTELPG   660
DAVQLAWVAA APSGVLVYQI TWTPLGEGKA HEISVPGNLG TAVLPGLGRH TEYDVTILAY   720
YRDGARSDPV SLRYTPSTVS RSPPSNLALA SETPDSLQVS WTPPLGRVLH YWLTYAPASG   780
LGPEKSVSVP GARSHVTLPD LQAATKYRVL VSAIYAAGRS EAVSATGQTA CPALRPDGSL   840
PGFDLMVAFS LVKEKAYASIR GVAMEPSAFG GTPFTFLFKD AQLTRRVSDV YPAPLPPEHT   900
IVFLVRLLPE TPREAFALWQ MTAEDFQPLL GVLLDAGKKS LTYFHRDPRA ALQEATFDPQ   960
EVRKIFFGSF HKVHVAVGRS KVRLYVDCRK VAERPLGEMG SPPAAGFVTL GRLAKARGPR  1020
SSSAAFQLQM LQIVCSDTWA DEDRCCELPA SRDGETCPAF VSACSCSSET PGPPGPQGPP  1080
GLPGRNGTPG EQGFPGPRGP PGVKGEKGDH GLPGLQGHPG HQGIPGRVGL QGPKGMRGLE  1140
GTAGLPGPPG PRGFQGMAGA RGTSGERGPP GTVGPTGLPG PKGERGEKGE PQSLATLYQL  1200
VSQASHSKF DSFHENTRPP MPILEQKLEP GTEPLGSPGT RSKALVPGEW GRGGRHLEGR  1260
GEPGAVGQMG SPGQQGASTQ GLWE                                        1284

SEQ ID NO: 19              moltype = AA  length = 626
FEATURE                    Location/Qualifiers
source                     1..626
                           mol_type = protein
                           organism = Homo sapiens
SEQUENCE: 19
MAARPAATLA WSLLLLSSAL LREGCRARFV AERDSEDDGE EPVVFPESPL QSPTVLVAVL    60
ARNAAHTLPH FLGCLERLDY PKSRMAIWAA TDHNVDNTTE IFREWLKNVQ RLYHYVEWRP   120
```

```
MDEPESYPDE IGPKHWPTSR FAHVMKLRQA ALRTAREKWS DYILFIDVDN FLTNPQTLNL    180
LIAENKTIVA PMLESRGLYS NFWCGITPKG FYKRTPDYVQ IREWKRTGCF PVPMVHSTFL    240
IDLRKEASDK LTFYPPHQDY TWTFDDIIVF AFSSRQAGIQ MYLCNREHYG YLPIPLKPHQ    300
TLQEDIENLI HVQIEAMIDR PPMEPSQYVS VVPKYPDKMG FDEIFMINLK RRKDRRDRML    360
RTLYEQEIEV KIVEAVDGKA LNTSQLKALN IEMLPGYRDP YSSRPLTRGE IGCFLSHYSV    420
WKEVIDRELE KTLVIEDDVR FEHQFKKKLM KLMDNIDQAQ LDWELIYIGR KRMQVKEPEK    480
AVPNVANLVE ADYSYWTLGY VISLEGAQKL VGANPFGKML PVDEFLPVMY NKHPVAEYKE    540
YYESRDLKAF SAEPLLIYPT HYTGQPGYLS DTETSTIWDN ETVATDWDRT HAWKSRKQSR    600
IYSNAKNTEA LPPPTSLDTV PSRDEL                                        626

SEQ ID NO: 20           moltype = AA  length = 610
FEATURE                 Location/Qualifiers
source                  1..610
                        mol_type = protein
                        organism = Homo sapiens
SEQUENCE: 20
MAQEIDLSAL KELEREAILQ VLYRDQAVQN TEEERTRKLK THLQHLRWKG AKNTDWEHKE    60
KCCARCQQVL GFLLHRGAVC RGCSHRVCAQ CRVFLRGTHA WKCTVCFEDR NVKIKTGEWF    120
YEEERAKKFPT GGKHETVGGQ LLQSYQKLSK ISVVPPTPPP VSESQCSRSP GRLQEFGQFR   180
GFNKSVENLF LSLATHVKKL SKSQNDMTSE KHLLATGPRQ CVGQTERRSQ SDTAVNVTTR    240
KVSAPDILKP LNQEDPKCST NPILKQQNLP SSPAPSTIFS GGFRHGSLIS IDSTCTEMGN    300
FDNANVTGEI EFAIHYCFKT HSLEICIKAC KNLAYGEEKK KKCNPYVKTY LLPDRSSQGK    360
RKTGVQRNTV DPTFQETLKY QVAPAQLVTR QLQVSVWHLG TLARRVFLGE VIIPLATWDF    420
EDSTTQSFRW HPLRAKAEKY EDSVPQSNGE LTVRAKLVLP SRPRKLQEAQ EGTDQPSLHG    480
QLCLVVLGAK NLPVRPDGTL NSFVKGCLTL PDQQKLRLKS PVLRKQACPQ WKHSFVFSGV    540
TPAQLRQSSL ELTVWDQALF GMNDRLLGGT RLGSKGDTAV GGDACSLSKL QWQKVLSSPN    600
LWTDMTLVLH                                                          610

SEQ ID NO: 21           moltype = AA  length = 775
FEATURE                 Location/Qualifiers
source                  1..775
                        mol_type = protein
                        organism = Homo sapiens
SEQUENCE: 21
MDCRTKANPD RTFDLVLKVK CHASENEDPV VLWKFPEDFG DQEILQSVPK FCFPFDVERV    60
SQNQVGQHFT FVLTDIESKQ RFGFCRLTSG GTICLCILSY LPWFEVYYKL LNTLADYLAK    120
ELENDLNETL RSLYNHPVPK ANTPVNLSVN QEIFIACEQV LKDQPALVPH SYFIAPDVTG    180
LPTIPESRNL TEYFVAVDVN NMLQLYASML HERRIVIASS KLSTLTACIH GSAALLYPMY    240
WQHIYIPVLP PHLLDYCCAP MPYLIGIHSS LIERVKNKSL EDVVMLNVDT NTLESPFSDL    300
NNLPSDVVSA LKNKLKKQST ATGDGVARAF LRAQAALFGS YRDALRYKPG EPITFCEESF    360
VKHRSSVMKQ FLETAINLQL FKQFIDGRLA KLNAGRGFSD VFEEEITSGG FCGGNPRSYQ    420
QWVHTVKKGG ALFNTAMTKA TPAVRTAYKF AKNHAKLGLK EVKSKLHKE NEEDYGTCSS     480
SVQYTPVYKL HNEKGGNSEK RKLAQARLKR PLKSLDGALY DDEDDDDIER ASKLSSEDGE    540
EASAYLYESD DSVETRVKTP YSGEMDLLGE ILDTLSTHSS DQGKLAAAKS LDFFRSMDDI    600
DYKPTNKSNA PSENNLAFLC GGSGDQAEWN LGQDDSALHG KHLPPSPRKR VSSSGLTDSL    660
FILKEENSNK HLGADNVSDP TSGLDFQLTS PEVSQTDKGK TEKRETLSQI SDDLLIPGLG    720
RHSSTFVPWE KEGKEAKETS EDIGLLHEVV SLCHMTSDFQ QSLNISDKNT NGNQT         775

SEQ ID NO: 22           moltype = AA  length = 8797
FEATURE                 Location/Qualifiers
source                  1..8797
                        mol_type = protein
                        organism = Homo sapiens
SEQUENCE: 22
MATSRGASRC PRDIANVMQR LQDEQEIVQK RTFTKWINSH LAKRKPPMVV DDLFEDMKDG    60
VKLLALLEVL SGQKLPCEQG RRMKRIHAVA NIGTALKFLE GRKIKLVNIN STDIADGRPS    120
IVLGLMWTII LYFQIEELTS NLPQLQSLSS SASSVDSIVS SETPSPPSKR KVTTKIQGNA    180
KKALLKWVQY TAGKQTGIEV KDFGKSWRSG VAFHSVIHAI RPELVDLETV KGRSNRENLE    240
DAFTIAETEL GIPRLLDPED VDVDKPDEKS IMTYVAQFLK HYPDIHNAST DGQEDDEILP    300
GFPSFANSVQ NFKKREDRVIF KEMKVWIEQF ERDLTRAQMV ESNLQDKYQS FKHFRVQYEM    360
KRKQIEHLIQ PLHRDGKLSL DQALVKQSWD RVTSRLFDWH IQLDKSLPAP LGTIGAWLYR    420
AEVALREEIT VQQVHEETAN TIQRKLEQHK DLLQNTDAHK RAFHEIYRTR SVNGIPVPPD    480
QLEDMAERFH FVSSTSELHL MKMEFLELKY RLLSLLVLAE SLKKSWIIKY GRRESVEQLL    540
QNYVSFIENS KFFEQYEVTY QILKQTAEMY VKADGSVEEA ENVMKFMNET TAQWRNLSVE    600
VRSVRSMLEE VISNWDRYGN TVASLQAWLE DAEKMLNQSE NAKKDFFRNL PHWIQQHTAM    660
NDAGNFLIET CDEMVSRDLK QQLLLLNGRW RELFMEVKQY AQADEMDRMK KEYTDCVVTL    720
SAFATEAHKK LSEPLEVSFM NVKLLIQDLE DIEQRVPVMD AQYKIITKTA HLITKESPQE    780
EGKEMPATMS KLKEQLTKVK ECYSPLLYES QQLLIPLEEL EKQMTSFYDS LGKINEIITV    840
LEREAQSSAL FKQKHQELLA CQENCKKTLT LIEKGSQSVQ KFVTLSNVLK HFDQTRLQRQ    900
IADIHVAFQS MVKKTGDWKK HVETNSRLMK KFEESRAELE KVLRIAQEGL EEKGDPEELL    960
RRHTEFFSQL DQRVLNAFLK ACDELTDILP EQEQQGLQEA VRKLHKQWKD LQGEAPYHLL   1020
HLKIDVEKNR FLASVEECRT ELDRETKLMP QEGSEKIIKE HRVFFSDKGP HHLCEKRLQL   1080
IEELCVKLPV RDPVRDTPGT CHVTLKELRA AIDSTYRKLM EDPDKWKDYT SRFSEFSSWI   1140
STNETQLKGI KGEAIDTANH GEVKRAVEEI RNGVTKRGET LSWLKSRLKV LTEVSSENEA   1200
QKQGDELAKL SSSFKALVTL LSEVEKMLSN FGDCVQYKEI VKNSLEELIS GSKEVQEQAE   1260
KILDTENLFE AQQLLLHHQQ KTKRISAKKR DVQQQIAQAQ QGEGGLPDRG HEELRKLEST   1320
LDGLERSRER QERRIQVTLR KWERFETNKE TVVRYLFQTG SSHERFLSFS SLESLSSELE   1380
QTKEFSKRTE SIAVQAENLV KEASEIPLGP QNKQLLQQQA KSIKEQVKKL EDTLEEDIKT   1440
MEMVKTKWDH FGSNFETLSV WITEKEKELN ALETSSSAMD MQISQIKVTI QEIESKLSSI   1500
```

```
VGLEEEAQSF AQFVTTGESA RIKAKLTQIR RYGEELREHA QCLEGTILGH LSQQQKFEEN   1560
LRKIQQSVSE FEDKLAVPIK ICSSATETYK VLQEHMDLCQ ALESLSSAIT AFSASARKVV   1620
NRDSCVQEAA ALQQQYEDIL RRAKERQTAL ENLLAHWQRL EKELSSFLTW LERGEAKASS   1680
PEMDISADRV KVEGELQLIQ ALQNEVVSQA SFYSKLLQLK ESLFSVASKD DVKMMKLHLE   1740
QLDERWRDLP QIINKRINFL QSVVAEHQQF DELLLSFSVW IKLFLSELQT TSEISIMDHQ   1800
VALTRHKDHA AEVESKKGEL QSLQGHLAKL GSLGRAEDLH LLQGKAEDCF QLFEEASQVV   1860
ERRQLALSHL AEFLQSHASL SGILRQLRQT VEATNSMNKN ESDLIEKDLN DALQNAKALE   1920
SAAVSLDGIL SKAQYHLKIG SSEQRTSCRA TADQLCGEVE RIQNLLGTKQ SEADALAVLK   1980
KAFQDQKEEL LKSIEDIEER TDKERLKEPT RQALQQRLRV FNQLEDELNS HEHELCWLKD   2040
KAKQIAQKDV AFAPEVDREI NRLEVTWDDT KRLIHENQGQ CCGLIDLMRE YQNLKSAVSK   2100
VLENASSVIV TRTTIKDQED LKWAFSKHET AKNKMNYKQK DLDNFTSKGK HLLSELKKIH   2160
SSDFSLVKTD MESTVDKWLD VSEKLEENMD RLRVSLSIWD DVLSTRDEIE GWSNNCVPQM   2220
AENISNLDNH LRAEELLKEF ESEVKNKALR LEELHSKVND LKELTKNLET PPDLQFIEAD   2280
LMQKLEHAKE ITEVAKGTLK DFTAQSTQVE KFINDITTWF TKVEESLMNC AQNETCEALK   2340
KVKDIQKELQ SQQSNISSTQ ENLNSLCRKY HSAELESLGR AMTGLIKKHE AVSQLCSKTQ   2400
ASLQESLEKH FSESMQEFQE WFLGAKAAAK ESSDRTGDSK VLEAKLHDLQ NILDSVSDGQ   2460
SKLDAVTQEG QTLYAHLSKQ IVSSIQEQIT KANEEFQAFL KQCLKDKQAL QDCASELGSF   2520
EDQHRKLNLW IHEMEERFNT ENLGESKQHI PEKKNEVHKV EMFLGELLAA RESLDKLSQR   2580
GQLLSEEGHG AGQEGRLCSQ LLTSHQNLLR MTKEKLRSCQ VALQEHEALE EALQSMWFWV   2640
KAIQDRLACA ESTLGSKDTL EKRLSQIQDI LLMKGEGEVK LNMAIGKGEQ ALRSSNKEGQ   2700
RVIQTQLETL KEVWADIMSS SVHAQSTLES VISQWNDYVE RKNQLEQWME SVDQKIEHPL   2760
QPQPGLKEKF VLLDHLQSIL SEAEDHTRAL HRLIAKSREL YEKTEDESFK DTAQEELKTQ   2820
FNDIMTVAKE KMRKVEEIVK DHLMYLDAVH EFTDWLHSAK EELHRWSDMS GDSSATQKKL   2880
SKIKELIDSR EIGASRLSRV ESLAPEVKQN TTASGCELMH TEMQALRADW KQWEDSVFQT   2940
QSCLENLVSQ MALSEQEFSG QVAQLEQALE QFSALLKTWA QQLTLLEGKN TDEEIVECWH   3000
KGQEILDALQ KAEPRTEDLK SQLNELCRFS RDLSTYSGKV SGLIKEYNCL CLQASKGCQN   3060
KEQILQQRFR KAFRDFQQWL VNAKITTAKC FDIPQNISEV STSLQKIQEF LSESENGQHK   3120
LNMMLSKGEL LSTLLTKEKA KGIQAKVTAA KEDWKNFHSN LHQKESALEN LKIQMKDFEV   3180
SAEPIQDWLS KTEKMVHESS NRLYDLPAKR REQQKLQSVL EEIHCYEPQL NRLKEKAQQL   3240
WEGQAASKSF RHRVSQLSSQ YLALSNLTKE KVSRLDRIVA EHNQFSLGIK ELQDWMTDAI   3300
HMLDSYCHPT SDKSVLDSRT LKLEALLSVK QEKEIQMKMI VTRGESVLQN TSPEGIPTIQ   3360
QQLQSVKDMW ASLLSAGIRC KSQLEGALSK WTSYQDGVRQ FSGWMDSMEA NLNESERQHA   3420
ELRDKTTMLG KAKLLNEEVL SYSSLLETIE VKGAGMTEHY VTQLELQDLQ ERYRAIQERA   3480
KEAVTKSEKL VRLHQEYQRD LKAFEVWLGQ EQEKLDQSVY LEGDAHTHET TLRDLQELQV   3540
HCAEGQALLN SVLHTREDVI PSGIPQAEDR ALESLRQDWQ AYQHRLSETR TQFNNVVNKL   3600
RLMEQKFQQV DEWLKTAEEK VSPRTRRQSN RATKEIQLHQ MKKWHEEVTA YRDEVEEVGA   3660
RAQEILDESH VNSRMGCQAT QLTSRYQALL LQVLEQIKFL EEEIQSLEES ESSLSSYSDW   3720
YGSTHKNFKN VATKIDKVDT VMMGKKLKTL EVLLKDMEKG HSLLKSAREK GERAVKYLEE   3780
GEAERLRKEI HDHMEQLKEL TSTVRKEHMT LEKGLHLAKE FSDKCKALTQ WIAEYQEILH   3840
VPEEPKMELY EKKAQLSKYK SLQQTVLSHE PSVKSVREKG EALLELVQDV TLKDKIDQLQ   3900
SDYQDLCSIG KEHVFSLEAK VKDHEDYNSE LQEVEKWLLQ MSGRLVAPDL LETSSLETIT   3960
QQLAHHKAMM EEIAGFEDRL NNLQMKGDTL IGQCADHLQA KLKQNVHAHL QGTKDSYSAI   4020
CSTAQRMYQS LEHELQKHVS RQDTLQQCQA WLSAVQPDLE PSPQPPLSRA EAIKQVKHFR   4080
ALQEQARTYL DLLCSMCDLS NASVKTTAKD IQQTEQTIEQ KLVQAQNLTQ GWEEIKHLKS   4140
ELWIYLQDAD QQLQNMKRRH SELELNIAQN MVSQVKDFVK KLQSKQASVN TIIEKVNKLT   4200
KKEESPEHKE INHLNDQWLD LCRQSNNLCL QREEDLQRTR DYHDCMNVVE VFLEKFTTEW   4260
DNLARSDAES TAVHLEALKK LALALQERKY AIEDLKDQKQ KMIEHLNLDD KELVKEQTSH   4320
LEQRWFQLED LIKRKIQVSV TNLEELNVVQ SRFQELMEWA EEQQPNIAEA LKQSPPPDMA   4380
QNLLMDHLAI CSELEAKQML LKSLIKDADR VMADLGLNER QVIQKALSDA QSHVNCLSDL   4440
VGQRRKYLNK ALSEKTQFLM AVFQATSQIQ QHERKIMFRE HICLLPDDVS KQVKTCKSAQ   4500
ASLKTYQNEV TGLWAQGREL MKEVTEQEKS EVLGKLQELC SVYDSVLQKC SHRLQELEKN   4560
LVSRKHFKED FDKACHWLKQ ADIVTFPEIN LMNESSELHT QLAKYQNILE QSPEYENLLL   4620
TLQRTGQTIL PSLNEVDHSY LSEKLNALPR QFNVIVALAK DKFYKVQEAI LARKEYASLI   4680
ELTTQSLSEL EAQFLRMSKV PTDLAVEEAL SLQDGCRAIL DEVAGLGEAV DELNQKKEGF   4740
RSTGQPWQPD KMLHLVTLYH RLKRQTEQRV SLLEDTTSAY QHEKMCQQL ERQLKSVKEE   4800
QSKVNEETLP AEEKLKMYHS LAGSLQDSGI VLKRVTIHLE DLAPHLDPLA YEKARHQIQS   4860
WQGELKLLTS AIGETVTECE SRMVQSIDFQ TEMSRSLDWL RRVKAELSGP VYLDLNLQDI   4920
QEEIRKIQIH QEEVQSSLRI MNALSHKEKE KFTKAKELIS ADLEHSLAEL SELDGDIQEA   4980
LRTRQATLTE IYSQCQRYYQ VFQAANDWLE DAQELLQLAG NGLDVESAEE NLKSHMEFFS   5040
TEDQFHSNLE ELHSLVATLD PLIKPTGKED LEQKVASLEL RSQRMSRDSG AQVDLLQRCT   5100
AQWHDYQKAR EEVIELMNDT EKKLSEFSLL KTSSSHEAEE KLSEHKALVS VVNSPHEKIV   5160
ALEEKASQLE KTGNDASKAT LSRSMTTVWQ RWTRLRAVAQ DQEKILEDAV DEWTGFNNKV   5220
KKATEMIDQL QDKLPGSSAE KASKAELLTL LEYHDTFVLE LEQQQSALGM LRQQTLSMLQ   5280
DGAAPTPGEE PPLMQEITAM QDRCLNMQEK VKTNGKLVKQ ELKDREMVET QINSVKCWVQ   5340
ETKEYLGNPT IEIDAQLEEL QILLTEATNH RQNIEKMAEE QKEKYLGLYT ILPSELSLQL   5400
AEVALDLKIR DQIQDKIKEV EQSKATSQEL SRQIQKLAKD LTTILTKLKA KTDNVVQAKT   5460
DQKVLGEELD GCNSKLMELD AAVQKFLEQN GQLGKPLAKK IGKLTELHQQ TIRQAENRLS   5520
KLNQAASHLE EYNEMLELIL KWIEKAKVLA HGTIAWNSAS QLREQYILHQ TLLEESKEID   5580
SELEAMTEKL QYLTSVYCTE KMSQQVAELG RETEELRQMI KIRLQNLQDA AKDMKKFEAE   5640
LKKLQAALEQ AQATLTSPEV GRLSLKEQLS HRQHLLSEME SLKPKVQAVQ LCQSSALRIPE  5700
DVVASLPLCH AALRLQEEAS RLQHTAIQQC NIMQEAVVQY EQYEQEMKHL QQLIEGAHRE   5760
IEDKPVATSN IQELQAQISR HEELAQKIKG YQEQIASLNS KCKMLTMKAK HATMLLTVTE   5820
VEGLAEGTED LDGELLPTPS AHPSVVMMTA GRCHTLLSPV TEESGEEGTN SEISSPPACR   5880
SPSPVANTDA SVNQDIAYYQ ALSAERLQTD AAKIHPSTSA SQEFYEPGLE PSATAKLGDL   5940
QRSWETLKNV ISEKQRTLYE ALERQQKYQD SLQSISTKME AIELKLSESP EPGRSPESQM   6000
AEHQALMDEI LMLQDEINEL QSSLAEELVS ESCEADPAEQ LALQSTLTVL AERMSTIRMK   6060
ASGKRQLLEE KLNDQLEEQR QEQALQRYRC EADELDSWLL STKATLDTAL SPPKEPMDME   6120
AQLMDCQNML VEIEQKVVAL SELSVHNENL LLEGKAHTKD EAEQLAGKLR RLKGSLLELQ   6180
RALHDKQLNM QGTAQEKEES DVDLTATQSP GVQEWLAQAR TTWTQQRQSS LQQQKELEQE   6240
```

```
LAEQKSLLRS VASRGEEILI QHSAAETSGD AGEKPDVLSQ ELGMEGEKSS AEDQMRMKWE    6300
SLHQEFSTKQ KLLQNVLEQE QEQVLYSRPN RLLSGVPLYK GDVPTQDKSA VTSLLDGLNQ    6360
AFEEVSSQSG GAKRQSIHLE QKLYDGVSAT STWLDDVEER LFVATALLPE ETETCLFNQE    6420
ILAKDIKEMS EEMDKNKNLF SQAFFPENGDN RDVIEDTLGC LLGRLSLLDS VVNQRCHQMK   6480
ERLQQILNFQ NDLKVLFTSL ADNKYIILQK LANVFEQPVA EQIEAIQQAE DGLKEFDAGI    6540
IELKRRGDKL QVEQPSMQEL SKLQDMYEDL MMIIGSRRSG LNQNLTLKSQ YERALQDLAD    6600
LLETGQEKMA GDQKIIVSSK EEIQQLLDKH KEYFQGLESH MILTETLFRK IISFAVQKET    6660
QFHTELMAQA SAVLKRAHKR GVELEYILET WSHLDEDQQE LSRQLEVVES SIPSVGLVEE    6720
NEDRLIDRIT LYQHLKSSLN EYQPKLYQVL DDGKRLLISI SCSDSLESQLN QLGECWLSNT   6780
NKMSKELHRL ETILKHWTRY QSESADLIHW LQSAKDRLEF WTQQSVTVPQ ELEMVRDHLN    6840
AFLEFSKEVD AQSSLKSSVL STGNQLLRLK KVDTATLRSE LSRIDSQWTD LLTNIPAVQE    6900
KLHQLQMDKL PSRHAISEVM SWISLMENVI QKDEDNIKNS IGYKAIHEYL QKYKGFKIDI    6960
NCKQLTVDFV NQSVLQISSQ DVESKRSDKT DFAEQLGAMN KSWQILQGLV TEKIQLLEGL    7020
LESWSEYENN VQCLKTWFET QEKRLKQQHR IGDQASVQNA LKDCQDLEDL IKAKEKEVEK    7080
IEQNGLALIQ NKKEDVSSIV MSTLRELGQT WANLDHMVGQ LKILLKSVLD QWSSHKVAFD    7140
KINSYLMEAR YSLSRFRLLT GSLEAVQVQV DNLQNLQDDL EKQERSLQKF GSITNQLLKE    7200
CHPPVTETLT NTLKEVNMRW NNLLEEIAEQ LQSSKALLQL WQRYKDYSKQ CASTVQQQED    7260
RTNELLKAAT NKDIADDEVA TWIQDCNDLL KGLGTVKDSL FFLHELGEQL KQQVDASAAS    7320
AIQSDQLSLS QHLCALEQAL CKQQTSLQAG VLDYETFAKS LEALEAWIVE AEEILQGQDP    7380
SHSSDLSTIQ ERMEELKGQM LKFSSMAPDL DRLNELGYRL PLNDKEIKRM QNLNRHWSLI    7440
SSQTTERFSK LQSFLLQHQT FLEKCETWME FLVQTEQKLA VEISGNYQHL LEQQRAHELF    7500
QAEMFSRQQI LHSIIIDGQR LLEQGQVDDR DEFNLKLTLL SNQWQGVIRR AQQRRGIIDS    7560
QIRQWQRYRE MAEKLRKWLV EVSYLPMSGL GSVPIPLQQA RTLFDEVQFK EKVFLRQQGS    7620
YILTVEAGKQ LLLSADSGAE AALQAELAEI QEKWKSASMR LEEQKKKLAF LLKDWEKCEK    7680
GIADSLEKLR TFKKKLSQSL PDHHEELHAE QMRCKELENA VGSWTDDLTQ LSLLKDTLSA    7740
YISADDISIL NERVELLQRQ WEELCHQLSL RRQQIGERLN EWAVFSEKNK ELCEWLTQME    7800
SKVSQNGDIL IEEMIEKLKK DYQEEIAIAQ ENKIQLQQMG ERLAKASHES KASEIEYKLG    7860
KVNDRWQHLL DLIAARVKKL KETLVAVQQL DKNMSSLRTW LAHIESELAK PIVYDSCNSE    7920
EIQRKLNEQQ ELQRDIEKHS TGVASVLNLC EVLLHDCDAC ATDAECDSIQ QATRNLDRRW    7980
RNICAMSMER RLKIEETWRL WQKFLDDYSR FEDWLKSSER TAAFPSSSGV IYTVAKEELK    8040
KFEAFQRQVH ECLTQLELIN KQYRRLAREN RTDSACSLKQ MVHEGNQRWD NLQKRVTSIL    8100
RRLKHFIGQR EEFETARDSI LVWLTEMDLQ LTNIEHFSEC DVQAKIKQLK AFQQEISLNH    8160
NKIEQIIAQG EQLIEKSEPL DAAIIEEELD ELRRYCQEVF GRVERYHKKL IRLPLPDDEH    8220
DLSDRELELE DSAALSDLHW HDRSADSLLS PQPSSNLSLS LAQPLRSERS GRDTPASVDS    8280
IPLEWDHDYD LSRDLESAMS RALPSEDEEG QDDKDFYLRG AVGLSGDHSA LESQIRQLGK    8340
ALDDSRFQIQ QTENIIRSKT PTGPELDTSY KGYMKLLGEC SSSIDSVKRL EHKLEKEEES    8400
LPGFVNLHST ETQTAGVIDR WELLQAQALS KELRMKQNLQ KWQQFNSDLN SIWAWLGDTE    8460
EELEQLQRLE LSTDIQTIEL QIKKLKELQK AVDHRKAIIL SINLCSPEFT QADSKESRDL    8520
QDRLSQMNGR WDRVCSLLEE WRGLLQDALM QCQGFHEMSH GLLLMLENID RRKNEIVPID    8580
SNLDAEILQD HHKQLMQIKH ELLESQLRVA SLQDMSCQLL VNAEGTDCLE AKEKVHVIGN    8640
RLKLLLKEVS RHIKELEKLL DVSSSQQDLS SWSSADELDT SGSVSPTSGR STPNRQKTPR    8700
GKCSLSQPGP SVSSPHSRST KGGSDSSLSE PGPGRSGRGF LFRVLRAALP LQLLLLLLIG    8760
LACLVPMSEE DYSCALSNNF ARSFHPMLRY TNGPPPL                            8797

SEQ ID NO: 23           moltype = AA  length = 431
FEATURE                 Location/Qualifiers
source                  1..431
                        mol_type = protein
                        organism = Homo sapiens
SEQUENCE: 23
MRRLRRLAHL VLFCPFSKRL QGRLPGLRVR CIFLAWLGVF AGSWLVYVHY SSYSERCRGH    60
VCQVVICDQY RKGIISGSVC QDLCELHMVE WRTCLSVAPG QQVYSGLWRD KDVTIKCGIE    120
ETLDSKARSD AAPRRELVLF DKPTRGTSIK EFREMTLSFL KANLGDLPSL PALVGQVLLM    180
ADFNKDNRVS LAEAKSVWAL LQRNEFLLLL SLQEKEHASR LLGYCGDLYL TEGVPHGAWH    240
AAALPLLRP LLPPALQGAL QQWLGPAWPW RAKIAIGLLE FVEELFHGSY GTFYMCETTL    300
ANVGYTATYD FKMADLQQVA PEATVRRFLQ GRRCEHSTDC TYGRDCRAPC DRLMRQCKGD    360
LIQPNLAKVC ALLRGYLLPG APADLREELG TQLRTCTTLS GLASQVEAHH SLVLSHLKTL    420
LWKKISNTKY S                                                       431

SEQ ID NO: 24           moltype = AA  length = 441
FEATURE                 Location/Qualifiers
source                  1..441
                        mol_type = protein
                        organism = Homo sapiens
SEQUENCE: 24
MGGPRAWALL CLGLLLPGGG AAWSIGAAPF SGRRNWCSYV VTRTISCHVQ NGTYLQRVLQ    60
NCPWPMSCPG SSYRTVVRPT YKVMYKIVTA REWRCCPGHS GVSCEEASSA SLEPMWSGST    120
MRRMALRPTA FSGCLNCSKV SELTERLKVL EAKMTMLTVI EQPVPPTPAT PEDPAPLWGP    180
PPAQGSPGDG GLQDVGAWG LPGPTGPKGD AGSRGPMGMR GPPGPQGPPG SPGRAGAVGT    240
PGERGPPGPP GPGPPGPPA PVGPPHARIS QHGDPLLSNT FTETNNHWPQ GPTGPPGPPG    300
PMGPPGPPGP TGVPGSPGHI GPPGPTGPKG ISGHPGEKGE RGLRGEPGPQ GSAGQRGEPG    360
PKGDPGEKSH WGEGLHQLRE ALKILAERVL ILETMIGLYE PELGSGAGPA GTGTPSLLRG    420
KRGGHATNYR IVAPRSRDER G                                            441

SEQ ID NO: 25           moltype = AA  length = 409
FEATURE                 Location/Qualifiers
source                  1..409
                        mol_type = protein
                        organism = Homo sapiens
```

```
SEQUENCE: 25
MEESWEAAPG  GQAGAELPME  PVGSLVPTLE  QPQVPAKVRQ  PEGPESSPSP  AGAVEKAAGA   60
GLEPSSKKKP  PSPRPGSPRV  PPLSLGYGVC  PEPPSPGPAL  VKLPRNGEAP  GAEPAPSAWA  120
PMELQVDVRV  KPVGAAGGSS  TPSPRPSTRF  LKVPVPESPA  FSRHADPAHQ  LLLRAPSQGG  180
TWGRRSPLAA  ARTESGCDAE  GRASPAEGSA  GSPGSPTCCR  CKELGLEKED  AALLPRAGLD  240
GDEKLPRAVT  LTGLPMYVKS  LYWALAFMAV  LLAVSGVVIV  VLASRAGARC  QQCPPGWVLS  300
EEHCYYFSAE  AQAWEASQAF  CSAYHATLPL  LSHTQDFLGR  YPVSRHSWVG  AWRGPQGWHW  360
IDEAPLPPQL  LPEDGEDNLD  INCGALEEGT  LVAANCSTPR  PWVCAKGTQ              409

SEQ ID NO: 26           moltype = AA   length = 904
FEATURE                 Location/Qualifiers
source                  1..904
                        mol_type = protein
                        organism = Homo sapiens
SEQUENCE: 26
MEWGSESAAV  RRHRVGVERR  EGAAAAPPPE  REARAQEPLV  DGCSGGGRTR  KRSPGGSGGA   60
SRGAGTGLSE  VRAALGLALY  LIALRTLVQL  SLQQLVLRGA  AGHRGEFDAL  QARDYLEHIT  120
SIGPRTTGSP  ENEILTVHYL  LEQIKLIEVQ  SNSLHKISVD  VQRPTGSFSI  DFLGGFTSYY  180
DNITNVVVKL  EPRDGAQHAV  LANCHFDSVA  NSPGASDDAV  SCSVMLEVLR  VLSTSSEALH  240
HAVIFLFNGA  EENVLQASHG  FITQHPWASL  IRAFINLEAA  GVGGKELVFQ  TGPENPWLVQ  300
AYVSAAKHPF  ASVVAQEVFQ  SGIIPSDTDF  RIYRDFGNIP  GIDLAFIENG  YIYHTKYDTA  360
DRILTDSIQR  AGDNILAVLK  HLATSDMLAA  ASKYRHGNMV  FFDVLGLFVI  AYPSRIGSII  420
NYMVVMGVVL  YLGKKFLQPK  HKTGNYKKDF  LCGLGITLIS  WFTSLVTVLI  IAVFISLIGQ  480
SLSWYNHFYV  SVCLYGTATV  AKIILIHTLA  KRFYYMNASA  QYLGEVFFDI  SLFVHCCFLV  540
TLTYQGLCSA  FISAVWVAFP  LLTKLCVHKD  FKQHGAQGKF  IAFYLLGMFI  PYLYALYLIW  600
AVFEMFTPIL  GRSGSEIPPD  VVLASILAGC  TMILSSYFIN  FIYLAKSTKK  TMLTLTLVCA  660
ITFLLVCSGT  FFPYSSNPAN  PKPKRVFLQH  MTRTFHDLEG  NAVKRDSGIW  INGFDYTGIS  720
HITPHIPEIN  DSIRAHCEEN  APLCGFPWYL  PVHFLIRKNW  YLPAPEVSPR  NPPHFRLISK  780
EQTPWDSIKL  TFEATGPSHM  SFYVRAHKGS  TLSQWSLGNG  TPVTSKGGDY  FVFYSHGLQA  840
SAWQFWIEVQ  VSEEHPEGMV  TVAIAAHYLS  GEDKRSPQLD  ALKEKFPDWT  FPSAWVCTYD  900
LFVF                                                                   904

SEQ ID NO: 27           moltype = AA   length = 202
FEATURE                 Location/Qualifiers
source                  1..202
                        mol_type = protein
                        organism = Homo sapiens
SEQUENCE: 27
MERGAGAKLL  PLLLLLRATG  FTCAQTDGRN  GYTAVIEVTS  GGPWGDWAWP  EMCPDGFFAS   60
GFSLKVEPPQ  GIPGDDTALN  GIRLHCARGN  VLGNTHVVES  QSGSWGEWSE  PLWCRGGAYL  120
VAFSLRVEAP  TTLGDNTAAN  NVRFRCSDGE  ELQGPGLSWG  DFGDWSDHCP  KGACGLQTKI  180
QGPRGLGDDT  ALNDARLFCC  RS                                             202

SEQ ID NO: 28           moltype = AA   length = 147
FEATURE                 Location/Qualifiers
source                  1..147
                        mol_type = protein
                        organism = Homo sapiens
SEQUENCE: 28
MGFIFSKSMN  ESMKNQKEFM  LMNARLQLER  QLIMQSEMRE  RQMAMQIAWS  REFLKYFGTF   60
FGLAAISLTA  GAIKKKKPAF  LVPIVPLSFI  LTYQYDLGYG  TLLERMKGEA  EDILETEKSK  120
LQLPRGMITF  ESIEKARKEQ  SRFFIDK                                        147

SEQ ID NO: 29           moltype = AA   length = 758
FEATURE                 Location/Qualifiers
source                  1..758
                        mol_type = protein
                        organism = Homo sapiens
SEQUENCE: 29
MRKQGVSSKR  LQSSGRSQSK  GRRGASLARE  PEVEEEMEKS  ALGGGKLPRG  SWRSSPGRIQ   60
SLKERKGLEL  EVVAKTFLLG  PFQFVRNSLA  QLREKVQELQ  ARRFSSRTTL  GIAVFVAILH  120
WLHLVTLFEN  DRHFSHLSSL  EREMTFRTEM  GLYYSYFKTI  IEAPSFLEGL  WMIMNDRLTE  180
YPLIINAIKR  FHLYPEVIIA  SWYCTFMGIM  NLFGLETKTC  WNVTRIEPLN  EVQSCEGLGD  240
PACFYVGVIF  ILNGLMMGLF  FMYGAYLSGT  QLGGLITVLC  FFFNHGEATR  VMWTPPLRES  300
FSYPFLVLQM  CILTLILRTS  SNDRRPFIAL  CLSNVAFMLP  WQFAQFILFT  QIASLFPMYV  360
VGYIEPSKFQ  KIIYMNMISV  TLSFILMFGN  SMYLSSYYSS  SLLMTWAIIL  KRNEIQKLGV  420
SKLNFWLIQG  SAWWCGTIIL  KFLTSKILGV  SDHIRLSDLI  AARILRYTDF  DTLIYTCAPE  480
PDFMEKATPL  RYTKTLLLPV  VMVITCFIPK  KTVRDISYVL  ATNIYLRKQL  LEHSELAFHT  540
LQLLVFTALA  ILIMRLKMFL  TPHMCVMASL  ICSRQLFGWL  FRRVRFEKVI  FGILTVMSIQ  600
GYANLRNQWS  IIGEFNNLPQ  EELLQWIKYS  TTSDAVFAGA  MPTVRASIKLS  TLHPIVNHPH  660
YEDADLRART  KIVYSTYSRK  SAKEVRDKLL  ELHVNYYVLE  EAWCVVRTKP  GCSMLEIWDV  720
EDPSNAANPP  LCSVLLEDAR  PYFTTVFQNS  VYRVLKVN                           758

SEQ ID NO: 30           moltype = AA   length = 316
FEATURE                 Location/Qualifiers
source                  1..316
                        mol_type = protein
                        organism = Homo sapiens
SEQUENCE: 30
```

```
MASADELTFH EFEEATNLLA DTPDAATTSR SDQLTPQGHV AVAVGSGGSY GAEDEVEEES      60
DKAALLQEQQ QQQQPGFWTF SYYQSFFDVD TSQVLDRIKG SLLPRPGHNF VRHHLRNRPD     120
LYGPFWICAT LAFVLAVTGN LTLVLAQRRD PSIHYSPQFH KVTVAGISIY CYAWLVPLAL     180
WGFLRWRKGV QERMGPYTFL ETVCIYGYSL FVFIPMVVLW LIPVPWLQWL FGALALGLSA     240
AGLVFTLWPV VREDTRLVAT VLLSVVVLLH ALLAMGCKLY FFQSLPPENV APPPQITSLP     300
SNIALSPTLP QSLAPS                                                    316

SEQ ID NO: 31           moltype = AA  length = 241
FEATURE                 Location/Qualifiers
source                  1..241
                        mol_type = protein
                        organism = Homo sapiens
SEQUENCE: 31
MKFILLWALL NLTVALAFNP DYTVSSTPPY LVYLKSDYLP CAGVLIHPLW VITAAHCNLP      60
KLRVILGVTI PADSNEKHLQ VIGYEKMIHH PHFSVTSIDH DIMLIKLKTE AELNDYVKLA     120
NLPYQTISEN TMCSVSTWSY NVCDIYKEPD SLQTVNISVI SKPQCRDAYK TYNITENMLC     180
VGIVPGRRQP CKEVSAAPAI CNGMLQGILS FADGCVLRAD VGIYAKIFYY IPWIENVIQN     240
N                                                                    241

SEQ ID NO: 32           moltype = AA  length = 1172
FEATURE                 Location/Qualifiers
source                  1..1172
                        mol_type = protein
                        organism = Homo sapiens
SEQUENCE: 32
MSPDVPLLND YKQDFFLKRF PQTVLGGPRF KLGYCAPPYI YVNQIILFLM PWVWGGVGTL      60
LYQLGILKDY YTAALSGGLM LFTAFVIQFT SLYAKNKSTT VERILTTDIL AEEDEHEFTS     120
CTGAETVKFL IPGKKYVANT VFHSILAGLA CGLGTWYLLP NRITLLYGST GGTALLFFFG     180
WMTLCIAEYS LIVNTATETA TFQTQDTYEI IPLMRPLYIF FFVSVDLAHR FVVNMPALEH     240
MNQILHILFV FLPFLWALGT LPPPDALLLW AMEQVLEFGL GGSSMSTHLR LLVMFIMSAG     300
TAIASYFIPS TVGVVLFMTG FGFLLSNLS  DMGHKIGTKS KDLPSGPEKH FSWKECLFYI     360
IILVLALLET SLLHHPAGFS QISKSNSQAI VGYGLMILLI ILWILREIQS VYIIGIFRNP     420
FYPKDVQTVT VFFEKQTRLM KIGIVRRILL TLVSPFAMIA FLSLDSSLQG LHSVSVCIGF     480
TRAFRMVWQN TENALLETVI VSTVHLISST DIWWNRSLDT GLRLLLVGII RDRLIQFISK     540
LQFAVTVLLT SWTEKKQRRK TTATLCILNI VFSPFVLVII VFSTLLSSPL LPLFTLPVFL     600
VGFPRPIQSW PGAAGTTACV CADTVYYYQM VPRLTAVLQT AMAAGSLGLL LPGSHYLGRF     660
QDRLMWIMIL ECGYTYCSIN IKGLELQETS CHTAEARRVD EVFEDAFEQE YTRVCSLNEH     720
FGNVLTPCTV LPVKLYSDAR NVLSGIIDSH ENLKEFKGDL IKVLVWILVQ YCSKRPGMKE     780
NVHNTENKGK APLMLPALNT LPPPKSPEDI DSLNSETFND WSDDNIFDDE PTIKKVIEEK     840
HQLKDLPGTN LFIPGSVESQ RVGDHSTGTV PENDLYKAVL LGYPAVDKGK QEDMPYIPLM     900
EFSCSHSHLV CLPAEWRTSC MPSSKMKEMS SLFPEDWYQF VLRQLECYHS EEKASNVLEE     960
IAKDKVLKDF YVHTVMTCYF SLFGIDNMAP SPGHILRVYG GVLPWSVALD WLTEKPELFQ    1020
LALKAFRYTL KLMIDKASLG PIEDFRELIK YLEEYERDWY IGLVSDEKWK EAILQEKPYL    1080
FSLGYDSNMG IYTGRVLSLQ ELLIQVGKLN PEAVRGQWAN LSWELLYATN DDEERYSIQA    1140
HPLLLRNLTV QAAEPPLGYP IYSSKPLHIH LY                                  1172

SEQ ID NO: 33           moltype = AA  length = 346
FEATURE                 Location/Qualifiers
source                  1..346
                        mol_type = protein
                        organism = Homo sapiens
SEQUENCE: 33
MLKKPLSAVT WLCIFIVAFV SHPAWLQKLS KHKTPAQPQL KAANCCEEVK ELKAQVANLS      60
SLLSELNKKQ ERDWVSVVMQ VMELESNSKR MESRLTDAES KYSEMNNQID IMQLQAAQTV     120
TQTSADAIYD CSSLYQKNYR ISGVYKLPPD DFLGSPELEV FCDMETSGGG WTIIQRRKSG     180
LVSFYRDWKQ YKQGFGSIRG DFWLGNEHIH RLSRQPTRLR VEMEDWEGNL RYAEYSHFVL     240
GNELNSYRLF LGNYTGNVGN DALQYHNNTA FSTKDKDNDN CLDKCAQLRK GGYWYNCCTD     300
SNLNGVYYRL GEHNKHLDGI TWYGWHGSTY SLKRVEMKIR PEDFKP                    346

SEQ ID NO: 34           moltype = AA  length = 752
FEATURE                 Location/Qualifiers
source                  1..752
                        mol_type = protein
                        organism = Homo sapiens
SEQUENCE: 34
MAEPQAESEP LLGGARGGGG DWPAGLTTYR SIQVGPGAAA RWDLCIDQAV VFIEDAIQYR      60
SINHRVDASS MWLYRRYYSN VCQRTLSFTI FLILFLAFIE TPSSLTSTAD VRYRAAPWEP     120
PCGLTESVEV LCLLVPAADL SVKGYLFGWA HFQKNLWLLG YLVVLVVSLV DWTVSLSLVC     180
HEPLRIRRLL RPFFLLQNSS MMKKTLKCIR WSLPEMASVG LLLAIHLCLF TMFGMLLFAG     240
GKQDDGQDRE RLTYFQNLPE SLTSLLVLLT TANNPDVMIP AYSKNRAYAI FFIVFTVIGS     300
LFLMNLLTAI IYSQFRGYLM KSLQTSLFRR RLGTRAAFEV LSSMVGEGGA FPQAVGVKPQ     360
NLLQVLQKVQ LDSSHKQAMM EKVRSYGSVL LSAEEFQKLF NELDRSVVKE HPPRPEYQSP     420
FLQSAQFLFG HYYFDYLGNL IALANLVSIC VFLVLDADVL PAERDDFILG ILNCVFIVYY     480
LLEMLLKVFA LGLRGYLSYP SNVFDGLLTV VLLVLEISTL AVYRLPHPGW RPEMVGLLSL     540
WDMTRMLNML IVFRFLRIIP SMKLMAVVAS TVLGLVQNMR AFGGILVVVY YVFAIIGINL     600
FRGVIVALPG NSSLAPANGS APCGSFEQLE YWANNFDDPA AALVTWNLM  VVNNWQVFLD     660
AYRRYSGPWS KIYFVLWWLV SSVIWVNLFL ALILENFLHK WDPRSHLQPL AGTPEATYQM     720
TVELLFRDIL EEPGEDELTE RLSQHPHLWL CR                                   752
```

```
SEQ ID NO: 35              moltype = AA  length = 272
FEATURE                    Location/Qualifiers
source                     1..272
                           mol_type = protein
                           organism = Homo sapiens
SEQUENCE: 35
MQWNVPRTVS RLARRTCLEP HNAGLFGHCQ NVKGPLLLYN AESKVVLVQG PQKQWLHLSA    60
AQCVAKERRP LDAHPPQPGV LRHKQGKQHV SFRRVFSSSA TAQGTPEKKE EPDPLQDKSI   120
SLYQRFKKTF RQYGKVLIPV HLITSGVWFG TFYYAALKGV NVVPFLELIG LPDSVVSILK   180
NSQSGNALTA YALFKIATPA RYTVTLGGTS VTVKYLRSHG YMSTPPPVKE YLQDRMEETK   240
ELITEKMEET KDRLTEKLQE TKEKVSFKKK VE                                 272

SEQ ID NO: 36              moltype = AA  length = 402
FEATURE                    Location/Qualifiers
source                     1..402
                           mol_type = protein
                           organism = Homo sapiens
SEQUENCE: 36
MMVALRGASA LLVLFLAAFL PPPQCTQDPA MVHYIYQRFR VLEQGLEKCT QATRAYIQEF    60
QEFSKNISVM LGRCQTYTSE YKSAVGNLAL RVERAQREID YIQYLREADE CIESEDKTLA   120
EMLLQEAEEE KKIRTLLNAS CDNMLMGIKS LKIVKKMMDT HGSWMKDAVY NSPKVYLLIG   180
SRNNTVWEFA NIRAFMEDNT KPAPRKQILT LSWQGTGQVI YKGFLFFHNQ ATSNEIIKYN   240
LQKRTVEDRM LLPGGVGRAL VYQHSPSTYI DLAVDEHGLW AIHSGPGTHS HLVLTKIEPG   300
TLGVEHSWDT PCRSQDAEAS FLLCGVLYVV YSTGGQGPHR ITCIYDPLGT ISEEDLPNLF   360
FPKRPRSHSM IHYNPRDKQL YAWNEGNQII YKLQTKRKLP LK                      402

SEQ ID NO: 37              moltype = AA  length = 246
FEATURE                    Location/Qualifiers
source                     1..246
                           mol_type = protein
                           organism = Homo sapiens
SEQUENCE: 37
MGPQHLRLVQ LFCLLGAIST LPRAGALLCY EATASRFRAV AFHNWKWLLM RNMVCKLQEG    60
CEETLVFIET GTARGVVGFK GCSSSSSYPA QISYLVSPPG VSIASYSRVC RSYLCNNLTN   120
LEPFVKLKAS TPKSITSASC SCPTCVGEHM KDCLPNFVTT NSCPLAASTC YSSTLKFQAG   180
FLNTTFLLMG CAREHNQLLA DFHHIGSIKV TEVLNILEKS QIVGAASSRQ DPAWGVVLGL   240
LFAFRD                                                              246

SEQ ID NO: 38              moltype = AA  length = 2845
FEATURE                    Location/Qualifiers
source                     1..2845
                           mol_type = protein
                           organism = Homo sapiens
SEQUENCE: 38
MALGKVLAMA LVLALAVLGS LSPGARAGDC KGQRQVLREA PGFVTDGAGN YSVNGNCEWL    60
IEAPSPQHRI LLDFLFLDTE CTYDYLFVYD GDSPRGPLLA SLSGSTRPPP IEASSGKMLL   120
HLFSDANYNL LGFNASFRFS LCPGGCQSHG QCQPPGVCAC EPGWGGPDCG LQECSAYCGS   180
HGTCASPLGP CRCEPGFLGR ACDLHLWENQ GAGWWHNVSA RDPAFSARIG AAGAFLSPPG   240
LLAVFGGQDL NNALGDLVLY NFSANTWESW DLSPAPAARH SHVAVAWAGS LVLMGGELAD   300
GSLTNDVWAF SPLGRGHWEL LAPPASSSSG PPGLAGHAAA LVDDVWLYVS GGRTPHDLFS   360
SGLFRFRLDS TSGGYWEQVI PAGGRPPAAT GHSMVFHAPS RALLVHGGHR PSTARFSVRV   420
NSTELFHVDR HVWTTLKGRD GLQGPRERAF HTASVLGNYM VVYGGNVHTH YQEEKCYEDG   480
IFFYHLGCHQ WVSGAELAPP GTPEGRAAPP SGRYSHVAAV LGGSVLLVAG GYSGRPRGDL   540
MAYKVPPFVF QAPAPDYHLD YCSMYTDHSV CSRDPECSWC QGACQAAPPP GTPLGACPAA   600
SCLGLGRLLG DCQACLAFSS PTAPPRGPGT LGWCVHNESC LPRPEQARCR GEQISGTVGW   660
WGPAPVFVTS LEACVTQSFL PGLHLLTFQQ PPNTSQPDKV SIVRSTTITL TPSAETDVSL   720
VYRGFIYPML PGGPGGPGAE DVAVWTRAQR LHVALARMARG PDTENMEEVG RWVAHQEKET   780
RRLQRPSGAR LFPLPGRDHK YAVEIQGQLN GSAGPGHSEL TLLWDRTGVP GGSEISFFFL   840
EPYRSSSCTS YSSCLGCLAD QGCGWCLTSA TCHLRQGGAL CGDDGAGGSL LVLVPTLCPL   900
CEEHRDCHAC TQDPFCEWHQ STSRKGDAAC SRRGRGRGAL KSPEECPPLC SQRLTCEDCL   960
ANSSQCAWCQ STHTCFLFAA YLARYPHGGC RGWDDSVHSE PRCRSCDGFL TCHECLQSHE  1020
CGWCGNEDNP TLGRCLQGDF SGPLGGGNCS LWVGEGLGLP VALPARWAYA RCPDVDECRL  1080
GLARCHPRAT CLNTPLSYEC HCQRGYQGDG ISHCNRTCLE DCGHGVCSGP PDFTCVCDLG  1140
WTSDLPPPTP APGPPAPRCS RDCGCSFHSH CRKRGPGFCD ECQDFTWGEH CERCRPGSFG  1200
NATGSRGCRP CQCNGHGDPR RGHCDNLSGL CFCQDHTEGA HCQLCSPGYY GDPRAGGSCF  1260
RECGGRALLT NVSSVALGSR RVGGLLPPGG GAARAGPGLS YCVWVVSATE ELQPCAPGTL  1320
CPPLTLTFSP DSSTPCTLSY VLAFDGFPRF LDTGVVQSDR SLIAAFCGQR RDRPLTVQAL  1380
SGLLVLHWEA NGSSSWGFNA SVGSARCGSS GPGSCPVPQE CVPQDGAAGA GLCRCPQGWA  1440
GPHCRMALCP ENCNAHTGAG TCNQSLGVCI CAEGFGGPDC ATKLDGGQLV WETLMDSRLS  1500
ADTASRFLHR LGHTMVDGPD ATLWMFGGLG LPQGLLGNLY RYSVSERRWT QMLAGAEDGG  1560
PGPSPRSFHA AAYVPAGRGA MYLLGGLTAG GVTRDFWVLN LTTLQWRQEK APQTVELPAV  1620
AGHTLTARRG LSLLLVGGYS PENGFNQQLL EYQLATGTWV SGAQSGTPPT GLYGHSAVYH  1680
EATDSLYVFG GFRFHVELAA PSPELYSLHC PDRTWSLLAP SQGAKRDRMR NVRGSSRGLG  1740
QVPGEQPGSW GFREVRKKMA LWAALAGTGG FLEEISPHLK EPRRPRLFHAS ALLGDTMVVL  1800
GGRSDPDEFS SDVLLYQVNC NAWLLPDLTR SASVGPPMEE SVAHAVAAVG SRLYISGGFG  1860
GVALGRLLAL TLPPDPCRLL SSPEACNQSG ACTWCHGACL SGDQAHRLGC GGSPCSPMPR  1920
SPEECRRLRT CSECLARHPR TLQPGDGEAS TPRCKWCTNC PEGACIGRNG SCTSENDCRI  1980
NQREVFWAGN CSEAACGAAD CEQCTREGKC MWTRQFKRTG ETRRILSVQP TYDWTCFSHS  2040
LLNVSPMPVE SSPPLPCPTP CHLLPNCTSC LDSKGADGGW QHCVWSSSLQ QCLSPSYLPL  2100
```

```
RCMAGGCGRL LRGPESCSLG CAQATQCALC LRRPHCGWCA WGGQDGGGRC MEGGLSGPRD   2160
GLTCGRPGAS WAFLSCPPED ECANGHHDCN ETQNCHDQPH GYECSCKTGY TMDNMTGLCR   2220
PVCAQGCVNG SCVEPDHCRC HFGFVGRNCS TECRCNRHSE CAGVGARDHC LLCRNHTKGS   2280
HCEQCLPLFV GSAVGGGTCR PCHAFCRGNS HICISRKELQ MSKGEPKKYS LDPEEIENWV   2340
TEGPSEDEAV CVNCQNNSYG EKCESCLQGY FLLDGKCTKC QCNGHADTCN EQDGTGCPCQ   2400
NNTETGTCQG SSPSDRRDCY KYQCAKCRES FHGSPLGGQQ CYRLISVEQE CCLDPTSQTN   2460
CFHEPKRRAL GPGRTVLFGV QPKFTNVDIR LTLDVTFGAV DLYVSTSYDT FVVRVAPDTG   2520
VHTVHIQPPP APPPPPPPAD GGPRGAGDPG GAGASSGPGA PAEPRVREVW PRGLITYVTV   2580
TEPSAVLVVR GVRDRLVITY PHEHHALKSS RFYLLLLGVG DPSGPGANGS ADSQGLLFFR   2640
QDQAHIDLFV FFSVFFSCFF LFLSLCVLLW KAKQALDQRQ EQRRHLQEMT KMASRPFAKV   2700
TVCFPPDPTA PASAWKPAGL PPPAFRRSEP FLAPLLLTGA GGPWGPMGGG CCPPAIPATT   2760
AGLRAGPITL EPTEDGMAGV ATLLLQLPGG PHAPNGACLG SALVTLRHRL HEYCGGGGGA   2820
GGSGHGTGAG RKGLLSQDNL TSMSL                                        2845

SEQ ID NO: 39          moltype = AA  length = 586
FEATURE                Location/Qualifiers
source                 1..586
                       mol_type = protein
                       organism = Homo sapiens
SEQUENCE: 39
MAEGVPASPS SGEGSRGPHS GVIQWLVDNF CICEECSVPR CLMYEIYVET CGQNTENQVN    60
PATFGKLVRL VFPDLGTRRL GTRGSARYHY DGICIKKSSF FYAQYCYLIG EKRYHSGDAI   120
AFEKSTNYNS IIQQEATCED HSPMKTDPVG SPLSEFRRCP FLEQEQAKKY SCNMMAFLAD   180
EYCNYCRDIL RNVEDLLTSF WKSLQQDTVM LMSLPDVCQL FKCYDVQLYK GIEDVLLHDF   240
LEDVSIQYLK SVQLFSKKFK LWLLLNALEGV PALLQISKLK EVTLFVKRLR RKTYLSNMAK   300
TMRMVLKSKR RVSVLKSDLQ AIINQGTLAT SKKALASDRS GADELENNPE MKCLRNLISL   360
LGTSTDLRVF LSCLSSHLQA FVFQTSRSKE EFTKLAASFQ LRWNLLLTAV SKAMTLCHRD   420
SFGSWHLFHL LLLEYMIHIL QSCLEEEEEE EDMGTVKEML PDDPTLGQPD QALFHSLNSS   480
LSQACASPSM EPLGVMPTHM GQGRYPVGVS NMVLRILGFL VDTAMGNKLI QVLLEDETTE   540
SAVKLSLPMG QEALITLKDG QQFVIQISDV PQSSEDIYFR ENNANV                  586

SEQ ID NO: 40          moltype = AA  length = 459
FEATURE                Location/Qualifiers
source                 1..459
                       mol_type = protein
                       organism = Homo sapiens
SEQUENCE: 40
MEGSASPPEK PRARPAAAVL CRGPVEPLVF LANFALVLQG PLTTQYLWHR FSADLGYNGT    60
RQRGGCSNRS ADPTMQEVET LTSHWTLYMN VGGFLVGLFS STLLGAWSDS VGRRPLLVLA   120
SLGLLLQALV SVFVVQLQLH VGYFVLGRIL CALLGDFGGL LAASFASVAD VSSSRSRTFR   180
MALLEASIGV AGMLASLLGG HWLRAQGYAN PFWLALALLI AMTLYAAFCF GETLKEPKST   240
RLFTFRHHRS IVQLYVAPAP EKSRKHLALY SLAIFVVITV HFGAQDILTL YELSTPLCWD   300
SKLIGYGSAA QHLPYLTSLL ALKLLQYCLA DAWVAEIGLA FNILGMVVFA FATITPLMFT   360
GYGLLFLSLV ITPVIRAKLS KLVRETEQGA LFSAVACVNS LAMLTASGIF NSLYPATLNF   420
MKGFPFLLGA GLLLIPAVLI GMLEKADPHL EFQQFPQSP                          459

SEQ ID NO: 41          moltype = AA  length = 173
FEATURE                Location/Qualifiers
source                 1..173
                       mol_type = protein
                       organism = Homo sapiens
SEQUENCE: 41
MHWKMLLLLL LYYNAEASMC HRWSRAVLFP AAHRPKRSSS LPLNPVLQTS LEEVELLYEF    60
LLAELEISPD LQISIKDEEL ASLRKASDFR TVCNNVIPKS IPDIRRLSAS LSSHPGILKK   120
EDFERTVLTL AYTAYRTALS HGHQKDIWAQ SLVSLFQALR HDLMRSSQPG VPP          173

SEQ ID NO: 42          moltype = AA  length = 245
FEATURE                Location/Qualifiers
source                 1..245
                       mol_type = protein
                       organism = Homo sapiens
SEQUENCE: 42
MTLFPVLLFL VAGLLPSFPA NEDKDPAFTA LLTTQTQVQR EIVNKHNELR RAVSPPARNM    60
LKMEWNKEAA ANAQKWANQC NYRHSNPKDR MTSLKCGENL YMSSASSSWS QAIQSWFDEY   120
NDFDFGVGPK TPNAVVGHYT QVVWYSSYLV GCGNAYCPNQ KVLKYYYVCQ YCPAGNWANR   180
LYVPYEQGAP CASCPDNCDD GLCTNGCKYE DLYSNCKSLK LTLTCKHQLV RDSCKASCNC   240
SNSIY                                                               245

SEQ ID NO: 43          moltype = AA  length = 13
FEATURE                Location/Qualifiers
REGION                 1..13
                       note = Synthetically generated peptide
source                 1..13
                       mol_type = protein
                       organism = synthetic construct
SEQUENCE: 43
KKSRGDYMTM QIG                                                       13

SEQ ID NO: 44          moltype = AA  length = 16
```

```
FEATURE            Location/Qualifiers
REGION             1..16
                   note = Synthetically generated peptide
source             1..16
                   mol_type = protein
                   organism = synthetic construct
SEQUENCE: 44
GGMEDIYFEF MGGKKK                                          16

SEQ ID NO: 45      moltype = AA  length = 13
FEATURE            Location/Qualifiers
REGION             1..13
                   note = Synthetically generated peptide
source             1..13
                   mol_type = protein
                   organism = synthetic construct
SEQUENCE: 45
KKKGQEEEYV FIE                                             13
```

COMPOUNDS FOR THE TREATMENT OF KINASE-DEPENDENT DISORDERS

CROSS-REFERENCE TO RELATED APPLICATIONS

This application is a continuation application of U.S. application Ser. No. 16/964,228, filed Jul. 23, 2020, which is a United States National Phase of PCT/US2019/015289, filed Jan. 25, 2019, which claims the benefit of priority to U.S. Provisional Application No. 62/622,626, filed Jan. 26, 2018, and to U.S. Provisional Application Ser. No. 62/622,629, filed Jan. 26, 2018, the entire contents of which are incorporated herein.

FIELD OF THE INVENTION

The invention relates to compounds for modulating protein kinase enzymatic activity for modulating cellular activities such as proliferation, differentiation, programmed cell death, migration, and chemoinvasion. Even more specifically, the invention relates to compounds which inhibit, regulate, and/or modulate Axl and Mer receptor tyrosine kinases, compositions which contain these compounds, methods of using them to treat kinase-dependent diseases and conditions, synthesis of the compounds, and processes for formulating the compounds for pharmaceutical purposes.

The instant application contains a Sequence Listing which has been submitted electronically in XML format and which is hereby incorporated by reference in its entirety. Said XML copy, created on Jun. 12, 2023, is named "EX18-001C2-US_Sequence-listing_ST26" and is 72,176 bytes in size.

BACKGROUND OF THE INVENTION

Human Axl belongs to the TAM subfamily of receptor tyrosine kinases that includes Mer. TAM kinases are characterized by an extracellular ligand binding domain consisting of two immunoglobulin-like domains and two fibronectin type III domains. Axl is overexpressed in a number of tumor cell types and was initially cloned from patients with chronic myelogenous leukemia. When overexpressed, Axl exhibits transforming potential. Axl signaling is believed to cause tumor growth through activation of proliferative and anti-apoptotic signaling pathways. Axl has been associated with cancers such as lung cancer, myeloid leukemia, uterine cancer, ovarian cancer, gliomas, melanoma, thyroid cancer, renal cell carcinoma, osteosarcoma, gastric cancer, prostate cancer, and breast cancer. The over-expression of Axl results in a poor prognosis for patients with the indicated cancers.

Activation of Mer, like Axl, conveys downstream signaling pathways that cause tumor growth and activation. Mer binds ligands such as the soluble protein Gas-6. Gas-6 binding to Mer induces autophosphorylation of Mer on its intracellular domain, resulting in downstream signal activation. Over-expression of Mer in cancer cells leads to increased metastasis most likely by generation of soluble Mer extracellular domain protein as a decoy receptor. Tumor cells secrete a soluble form of the extracellular Mer receptor which reduces the ability of soluble Gas-6 ligand to activate Mer on endothelial cells leading to cancer progression.

Therefore a need exists for compounds that inhibit TAM receptor tyrosine kinases such as Axl and Mer for the treatment of selected cancers.

SUMMARY OF THE INVENTION

In one aspect, the present invention comprises a compound for modulating kinase activity according to Formula I', Formula I, or Formula II.

In one aspect, the invention includes a compound of Formula I':

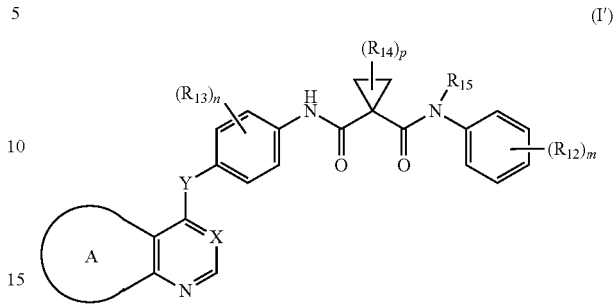

(I')

or a pharmaceutically acceptable salt thereof, wherein:
X is N or CH;
Y is selected from O, S, SO, SO$_2$, NH, and —N(C$_{1-6}$ alkyl)-;
(i) ring A is

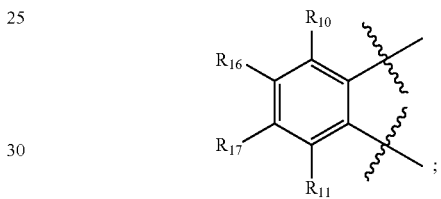

;

R$_{16}$ is selected from the group consisting of (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; and
R$_{17}$ is selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$, —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{16}$ or R$_{17}$ are each optionally substituted with 1, 2, 3, 4, or 5 independently selected R$^b$ substituents, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ is selected from —H; halo; $(C_1-C_6)$ alkyl; $(C_2-C_6)$ alkenyl; $(C_2-C_6)$ alkynyl; $(C_1-C_6)$ haloalkyl; $(C_1-C_6)$ haloalkoxy; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the $(C_1-C_6)$ alkyl; $(C_2-C_6)$ alkenyl; $(C_2-C_6)$ alkynyl; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; and (4-14 membered heterocycloalkyl)-$(C_1-C_4)$ alkylene- of $R_{16}$ is each optionally substituted with 1, 2, 3, 4, or 5 independently selected R$^b$ substituents; and $R_{17}$ is selected from the group consisting of $(C_2-C_6)$ alkenyl; $(C_2-C_6)$ alkynyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ and $R_{17}$ taken together with the atoms to which they are attached form a fused $C_{3-7}$ cycloalkyl ring or a fused 4- to 10-membered heterocycloalkyl ring; wherein the fused $C_{3-7}$ cycloalkyl ring and fused 4- to 10-membered heterocycloalkyl ring are each optionally substituted with 1, 2, or 3 independently selected R$^b$ substituents; or (ii) ring A is

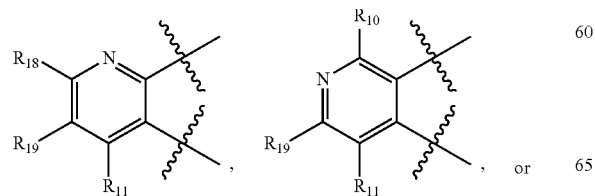

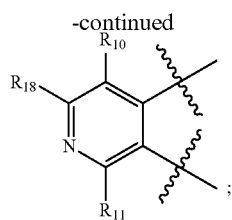

$R_{18}$ and $R_{19}$ are each independently selected from —H; halo; $(C_1-C_6)$ alkyl; $(C_2-C_6)$ alkenyl; $(C_2-C_6)$ alkynyl; $(C_1-C_6)$ haloalkyl; $(C_1-C_6)$haloalkoxy; $(C_6-C_{10})$ aryl; $(C_3-C_{10})$ cycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the $(C_1-C_6)$ alkyl; $(C_2-C_6)$ alkenyl; $(C_2-C_6)$ alkynyl; $(C_6-C_{10})$ aryl; $(C_3-C_{10})$ cycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; and (4-14 membered heterocycloalkyl)-$(C_1-C_4)$ alkylene- of $R_{18}$ or $R_{19}$ are each optionally substituted with 1, 2, 3, 4, or 5 independently selected R$^b$ substituents; or $R_{18}$ and $R_{19}$ taken together with the atoms to which they are attached form a fused $C_{3-7}$ cycloalkyl ring or a fused 4- to 10-membered heterocycloalkyl ring; wherein the fused $C_{3-7}$ cycloalkyl ring and fused 4- to 10-membered heterocycloalkyl ring are each optionally substituted with 1, 2, or 3 independently selected R$^b$ substituents;

$R_{10}$ and $R_{11}$ are each independently selected from the group consisting of —H; halo; $(C_1-C_6)$ alkyl; $(C_1-C_6)$ haloalkyl; $(C_1-C_6)$haloalkoxy; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^a$; —C(O)R$^a$; —C(O)NR$^a$R$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; wherein the $(C_1-C_6)$ alkyl; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; and (4-14 membered heterocycloalkyl)-

($C_1$-$C_4$) alkylene- of $R_1$ or $R_2$ are each optionally substituted with 1, 2, 3, 4, or 5 independently selected $R^b$ substituents;

each $R_{13}$ is independently selected from the group consisting of —H; halo; —OH; —CN; optionally substituted ($C_1$-$C_6$) alkyl; ($C_1$-$C_6$) alkoxy; ($C_1$-$C_6$) haloalkoxy; —NH$_2$; —NH($C_1$-$C_6$)alkyl; —N($C_1$-$C_6$ alkyl)$_2$; and ($C_3$-$C_6$) cycloalkyl; wherein the ($C_1$-$C_6$) alkoxy; —NH($C_1$-$C_6$)alkyl; —N($C_1$-$C_6$ alkyl)$_2$; and ($C_3$-$C_6$) cycloalkyl of $R_3$ are each optionally substituted with 1, 2, or 3 independently selected $R^b$ substituents;

each $R_{14}$ is independently selected from the group consisting of halo; —OH; —NH$_2$; —CN; ($C_1$-$C_6$) alkyl; ($C_1$-$C_6$) alkoxy; ($C_1$-$C_6$) haloalkyl; ($C_1$-$C_6$) haloalkoxy; —COOH; —NH($C_1$-$C_6$)alkyl; —N($C_1$-$C_6$ alkyl)$_2$; phenyl; phenyl-($C_1$-$C_2$) alkylene; ($C_3$-$C_6$) cycloalkyl; ($C_3$-$C_6$) cycloalkyl-($C_1$-$C_4$) alkylene-; 4- to 6-membered heterocycloalkyl; (4- to 6-membered heterocycloalkyl)-($C_1$-$C_4$) alkylene-; 5- to 6-membered heteroaryl; (5- to 6-membered heteroaryl)-($C_1$-$C_4$) alkylene-; and —OR$^e$; wherein the ($C_1$-$C_6$) alkyl; phenyl; phenyl-($C_1$-$C_2$) alkylene; ($C_3$-$C_6$) cycloalkyl; ($C_3$-$C_6$) cycloalkyl-($C_1$-$C_4$) alkylene-; 4- to 6-membered heterocycloalkyl; (4- to 6-membered heterocycloalkyl)-($C_1$-$C_4$) alkylene-; 5- to 6-membered heteroaryl; and (5- to 6-membered heteroaryl)-($C_1$-$C_4$) alkylene- of $R_{14}$ are each optionally substituted with 1, 2, or 3 independently selected $R^g$ substituents;

$R_{15}$ is H;

each $R_{12}$ is independently selected from the group consisting of —H; halo; —OH; —COOR$^e$; —CONR$^e$R$^e$; —CN; —NH$_2$; —NH(($C_1$-$C_6$) alkyl); —N(($C_1$-$C_6$) alkyl)$_2$; ($C_1$-$C_6$) alkyl; ($C_1$-$C_6$) alkoxy; ($C_1$-$C_6$) haloalkyl; ($C_1$-$C_6$) haloalkoxy; —CONR$^a$R$^a$; —NR$^a$COR$^a$; —NR$^a$CONR$^a$R$^a$; —SO$_2$R$^a$; —NR$^a$S(O)$_2$R$^a$; —NR$^a$S(O)$_2$NR$^a$R$^a$; ($C_3$-$C_6$) cycloalkyl; 4- to 6-membered heterocycloalkyl; phenyl; 5- or 6-membered heteroaryl; ($C_3$-$C_6$) cycloalkyl-($C_1$-$C_4$) alkylene-; (4- to 6-membered heterocycloalkyl)-($C_1$-$C_4$) alkylene-; phenyl-($C_1$-$C_2$) alkylene; and (5- or 6-membered heteroaryl)-($C_1$-$C_4$) alkylene-; wherein the ($C_1$-$C_6$) alkyl; ($C_3$-$C_6$) cycloalkyl; 4- to 6-membered heterocycloalkyl; phenyl; 5- or 6-membered heteroaryl; ($C_3$-$C_6$) cycloalkyl-($C_1$-$C_4$) alkylene-; (4- to 6-membered heterocycloalkyl)-($C_1$-$C_4$) alkylene-; phenyl-($C_1$-$C_2$) alkylene; and (5- or 6-membered heteroaryl)-($C_1$-$C_4$) alkylene- of $R_{12}$ are each optionally substituted with 1, 2, or 3 independently selected $R^f$ substituents;

each $R^a$ is independently selected from the group consisting of —H; —CN; ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; and (4-14 membered heterocycloalkyl)-($C_1$-$C_4$) alkylene-; wherein the ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; and (4-14 membered heterocycloalkyl)-($C_1$-$C_4$) alkylene- of $R^a$ are each optionally substituted with 1, 2, 3, 4, or 5 independently selected $R^d$ substituents;

each $R^b$ is independently selected from the group consisting of halo; ($C_1$-$C_6$) alkyl; ($C_2$-$C_6$) alkenyl; ($C_2$-$C_6$) alkynyl; ($C_1$-$C_6$) haloalkyl; ($C_1$-$C_6$) haloalkoxy; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; (4-10 membered heterocycloalkyl)-($C_1$-$C_4$) alkylene-; —CN; —OH; —NH$_2$; —NO$_2$; —NHOR$^c$; —OR$^c$; —SR$^c$; —C(O)R$^c$; —C(O)NR$^c$R$^c$; —C(O)OR$^c$; —C(O)NR$^c$S(O)$_2$R$^c$; —OC(O)R$^c$; —OC(O)NR$^c$R$^c$; —C(=NOH)R$^c$; —C(=NOH)NR$^c$; —C(=NCN)NR$^c$R$^c$; —NR$^c$C(=NCN)NR$^c$R$^c$; —C(=NR$^c$)NR$^c$R$^c$; —NR$^c$C(=NR$^c$)NR$^c$R$^c$; —NHR$^c$; —NR$^c$R$^c$; —NR$^c$C(O)R$^c$; —NR$^c$C(=NR$^c$)R$^c$; —NR$^c$C(O)OR$^c$; —NR$^c$C(O)NR$^c$R$^c$; —NR$^c$S(O)R$^c$; —NR$^c$S(O)$_2$R$^c$; —NR$^c$S(O)$_2$NR$^c$R$^c$; —S(O)R$^c$; —S(O)NR$^c$R$^c$; —S(O)$_2$R$^c$; —S(O)$_2$NR$^c$C(O)R$^c$; —Si(R$^c$)$_3$; —P(O)R$^c$R$^c$; —P(O)(OR$^c$)(OR$^c$); —B(OH)$_2$; —B(OR$^c$)$_2$; and —S(O)$_2$NR$^c$R$^c$; wherein the ($C_1$-$C_6$) alkyl; ($C_1$-$C_6$) haloalkyl; ($C_1$-$C_6$) haloalkoxy; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalky-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^b$ are each further optionally substituted with 1, 2, or 3 independently selected $R^d$ substituents;

each $R^c$ is independently selected from the group consisting of —H; ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene-; wherein the ($C_1$-$C_6$) alkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^c$ are each optionally substituted with 1, 2, 3, 4, or 5 independently selected $R^f$ substituents;

each $R^d$ is independently selected from the group consisting of ($C_1$-$C_6$) alkyl; ($C_1$-$C_6$) haloalkyl; halo; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; (4-10 membered heterocycloalkyl)-($C_1$-$C_4$) alkylene-; —CN; —NH$_2$; —NHOR$^e$; —OR$^e$; —SR$^e$; —C(O)R$^e$; —C(O)NR$^e$R$^e$; —C(O)OR$^e$; —OC(O)R$^e$; —OC(O)NR$^e$R$^e$; —NR$^e$; —NR$^e$R$^e$; —NR$^e$C(O)R$^e$; —NR$^e$C(O)NR$^e$R$^e$; —NR$^e$C(O)OR$^e$; —C(=NR$^e$)NR$^e$R$^e$; —NR$^e$C(=NR$^e$)NR$^e$R$^e$; —NR$^e$C(=NOH)NR$^e$R$^e$; —NR$^e$C(=NCN)NR$^e$R$^e$; —S(O)R$^e$; —S(O)NR$^e$R$^e$; —S(O)$_2$R$^e$; —NR$^e$S(O)$_2$R$^e$; —NR$^e$S(O)$_2$NR$^e$R$^e$; and —S(O)$_2$NR$^e$R$^e$; wherein the ($C_1$-$C_6$) alkyl; ($C_1$-$C_6$) haloalkyl; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^d$ are each optionally substituted with 1, 2, or 3 independently selected $R^f$ substituents;

each $R^e$ is independently selected from the group consisting of —H; ($C_1$-$C_6$) alkyl; ($C_3$-$C_6$) cycloalkyl; ($C_3$-$C_6$)

cycloalkyl-(C$_1$-C$_4$) alkylene-; (C$_6$-C$_{10}$) aryl; (C$_6$-C$_{10}$) aryl-(C$_1$-C$_4$) alkylene-; 5- or 6-membered heteroaryl; (5- or 6-membered heteroaryl)-(C$_1$-C$_4$) alkylene-; 4-7-membered heterocycloalkyl; (4-7-membered heterocycloalkyl)-(C$_1$-C$_4$) alkylene-; (C$_1$-C$_6$) haloalkyl; (C$_1$-C$_6$) haloalkoxy; (C$_2$-C$_4$) alkenyl; and (C$_2$-C$_4$) alkynyl; wherein the (C$_1$-C$_4$) alkyl; (C$_3$-C$_6$) cycloalkyl; (C$_6$-C$_{10}$) aryl; 5 or 6-membered heteroaryl; 4-7-membered heterocycloalkyl; (C$_6$-C$_{10}$) aryl-(C$_1$-C$_4$) alkylene-; (5- or 6-membered heteroaryl)-(C$_1$-C$_4$) alkylene-; (4-7-membered heterocycloalkyl)-(C$_1$-C$_4$) alkylene-; (C$_2$-C$_4$) alkenyl; and (C$_2$-C$_4$) alkynyl of R$^e$ are each optionally substituted with 1, 2, or 3 R$^f$ substituents;

or any two R$^a$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

or any two R$^c$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

or any two R$^e$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

each R$^f$ is independently selected from the group consisting of halo; —OH; —CN; —COOH; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$)haloalkyl; (C$_1$-C$_6$)haloalkoxy; phenyl; 5-6 membered heteroaryl; 4-6 membered heterocycloalkyl; and (C$_3$-C$_6$) cycloalkyl; wherein the (C$_1$-C$_6$) alkyl; phenyl; (C$_3$-C$_6$) cycloalkyl; 4-6 membered heterocycloalkyl; and 5-6 membered heteroaryl of R$^f$ are each optionally substituted with 1, 2, or 3 substituents selected from halo; —OH; —CN; —COOH; —NH$_2$; (C$_1$-C$_4$) alkyl; (C$_1$-C$_4$) alkoxy; (C$_1$-C$_4$) haloalkyl; (C$_1$-C$_4$) haloalkoxy; phenyl; (C$_3$-C$_{10}$) cycloalkyl; 5-6 membered heteroaryl; and 4-6 membered heterocycloalkyl;

each R$^g$ is independently selected from the group consisting of halo; —OH; —CN; —COOH; —COO—(C$_1$-C$_4$) alkyl; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$)haloalkyl; (C$_1$-C$_6$)haloalkoxy; phenyl; 5-6 membered heteroaryl; 4-6 membered heterocycloalkyl; and (C$_3$-C$_6$) cycloalkyl;

the ring nitrogen atom on the quinoline moiety in Formula A is optionally oxidized;

the subscript n is an integer of 1, 2, 3, or 4;

the subscript m is an integer of 1, 2, 3, 4, or 5; and the subscript p is an integer of 0, 1, 2, 3, or 4;

provided that when X is C—H, Ring A is

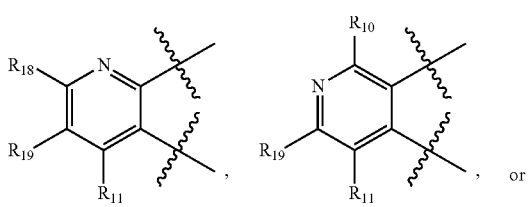 , 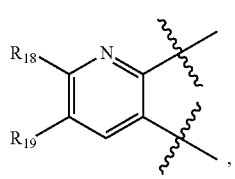 or 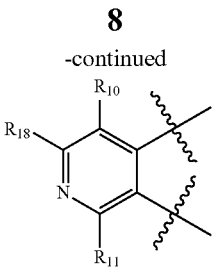.

In one embodiment, the compound of Formula I' is a compound of Formula I:

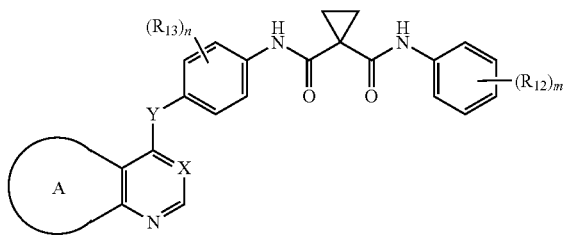

wherein:

X is selected from N and C—H;

Y is O, S, SO, SO$_2$, NH, or N—(C$_1$-C$_6$ alkyl);

R$_{13}$ is selected from —H, halo, —CN, and optionally substituted C$_{1-6}$ alkyl;

R$_{12}$ is —H or halo;

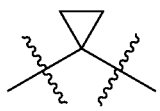

is optionally substituted with one, two, three, or four groups independently selected from the group consisting of halo, and C$_1$-C$_6$ alkyl, wherein " ∿∿∿ " indicate points of attachment;

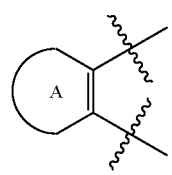

is selected from the group consisting of

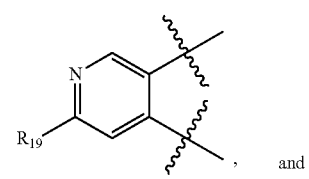 and

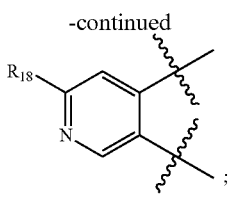

wherein $R_{18}$ and $R_{19}$ are selected from the group consisting of H, halo, —CN, optionally substituted $C_1$-$C_6$ alkyl, $C(O)NR_5R_6$, optionally substituted 5 or 6-membered heteroaryl, and optionally substituted $C_1$-$C_6$ alkoxy; or
when

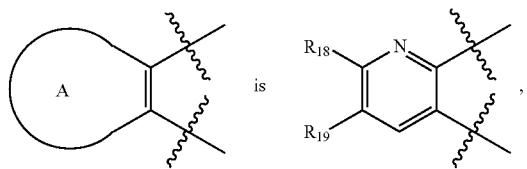

$R_{18}$ and $R_{19}$ can be joined together to form a 5 or 6-membered optionally substituted cycloalkyl or heterocycloalkyl;

$R_5$ and $R_6$ are selected from the group consisting of H, optionally substituted $C_{1-6}$ alkyl, or $R_5$ and $R_6$ taken together with the nitrogen to which they are attached to form a 5- or 6-membered optionally substituted heterocycle; and m and n are each independently 1 or 2;
provided that when

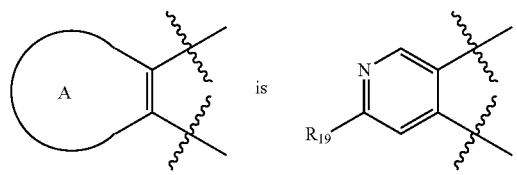

and X is C—H, $R_{19}$ is not optionally substituted $C_1$-$C_6$ alkyl, halo, or optionally substituted $C_1$-$C_6$ alkoxy.

In one embodiment, the compound of Formula I' is a compound of Formula II:

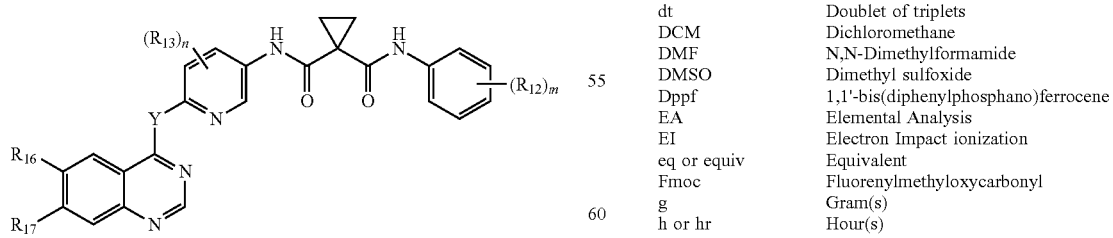

or a pharmaceutically acceptable salt thereof, wherein:
$R_{16}$ is selected from the group consisting of —CN and —CO—$NR_5R_6$;
$R_{17}$ is selected from H and optionally substituted $C_1$-$C_6$ alkoxy;

$R_{13}$ is selected from the group consisting of —H, halo, —CN, or optionally substituted $C_{1-6}$ alkyl;
$R_{12}$ is —H or halo;

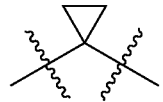 [SMILES: *C1(*)CC1]

is optionally substituted with one, two, three, or four groups independently selected from the group consisting of halo, and $C_1$-$C_6$ alkyl, wherein " ~~~ " indicate points of attachment;

$R_5$ and $R_6$ are each independently selected from the group consisting of H, optionally substituted $C_1$-$C_6$ alkyl, optionally substituted $C_3$-$C_6$ heterocycloalkyl, and optionally substituted $C_1$-$C_6$ cycloalkyl;
Y is O, S, SO, $SO_2$, NH, or N—($C_1$-$C_6$ alkyl); and
m and n are each independently 1 or 2.

In one aspect, the invention includes a pharmaceutical composition comprising a compound described herein, and a pharmaceutically acceptable carrier or excipient.

In another aspect, the invention includes a method of treating a disease, disorder, or syndrome mediated at least in part by modulating in vivo activity of a protein kinase, comprising administering to a subject in need thereof a therapeutically effective amount of a compound described herein, or a pharmaceutical composition thereof.

DETAILED DESCRIPTION OF THE INVENTION

Abbreviations and Definitions

The following abbreviations and terms have the indicated meanings throughout:

| Abbreviation | Meaning |
| --- | --- |
| Ac | Acetyl |
| anhyd | Anhydrous |
| Aq | Aqueous |
| Ar | Argon |
| Boc | Tert-butoxycarbonyl |
| Br | Broad |
| ° C. | Degrees Celsius |
| c- | Cyclo |
| calcd | Calculated |
| CBZ | CarboBenZoxy = benzyloxycarbonyl |
| d | Doublet |
| dd | Doublet of doublets |
| ddd | Doublet of doublets of doublets |
| dt | Doublet of triplets |
| DCM | Dichloromethane |
| DMF | N,N-Dimethylformamide |
| DMSO | Dimethyl sulfoxide |
| Dppf | 1,1'-bis(diphenylphosphano)ferrocene |
| EA | Elemental Analysis |
| EI | Electron Impact ionization |
| eq or equiv | Equivalent |
| Fmoc | Fluorenylmethyloxycarbonyl |
| g | Gram(s) |
| h or hr | Hour(s) |
| HPLC | High pressure liquid chromatography |
| $H_2$ | Hydrogen |
| L | Liter(s) |
| LiHMDS | Lithium bis(trimethylsilyl)azide |
| M | Molar or molarity |
| m | Multiplet |
| MHz | Megahertz (frequency) |

| Abbreviation | Meaning |
| --- | --- |
| Min | Minute(s) |
| mL | Milliliter(s) |
| Mp | Melting point |
| m/z | Mass to charge ratio |
| μL | Microliter(s) |
| Mol | Mole(s) |
| MS | Mass spectral analysis |
| $N_2$ | Nitrogen |
| N | Normal or normality |
| nM | Nanomolar |
| NMR | Nuclear magnetic resonance spectroscopy |
| Pd/C | Palladium on carbon |
| Q | Quartet |
| RT | Room temperature |
| s | Singlet |
| soln | Solution |
| S/C | Substrate/catalyst ratio |
| t or tr | Triplet |
| THF | Tetrahydrofuran |
| TLC | Thin layer chromatography |
| v/v | Volume to volume |

The symbol "-" means a single bond, and "=" means a double bond.

As used herein, the singular forms "a," "an," and "the" include plural reference unless the context clearly dictates otherwise.

When a variable is defined generically, with a number of possible substituents, each individual radical can be defined with or without the bond. For example, if $R^z$ can be hydrogen, this can be indicated as "—H" or "H" in the definition of $R^z$.

When chemical structures are depicted or described, unless explicitly stated otherwise, all carbons are assumed to have hydrogen substitution to conform to a valence of four. For example, in the structure on the left-hand side of the schematic below, there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

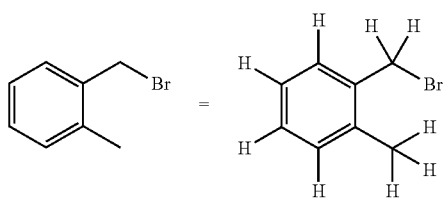

If a group "R" is depicted as "floating" on a ring system, as for example in the formula:

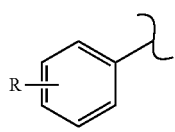

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

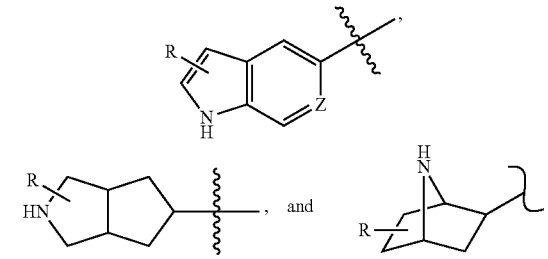

then, unless otherwise defined, a substituent "R" may reside on any atom of the fused ring system, assuming replacement of a depicted hydrogen (for example the —NH— in the formula above), implied hydrogen (for example, in the formula above, where the hydrogens are not shown but understood to be present), or expressly defined hydrogen (for example, where in the formula above, "Z" equals=CH—) from one of the ring atoms, so long as a stable structure is formed. In the example depicted, the "R" group may reside on either the 5-membered or the 6-membered ring of the fused ring system. When a group "R" is depicted as existing on a ring system containing saturated carbons, for example in the formula:

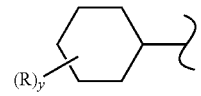

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group, there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

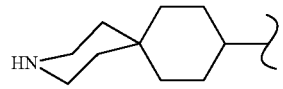

"Halogen" or "halo" refers to fluorine, chlorine, bromine, or iodine.

The term "$C_{n-m}$" or "$C_n$-$C_m$" indicates a range which includes the endpoints, wherein n and m are integers and indicate the number of carbons. Examples include $C_{1-4}$, $C_1$-$C_4$, $C_{1-6}$, $C_1$-$C_6$, and the like.

"Alkyl" refers to a branched or straight hydrocarbon chain of one to eight carbon atoms, such as methyl, ethyl, n-propyl, isopropyl, n-butyl, isobutyl, sec-butyl, t-butyl, pentyl, hexyl, and heptyl. ($C_1$-$C_6$)alkyl is preferred. The term "$C_{n-m}$ alkyl" or ($C_n$-$C_m$) alkyl, refers to an alkyl group having n to m carbon atoms. When optionally substituted, one or more hydrogen atoms of the alkyl group (e.g., from 1 to 4, from 1 to 2, or 1) may be replaced with a moiety as described below under "Optional Substitution." In some aspects, the alkyl group is unsubstituted or not optionally substituted.

"Alkylene" refers to an optionally substituted bivalent saturated aliphatic radical having from 1 to 10 carbon atoms, 1 to 8 carbon atoms, 1 to 6 carbon atoms, 1 to 4 carbon atoms, or 1 to 2 carbon atoms. When optionally substituted, one or more hydrogen atoms of the alkylene group (e.g., from 1 to 4, from 1 to 2, or 1) may be replaced with a moiety as described below under "Optional Substitution." In some aspects, the alkylene group is unsubstituted or not optionally substituted. The term "Cn-m alkylene" refers to an alkylene group having n to m carbon atoms. Examples of alkylene groups include, but are not limited to, methylene, ethan-1, 2-diyl, propan-1,3-diyl, propan-1,2-diyl, butan-1,4-diyl, butan-1,3-diyl, butan-1,2-diyl, 2-methyl-propan-1,3-diyl, and the like.

The term "alkenyl" refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" or ($C_n$-$C_m$) alkenyl refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

The term "alkynyl" refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" or ($C_n$-$C_m$) alkynyl refers to an alkynyl group having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

"Alkoxy" refers to a moiety of the formula —OR', wherein R' is an ($C_1$-$C_6$)alkyl moiety as defined herein. The term "$C_{n-m}$ alkoxy" or ($C_n$-$C_m$) alkoxy refers to an alkoxy group, the alkyl group of which has n to m carbons. Examples of alkoxy moieties include, but are not limited to, methoxy, ethoxy, isopropoxy, and the like.

An alkoxy group can be unsubstituted or optionally substituted. When optionally substituted, one or more hydrogen atoms of the alkoxy group (e.g., from 1 to 4, from 1 to 2, or 1) may be replaced with a moiety as described below under "Optional Substitution," with the proviso that no hydrogen atom alpha to the ether oxygen is replaced by a hydroxy, amino, or thio group. In some aspects, the alkoxy group is unsubstituted or not optionally substituted.

"Alkoxycarbonyl" refers to a group —C(O)—R' wherein R' is ($C_1$-$C_6$)alkoxy as defined herein.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN or CN.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfide" refers to a sulfur atom as a divalent substituent, forming a thiocarbonyl group (C=S) when attached to carbon.

The term "heteroatom" used herein is meant to include boron, phosphorus, sulfur, oxygen, and nitrogen.

The term "haloalkyl" as used herein refers to an alkyl group in which one or more of the hydrogen atoms has been replaced by a halogen atom. The term "$C_{n-m}$ haloalkyl" or ($C_n$-$C_m$) haloalkyl refers to a $C_{n-m}$ alkyl group having n to m carbon atoms and from at least one up to $\{2(n\ to\ m)+1\}$ halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" or ($C_n$-$C_m$) haloalkoxy refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

"Aryl" means a monovalent six- to fourteen-membered, mono- or bi-carbocyclic ring (e.g., having two fused rings), wherein the monocyclic ring is aromatic and at least one of the rings in the bicyclic ring is aromatic. The term "$C_{n-m}$ aryl" or "($C_n$-$C_m$) aryl" refers to an aryl group having from n to m ring carbon atoms. In some embodiments, aryl groups have from 6 to about 10 carbon atoms. In some embodiments aryl groups have 6 carbon atoms. In some embodiments aryl groups have 10 carbon atoms. Unless stated otherwise, the valency of the group may be located on any atom of any ring within the radical, valency rules permitting. Representative examples include phenyl, naphthyl, and indanyl, and the like.

An aryl group can be unsubstituted or optionally substituted. When optionally substituted, one or more hydrogen atoms of the aryl group (e.g., from 1 to 5, from 1 to 2, or 1) may be replaced with a moiety as described below under "Optional Substitution." In some aspects, the alkoxy group is unsubstituted or not optionally substituted.

"Arylene" means a divalent six- to fourteen-membered, mono- or bi-carbocyclic ring, wherein the monocyclic ring is aromatic and at least one of the rings in the bicyclic ring is aromatic. Representative examples include phenylene, naphthylene, and indanylene, and the like.

"Cycloalkyl" refers to a non-aromatic hydrocarbon ring system (monocyclic, bicyclic, or polycyclic), including cyclized alkyl and alkenyl groups. The term "$C_{n-m}$ cycloalkyl" or "($C_n$-$C_m$) cycloalkyl" refers to a cycloalkyl that has n to m ring member carbon atoms. Cycloalkyl groups can include mono- or polycyclic (e.g., having 2, 3, or 4 fused rings) groups and spirocycles. Cycloalkyl groups can have 3, 4, 5, 6, 7, 8, 9, 10, 11, 12, 13, or 14 ring-forming carbons ($C_{3-14}$). In some embodiments, the cycloalkyl group has 3 to 14 members, 3 to 10 members, 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl, or cyclohexyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl. In some embodiments, cycloalkyl includes a single saturated carbocyclic ring of three to eight ring carbons, such as cyclopropyl, cyclobutyl, cyclopentyl, and cyclohexyl.

Cycloalkyl may optionally be substituted with one or more substituents, such as one, two, or three substituents. In some embodiments, the cycloalkyl substituent is selected from the group consisting of $(C_1-C_6)$alkyl, hydroxy, $(C_1-C_6)$alkoxy, halo$(C_1-C_6)$alkyl, halo$(C_1-C_6)$alkoxy, halo, amino, mono- and di$(C_1-C_6)$alkylamino, hetero$(C_1-C_6)$alkyl, acyl, aryl, and heteroaryl.

A cycloalkyl group can be unsubstituted or optionally substituted. When optionally substituted, one or more hydrogen atoms of the cycloalkyl group (e.g., from 1 to 4, from 1 to 2, or 1) may be replaced with a moiety as described below under "Optional Substitution." In some aspects, a substituted cycloalkyl group can incorporate an exo- or endocyclic alkene (e.g., cyclohex-2-en-1-yl). In some aspects, a cycloalkyl group is unsubstituted or not optionally substituted.

"Cycloalkyloxycarbonyl" means a group —C(O)—OR' wherein R' is $(C_3-C_6)$cycloalkyl as defined herein.

"Phenyloxycarbonyl" refers to a group —C(O)—Ophenyl.

"Heteroaryl" means a monocyclic, fused bicyclic, or fused tricyclic, monovalent radical of 5 to 14 ring atoms containing one or more, preferably one, two, three, or four ring heteroatoms independently selected from —O—, —S(O)$_n$— (n is 0, 1, or 2), —N—, and —N(R')—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R' is hydrogen, alkyl, hydroxy, alkoxy, acyl, or alkylsulfonyl. Unless stated otherwise, the valency may be located on any atom of any ring of the heteroaryl group, valency rules permitting. In particular, when the point of valency is located on the nitrogen, an additional nitrogen substituent is not present. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, and N-oxide or a protected derivative thereof.

A five-membered heteroaryl ring is a heteroaryl group having five ring atoms wherein one or more (e.g., 1, 2, 3, or 4) ring atoms are independently selected from N, O, and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl group having six ring atoms wherein one or more (e.g., 1, 2, 3, or 4) ring atoms are independently selected from N, O, and S.

Exemplary six-membered ring heteroaryls are pyridyl, pyrazinyl, pyrimidinyl, triazinyl, and pyridazinyl.

"Heteroarylene" means a monocyclic, fused bicyclic, or fused tricyclic, divalent radical of 5 to 14 ring atoms containing one or more, preferably one, two, three, or four ring heteroatoms independently selected from —O—, —S(O)$_n$— (n is 0, 1, or 2), —N—, and —N(R$^{19}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^{19}$ is hydrogen, alkyl, or alkenyl. Unless stated otherwise, the valencies may be located on any atom of any ring of the heteroarylene group, valency rules permitting. In particular, when the point of valency is located on the nitrogen, an additional nitrogen substituent is not present. More specifically, the term heteroaryl includes, but is not limited to, thien-diyl, benzo[d]isoxazol-diyl, benzo[d]isothiazol-diyl, 1H-indazol-diyl (optionally substituted at the N1 position with R$^{19}$), benzo[d]oxazol-diyl, benzo[d]thiazol-diyl, 1H-benzo[d]imidazol-diyl (optionally substituted at the N1 position with R$^{19}$), 1H-benzo[d][1,2,3]triazol-diyl (optionally substituted at the N1 position with R$^{19}$), imidazo[1,2-a]pyridin-diyl, cinnolin-diyl, quinolin-diyl, pyridin-diyl, 1-oxido-pyridin-diyl, [1,2,4]triazolo[4,3-a]pyridin-diyl, and 2,3-dihydroimidazo[1,2-a]pyridin-diyl, and the like.

As used herein, "heterocycloalkyl" or "heterocyclo" refer to a non-aromatic ring or ring system, which may optionally contain one or more alkenylene groups as part of the ring structure, which has at least one heteroatom ring member independently selected from boron, nitrogen, sulfur, oxygen, and phosphorus, and which has 4-14 ring members, 4-10 ring members, 4-7 ring members, or 4-6 ring members. Included within the term "heterocycloalkyl" are monocyclic 4-, 5-, 6-, and 7-membered heterocycloalkyl groups.

Heterocycloalkyl groups can include mono- or bicyclic or polycyclic (e.g., having two or three fused or bridged rings) ring systems or spirorcycles. In some embodiments, the heterocycloalkyl group is a monocyclic group having 1, 2, or 3 heteroatoms independently selected from nitrogen, sulfur, and oxygen. Ring-forming carbon atoms and heteroatoms of a heterocycloalkyl group can be optionally oxidized to form an oxo or sulfido group or other oxidized linkage (e.g., C(O), S(O), C(S), S(O)$_2$, N-oxide, and the like.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, and the like. A heterocycloalkyl group containing a fused aromatic ring can be attached through any ring-forming atom, including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 4,5,6,7-tetrahydrothiazolo[5,4-c]pyridinyl, and thiomorpholino.

"Heterocycloalkyl" or "heterocyclo," can be unsubstituted or optionally substituted. When optionally substituted, one or more hydrogen atoms of the group (e.g., from 1 to 4, from 1 to 2, or 1) may be replaced with a moiety independently selected from fluoro, hydroxy, alkoxy, amino, alkylamino, acylamino, thio, and alkylthio. In some aspects, a substituted heterocycyl group can incorporate an exo- or endocyclic alkene (e.g., cyclohex-2-en-1-yl). In some aspects, the heterocycyl group is unsubstituted or not optionally substituted.

Optional Substitution

A group is optionally substituted herein unless expressly provided otherwise. The term "optionally substituted" refers to being substituted or unsubstituted. In certain embodiments, alkyl, alkenyl, alkynyl, carbocycloalkyl, heterocyclyoalkyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" "substituted" or "unsubstituted" cycyloalkyl, "substituted" or "unsubstituted" heterocycloalkyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen (halo), —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^c$)R$^{bb}$, —SH, —SR$^{aa}$, —SSR$^{cc}$, —C(=O)R$^{aa}$, —CO$_2$H, —CHO, —C(OR$^c$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —R$^b$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^a$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, OP(=O)(NR$^{bb}$)$_2$, —NR$^{bb}$P(=O)(OR$^{cc}$)$_2$, —NR$^{bb}$P(=O)(NR$^{bb}$)$_2$, —OP(R$^{cc}$)$_2$, —OP(R$^{cc}$)$_3$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, (C$_3$-C$_{10}$) carbocycloalkyl, 3-14 membered heterocycloalkyl, (C$_6$-C$_{14}$) aryl, and 5-14 membered heteroaryl, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from (C$_1$-C$_{10}$) alkyl, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl, or two R$^{aa}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

each instance of R$^{bb}$ is, independently, selected from hydrogen, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, C$_{6-14}$ aryl, and 5-14 membered heteroaryl, or two R$^{bb}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

each instance of R$^{cc}$ is, independently, selected from hydrogen, (C$_1$-C$_{10}$) alkyl, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl, or two R$^{cc}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^e$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^f$)$_2$, —SO$_2$R$^{ee}$, —SO$_2$OR$^e$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)

$_2$, ($C_1$-$C_{10}$) alkyl, ($C_1$-$C_{10}$) perhaloalkyl, ($C_2$—$C_{10}$) alkenyl, ($C_2$-$C_{10}$) alkynyl, ($C_3$-$C_{10}$) cycloalkyl, 3-10 membered heterocycloalkyl, ($C_6$-$C_{10}$) aryl, 5-10 membered heteroaryl, wherein each alkyl, alkenyl, alkynyl, cycloalkyl, heterocycloalkyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from ($C_1$-$C_6$) alkyl, ($C_1$-$C_6$) perhaloalkyl, ($C_2$-$C_6$) alkenyl, ($C_2$-$C_6$) alkynyl, ($C_3$-$C_{10}$) cycloalkyl, ($C_6$-$C_{10}$) aryl, 3-10 membered heterocycloalkyl, and 3-10 membered heteroaryl, wherein each alkyl, alkenyl, alkynyl, heteroalkyl, heteroalkenyl, heteroalkynyl, cycloalkyl, heterocycloalkyl, aryl, and heteroaryl is independently substituted with 0, 1, 2, 3, 4, or 5 $R^{gg}$ groups;

each instance of $R^{ff}$ is, independently, selected from hydrogen, ($C_1$-$C_6$) alkyl, ($C_1$-$C_6$) perhaloalkyl, ($C_2$-$C_6$) alkenyl, ($C_2$-$C_6$) alkynyl, ($C_3$-$C_{10}$) cycloalkyl, ($C_6$-$C_{10}$) aryl, and 5-10 membered heteroaryl, or two $R^f$ groups are joined to form a 3-10 membered heterocycloalkyl or 5-10 membered heteroaryl ring, wherein each alkyl, alkenyl, alkynyl, cycloalkyl, heterocycloalkyl, aryl, and heteroaryl is independently substituted with 0, 1, 2, 3, 4, or 5 $R^{gg}$ groups; and each instance of $R^{gg}$ is, independently, halogen, —CN, —NO$_2$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —CO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, (C$_1$-C$_6$) alkyl, (C$_1$-C$_6$) perhaloalkyl, (C$_2$-C$_6$) alkenyl, (C$_2$-C$_6$) alkynyl, (C$_3$-C$_{10}$) cycloalkyl, (C$_6$-C$_{10}$) aryl, 3-10 membered heterocycloalkyl, 5-10 membered heteroaryl; or two geminal $R^{gg}$ substituents can be joined to form =O or =S; wherein X$^-$ is a counterion.

As noted previously, nitrogen atoms can be substituted or unsubstituted as valency permits and include primary, secondary, tertiary, and quaternary nitrogen atoms. Exemplary nitrogen atom substituents include, but are not limited to, hydrogen, —OH, —OR$^{aa}$, —N(R$^{cc}$)$_2$—CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^c$)OR$^{aa}$, —C(=NR$^{cc}$)N(R$^{cc}$)$_2$, —SO$_2$N(R$^c$)$_2$, —SO$_2$R$^{cc}$, —SO$_2$OR$^c$, —SOR$^{aa}$, —C(=S)N(R$^c$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^c$)$_2$, —P(=O)(NR$^{cc}$)$_2$, (C$_1$-C$_{10}$) alkyl, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl, or two R$^{cc}$ groups attached to an N atom are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$—CO$_2$R$^{aa}$, —SO$_2$R$^{aa}$, —C(=NR$^{cc}$)R$^a$, —C(=NR$^{cc}$)OR$^{aa}$, —C(=NR$^{cc}$)N(R$^c$)$_2$—SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, (C$_1$-C$_{10}$) alkyl (e.g., aralkyl, heteroaralkyl), (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl groups, wherein each alkyl, alkenyl, alkynyl, cycloalkyl, heterocycloalkyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DN/IBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'- pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), —$OR^{aa}$ (when the 0 atom is attached to a carbonyl group, wherein $R^{aa}$ is as defined herein), —$O(C=O)R^{LG}$, or —$O(SO)_2R^{LG}$ (e.g., tosyl, mesyl, besyl), wherein $R^{LG}$ is optionally substituted alkyl, optionally substituted aryl, or optionally substituted heteroaryl. In certain embodiments, the leaving group is a halogen.

The terms for which definitions are given above are specifically exemplified in the Examples.

"Yield" for each of the reactions described herein is expressed as a percentage of the theoretical yield.

"Patient" for the purposes of the present invention includes humans and any other animals, particularly mammals, and other organisms. Thus the methods are applicable to both human therapy and veterinary applications. In a preferred embodiment the patient is a mammal, and in a most preferred embodiment the patient is human. Examples of the preferred mammals include mice, rats, other rodents, rabbits, dogs, cats, swine, cattle, sheep, horses, and primates.

"Kinase-dependent diseases or conditions" refer to pathologic conditions that depend on the activity of one or more kinases. Kinases either directly or indirectly participate in the signal transduction pathways of a variety of cellular activities including proliferation, adhesion, migration, differentiation, and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

"Therapeutically effective amount" is an amount of a compound of the invention that, when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Head and neck: squamous cell carcinomas of the head and neck, laryngeal and hypopharyngeal cancer, nasal cavity and paranasal sinus cancer, nasopharyngeal cancer, salivary gland cancer, oral and orppharyngeal cancer; Lung: bronchogenic carcinoma (squamous cell, undifferentiated small cell, undifferentiated large cell, adenocarcinoma, non-small cell lung cancer), alveolar (bronchiolar) carcinoma, bronchial adenoma, sarcoma, lymphoma, chondromatous hamartoma, mesothelioma; Colon: colorectal cancer, adenocarcinoma, gastrointestinal stromal tumors, lymphoma, carcinoids, Turcot Syndrome; Gastrointestinal: gastric cancer, gastroesophageal junction adenocarcinoma, esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Breast: metastatic breast cancer, ductal carcinoma in situ, invasive ductal carcinoma, tubular carcinoma, medullary carcinoma, mucinous carcinoma, lobular carcinoma in situ, triple negative breast cancer; Genitourinary tract: kidney (adenocarcinoma, Wilm's tumor [nephroblastoma], lymphoma, leukemia, renal cell carcinoma), bladder and urethra (squamous cell carcinoma, transitional cell carcinoma, adenocarcinoma, urothelial carcinoma), prostate (adenocarcinoma, sarcoma, castrate resistant prostate cancer), testis (seminoma, teratoma, embryonal carcinoma, teratocarcinoma, choriocarcinoma, sarcoma, interstitial cell carcinoma, fibroma, fibroadenoma, adenomatoid tumors, lipoma), clear cell carcinoma, papillary carcinoma; Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma, and giant cell tumors; Thyroid: medullary thyroid cancer, differentiated thyroid cancer, papillary thyroid cancer, follicular thyroid cancer, hurthle cell cancer, and anaplastic thyroid cancer; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial cancer), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable salts" includes "pharmaceutically acceptable acid addition salts" and "pharmaceutically acceptable base addition salts." "Pharmaceutically acceptable acid addition salts" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salts" include those derived from inorganic bases such as sodium, potassium, lithium, ammonium, calcium, magnesium, iron, zinc, copper, manganese, aluminum salts, and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

The term compound as used herein is meant to include all stereoisomers, geometric isomers, tautomers, and isotopes of the structures depicted. The term is also meant to refer to compounds of the inventions, regardless of how they are prepared, e.g., synthetically, through biological process (e.g., metabolism or enzyme conversion), or a combination thereof.

Compounds of the invention can also include all isotopes of atoms occurring in the intermediates or final compounds. Isotopes include those atoms having the same atomic number but different mass numbers. For example, isotopes of hydrogen include tritium and deuterium.

Any one of the process steps or sequences disclosed and/or claimed herein can be performed under an inert gas atmosphere, more particularly under argon or nitrogen. In addition, the methods of the present invention may be carried out as semi-continuous or continuous processes, more preferably as continuous processes.

Moreover, many of the process steps and sequences that are described herein can be telescoped.

In general, the nomenclature used in this Application is based on naming conventions adopted by the International Union of Pure and Applied Chemistry (IUPAC).

Chemical structures shown herein were prepared using CHEMDRAW®. Any open valency appearing on a carbon, oxygen, or nitrogen atom in the structures herein indicates the presence of a hydrogen atom.

EMBODIMENTS OF THE INVENTION

In one aspect, the present invention comprises a compound for modulating kinase activity according to Formula I', Formula I, or Formula II.

In one aspect, the invention includes a compound of Formula I':

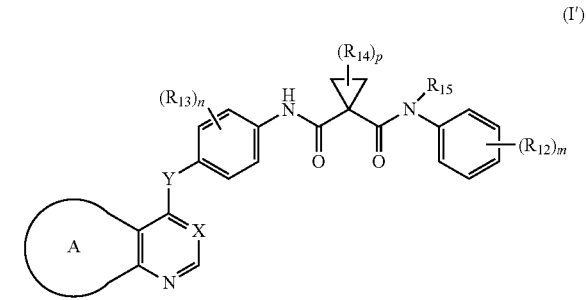

or a pharmaceutically acceptable salt thereof, wherein:

Y is selected from O, S, SO, $SO_2$, NH, and —N($C_{1-6}$ alkyl)-;

(i) ring A is

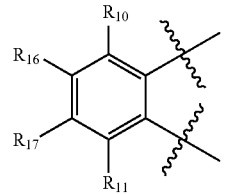

and X is N;

$R_{16}$ is selected from the group consisting of ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; —CN; —NHOH, —C(O)$R^a$; —C(O)NR$R^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; and $R_{17}$ is selected from —H; halo; ($C_1$-$C_6$) alkyl; ($C_2$-$C_6$) alkenyl; ($C_2$-$C_6$) alkynyl; ($C_1$-$C_6$) haloalkyl; ($C_1$-$C_6$) haloalkoxy; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; (4-14 membered heterocycloalkyl)-($C_1$-$C_4$) alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$, —NR$^a$R$^a$, —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the ($C_1$-$C_6$) alkyl; ($C_2$-$C_6$) alkenyl; ($C_2$-$C_6$) alkynyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; and (4-14 membered heterocycloalkyl)-($C_1$-$C_4$) alkylene- of $R_{16}$ or $R_{17}$ are each optionally substituted with 1, 2, 3, 4, or 5 independently selected $R^b$ substituents, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ is selected from —H; halo; ($C_1$-$C_6$) alkyl; ($C_2$-$C_6$) alkenyl; ($C_2$-$C_6$) alkynyl; ($C_1$-$C_6$) haloalkyl; ($C_1$-$C_6$) haloalkoxy; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; (4-14 membered heterocycloalkyl)-($C_1$-$C_4$) alkylene-; —CN; —NO$_2$; —OR$^a$; —SR$^a$; —NHOR$^a$; —C(O)R$^a$; —C(O)NHOR$^a$; —C(O)OR$^a$; —C(O)NR$^a$S(O)$_2$R$^a$; —OC(O)R$^a$; —OC(O)NR$^a$R$^a$; —NR$^a$, —NR$^a$R$^a$, —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the ($C_1$-$C_6$) alkyl; ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; and (4-14 membered heterocycloalkyl)-($C_1$-$C_4$) alkylene- of $R_{16}$ is each optionally substituted with 1, 2, 3, 4, or 5 independently selected $R^b$ substituents; and $R_{17}$ is selected from the group consisting of ($C_2$-$C_6$) alkenyl; ($C_2$-$C_6$) alkynyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ and $R_{17}$ taken together with the atoms to which they are attached form a fused $C_{3-7}$ cycloalkyl ring or a fused 4- to 10-membered heterocycloalkyl ring; wherein the fused $C_{3-7}$ cycloalkyl ring and fused 4- to 10-membered heterocycloalkyl ring are each optionally substituted with 1, 2, or 3 independently selected $R^b$ substituents; or (ii) ring A is

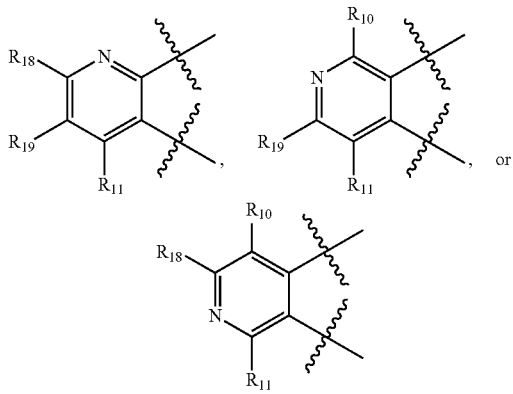

and X is N or CH, wherein $R_{18}$ and $R_{19}$ are each independently selected from —H; halo; ($C_1$-$C_6$) alkyl; ($C_2$-$C_6$) alkenyl; ($C_2$-$C_6$) alkynyl; ($C_1$-$C_6$) haloalkyl; ($C_1$-$C_6$) haloalkoxy; ($C_6$-$C_{10}$) aryl; ($C_3$-$C_{10}$) cycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; (4-14 membered heterocycloalkyl)-($C_1$-$C_4$) alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$, —NR$^a$R$^a$; —NR$^a$C(O)R$^a$; —NR$^a$C(=NR$^a$)R$^a$; —NR$^a$C(O)OR$^a$;

—NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl; (C$_3$-C$_{10}$) cycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{18}$ or R$_{19}$ are each optionally substituted with 1, 2, 3, 4, or 5 independently selected R$^b$ substituents; or R$_{18}$ and R$_{19}$ taken together with the atoms to which they are attached form a fused C$_{3-7}$ cycloalkyl ring or a fused 4- to 10-membered heterocycloalkyl ring; wherein the fused C$_{3-7}$ cycloalkyl ring and fused 4- to 10-membered heterocycloalkyl ring are each optionally substituted with 1, 2, or 3 independently selected R$^b$ substituents;

R$_{10}$ and R$_{11}$ are each independently selected from the group consisting of —H; halo; (C$_1$-C$_6$) alkyl; (C$_1$-C$_6$) haloalkyl; (C$_1$-C$_6$)haloalkoxy; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^a$; —C(O)R$^a$; —C(O)NR$^a$R$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; wherein the (C$_1$-C$_6$) alkyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_1$ or R$_2$ are each optionally substituted with 1, 2, 3, 4, or 5 independently selected R$^b$ substituents;

each R$_{13}$ is independently selected from the group consisting of —H; halo; —OH; —CN; optionally substituted (C$_1$-C$_6$) alkyl; (C$_1$-C$_6$) alkoxy; (C$_1$-C$_6$) haloalkoxy; —NH$_2$; —NH(C$_1$-C$_6$)alkyl; —N(C$_1$-C$_6$ alkyl)$_2$; and (C$_3$-C$_6$) cycloalkyl; wherein the (C$_1$-C$_6$) alkoxy; —NH(C$_1$-C$_6$)alkyl; —N(C$_1$-C$_6$ alkyl)$_2$; and (C$_3$-C$_6$) cycloalkyl of R$_3$ are each optionally substituted with 1, 2, or 3 independently selected R$^g$ substituents;

each R$_{14}$ is independently selected from the group consisting of halo; —OH; —NH$_2$; —CN; (C$_1$-C$_6$) alkyl; (C$_1$-C$_6$) alkoxy; (C$_1$-C$_6$) haloalkyl; (C$_1$-C$_6$) haloalkoxy; —COOH; —NH(C$_1$-C$_6$)alkyl; —N(C$_1$-C$_6$ alkyl)$_2$; phenyl; phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; (5- to 6-membered heteroaryl)-(C$_1$-C$_4$) alkylene-; and —OR$^e$; wherein the (C$_1$-C$_6$) alkyl; phenyl; phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; and (5- to 6-membered heteroaryl)-(C$_1$-C$_4$) alkylene- of R$_{14}$ are each optionally substituted with 1, 2, or 3 independently selected R$^g$ substituents;

R$_{15}$ is H;

each R$_{12}$ is independently selected from the group consisting of —H; halo; —OH; —COOR$^e$; —CONR$^e$R$^e$; —CN; —NH$_2$; —NH((C$_1$-C$_6$) alkyl); —N((C$_1$-C$_6$) alkyl)$_2$; (C$_1$-C$_6$) alkyl; (C$_1$-C$_6$) alkoxy; (C$_1$-C$_6$) haloalkyl; (C$_1$-C$_6$) haloalkoxy; —CONR$^a$R$^a$; —NR$^a$COR$^a$; —NR$^a$CONR$^a$R$^a$; —SO$_2$R$^a$; —NR$^a$S(O)$_2$R$^a$; —NR$^a$S(O)$_2$NR$^a$R$^a$; (C$_3$-C$_6$) cycloalkyl; 4- to 6-membered heterocycloalkyl; phenyl; 5- or 6-membered heteroaryl; (C$_3$-C$_6$) cycloalkyl-(C$_1$-C$_4$) alkylene-; (4- to 6-membered heterocycloalkyl)-(C$_1$-C$_4$) alkylene-; phenyl-(C$_1$-C$_2$) alkylene; and (5- or 6-membered heteroaryl)-(C$_1$-C$_4$) alkylene-; wherein the (C$_1$-C$_6$) alkyl; (C$_3$-C$_6$) cycloalkyl; 4- to 6-membered heterocycloalkyl; phenyl; 5- or 6-membered heteroaryl; (C$_3$-C$_6$) cycloalkyl-(C$_1$-C$_4$) alkylene-; (4- to 6-membered heterocycloalkyl)-(C$_1$-C$_4$) alkylene-; phenyl-(C$_1$-C$_2$) alkylene; and (5- or 6-membered heteroaryl)-(C$_1$-C$_4$) alkylene- of R$_{12}$ are each optionally substituted with 1, 2, or 3 independently selected R$^f$ substituents;

each R$^a$ is independently selected from the group consisting of —H; —CN; (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene-; wherein the (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$^a$ are each optionally substituted with 1, 2, 3, 4, or 5 independently selected R$^d$ substituents;

each R$^b$ is independently selected from the group consisting of halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; (4-10 membered heterocycloalkyl)-(C$_1$-C$_4$) alkylene-; —CN; —OH; —NH$_2$; —NO$_2$; —NHOR$^c$; —OR$^c$; —SR$^c$; —C(O)R$^c$; —C(O)NR$^c$R$^c$; —C(O)OR$^c$; —C(O)NR$^c$S(O)$_2$R$^c$; —OC(O)R$^c$; —OC(O)NR$^c$R$^c$; —C(=NOH)R$^c$; —C(=NOH)NR$^c$; —C(=NCN)NR$^c$R$^c$; —NR$^c$C(=NCN)NR$^c$R$^c$; —C(=NR$^c$)NR$^c$R$^c$; —NR$^c$C(=NR$^c$)NR$^c$R$^c$; —NHR$^c$; —NR$^c$R$^c$; —NR$^c$C(O)R$^c$; —NR$^c$C(=NR$^c$)R$^c$; —NR$^c$C(O)OR$^c$; —NR$^c$C(O)NR$^c$R$^c$; —NR$^c$S(O)R$^c$; —NR$^c$S(O)$_2$R$^c$; —NR$^c$S(O)$_2$NR$^c$R$^c$; —S(O)R$^c$; —S(O)NR$^c$R$^c$; —S(O)$_2$R$^c$; —S(O)$_2$NR$^c$C(O)R$^c$; —Si(R$^c$)$_3$; —P(O)R$^c$R$^c$; —P(O)(OR$^c$)(OR$^c$); —B(OH)$_2$; —B(OR$^c$)$_2$; and —S(O)$_2$NR$^c$R$^c$; wherein the (C$_1$-C$_6$) alkyl; (C$_1$-C$_6$) haloalkyl; (C$_1$-C$_6$) haloalkoxy; (C$_2$-C$_6$) alkenyl; (C$_2$-C$_6$) alkynyl; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-

$C_{10}$) cycloalky-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^b$ are each further optionally substituted with 1, 2, or 3 independently selected $R^d$ substituents;

each $R^c$ is independently selected from the group consisting of —H; ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene-; wherein the ($C_1$-$C_6$) alkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^c$ are each optionally substituted with 1, 2, 3, 4, or 5 independently selected $R^f$ substituents;

each $R^d$ is independently selected from the group consisting of ($C_1$-$C_6$) alkyl; ($C_1$-$C_6$) haloalkyl; halo; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; (4-10 membered heterocycloalkyl)-($C_1$-$C_4$) alkylene-; —CN; —$NH_2$; —$NHOR^e$; —$OR^e$; —$SR^e$; —C(O)$R^e$; —C(O)$NR^eR^e$; —C(O)$OR^e$; —OC(O)$R^e$; —OC(O)$NR^eR^e$; —$NR^e$; —$NR^eR^e$; —$NR^eC(O)R^e$; —$NR^eC(O)NR^eR^e$; —$NR^eC(O)OR^e$; —C(=$NR^e$)$NR^eR^e$; —$NR^eC(=NR^e)NR^eR^e$; —$NR^eC(=NOH)NR^eR^e$; —$NR^eC(=NCN)NR^eR^e$; —S(O)$R^e$; —S(O)$NR^eR^e$; —S(O)$_2R^e$; —$NR^eS(O)_2R^e$; —$NR^eS(O)_2NR^eR^e$; and —S(O)$_2NR^eR^e$; wherein the ($C_1$-$C_6$) alkyl; ($C_1$-$C_6$) haloalkyl; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^d$ are each optionally substituted with 1, 2, or 3 independently selected $R^f$ substituents;

each $R^e$ is independently selected from the group consisting of —H; ($C_1$-$C_6$) alkyl; ($C_3$-$C_6$) cycloalkyl; ($C_3$-$C_6$) cycloalkyl-($C_1$-$C_4$) alkylene-; ($C_6$-$C_{10}$) aryl; ($C_6$-$C_{10}$) aryl-($C_1$-$C_4$) alkylene-; 5- or 6-membered heteroaryl; (5- or 6-membered heteroaryl)-($C_1$-$C_4$) alkylene-; 4-7-membered heterocycloalkyl; (4-7-membered heterocycloalkyl)-($C_1$-$C_4$) alkylene-; ($C_1$-$C_6$) haloalkyl; ($C_1$-$C_6$) haloalkoxy; ($C_2$-$C_4$) alkenyl; and ($C_2$-$C_4$) alkynyl; wherein the ($C_1$-$C_4$) alkyl; ($C_3$-$C_6$) cycloalkyl; ($C_6$-$C_{10}$) aryl; 5 or 6-membered heteroaryl; 4-7-membered heterocycloalkyl; ($C_6$-$C_{10}$) aryl-($C_1$-$C_4$) alkylene-; (5- or 6-membered heteroaryl)-($C_1$-$C_4$) alkylene-; (4-7-membered heterocycloalkyl)-($C_1$-$C_4$) alkylene-; ($C_2$-$C_4$) alkenyl; and ($C_2$-$C_4$) alkynyl of $R^e$ are each optionally substituted with 1, 2, or 3 $R^f$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

or any two $R^e$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo; —OH; —CN; —COOH; —$NH_2$; —NH—($C_1$-$C_6$) alkyl; —N(($C_1$-$C_6$) alky)$_2$; ($C_1$-$C_6$) alkyl; ($C_1$-$C_6$) alkoxy; ($C_1$-$C_6$) alkylthio; ($C_1$-$C_6$)haloalkyl; ($C_1$-$C_6$)haloalkoxy; phenyl; 5-6 membered heteroaryl; 4-6 membered heterocycloalkyl; and ($C_3$-$C_6$) cycloalkyl; wherein the ($C_1$-$C_6$) alkyl; phenyl; ($C_3$-$C_6$) cycloalkyl; 4-6 membered heterocycloalkyl; and 5-6 membered heteroaryl of $R^f$ are each optionally substituted with 1, 2, or 3 substituents selected from halo; —OH; —CN; —COOH; —$NH_2$; ($C_1$-$C_4$) alkyl; ($C_1$-$C_4$) alkoxy; ($C_1$-$C_4$) haloalkyl; ($C_1$-$C_4$) haloalkoxy; phenyl; ($C_3$-$C_{10}$) cycloalkyl; 5-6 membered heteroaryl; and 4-6 membered heterocycloalkyl;

each $R^g$ is independently selected from the group consisting of halo; —OH; —CN; —COOH; —COO—($C_1$-$C_4$) alkyl; —$NH_2$; —NH—($C_1$-$C_6$) alkyl; —N(($C_1$-$C_6$) alky)$_2$; ($C_1$-$C_6$) alkyl; ($C_1$-$C_6$) alkoxy; ($C_1$-$C_6$) alkylthio; ($C_1$-$C_6$)haloalkyl; ($C_1$-$C_6$)haloalkoxy; phenyl; 5-6 membered heteroaryl; 4-6 membered heterocycloalkyl; and ($C_3$-$C_6$) cycloalkyl;

the ring nitrogen atom on the quinoline moiety in Formula A is optionally oxidized;

the subscript n is an integer of 1, 2, 3, or 4;

the subscript m is an integer of 1, 2, 3, 4, or 5; and the subscript p is an integer of 0, 1, 2, 3, or 4;

provided that when X is C—H, Ring A is

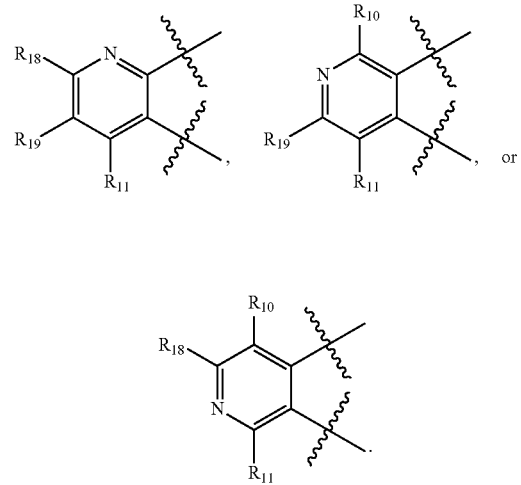

In one aspect, the invention includes a compound of Formula I':

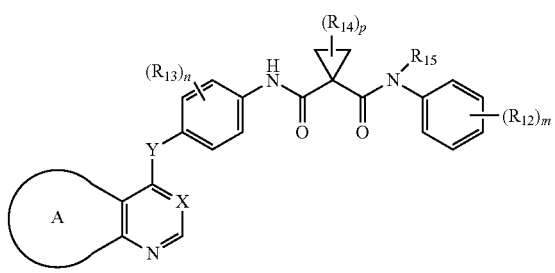

(I')

or a pharmaceutically acceptable salt thereof, wherein:
X is N or CH;
Y is selected from O, S, SO, SO$_2$, NH, and —N(C$_{1-6}$ alkyl)-;
(i) ring A is

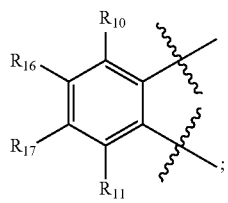
;

$R_{16}$ is selected from the group consisting of (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; and $R_{17}$ is selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{16}$ or R$_{17}$ are each optionally substituted with 1, 2, 3, 4, or 5 independently selected R$^b$ substituents, provided when R$_{16}$ or R$_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ is selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{16}$ is each optionally substituted with 1, 2, 3, 4, or 5 independently selected R$^b$ substituents; and $R_{17}$ is selected from the group consisting of (C$_2$-C$_6$) alkenyl; (C$_2$-C$_6$) alkynyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$, provided when R$_{16}$ or R$_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ and $R_{17}$ taken together with the atoms to which they are attached form a fused C$_{3-7}$ cycloalkyl ring or a fused 4- to 10-membered heterocycloalkyl ring; wherein the fused C$_{3-7}$ cycloalkyl ring and fused 4- to 10-membered heterocycloalkyl ring are each optionally substituted with 1, 2, or 3 independently selected R$^b$ substituents; or (ii) ring A is

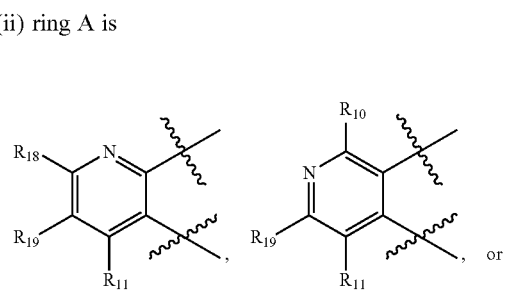

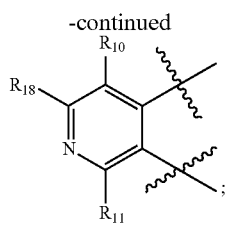

R$_{18}$ and R$_{19}$ are each independently selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$)haloalkoxy; (C$_6$-C$_{10}$) aryl; (C$_3$-C$_{10}$) cycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^a$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl; (C$_3$-C$_{10}$) cycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{18}$ or R$_{19}$ are each optionally substituted with 1, 2, 3, 4, or 5 independently selected R$^b$ substituents; or R$_{18}$ and R$_{19}$ taken together with the atoms to which they are attached form a fused C$_{3-7}$ cycloalkyl ring or a fused 4- to 10-membered heterocycloalkyl ring; wherein the fused C$_{3-7}$ cycloalkyl ring and fused 4- to 10-membered heterocycloalkyl ring are each optionally substituted with 1, 2, or 3 independently selected R$^b$ substituents;

R$_{10}$ and R$_{11}$ are each independently selected from the group consisting of —H; halo; (C$_1$-C$_6$) alkyl; (C$_1$-C$_6$) haloalkyl; (C$_1$-C$_6$) haloalkoxy; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^a$; —C(O)R$^a$; —C(O)NR$^a$R$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; wherein the (C$_1$-C$_6$) alkyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_1$ or R$_2$ are each optionally substituted with 1, 2, 3, 4, or 5 independently selected R$^b$ substituents;

each R$_{13}$ is independently selected from the group consisting of —H; halo; —OH; —CN; optionally substituted (C$_1$-C$_6$) alkyl; (C$_1$-C$_6$) alkoxy; (C$_1$-C$_6$) haloalkoxy; —NH$_2$; —NH(C$_1$-C$_6$)alkyl; —N(C$_1$-C$_6$ alkyl)$_2$; and (C$_3$-C$_6$) cycloalkyl; wherein the (C$_1$-C$_6$) alkoxy; —NH(C$_1$-C$_6$)alkyl; —N(C$_1$-C$_6$ alkyl)$_2$; and (C$_3$-C$_6$) cycloalkyl of R$_3$ are each optionally substituted with 1, 2, or 3 independently selected R$^g$ substituents;

each R$_{14}$ is independently selected from the group consisting of halo; —OH; —NH$_2$; —CN; (C$_1$-C$_6$) alkyl; (C$_1$-C$_6$) alkoxy; (C$_1$-C$_6$) haloalkyl; (C$_1$-C$_6$) haloalkoxy; —COOH; —NH(C$_1$-C$_6$)alkyl; —N(C$_1$-C$_6$ alkyl)$_2$; phenyl; phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; (5- to 6-membered heteroaryl)-(C$_1$-C$_4$) alkylene-; and —OR$^e$; wherein the (C$_1$-C$_6$) alkyl; phenyl; phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; and (5- to 6-membered heteroaryl)-(C$_1$-C$_4$) alkylene- of R$_{14}$ are each optionally substituted with 1, 2, or 3 independently selected R$^g$ substituents;

R$_{15}$ is H;

each R$_{12}$ is independently selected from the group consisting of —H; halo; —OH; —COOR$^e$; —CONR$^e$R$^e$; —CN; —NH$_2$; —NH((C$_1$-C$_6$) alkyl); —N((C$_1$-C$_6$) alkyl)$_2$; (C$_1$-C$_6$) alkyl; (C$_1$-C$_6$) alkoxy; (C$_1$-C$_6$) haloalkyl; (C$_1$-C$_6$) haloalkoxy; —CONR$^a$R$^a$; —NR$^a$COR$^a$; —NR$^a$CONR$^a$R$^a$; —SO$_2$R$^a$; —NR$^a$S(O)$_2$R$^a$; —NR$^a$S(O)$_2$NR$^a$R$^a$; (C$_3$-C$_6$) cycloalkyl; 4- to 6-membered heterocycloalkyl; phenyl; 5- or 6-membered heteroaryl; (C$_3$-C$_6$) cycloalkyl-(C$_1$-C$_4$) alkylene-; (4- to 6-membered heterocycloalkyl)-(C$_1$-C$_4$) alkylene-; phenyl-(C$_1$-C$_2$) alkylene; and (5- or 6-membered heteroaryl)-(C$_1$-C$_4$) alkylene-; wherein the (C$_1$-C$_6$) alkyl; (C$_3$-C$_6$) cycloalkyl; 4- to 6-membered heterocycloalkyl; phenyl; 5- or 6-membered heteroaryl; (C$_3$-C$_6$) cycloalkyl-(C$_1$-C$_4$) alkylene-; (4- to 6-membered heterocycloalkyl)-(C$_1$-C$_4$) alkylene-; phenyl-(C$_1$-C$_2$) alkylene; and (5- or 6-membered heteroaryl)-(C$_1$-C$_4$) alkylene- of R$_{12}$ are each optionally substituted with 1, 2, or 3 independently selected R$^f$ substituents;

each R$^a$ is independently selected from the group consisting of —H; —CN; (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene-; wherein the (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$^a$ are each optionally substituted with 1, 2, 3, 4, or 5 independently selected R$^d$ substituents;

each R$^b$ is independently selected from the group consisting of halo; (C$_1$-C$_6$) alkyl; (C$_2$-C$_6$) alkenyl; (C$_2$-C$_6$)

alkynyl; (C$_1$-C$_6$) haloalkyl; (C$_1$-C$_6$) haloalkoxy; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; (4-10 membered heterocycloalkyl)-(C$_1$-C$_4$) alkylene-; —CN; —OH; —NH$_2$; —NO$_2$; —NHOR$^c$; —OR$^c$; —SR$^c$; —C(O)R$^c$; —C(O)NR$^c$R$^c$; —C(O)OR$^c$; —C(O)NR$^c$S(O)$_2$R$^c$; —OC(O)R$^c$; —OC(O)NR$^c$R$^c$; —C(=NOH)R$^c$; —C(=NOH)NR$^c$R$^c$; —C(=NCN)NR$^c$R$^c$; —NR$^c$C(=NCN)NR$^c$R$^c$; —C(=NR$^c$)NR$^c$R$^c$; —NR$^c$C(=NR$^c$)NR$^c$R$^c$; —NHR$^c$; —NR$^c$R$^c$; —NR$^c$C(O)R$^c$; —NR$^c$C(=NR$^c$)R$^c$; —NR$^c$C(O)OR$^c$; —NR$^c$C(O)NR$^c$R$^c$; —NR$^c$S(O)R$^c$; —NR$^c$S(O)$_2$R$^c$; —NR$^c$S(O)$_2$NR$^c$R$^c$; —S(O)R$^c$; —S(O)NR$^c$R$^c$; —S(O)$_2$R$^c$; —S(O)$_2$NR$^c$C(O)R$^c$; —Si(R$^c$)$_3$; —P(O)R$^c$R$^c$; —P(O)(OR$^c$)(OR$^c$); —B(OH)$_2$; —B(OR$^c$)$_2$; and —S(O)$_2$NR$^c$R$^c$; wherein the (C$_1$-C$_6$) alkyl; (C$_1$-C$_6$) haloalkyl; (C$_1$-C$_6$) haloalkoxy; (C$_2$-C$_6$) alkenyl; (C$_2$-C$_6$) alkynyl; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalky-(C$_1$-C$_4$) alkylene-; (5-10 membered heteroaryl)-(C$_1$-C$_4$) alkylene-; and (4-10 membered heterocycloalkyl)-(C$_1$-C$_4$) alkylene- of R$^b$ are each further optionally substituted with 1, 2, or 3 independently selected R$^d$ substituents;

each R$^c$ is independently selected from the group consisting of —H; (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; and (4-10 membered heterocycloalkyl)-(C$_1$-C$_4$) alkylene-; wherein the (C$_1$-C$_6$) alkyl; (C$_2$-C$_6$) alkenyl; (C$_2$-C$_6$) alkynyl; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; and (4-10 membered heterocycloalkyl)-(C$_1$-C$_4$) alkylene- of R are each optionally substituted with 1, 2, 3, 4, or 5 independently selected R$^f$ substituents;

each R$^d$ is independently selected from the group consisting of (C$_1$-C$_6$) alkyl; (C$_1$-C$_6$) haloalkyl; halo; (C$_6$-C$_{10}$) aryl; 5-10 membered heteroaryl; (C$_3$-C$_{10}$) cycloalkyl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; (4-10 membered heterocycloalkyl)-(C$_1$-C$_4$) alkylene-; —CN; —NH$_2$; —NHOR$^e$; —OR$^e$; —SR$^e$; —C(O)R$^e$; —C(O)NR$^e$R$^e$; —C(O)OR$^e$; —OC(O)R$^e$; —OC(O)NR$^e$R$^e$; —NR$^e$; —NR$^e$R$^e$; —NR$^e$C(O)R$^e$; —NR$^e$C(O)NR$^e$R$^e$; —NR$^e$C(O)OR$^e$; —C(=NR$^e$)NR$^e$R$^e$; —NR$^e$C(=NR$^e$)NR$^e$R$^e$; —NR$^e$C(=NOH)NR$^e$R$^e$; —NR$^e$C(=NCN)NR$^e$R$^e$; —S(O)R$^e$; —S(O)NR$^e$R$^e$; —S(O)$_2$R$^e$; —NR$^e$S(O)$_2$R$^e$; —NR$^e$S(O)$_2$NR$^e$R$^e$; and —S(O)$_2$NR$^e$R$^e$; wherein the (C$_1$-C$_6$) alkyl; (C$_1$-C$_6$) haloalkyl; (C$_6$-C$_{10}$) aryl; 5-10 membered heteroaryl; (C$_3$-C$_{10}$) cycloalkyl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; and (4-10 membered heterocycloalkyl)-(C$_1$-C$_4$) alkylene- of R$^d$ are each optionally substituted with 1, 2, or 3 independently selected R$^f$ substituents;

each R$^e$ is independently selected from the group consisting of —H; (C$_1$-C$_6$) alkyl; (C$_3$-C$_6$) cycloalkyl; (C$_3$-C$_6$) cycloalkyl-(C$_1$-C$_4$) alkylene-; (C$_6$-C$_{10}$) aryl; (C$_6$-C$_{10}$) aryl-(C$_1$-C$_4$) alkylene-; 5- or 6-membered heteroaryl; (5- or 6-membered heteroaryl)-(C$_1$-C$_4$) alkylene-; 4-7-membered heterocycloalkyl; (4-7-membered heterocycloalkyl)-(C$_1$-C$_4$) alkylene-; (C$_1$-C$_6$) haloalkyl; (C$_1$-C$_6$) haloalkoxy; (C$_2$-C$_4$) alkenyl; and (C$_2$-C$_4$) alkynyl; wherein the (C$_1$-C$_4$) alkyl; (C$_3$-C$_6$) cycloalkyl; (C$_6$-C$_{10}$) aryl; 5 or 6-membered heteroaryl; 4-7-membered heterocycloalkyl; (C$_6$-C$_{10}$) aryl-(C$_1$-C$_4$) alkylene-; (5- or 6-membered heteroaryl)-(C$_1$-C$_4$) alkylene-; (4-7-membered heterocycloalkyl)-(C$_1$-C$_4$) alkylene-; (C$_2$-C$_4$) alkenyl; and (C$_2$-C$_4$) alkynyl of R$^e$ are each optionally substituted with 1, 2, or 3 R$^f$ substituents;

or any two R$^a$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

or any two R$^c$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

or any two R$^e$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

each R$^f$ is independently selected from the group consisting of halo; —OH; —CN; —COOH; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$)haloalkyl; (C$_1$-C$_6$)haloalkoxy; phenyl; 5-6 membered heteroaryl; 4-6 membered heterocycloalkyl; and (C$_3$-C$_6$) cycloalkyl; wherein the (C$_1$-C$_6$) alkyl; phenyl; (C$_3$-C$_6$) cycloalkyl; 4-6 membered heterocycloalkyl; and 5-6 membered heteroaryl of R$^f$ are each optionally substituted with 1, 2, or 3 substituents selected from halo; —OH; —CN; —COOH; —NH$_2$; (C$_1$-C$_4$) alkyl; (C$_1$-C$_4$) alkoxy; (C$_1$-C$_4$) haloalkyl; (C$_1$-C$_4$) haloalkoxy; phenyl; (C$_3$-C$_{10}$) cycloalkyl; 5-6 membered heteroaryl; and 4-6 membered heterocycloalkyl;

each R$^g$ is independently selected from the group consisting of halo; —OH; —CN; —COOH; —COO—(C$_1$-C$_4$) alkyl; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$)haloalkyl; (C$_1$-C$_6$)haloalkoxy; phenyl; 5-6 membered heteroaryl; 4-6 membered heterocycloalkyl; and (C$_3$-C$_6$) cycloalkyl;

the ring nitrogen atom on the quinoline moiety in Formula A is optionally oxidized;

the subscript n is an integer of 1, 2, 3, or 4;

the subscript m is an integer of 1, 2, 3, 4, or 5; and the subscript p is an integer of 0, 1, 2, 3, or 4;

provided that when X is C—H, Ring A is

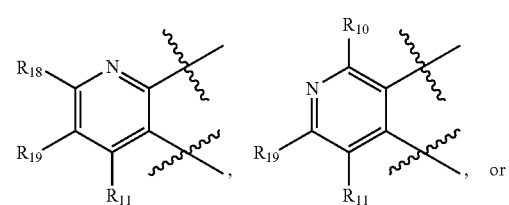

-continued

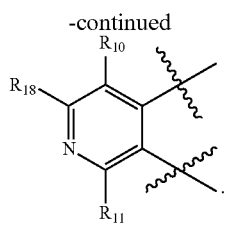

In one embodiment of this aspect, X is N. In another embodiment, X is CH;

In one embodiment of this aspect, Y is selected from O, NH, and —N($C_{1-6}$ alkyl)-. In a further aspect, Y is O.

In one embodiment of this aspect, $R_{16}$ is selected from —H, halo, —CN, ($C_1$-$C_6$) alkyl, ($C_6$-$C_{10}$) aryl, ($C_3$-$C_{10}$) cycloalkyl, 5-14 membered heteroaryl, 4-14 membered heterocycloalkyl, —CN, —NO$_2$, —OR$^a$, —SR$^a$, —NHOR$^a$, —C(O)R$^a$, —C(O)NR$^a$R$^a$, —C(O)NHOR$^a$, —C(O)OR$^a$, —C(O)NR$^a$S(O)$_2$R$^a$, —OC(O)R$^a$, —OC(O)NR$^a$R$^a$, —NHR$^a$, —NR$^a$R$^a$, and —NR$^a$C(O)R$^a$.

In a further embodiment, $R_{16}$ is selected from —H, halo, —CN, ($C_1$-$C_6$) alkyl, 5-14 membered heteroaryl, —O($C_1$-$C_6$), —C(O)($C_1$-$C_6$ alkyl), —C(O)N($C_1$-$C_6$ alkyl)$_2$, —C(O)NH($C_1$-$C_6$ alkyl), —C(O)NH$_2$, —C(O)NH(4-6 membered heterocycloalkyl), —C(O)NH($C_3$-$C_{10}$ cycloalkyl), —C(O)NH($C_1$-$C_4$ alkylene-(4-6 membered heterocycloalkyl)), —C(O)NH($C_1$-$C_4$ alkylene-($C_3$-$C_{10}$ cycloalkyl)), —C(O)O ($C_1$-$C_6$ alkyl), —NH($C_1$-$C_6$ alkyl), —N($C_1$-$C_6$ alkyl)$_2$, and —NHC(O)($C_1$-$C_6$ alkyl). In still a further embodiment, $R_{16}$ is selected from —H, —CN, 5-14 membered heteroaryl, —C(O)NH$_2$, —C(O)NH(4-6 membered heterocycloalkyl), —C(O)NH($C_3$-$C_{10}$ cycloalkyl), —C(O)NH($C_1$-$C_4$ alkylene-(4-6 membered heterocycloalkyl)), —C(O)O($C_1$-$C_6$ alkyl), —NH($C_1$-$C_6$ alkyl), —N($C_1$-$C_6$ alkyl)$_2$, and —NHC(O)($C_1$-$C_6$ alkyl).

In some embodiments, each ($C_1$-$C_6$) alkyl, ($C_6$-$C_{10}$) aryl, ($C_3$-$C_{10}$) cycloalkyl, 5-14 membered heteroaryl, or 4-14 membered heterocycloalkyl of $R_{16}$ is optionally substituted with 1, 2, 3, 4, or 5 substituents independently selected from halo, ($C_1$-$C_6$) alkyl, —CN, —NO$_2$, phenyl, ($C_1$-$C_6$) alkoxy, and oxo. In a further embodiment, each ($C_1$-$C_6$) alkyl, ($C_6$-$C_{10}$) aryl, ($C_3$-$C_{10}$) cycloalkyl, 5-14 membered heteroaryl, or 4-14 membered heterocycloalkyl of $R_{16}$ is optionally substituted with 1, 2, 3, 4, or 5 ($C_1$-$C_6$) alkyl substituents.

In one embodiment, $R_{16}$ is selected from H, —CN, (oxetan-3-yl)carbamoyl, cyclopropylcarbamoyl, carbamoyl, 2-(pyrrolidin-1-yl)ethylcarbamoyl, 1-(t-butoxycarbonylpyrrolidin-2-yl)methylcarbamoyl, 1-(pyrrolidin-2-yl)methylcarbamoyl, pyrazol-4-yl, 1-methyl-pyrazol-4-yl.

In some embodiments, $R_{17}$ is selected from the group consisting of —H, halo, ($C_1$-$C_6$) alkyl, ($C_2$-$C_6$) alkenyl, ($C_2$-$C_6$) alkynyl, —CN, —NO$_2$, —OR$^a$, —SR$^a$, —NHOH, —C(O)R$^a$, —C(O)NR$^a$R$^a$, —C(O)NHOR$^a$, —C(O)OR$^a$, —C(O)NR$^a$S(O)$_2$R$^a$, —OC(O)NR$^a$R$^a$, —C(=NR$^a$)R$^a$, —C(=NOH)R$^a$, —C(=NOH)NR$^a$, —C(=NCN)NR$^a$R$^a$, —NR$^a$C(=NCN)NR$^a$R$^a$, —C(=NR$^a$)NR$^a$R$^a$, —S(O)NR$^a$R$^a$, —S(O)$_2$NR$^a$C(O)R$^a$, —P(O)R$^a$R$^a$, —P(O)(OR$^a$)(OR$^a$), —B(OH)$_2$, —B(OR$^a$)$_2$, and S(O)$_2$NR$^a$R$^a$. In a further embodiment, $R_{17}$ is selected from the group consisting of —H, halo, ($C_1$-$C_6$) alkyl, —CN, —NO$_2$, —O($C_1$-$C_6$) alkyl, —C(O)($C_1$-$C_6$) alkyl, —C(O)NH($C_1$-$C_6$) alkyl, —C(O)N(($C_1$-$C_6$) alkyl)$_2$, and —C(O)O($C_1$-$C_6$) alkyl. In still a further embodiment, $R_{17}$ is selected from the group consisting of —H, halo, ($C_1$-$C_6$) alkyl, —CN, —NO$_2$, and —O($C_1$-$C_6$) alkyl. In yet a further embodiment, $R_{17}$ is selected from the group consisting of —H, halo, ($C_1$-$C_6$) alkyl, and —O($C_1$-$C_6$) alkyl. In yet a further embodiment, $R_{17}$ is selected from the group consisting of —H, and methoxy.

In one embodiment of this aspect, ring A is

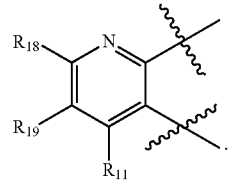

In another embodiment of this aspect, ring A is

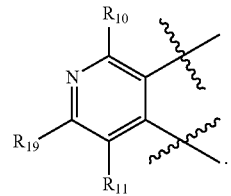

In yet another embodiment of this aspect, ring A is

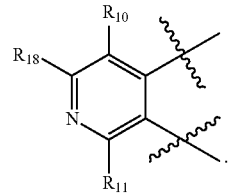

In one embodiment of this aspect, $R_{18}$ and $R_{19}$ are each independently selected from —H, halo, ($C_1$-$C_6$) alkyl, ($C_1$-$C_6$) haloalkyl, ($C_1$-$C_6$)haloalkoxy, ($C_6$-$C_{10}$) aryl, ($C_3$-$C_{10}$) cycloalkyl, 4-14 membered heterocycloalkyl, phenyl, 5-14 membered heteroaryl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, (4-14 membered heterocycloalkyl)-($C_1$-$C_4$) alkylene-, —CN, —NO$_2$, —OR$^a$, —SR$^a$, —NHOR$^a$, —C(O)R$^a$, —C(O)NR$^a$R$^a$, —C(O)NHOR$^a$, —C(O)OR$^a$, —C(O)NR$^a$S(O)$_2$R$^a$, —OC(O)R$^a$, —OC(O)NR$^a$R$^a$, —NHR$^a$, —NR$^a$R$^a$, —NR$^a$C(O)R$^a$, —NR$^a$C(=NR$^a$)R$^a$, —NR$^a$C(O)OR$^a$, and —NR$^a$C(O)NR$^a$R$^a$. In another embodiment, $R_{18}$ and $R_{19}$ are each independently selected from —H, halo, ($C_1$-$C_6$) alkyl, ($C_1$-$C_6$) haloalkyl, ($C_1$-$C_6$)haloalkoxy, ($C_6$-$C_{10}$) aryl, ($C_3$-$C_{10}$) cycloalkyl, 4-14 membered heterocycloalkyl, phenyl, 5-14 membered heteroaryl, —CN, —NO$_2$, —OR$^a$, —SR$^a$, —C(O)R$^a$, —C(O)NR$^a$R$^a$, —C(O)OR$^a$, —NH a —NR$^a$R$^a$, and —NR$^a$C(O)R$^a$. In a further embodiment, $R_{18}$ and $R_{19}$ are each independently selected from —H, halo, ($C_1$-$C_6$) alkyl, phenyl, ($C_3$-$C_{10}$) cycloalkyl, 4-14 membered heterocycloalkyl, 5-14 membered heteroaryl, —CN, —O($C_1$-$C_6$) alkyl, —C(O) ($C_1$-$C_6$) alkyl, —C(O)NH$_2$, —C(O)NH($C_1$-$C_6$) alkyl, —C(O)N(($C_1$-$C_6$) alkyl)$_2$, —C(O)O($C_1$-$C_6$) alkyl, —NH ($C_1$-$C_6$) alkyl, —N(($C_1$-$C_6$) alkyl)$_2$, and —NHC(O)($C_1$-$C_6$) alkyl. In a further embodiment, $R_{18}$ and $R_{19}$ are each independently selected from —H, halo, ($C_1$-$C_6$) alkyl, 5-14 membered heteroaryl, —CN, —O($C_1$-$C_4$ alkylene-(4-14 membered heterocycloalkyl)), O($C_1$-$C_6$ alkoxy-$C_1$-$C_6$ alkyl)), —C(O)NH$_2$, —C(O)NH($C_1$-$C_6$) alkyl, —C(O)N(($C_1$-$C_6$) alkyl)$_2$, and —NH$_2$.

In one embodiment, the ($C_1$-$C_6$) alkyl, ($C_1$-$C_6$) haloalkyl, ($C_1$-$C_6$)haloalkoxy, ($C_6$-$C_{10}$) aryl, ($C_3$-$C_{10}$) cycloalkyl, 4-14 membered heterocycloalkyl, phenyl, 5-14 membered heteroaryl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, or (4-14 membered heterocycloalkyl)-($C_1$-$C_4$) alkylene-, of $R_{18}$ or $R_{19}$ are each optionally substituted with 1, 2, 3, 4, or 5 substituents independently selected from halo, ($C_1$-$C_6$) alkyl, —CN, —OH, and —C(O)O$R_x$, wherein $R_x$ is ($C_1$-$C_6$) alkyl, phenyl, or benzyl. In a further embodiment, the ($C_1$-$C_6$) alkyl, ($C_1$-$C_6$) haloalkyl, ($C_1$-$C_6$)haloalkoxy, ($C_6$-$C_{10}$) aryl, ($C_3$-$C_{10}$) cycloalkyl, 4-14 membered heterocycloalkyl, phenyl, 5-14 membered heteroaryl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, or (4-14 membered heterocycloalkyl)-($C_1$-$C_4$) alkylene-, of $R_{18}$ or $R_{19}$ are each optionally substituted with —C(O)O$R_x$, wherein $R_x$ is ($C_1$-$C_6$) alkyl, phenyl, or benzyl.

In another embodiment, $R_{18}$ and $R_{19}$ taken together with the atoms to which they are attached form a fused $C_3$-$C_7$ cycloalkyl ring or a fused 4- to 10-membered heterocycloalkyl ring, wherein the fused $C_3$-$C_7$ cycloalkyl ring and fused 4- to 10-membered heterocycloalkyl ring are each optionally substituted with 1, 2, or 3 independently selected $R^b$ substituents. In a further embodiment, $R_{18}$ and $R_{19}$ taken together with the atoms to which they are attached form a fused $C_3$-$C_7$ cycloalkyl ring or a fused 4- to 10-membered heterocycloalkyl ring, wherein the fused $C_3$-$C_7$ cycloalkyl ring and fused 4- to 10-membered heterocycloalkyl ring are each optionally substituted with 1, 2, or 3 substituents independently selected from halo, —CN, —NO$_2$, —OH, oxo, ($C_1$-$C_6$) alkyl, —O($C_1$-$C_6$) alkyl, —C(O)($C_1$-$C_6$) alkyl, —C(O)NH$_2$, —C(O)NH($C_1$-$C_6$) alkyl, —C(O)N(($C_1$-$C_6$) alkyl)$_2$, —C(O)O($C_1$-$C_6$) alkyl, —NH($C_1$-$C_6$) alkyl, —N(($C_1$-$C_6$) alkyl)$_2$, and —NHC(O)($C_1$-$C_6$) alkyl. In still a further embodiment, $R_{18}$ and $R_{19}$ taken together with the atoms to which they are attached form a fused $C_3$-$C_7$ cycloalkyl ring or a fused 4- to 10-membered heterocycloalkyl ring, wherein the fused $C_3$-$C_7$ cycloalkyl ring and fused 4- to 10-membered heterocycloalkyl ring are each optionally substituted with 1, 2, or 3 substituents independently selected from halo, ($C_1$-$C_6$) alkyl, and —O($C_1$-$C_6$) alkyl. In yet a further embodiment, $R_{18}$ and $R_{19}$ taken together with the atoms to which they are attached form a fused ring selected from

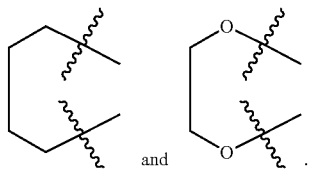 [SMILES: *CCCC* ; *OCCO*]

In one embodiment, $R_{18}$ is selected from H, halo, NH$_2$, methoxy, methyl, —CN, carbamoyl, dimethylcarbamoyl, methylcarbamoyl, pyrazol-4-yl, 1-methyl-pyrazol-4-yl, and 2-methyl-pyrazol-3-yl.

In one embodiment, $R_{19}$ is selected from H, halo, methoxy, methyl, 3-morphlinopropoxy, 2-methoxyethoxy, 1-methyl-pyrazol-4-yl.

In one embodiment of this aspect, each $R_{13}$ is independently selected from the group consisting of —H, halo, —OH, —CN, optionally substituted ($C_1$-$C_6$) alkyl, ($C_1$-$C_6$) alkoxy, ($C_1$-$C_6$) haloalkoxy, —NH$_2$, —NH($C_1$-$C_6$)alkyl, —N($C_1$-$C_6$ alkyl)$_2$, and ($C_3$-$C_6$) cycloalkyl, wherein the ($C_1$-$C_6$) alkyl, ($C_1$-$C_6$) alkoxy, —NH($C_1$-$C_6$)alkyl, —N($C_1$-$C_6$ alkyl)$_2$, and ($C_3$-$C_6$) cycloalkyl of $R_3$ are each optionally substituted with 1, 2, or 3 independently selected $R^g$ substituents. In a further embodiment of this aspect, each $R_{13}$ is independently selected from the group consisting of —H, halo, —OH, —CN, ($C_1$-$C_6$) alkyl, ($C_1$-$C_6$) alkoxy, —NH$_2$, —NH($C_1$-$C_6$)alkyl, and —N($C_1$-$C_6$ alkyl)$_2$, wherein the ($C_1$-$C_6$) alkyl, ($C_1$-$C_6$) alkoxy, —NH($C_1$-$C_6$)alkyl, and —N($C_1$-$C_6$ alkyl)$_2$ of $R_3$ are each optionally substituted with 1, 2, or 3 substituents independently selected from halo, —OH, —CN, ($C_1$-$C_6$) alkyl, and —NH$_2$. In still further embodiment of this aspect, each $R_{13}$ is independently selected from the group consisting of —H, halo, ($C_1$-$C_6$) alkyl, and ($C_1$-$C_6$) alkoxy.

In one embodiment of this aspect, each $R_{14}$ is independently selected from the group consisting of H, halo, —OH, —NH$_2$, —CN, ($C_1$-$C_6$) alkyl, ($C_1$-$C_6$) alkoxy, ($C_1$-$C_6$) haloalkyl, ($C_1$-$C_6$) haloalkoxy, —COOH, —NH($C_1$-$C_6$)alkyl, —N($C_1$-$C_6$ alkyl)$_2$, phenyl, phenyl-($C_1$-$C_2$) alkylene, ($C_3$-$C_6$) cycloalkyl, ($C_3$-$C_6$) cycloalkyl-($C_1$-$C_4$) alkylene-, and 4- to 6-membered heterocycloalkyl. In a further embodiment, each $R_{14}$ is independently selected from the group consisting of H, halo, —OH, —NH$_2$, —CN, ($C_1$-$C_6$) alkyl, ($C_1$-$C_6$) alkoxy, —COOH, —NH($C_1$-$C_6$)alkyl, —N($C_1$-$C_6$ alkyl)$_2$, and phenyl. In still further embodiment, each $R_{14}$ is independently selected from the group consisting of H, halo, and ($C_1$-$C_6$) alkyl. In yet a further embodiment, $R_{14}$ is H.

In one embodiment of this aspect, each $R_{12}$ is independently selected from the group consisting of —H, halo, —OH, —COO($C_1$-$C_6$) alkyl, —CN, —NH$_2$, —NH(($C_1$-$C_6$) alkyl), —N(($C_1$-$C_6$) alkyl)$_2$, —C(O)NH$_2$, —C(O)NH(($C_1$-$C_6$) alkyl), —C(O)N(($C_1$-$C_6$) alkyl)$_2$, ($C_1$-$C_6$) alkyl, ($C_1$-$C_6$) alkoxy, ($C_3$-$C_6$) cycloalkyl, 4- to 6-membered heterocycloalkyl, phenyl, 5- or 6-membered heteroaryl. In a further embodiment, each $R_{12}$ is independently selected from the group consisting of —H, halo, —OH, —CN, —NH$_2$, —NH(($C_1$-$C_6$) alkyl), —N(($C_1$-$C_6$) alkyl)$_2$, ($C_1$-$C_6$) alkyl, and ($C_1$-$C_6$) alkoxy. In still a further embodiment, each $R_{12}$ is independently selected from the group consisting of —H and halo. In yet a further embodiment, m is one and $R_{12}$ is F. In still a further embodiment, m is one and $R_{12}$ is F, which is para to the amine substituent on the phenyl ring.

In one embodiment of this aspect, each $R^a$ is independently selected from the group consisting of —H, —CN, ($C_1$-$C_6$) alkyl, ($C_3$-$C_{10}$) cycloalkyl, 5-14 membered heteroaryl, 4-14 membered heterocycloalkyl, ($C_3$-$C_{10}$) cycloalkyl-($C_1$-$C_4$) alkylene-, and (4-14 membered heterocycloalkyl)-($C_1$-$C_4$) alkylene-, wherein the ($C_1$-$C_6$) alkyl, ($C_3$-$C_{10}$) cycloalkyl, 5-14 membered heteroaryl, 4-14 membered heterocycloalkyl, ($C_3$-$C_{10}$) cycloalkyl-($C_1$-$C_4$) alkylene-, and (4-14 membered heterocycloalkyl)-($C_1$-$C_4$) alkylene- of $R^a$ are each optionally substituted with 1, 2, 3, 4, or 5 independently selected $R^d$ substituents. In one embodiment of this aspect, each $R^a$ is independently selected from the group consisting of —H, ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene-, wherein the ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene- of $R^a$ are each optionally substituted with 1, 2, 3, 4, or 5 substituents independently selected from ($C_1$-$C_6$) alkyl, ($C_1$-$C_6$) alkoxy, and —C(O)O($C_1$-$C_4$) alkyl.

In one embodiment of this aspect, each $R^b$ is independently selected from the group consisting of halo, $(C_1-C_6)$ alkyl, —CN, —OH, —NH$_2$, —NO$_2$, and —C(O)O(C$_1$-C$_4$) alkyl. In a further embodiment, each $R^b$ is independently selected from the group consisting of $(C_1-C_6)$ alkyl and —C(O)O(C$_1$-C$_4$) alkyl.

In one embodiment of this aspect, each $R^c$ is —H or $(C_1-C_6)$ alkyl.

In one embodiment of this aspect, each $R^d$ is independently selected from the group consisting of $(C_1-C_6)$ alkyl, halo, phenyl, 5-10 membered heteroaryl, $(C_3-C_{10})$ cycloalkyl, 4-10 membered heterocycloalkyl, (4-10 membered heterocycloalkyl)-$(C_1-C_4)$ alkylene-, —CN, and —C(O)O(C$_1$-C$_4$) alkyl.

In one embodiment of this aspect, each $R^e$ is —H or $(C_1-C_6)$ alkyl.

In another embodiment, any two $R^a$ substituents together with the nitrogen atom to which they are attached form a 5 or 6-membered heterocycloalkyl.

In another embodiment, any two $R^c$ substituents together with the nitrogen atom to which they are attached form a 5 or 6-membered heterocycloalkyl.

In another embodiment, any two $R^e$ substituents together with the nitrogen atom to which they are attached form a 5 or 6-membered heterocycloalkyl.

In one embodiment, each $R^f$ is independently selected from the group consisting of halo, —OH, —CN, —COOH, —NH$_2$, $(C_1-C_6)$ alkyl, and $(C_1-C_6)$ alkoxy.

In one embodiment, each $R^g$ is independently selected from the group consisting of halo, —OH, —CN, —COOH, $(C_1-C_6)$ alkyl, $(C_1-C_6)$ alkoxy, and —C(O)O(C$_1$-C$_4$) alkyl.

In one embodiment, n is 1 or 2;

In one embodiment, m is 1 or 2. In further embodiment, m is 1.

In one embodiment, p is 1 or 2.

In one embodiment of this aspect, the compound of Formula I' is a compound of Formula I'a, wherein the variables $R_{10}$—$R_{17}$ are defined herein:

(I'a)

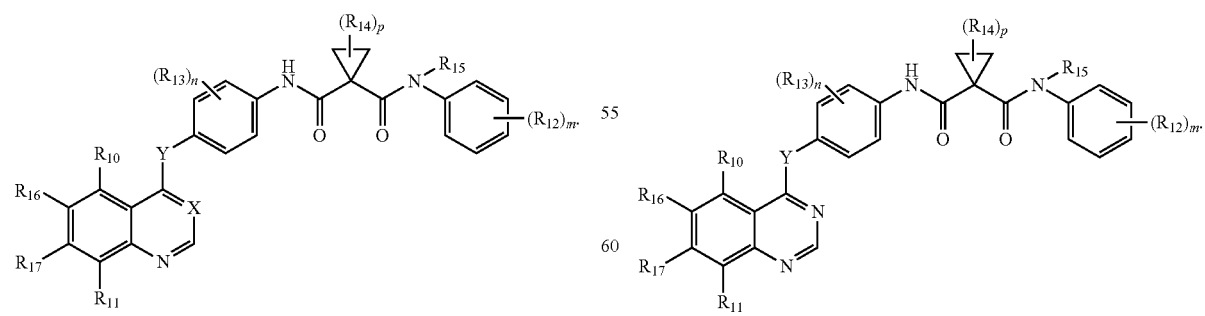

In another embodiment of this aspect, the compound of Formula I' is a compound of Formula I'b, I'c or I'd, wherein the variables $R_{10}$—$R_{19}$ are defined herein:

(I'b)

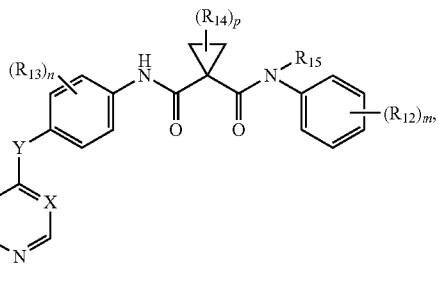

(I'c)

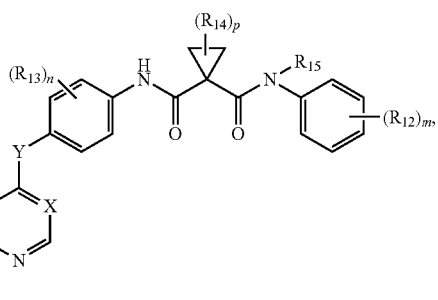

(I'd)

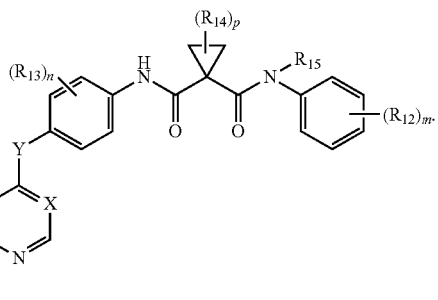

In another embodiment of this aspect, the compound of Formula I' is a compound of Formula (I'a-1), wherein the variables $R_{10}$—$R_{17}$ are defined herein:

(I'a-1)

In another embodiment of this aspect, the compound of Formula I' is a compound of Formula (I'b-1), wherein the variables $R_{10}$—$R_{19}$ are defined herein:

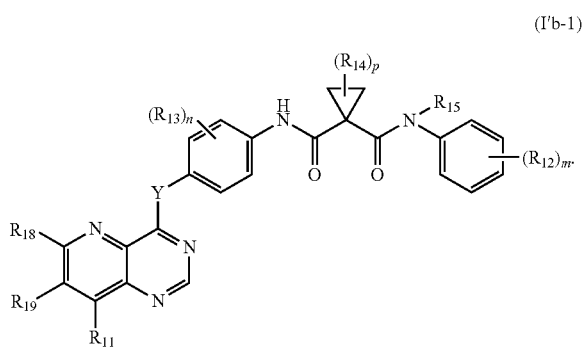
(I'b-1)

In another embodiment of this aspect, the compound of Formula I' is a compound of Formula (I'b-2), wherein the variables $R_{10}$—$R_{19}$ are defined herein:

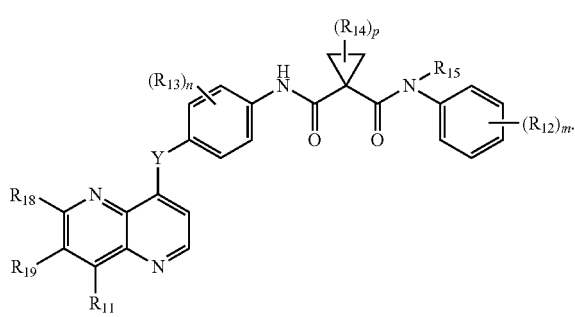
(I'b-2)

In another embodiment of this aspect, the compound of Formula I' is a compound of Formula (I'c-1) wherein the variables $R_{10}$—$R_{19}$ are defined herein:

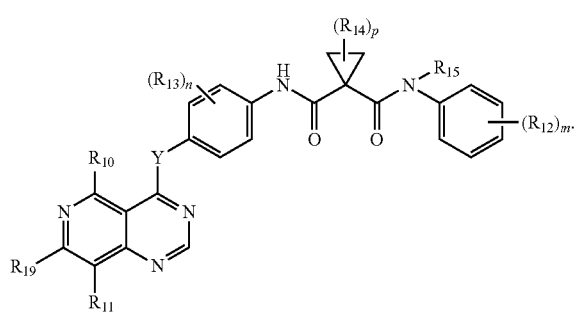
(I'c-1)

In another embodiment of this aspect, the compound of Formula I' is a compound of Formula (I'c-2) wherein the variables $R_{10}$—$R_{19}$ are defined herein:

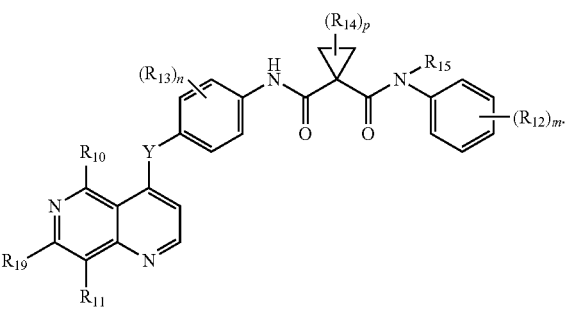
(I'c-2)

In another embodiment of this aspect, the compound of Formula I' is a compound of Formula (I'd-1), wherein the variables $R_{10}$—$R_{18}$ are defined herein:

(I'd-1)

In another embodiment of this aspect, the compound of Formula I' is a compound of Formula (I'd-2), wherein the variables $R_{10}$—$R_{18}$ are defined herein:

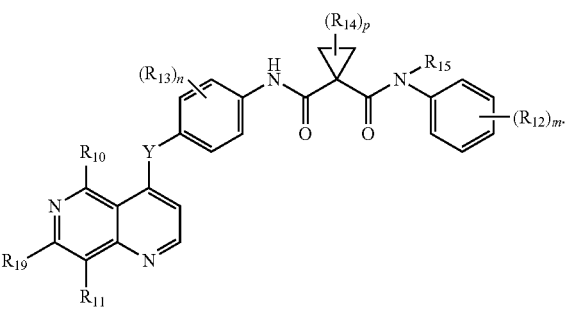
(I'd-2)

In one embodiment, $R_{16}$ is selected from —H, $(C_1$-$C_6)$ alkyl, $(C_2$-$C_6)$ alkenyl, $(C_2$-$C_6)$ alkynyl, —C(=NO—$(C_1$-$C_6)$ alkyl)$R^a$; halo, —CN, $OR^a$, —C(O)$OR^a$; —C(O)$NR^aR^a$, —C(O)NHOR$^a$, —S(O)$_2$NR$^a$R$^a$, phenyl, 5- to 6-membered heteroaryl, $(C_3$-$C_6)$ cycloalkyl, and 4- to 6-membered heterocycloalkyl, wherein the $(C_1$-$C_6)$ alkyl; $(C_2$-$C_6)$ alkenyl, $(C_2$-$C_6)$ alkynyl, phenyl, 5- to 6-membered heteroaryl, $(C_3$-$C_6)$ cycloalkyl, and 4- to 6-membered heterocycloalkyl of $R_{16}$ are each optionally substituted with 1, 2, or 3 $R^g$ substituents.

In one embodiment, $R_{17}$ is selected from —H, $(C_1$-$C_6)$ alkyl, $(C_2$-$C_6)$ alkenyl, $(C_2$-$C_6)$ alkynyl, —C(=NO—$(C_1$-

$C_6$) alkyl)$R^a$, halo, —CN, $OR^a$, —C(O)$OR^a$, —C(O)$NR^aR^a$, —C(O)$NHOR^a$, —S(O)$_2NR^aR^a$, phenyl, 5- to 6-membered heteroaryl, ($C_3$-$C_6$) cycloalkyl, and 4- to 6-membered heterocycloalkyl, wherein the ($C_1$-$C_6$) alkyl, ($C_2$-$C_6$) alkenyl, ($C_2$-$C_6$) alkynyl, phenyl, 5- to 6-membered heteroaryl, ($C_3$-$C_6$) cycloalkyl, and 4- to 6-membered heterocycloalkyl of $R_{17}$ are each optionally substituted with 1, 2, or 3 $R^g$ substituents.

In one embodiment, $R_{18}$ and $R_{19}$ are each independently selected from —H, ($C_1$-$C_6$) alkyl, ($C_2$-$C_6$) alkenyl, ($C_2$-$C_6$) alkynyl, —C(=NO—($C_1$-$C_6$) alkyl)$R^a$, halo, —CN, $OR^a$, —C(O)$OR^a$, —C(O)$NR^aR^a$, —C(O)$NHOR^a$, —S(O)$_2NR^aR^a$, phenyl, 5- to 6-membered heteroaryl, ($C_3$-$C_6$) cycloalkyl, and 4- to 6-membered heterocycloalkyl, wherein the ($C_1$-$C_6$) alkyl, ($C_2$-$C_6$) alkenyl, ($C_2$-$C_6$) alkynyl, phenyl, 5- to 6-membered heteroaryl, ($C_3$-$C_6$) cycloalkyl, and 4- to 6-membered heterocycloalkyl of $R_{18}$ or $R_{19}$ are each optionally substituted with 1, 2, or 3 $R^b$ substituents.

In one embodiment, $R_{16}$ is selected from H, halo, $NH_2$, NH($C_{1-6}$ alkyl), N($C_{1-6}$ alkyl), methoxy, methyl, CN, 3-morphlinopropoxy, 2-methoxyethoxy, (oxetan-3-yloxy) carbamoyl, cyclopropylcarbamoyl, carbamoyl, 2-(pyrrolidin-1-yl)ethylcarbamoyl, 1-(t-butoxycarbonylpyrrolidin-2-yl)methylcarbamoyl, 1-(pyrrolidin-2-yl)methylcarbamoyl, 2-methoxyethylamino, azetidin-1-yl, dimethylcarbamoyl, methylamino, 3-morpholinopropoxy, 2-methoxyethoxy, 2-hydroxyethoxy, propoxy, 2-hydroxypropoxy, methoxycarbonyl, carboxy, methylcarbamoyl, 2-oxazolyl, pyrazol-3-yl, pyrazol-4-yl, 4-isoxazolyl, 3,5-dimethylisoxazol-4-yl, 1-methyl-pyrazol-4-yl, 2-methyl-pyrazol-3-yl, 2-ethyl-pyrazol-3-yl, 2-(2-hydroxyethyl)-pyrazol-3-yl, 2-(2,2,2-trifluoroethyl)-pyrazol-3-yl, 2-(2-fluoroethyl)-pyrazol-3-yl, 2-(2,2-difluoroethyl)-pyrazol-3-yl, 2-trifluoromethyl-pyrazol-3-yl, 2-difluoromethyl-pyrazol-3-yl, 1-methyl-imidazol-4-yl, 1-methyl-imidazol-2-yl, 1H-imidazol-2-yl, (2-hydroxyethoxy)carbamoyl, (2,2-dihydroxyethoxy)carbamoyl, (oxetan-3-yl)carbamoyl, methoxycarbamoyl, 2-trimethylsilylethynyl, ethynyl, 1,3,4-oxadiazol-3-yl, 1H-1,2,3-triazol-5-yl, sulfamoyl, acetyl, and —C(=NOCH$_3$)CH$_3$.

In one embodiment, $R_{18}$ and $R_{19}$ are each independently selected from H, halo, $NH_2$, NH($C_{1-6}$ alkyl), N($C_{1-6}$ alkyl), methoxy, methyl, CN, 3-morphlinopropoxy, 2-methoxyethoxy, (oxetan-3-yloxy)carbamoyl, cyclopropylcarbamoyl, carbamoyl, 2-(pyrrolidin-1-yl)ethylcarbamoyl, 1-(t-butoxycarbonylpyrrolidin-2-yl)methylcarbamoyl, 1-(pyrrolidin-2-yl)methylcarbamoyl, 2-methoxyethylamino, azetidin-1-yl, dimethylcarbamoyl, methylamino, 3-morpholinopropoxy, 2-methoxyethoxy, 2-hydroxyethoxy, propoxy, 2-hydroxypropoxy, methoxycarbonyl, carboxy, methylcarbamoyl, 2-oxazolyl, pyrazol-3-yl, pyrazol-4-yl, 4-isoxazolyl, 3,5-dimethylisoxazol-4-yl, 1-methyl-pyrazol-4-yl, 2-methyl-pyrazol-3-yl, 2-ethyl-pyrazol-3-yl, 2-(2-hydroxyethyl)-pyrazol-3-yl, 2-(2,2,2-trifluoroethyl)-pyrazol-3-yl, 2-(2-fluoroethyl)-pyrazol-3-yl, 2-(2,2-difluoroethyl)-pyrazol-3-yl, 2-trifluoromethyl-pyrazol-3-yl, 2-difluoromethyl-pyrazol-3-yl, 1-methyl-imidazol-4-yl, 1-methyl-imidazol-2-yl, 1H-imidazol-2-yl, (2-hydroxyethoxy)carbamoyl, (2,2-dihydroxyethoxy)carbamoyl, (oxetan-3-yl)carbamoyl, methoxycarbamoyl, 2-trimethylsilylethynyl, ethynyl, 1,3,4-oxadiazol-3-yl, 1H-1,2,3-triazol-5-yl, sulfamoyl, acetyl, and —C(=NOCH$_3$)CH$_3$.

In one embodiment, $R_{16}$ is $R^a$NHC(O)— and $R_{17}$ is H or —$OR^a$.

In another embodiment, $R_{16}$ is 5- or 6-membered heteroaryl optionally substituted with 1, 2, or 3 independently selected R substituents and $R_{17}$ is H.

In another embodiment, $R_{16}$ is H and $R_{17}$ is 5- or 6-membered heteroaryl optionally substituted with 1, 2, or 3 independently selected $R^b$ substituents.

In one embodiment, $R_{18}$ and $R_{19}$ are each independently H, halo, CN, $R^a$NHC(O)—, —$OR^a$ or 5- or 6-membered heteroaryl optionally substituted with 1-3 independently selected R substituents.

In another embodiment, $R_{18}$ is H and $R_{19}$ is —$OR^a$.

In another embodiment, $R_{19}$ is and $R_{18}$ is —$OR^a$.

In another embodiment, $R_{18}$ and $R_{19}$ are each independently —$OR^a$.

In another embodiment, $R_{18}$ is 5- or 6-membered heteroaryl optionally substituted with 1-3 independently selected $R^b$ substituents and $R_{19}$ is H or —$OR^a$.

In another embodiment, $R_{18}$ is H or —$OR^a$ and $R_{19}$ is 5- or 6-membered heteroaryl optionally substituted with 1-3 independently selected $R^b$ substituents.

In another embodiment, $R_{18}$ is $R^a$NHC(O)— and $R_{19}$ is H or —$OR^a$.

In another embodiment, $R_{19}$ is $R^a$NHC(O)— and $R_{18}$ is H or —$OR^a$.

In one embodiment, $R_{10}$ and $R_{11}$ are each H.

In one embodiment, the subscript m is 1.

In another embodiment, the subscript n is 1.

In another embodiment, the subscript p is 1.

In some embodiments,

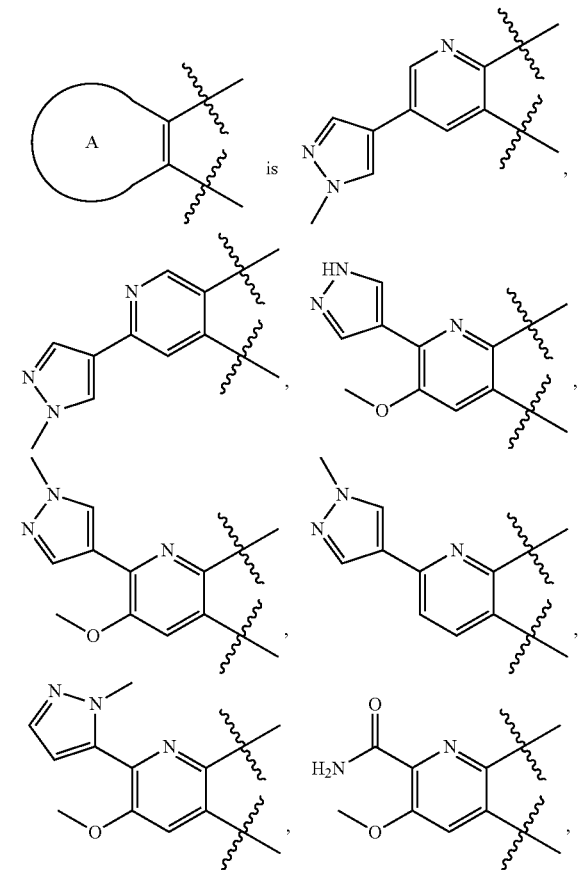

-continued
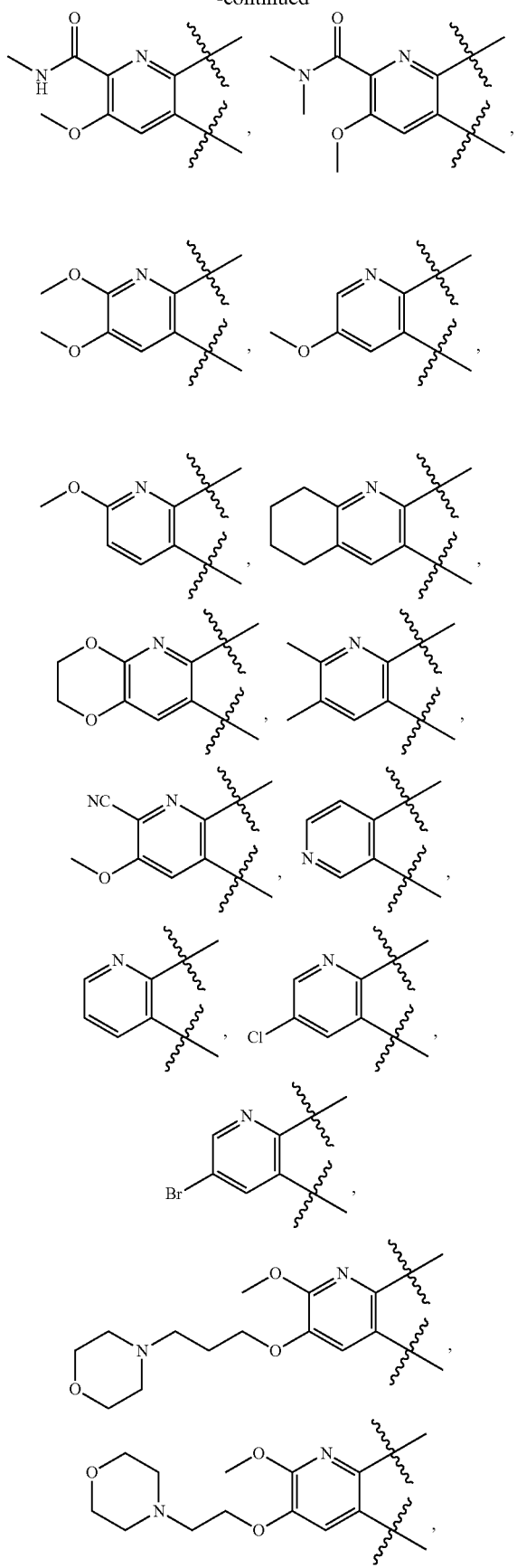
-continued
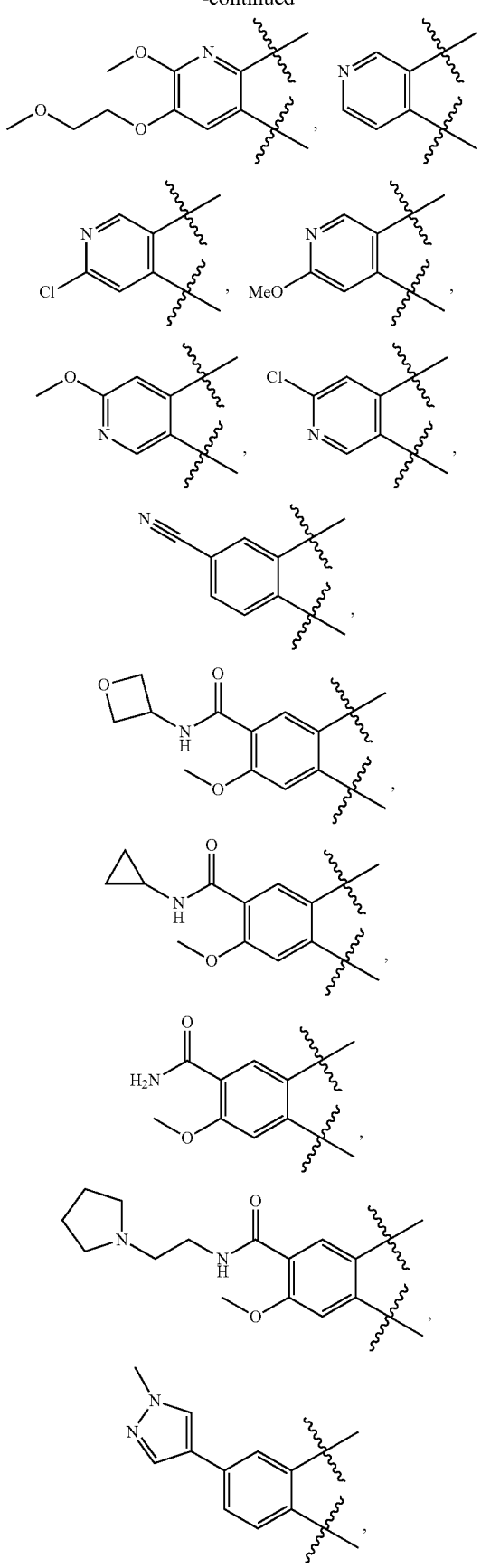

51

-continued

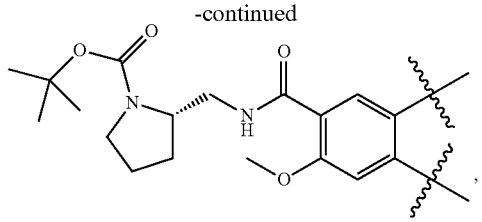

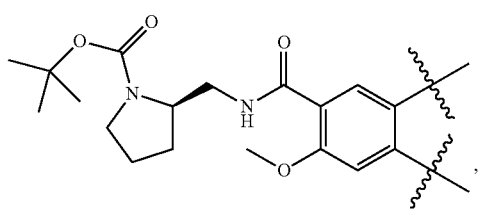

52

-continued

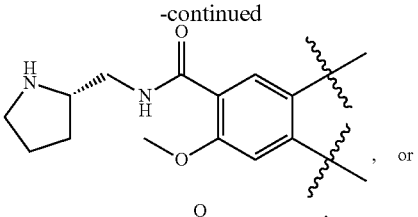

In some embodiments, the compound of Formula I', or a pharmaceutically acceptable salt thereof, is selected from the compounds listed in Table 1, or a pharmaceutically acceptable salt thereof.

TABLE 1

Compounds of Formula I'

| Comp. | Structure | IUPAC Name |
| --- | --- | --- |
| 7 | 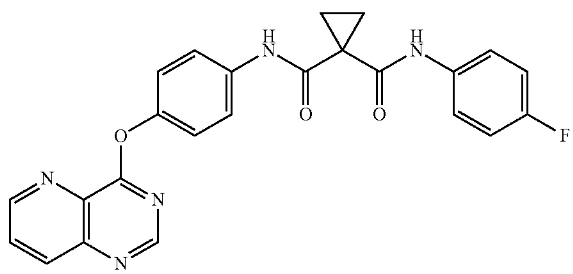 [SMILES: O=C(Nc1ccc(F)cc1)C1(C(=O)Nc2ccc(Oc3ncnc4cccnc34)cc2)CC1] | 1-N'-(4-fluorophenyl)-1-N-(4-pyrido[3,2-d]pyrimidin-4-yloxyphenyl)cyclopropane-1,1-dicarboxamide |
| 12 | 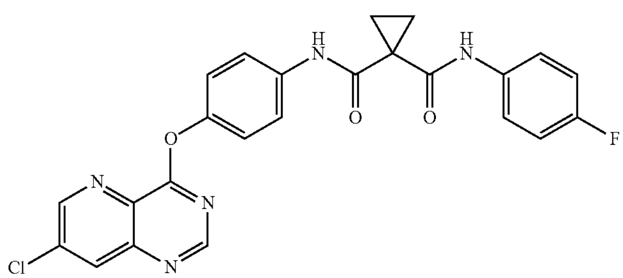 | 1-N-[4-(7-chloropyrido[3,2-d]pyrimidin-4-yl)oxyphenyl]-1-N'-(4-fluorophenyl)cyclopropane-1,1-dicarboxamide |
| 13 | 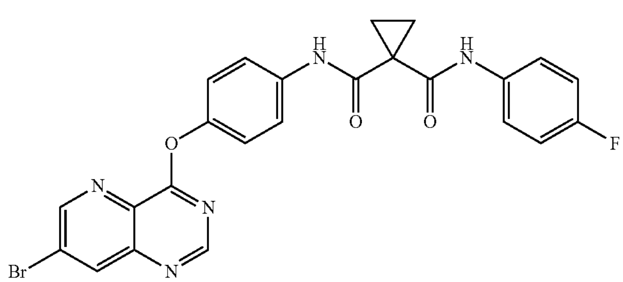 [SMILES: O=C(Nc1ccc(F)cc1)C1(C(=O)Nc2ccc(Oc3ncnc4cc(Cl)cnc34)cc2)CC1] | 1-N-[4-(7-bromopyrido[3,2-d]pyrimidin-4-yl)oxyphenyl]-1-N'-(4-fluorophenyl)cyclopropane-1,1-dicarboxamide |

TABLE 1-continued

Compounds of Formula I'

| Comp. | Structure | IUPAC Name |
|---|---|---|
| 16 | 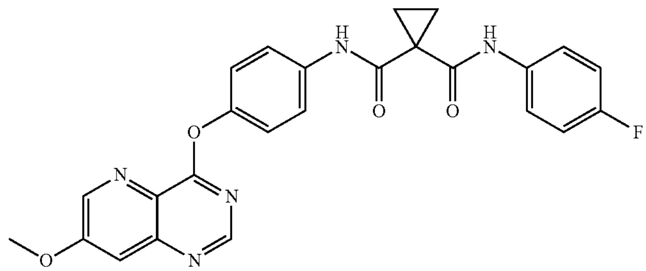 [SMILES: COc1cnc2c(Oc3ccc(NC(=O)C4(C(=O)Nc5ccc(F)cc5)CC4)cc3)ncnc2c1] | 1-N'-(4-fluorophenyl)-1-N-[4-(7-methoxypyrido[3,2-d]pyrimidin-4-yl)oxyphenyl]cyclopropane-1,1-dicarboxamide |
| 19 | 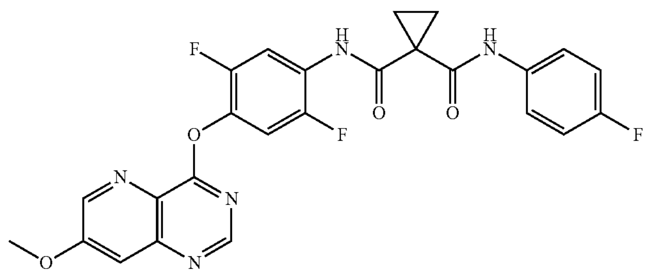 [SMILES: COc1cnc2c(Oc3cc(F)c(NC(=O)C4(C(=O)Nc5ccc(F)cc5)CC4)cc3F)ncnc2c1] | 1-N'-[2,5-difluoro-4-(7-methoxypyrido[3,2-d]pyrimidin-4-yl)oxyphenyl]-1-N-(4-fluorophenyl)cyclopropane-1,1-dicarboxamide |
| 28 | 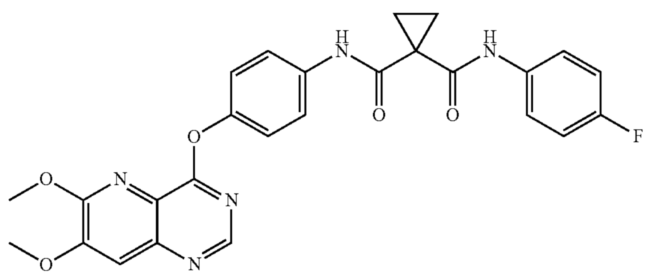 [SMILES: COc1cc2ncnc(Oc3ccc(NC(=O)C4(C(=O)Nc5ccc(F)cc5)CC4)cc3)c2nc1OC] | 1-N-[4-(6,7-dimethoxypyrido[3,2-d]pyrimidin-4-yl)oxyphenyl]-1-N'-(4-fluorophenyl)cyclopropane-1,1-dicarboxamide |
| 29 | 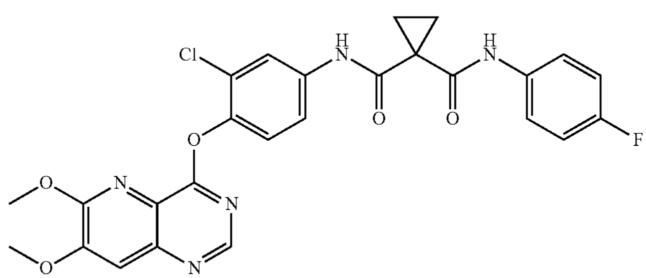 [SMILES: COc1cc2ncnc(Oc3ccc(NC(=O)C4(C(=O)Nc5ccc(F)cc5)CC4)cc3Cl)c2nc1OC] | 1-N'-[3-chloro-4-(6,7-dimethoxypyrido[3,2-d]pyrimidin-4-yl)oxyphenyl]-1-N-(4-fluorophenyl)cyclopropane-1,1-dicarboxamide |
| 30 | 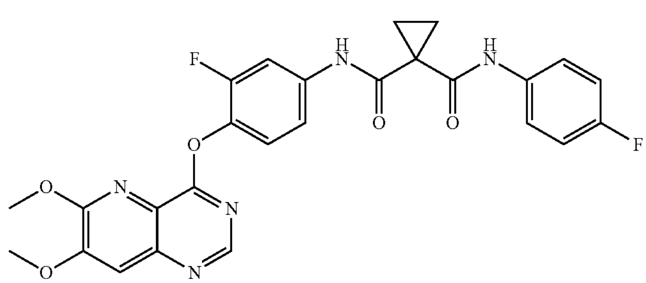 | 1-N'-[4-(6,7-dimethoxypyrido[3,2-d]pyrimidin-4-yl)oxy-3-fluorophenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 31 | 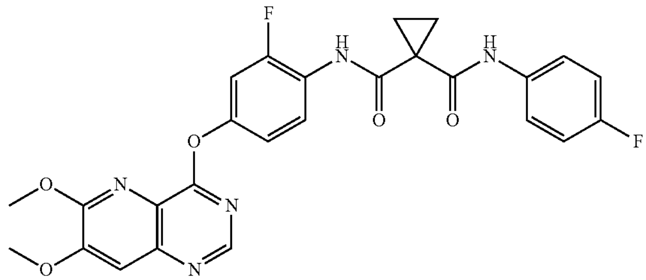 | 1-N'-[4-(6,7-dimethoxy-pyrido[3,2-d]pyrimidin-4-yl)oxy-2-fluorophenyl]-1-N-(4-fluorophenyl)cyclo-propane-1,1-dicarboxamide |
| 32 | 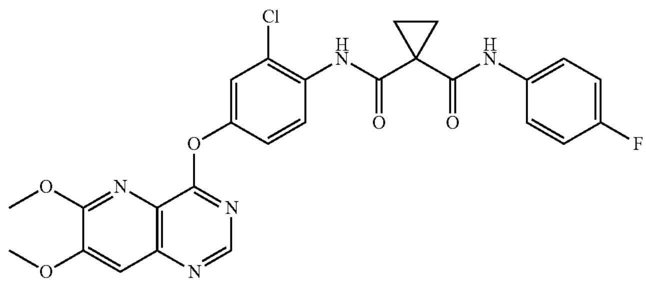 [SMILES: COc1cc2ncnc(Oc3ccc(NC(=O)C4(C(=O)Nc5ccc(F)cc5)CC4)c(F)c3)c2nc1OC] | 1-N'-[2-chloro-4-(6,7-dimethoxypyrido[3,2-d]pyrimidin-4-yl)oxyphenyl]-1-N-(4-fluorophenyl)cyclo-propane-1,1-dicarboxamide |
| 33 | 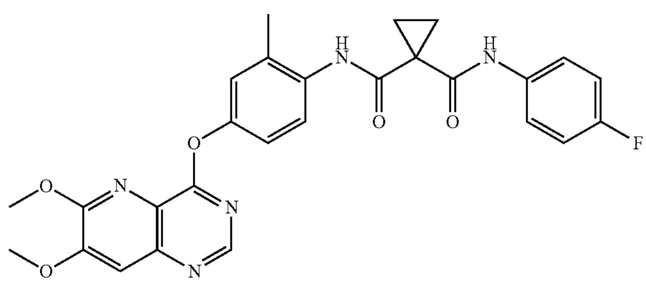 [SMILES: COc1cc2ncnc(Oc3ccc(NC(=O)C4(C(=O)Nc5ccc(F)cc5)CC4)c(C)c3)c2nc1OC] | 1-N'-[4-(6,7-dimethoxypyrido[3,2-d]pyrimidin-4-yl)oxy-2-methylphenyl]-1-N-(4-fluorophenyl)cyclopropane-1,1-dicarboxamide |
| 34 | 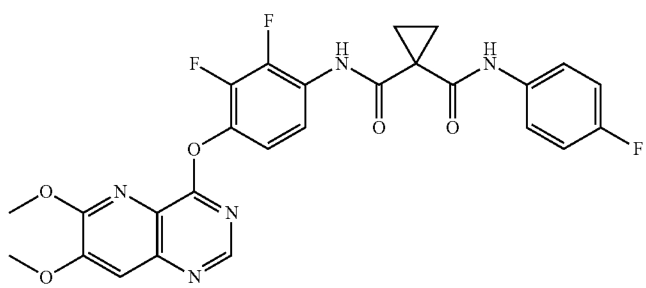 [SMILES: COc1cc2ncnc(Oc3ccc(NC(=O)C4(C(=O)Nc5ccc(F)cc5)CC4)c(F)c3F)c2nc1OC] | 1-N'-[4-(6,7-dimethoxypyrido[3,2-d]pyrimidin-4-yl)oxy-2,3-difluorophenyl]-1-N-(4-fluorophenyl)cyclo-propane-1,1-dicarbox-amide |
| 35 | 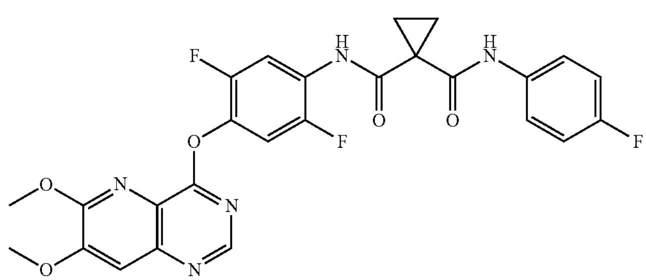 [SMILES: COc1cc2ncnc(Oc3cc(F)c(NC(=O)C4(C(=O)Nc5ccc(F)cc5)CC4)cc3F)c2nc1OC] | 1-N'-[4-(6,7-dimethoxypyrido[3,2-d]pyrimidin-4-yl)oxy-2,5-difluorophenyl]-1-N-(4-fluorophenyl)cyclo-propane-1,1-dicarboxamide |

TABLE 1-continued

Compounds of Formula I'

| Comp. | Structure | IUPAC Name |
|---|---|---|
| 43 | 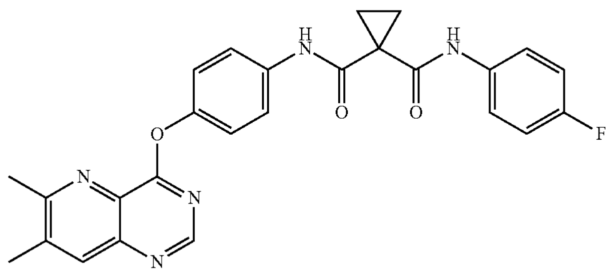 [SMILES: Cc1cc2ncnc(Oc3ccc(NC(=O)C4(C(=O)Nc5ccc(F)cc5)CC4)cc3)c2nc1C] | 1-N-[4-(6,7-dimethyl-pyrido[3,2-d]pyrimidin-4-yl)oxyphenyl]-1-N'-(4-fluorophenyl)cyclopropane-1,1-dicarboxamide |
| 52 | 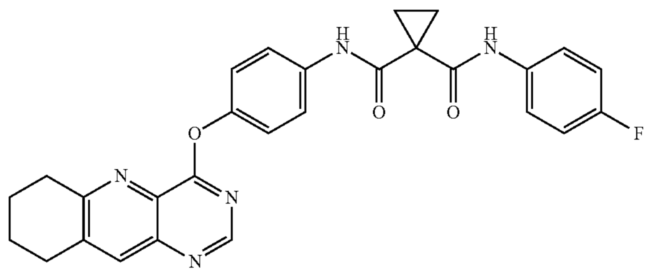 [SMILES: O=C(Nc1ccc(F)cc1)C1(C(=O)Nc2ccc(Oc3ncnc4cc5c(nc34)CCCC5)cc2)CC1] | 1-N'-(4-fluorophenyl)-1-N-[4-(6,7,8,9-tetrahydro-pyrimido[5,4-b]quinolin-4-yloxy)phenyl]cyclopropane-1,1-dicarboxamide |
| 57 | 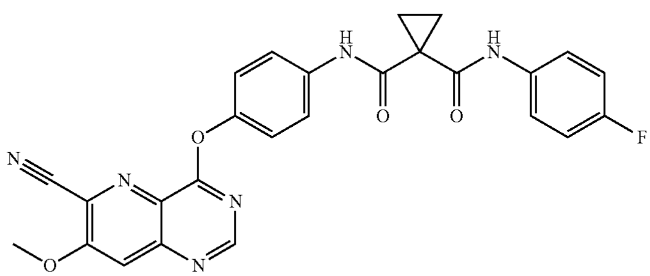 [SMILES: COc1cc2ncnc(Oc3ccc(NC(=O)C4(C(=O)Nc5ccc(F)cc5)CC4)cc3)c2nc1C#N] | 1-N-[4-(6-cyano-7-methoxypyrido[3,2-d]pyrimidin-4-yl)oxyphenyl]-1-N'-(4-fluorophenyl)cyclopropane-1,1-dicarboxamide |
| 65 | 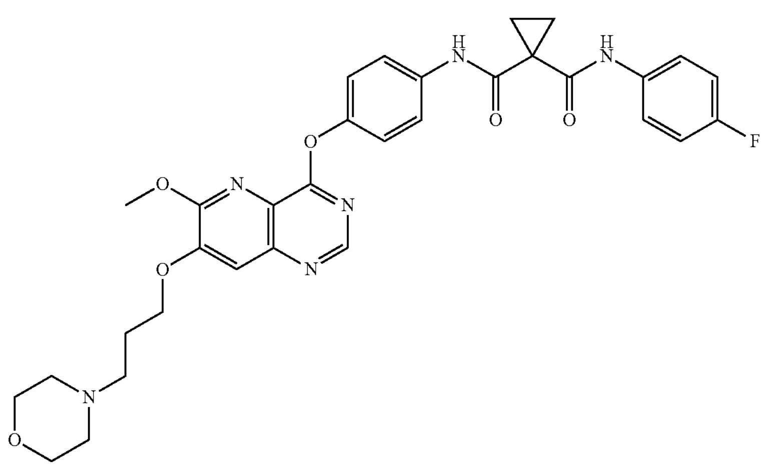 [SMILES: COc1nc2c(Oc3ccc(NC(=O)C4(C(=O)Nc5ccc(F)cc5)CC4)cc3)ncnc2cc1OCCCN1CCOCC1] | 1-N'-(4-fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide |

TABLE 1-continued

Compounds of Formula I'

| Comp. | Structure | IUPAC Name |
|---|---|---|
| 66 | 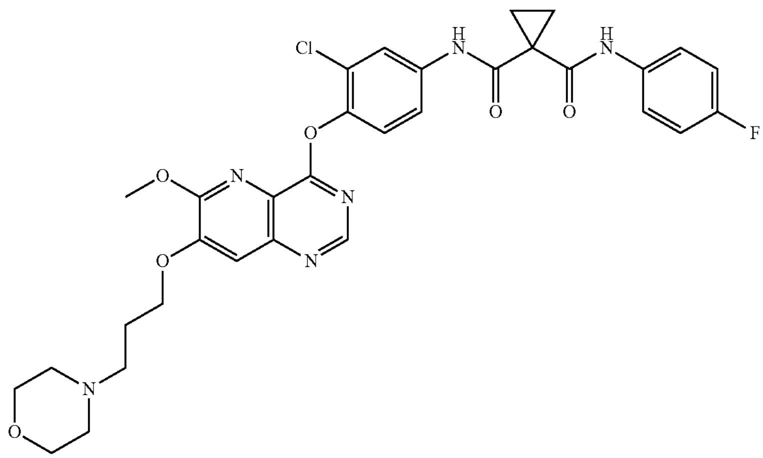 | 1-N'-[3-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 67 | 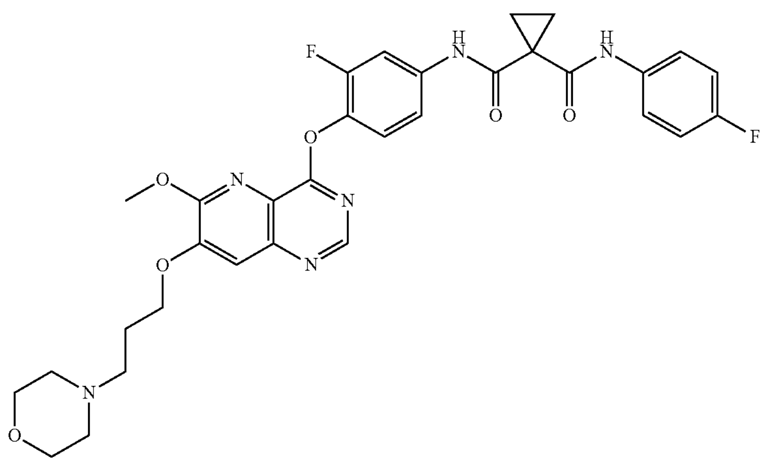 [SMILES: COc1nc2c(Oc3ccc(NC(=O)C4(C(=O)Nc5ccc(F)cc5)CC4)cc3F)ncnc2cc1OCCCN1CCOCC1] | 1-N'-[3-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 68 | 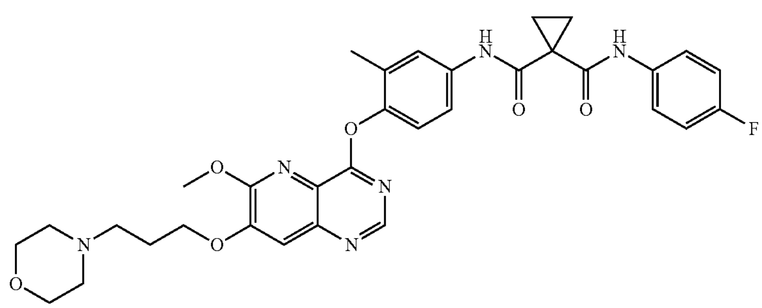 [SMILES: COc1nc2c(Oc3ccc(NC(=O)C4(C(=O)Nc5ccc(F)cc5)CC4)cc3C)ncnc2cc1OCCCN1CCOCC1] | 1-N-(4-fluorophenyl)-1-N'-[4-[6-methoxy-7-(3-morpholin-4-ylpropoxy)pyrido[3,2-d]pyrimidin-4-yl]oxy-3-methylphenyl]cyclopropane-1,1-dicarboxamide |
| 69 | 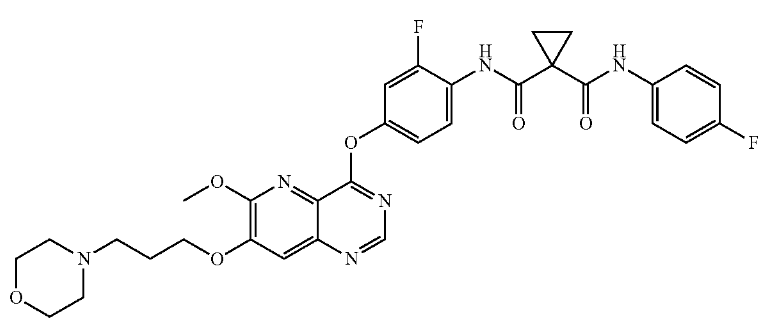 [SMILES: COc1nc2c(Oc3ccc(NC(=O)C4(C(=O)Nc5ccc(F)cc5)CC4)c(F)c3)ncnc2cc1OCCCN1CCOCC1] | 1-N'-[2-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 70 | 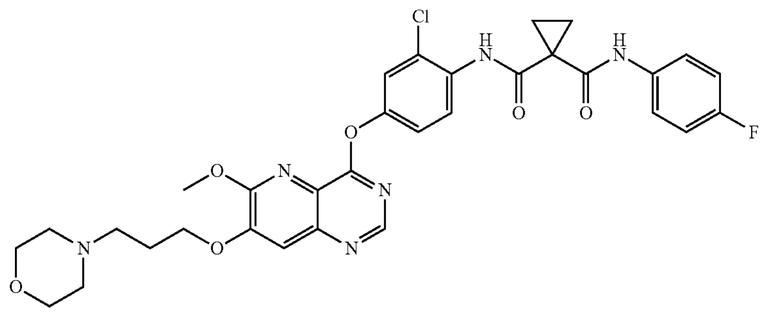 | 1-N'-[2-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 71 | 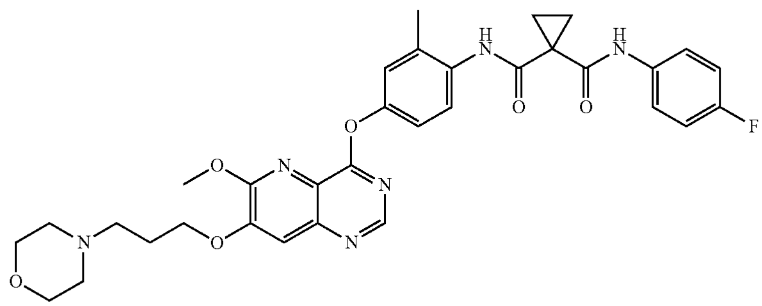 [SMILES: COc1nc2c(Oc3ccc(NC(=O)C4(C(=O)Nc5ccc(F)cc5)CC4)c(C)c3)ncnc2cc1OCCCN1CCOCC1] | 1-N-(4-fluorophenyl)-1-N'-[4-[6-methoxy-7-(3-morpholin-4-ylpropoxy)pyrido[3,2-d]pyrimidin-4-yl]oxy-2-methylphenyl]cyclopropane-1,1-dicarboxamide |
| 72 | 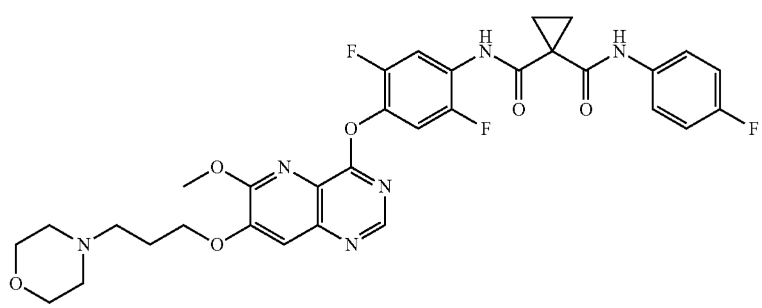 [SMILES: COc1nc2c(Oc3cc(F)c(NC(=O)C4(C(=O)Nc5ccc(F)cc5)CC4)cc3F)ncnc2cc1OCCCN1CCOCC1] | 1-N'-[2,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 73 | 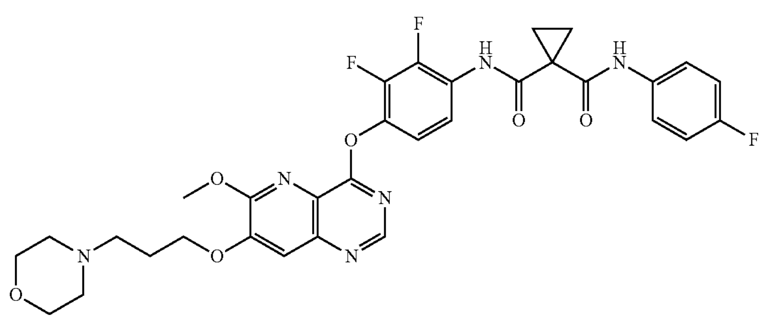 [SMILES: COc1nc2c(Oc3ccc(NC(=O)C4(C(=O)Nc5ccc(F)cc5)CC4)c(F)c3F)ncnc2cc1OCCCN1CCOCC1] | 1-N'-[2,3-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 74 | 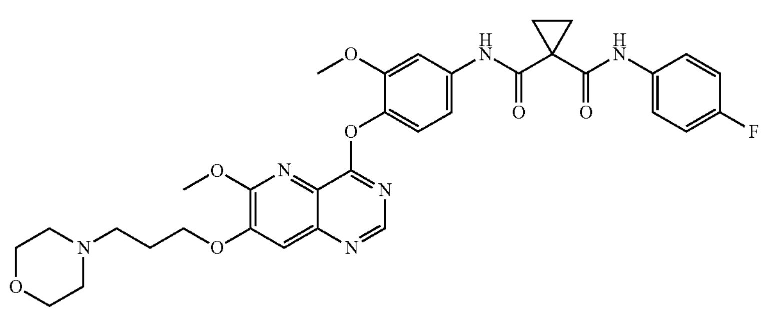 [SMILES: COc1cc(NC(=O)C2(C(=O)Nc3ccc(F)cc3)CC2)ccc1Oc1ncnc2cc(OCCCN3CCOCC3)c(OC)nc12] | 1-N-(4-fluorophenyl)-1-N'-[3-methoxy-4-[6-methoxy-7-(3-morpholin-4-ylpropoxy)pyrido[3,2-d]pyrimidin-4-yl]oxyphenyl]cyclopropane-1,1-dicarboxamide |

TABLE 1-continued

Compounds of Formula I'

| Comp. | Structure | IUPAC Name |
|---|---|---|
| 75 | 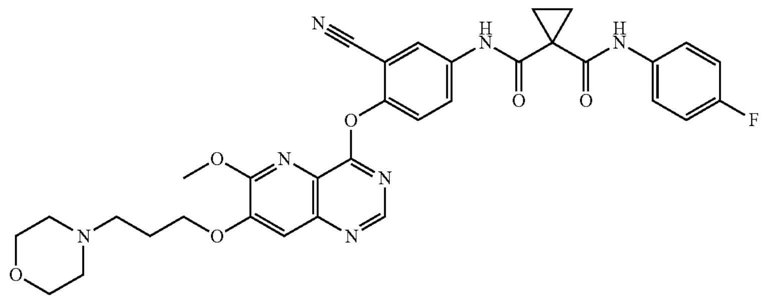 [SMILES: COc1nc2c(Oc3ccc(NC(=O)C4(C(=O)Nc5ccc(F)cc5)CC4)cc3C#N)ncnc2cc1OCCCN1CCOCC1] | 1-N'-[3-cyano-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 76 | 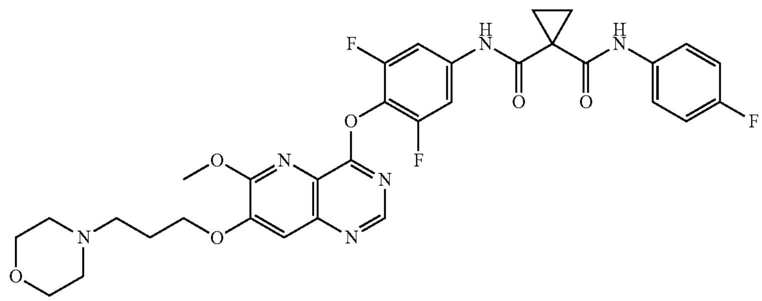 [SMILES: COc1nc2c(Oc3c(F)cc(NC(=O)C4(C(=O)Nc5ccc(F)cc5)CC4)cc3F)ncnc2cc1OCCCN1CCOCC1] | 1-N'-[3,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 78 | 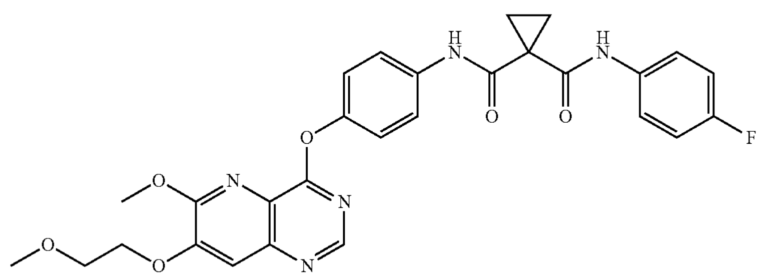 [SMILES: COCCOc1cc2ncnc(Oc3ccc(NC(=O)C4(C(=O)Nc5ccc(F)cc5)CC4)cc3)c2nc1OC] | 1-N'-(4-fluorophenyl)-1-N-[4-[6-methoxy-7-(2-methoxyethoxy)pyrido[3,2-d]pyrimidin-4-yl]oxyphenyl]cyclopropane-1,1-dicarboxamide |
| 79 | 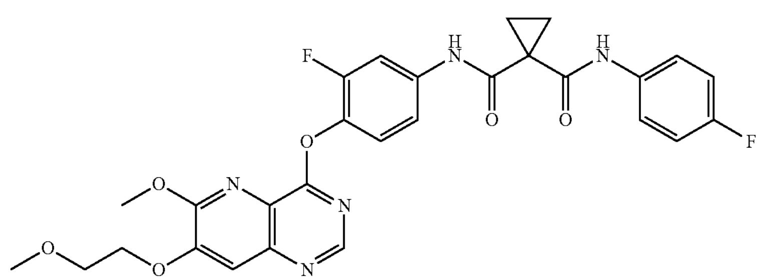 | 1-N'-[3-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 80 | 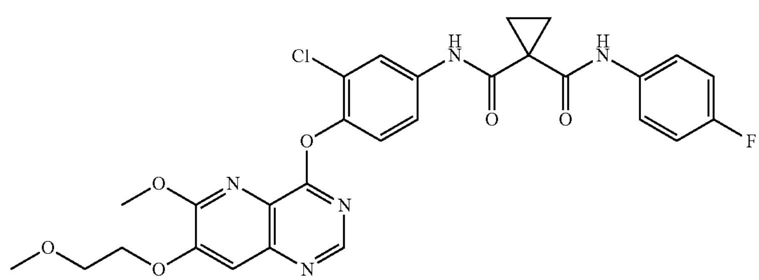 [SMILES: COCCOc1cc2ncnc(Oc3ccc(NC(=O)C4(C(=O)Nc5ccc(F)cc5)CC4)cc3Cl)c2nc1OC] | 1-N'-[3-chloro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 81 | 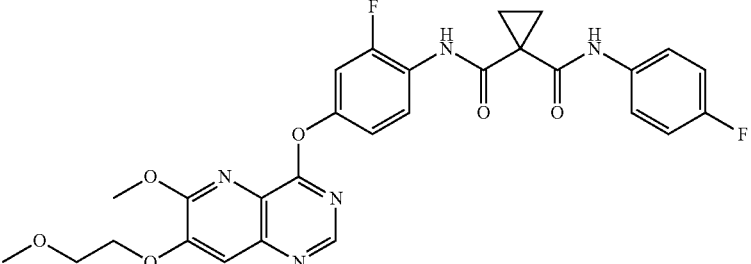 | 1-N'-[2-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 82 | 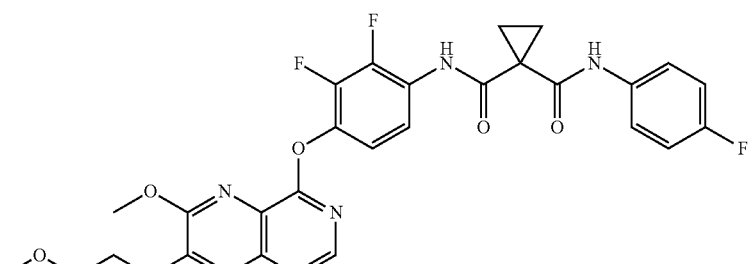 | 1-N'-[2,3-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 83 | 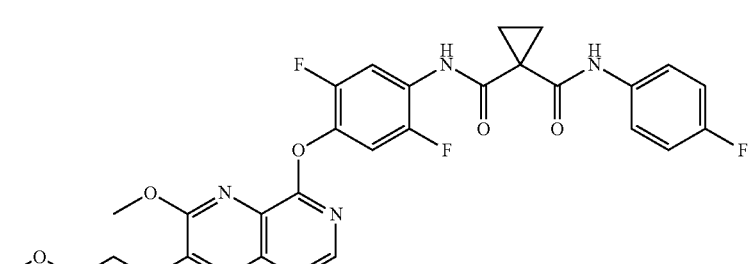 | 1-N'-[2,5-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 85 | 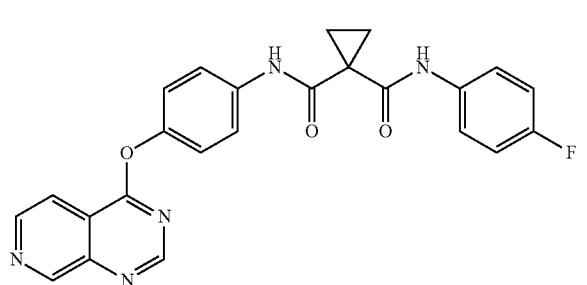 | 1-N'-(4-fluorophenyl)-1-N-(4-pyrido[3,4-d]pyrimidin-4-yloxyphenyl)cyclopropane-1,1-dicarboxamide |
| 88 | 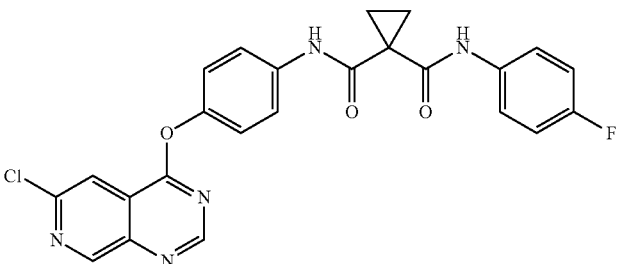 | 1-N-[4-(6-chloropyrido[3,4-d]pyrimidin-4-yl)oxyphenyl]-1-N'-(4-fluorophenyl)cyclopropane-1,1-dicarboxamide |

TABLE 1-continued

Compounds of Formula I'

| Comp. | Structure | IUPAC Name |
|---|---|---|
| 91 | 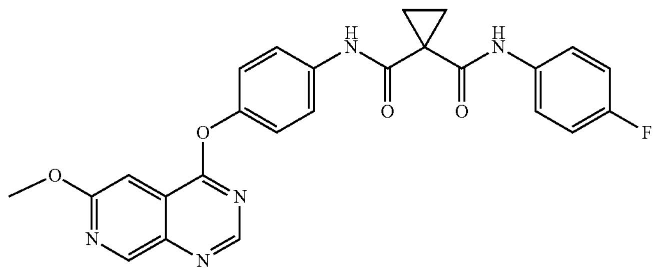 [SMILES: COc1cc2c(Oc3ccc(NC(=O)C4(C(=O)Nc5ccc(F)cc5)CC4)cc3)ncnc2cn1] | 1-N'-(4-fluorophenyl)-1-N-[4-(6-methoxypyrido[3,4-d]pyrimidin-4-yl)oxyphenyl]cyclopropane-1,1-dicarboxamide |
| 95 | 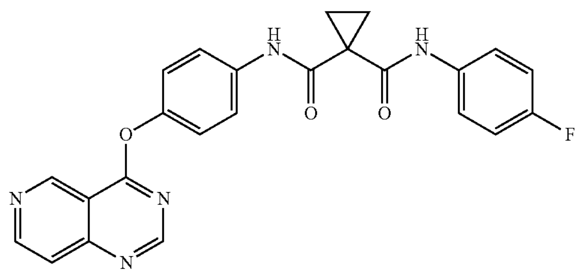 [SMILES: O=C(Nc1ccc(F)cc1)C1(C(=O)Nc2ccc(Oc3ncnc4ccncc34)cc2)CC1] | 1-N'-(4-fluorophenyl)-1-N-(4-pyrido[4,3-d]pyrimidin-4-yloxyphenyl)cyclopropane-1,1-dicarboxamide |
| 101 | 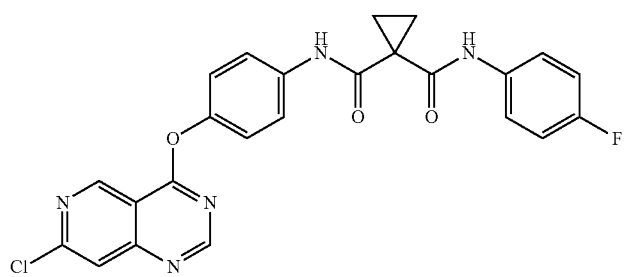 [SMILES: O=C(Nc1ccc(F)cc1)C1(C(=O)Nc2ccc(Oc3ncnc4cc(Cl)ncc34)cc2)CC1] | 1-N-[4-(7-chloropyrido[4,3-d]pyrimidin-4-yl)oxyphenyl]-1-N'-(4-fluorophenyl)cyclopropane-1,1-dicarboxamide |
| 104 | 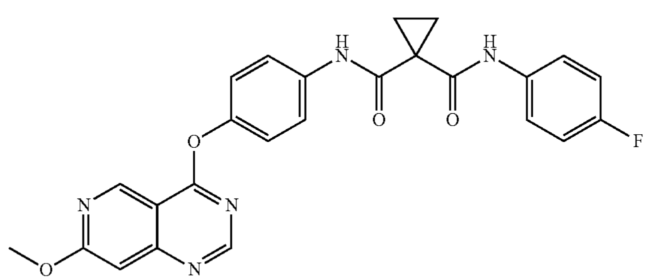 [SMILES: COc1cc2ncnc(Oc3ccc(NC(=O)C4(C(=O)Nc5ccc(F)cc5)CC4)cc3)c2cn1] | 1-N'-(4-fluorophenyl)-1-N-[4-(7-methoxypyrido[4,3-d]pyrimidin-4-yl)oxyphenyl]cyclopropane-1,1-dicarboxamide |
| 106 | 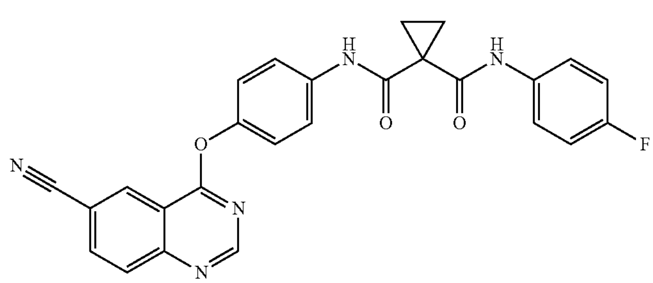 [SMILES: N#Cc1ccc2ncnc(Oc3ccc(NC(=O)C4(C(=O)Nc5ccc(F)cc5)CC4)cc3)c2c1] | 1-N-[4-(6-cyanoquinazolin-4-yl)oxyphenyl]-1-N'-(4-fluorophenyl)cyclopropane-1,1-dicarboxamide |

TABLE 1-continued

Compounds of Formula I'

| Comp. | Structure | IUPAC Name |
|---|---|---|
| 115 | 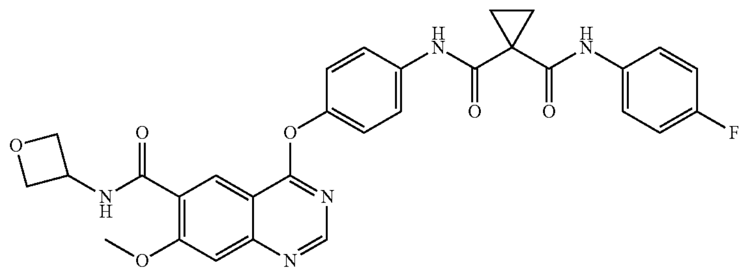 [SMILES: COc1cc2ncnc(Oc3ccc(NC(=O)C4(C(=O)Nc5ccc(F)cc5)CC4)cc3)c2cc1C(=O)NC1COC1] | 1-N'-(4-fluorophenyl)-1-N-[4-[7-methoxy-6-(oxetan-3-ylcarbamoyl)quinazolin-4-yl]oxyphenyl]cyclopropane-1,1-dicarboxamide |
| 116 | 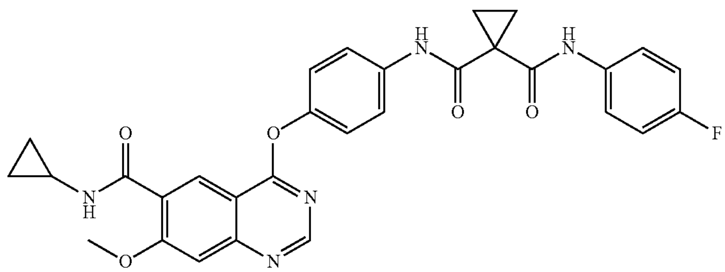 [SMILES: COc1cc2ncnc(Oc3ccc(NC(=O)C4(C(=O)Nc5ccc(F)cc5)CC4)cc3)c2cc1C(=O)NC1CC1] | 1-N-[4-[6-(cyclopropylcarbamoyl)-7-methoxyquinazolin-4-yl]oxyphenyl]-1-N'-(4-fluorophenyl)cyclopropane-1,1-dicarboxamide |
| 117 | 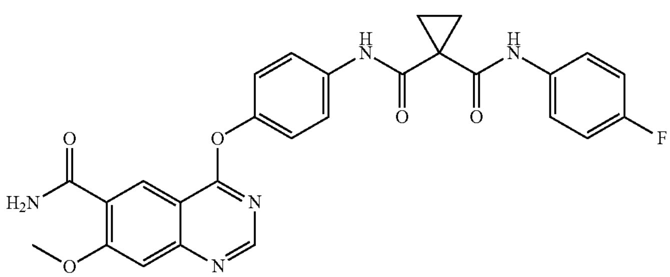 [SMILES: COc1cc2ncnc(Oc3ccc(NC(=O)C4(C(=O)Nc5ccc(F)cc5)CC4)cc3)c2cc1C(N)=O] | 1-N-[4-(6-carbamoyl-7-methoxyquinazolin-4-yl)oxyphenyl]-1-N'-(4-fluorophenyl)cyclopropane-1,1-dicarboxamide |
| 118 | 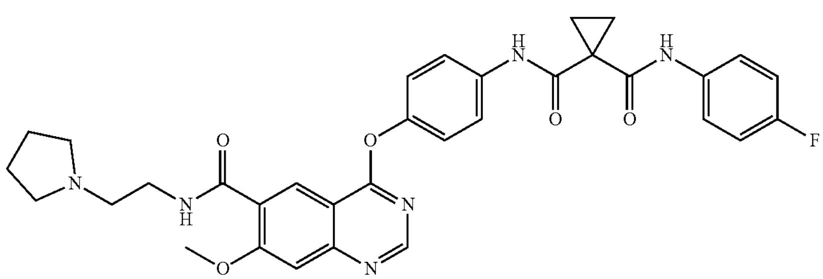 [SMILES: COc1cc2ncnc(Oc3ccc(NC(=O)C4(C(=O)Nc5ccc(F)cc5)CC4)cc3)c2cc1C(=O)NCCN1CCCC1] | 1-N'-(4-fluorophenyl)-1-N-[4-[7-methoxy-6-(2-pyrrolidin-1-ylethyl-carbamoyl)quinazolin-4-yl]oxyphenyl]cyclopropane-1,1-dicarboxamide |
| 119 | 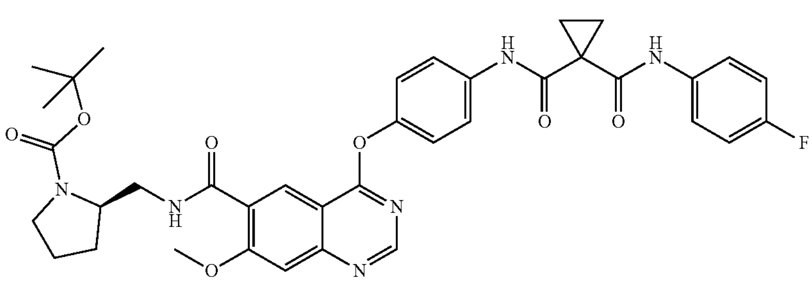 [SMILES: COc1cc2ncnc(Oc3ccc(NC(=O)C4(C(=O)Nc5ccc(F)cc5)CC4)cc3)c2cc1C(=O)NC[C@H]1CCCN1C(=O)OC(C)(C)C] | tert-butyl (2R)-2-[[[4-[4-[[1-[(4-fluoro-phenyl)carbamoyl]cyclo-propane-carbonyl]amino]phenoxy]-7-methoxyquinazoline-6-carbonyl]amino]methyl]pyr-rolidine-1-carboxylate |

TABLE 1-continued

Compounds of Formula I'

| Comp. | Structure | IUPAC Name |
|---|---|---|
| 120 | 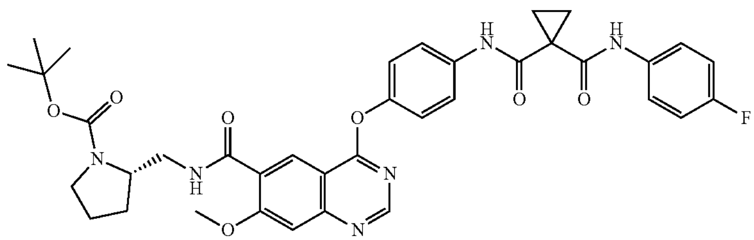 [SMILES: COc1cc2ncnc(Oc3ccc(NC(=O)C4(C(=O)Nc5ccc(F)cc5)CC4)cc3)c2cc1C(=O)NC[C@@H]1CCCN1C(=O)OC(C)(C)C] | tert-butyl (2S)-2-[[[4-[4-[[1-[(4-fluoro-phenyl)carbamoyl]cyclo-propane-carbonyl]amino]phenoxy]-7-methoxyquinazoline-6-carbonyl]amino]methyl]pyr-rolidine-1-carboxylate |
| 121 | 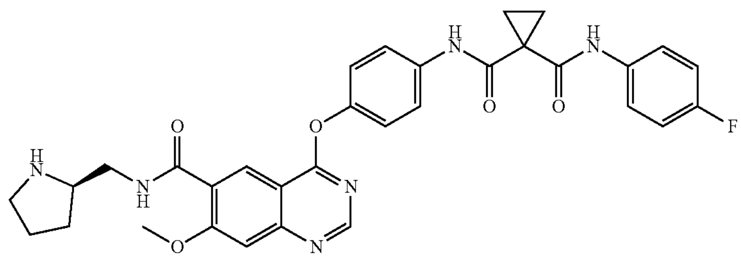 [SMILES: COc1cc2ncnc(Oc3ccc(NC(=O)C4(C(=O)Nc5ccc(F)cc5)CC4)cc3)c2cc1C(=O)NC[C@H]1CCCN1] | 1-N'-(4-fluorophenyl)-1-N-[4-[7-methoxy-6-[[(2R)-pyrrolidin-2-yl]methyl-carbamoyl]quinazolin-4-yl]oxyphenyl]cyclopropane-1,1-dicarboxamide |
| 122 | 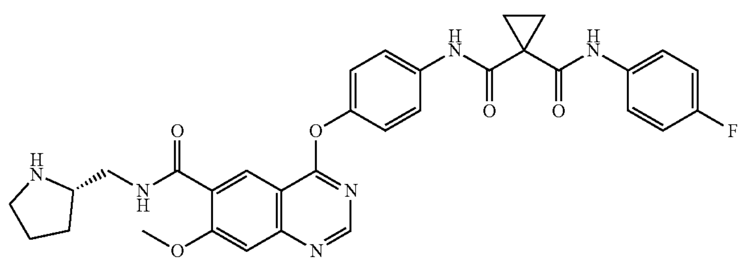 [SMILES: COc1cc2ncnc(Oc3ccc(NC(=O)C4(C(=O)Nc5ccc(F)cc5)CC4)cc3)c2cc1C(=O)NC[C@@H]1CCCN1] | 1-N'-(4-fluorophenyl)-1-N-[4-[7-methoxy-6-[[(2S)-pyrrolidin-2-yl]methyl-carbamoyl]quinazolin-4-yl]oxyphenyl]cyclopropane-1,1-dicarboxamide |
| 126 | 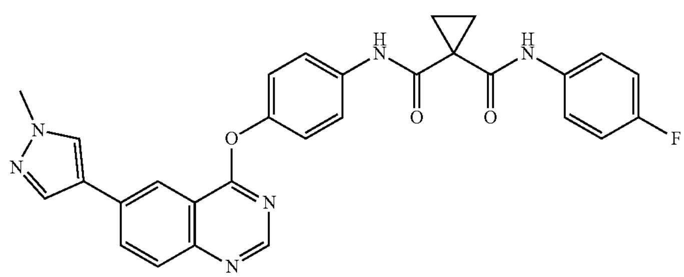 [SMILES: Cn1cc(-c2ccc3ncnc(Oc4ccc(NC(=O)C5(C(=O)Nc6ccc(F)cc6)CC5)cc4)c3c2)cn1] | 1-N'-(4-fluorophenyl)-1-N-[4-[6-(1-methylpyrazol-4-yl)quinazolin-4-yl]oxyphenyl]cyclo-propane-1,1-dicarboxamide |
| 129 | 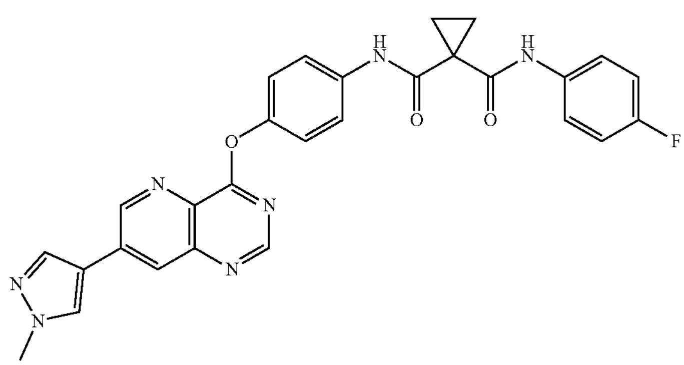 [SMILES: Cn1cc(-c2cnc3c(Oc4ccc(NC(=O)C5(C(=O)Nc6ccc(F)cc6)CC5)cc4)ncnc3c2)cn1] | 1-N'-(4-fluorophenyl)-1-N-[4-[7-(1-methylpyrazol-4-yl)pyrido[3,2-d]pyrimidin-4-yl]oxyphenyl]cyclo-propane-1,1-dicarboxamide |

TABLE 1-continued

Compounds of Formula I'

| Comp. | Structure | IUPAC Name |
|---|---|---|
| 130 | 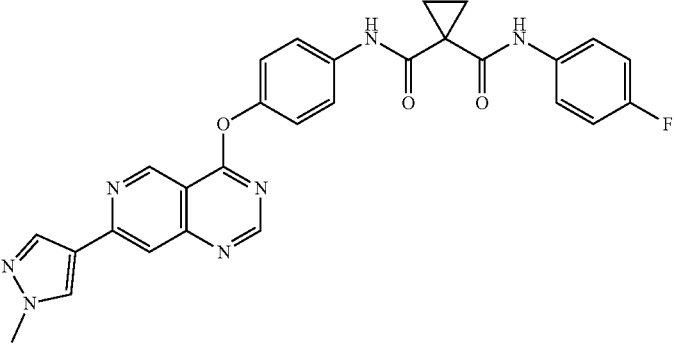 [SMILES: Cn1cc(-c2cc3ncnc(Oc4ccc(NC(=O)C5(C(=O)Nc6ccc(F)cc6)CC5)cc4)c3cn2)cn1] | 1-N'-(4-fluorophenyl)-1-N-[4-[7-(1-methylpyrazol-4-yl)pyrido[4,3-d]pyrimidin-4-yl]oxyphenyl]cyclopropane-1,1-dicarboxamide |
| 139 | 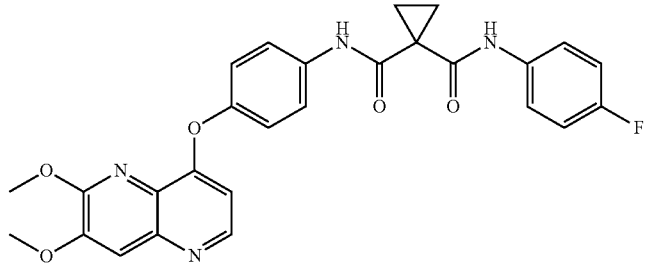 [SMILES: COc1cc2nccc(Oc3ccc(NC(=O)C4(C(=O)Nc5ccc(F)cc5)CC4)cc3)c2nc1OC] | 1-N-[4-[(6,7-dimethoxy-1,5-naphthyridin-4-yl)oxy]phenyl]-1-N'-(4-fluorophenyl)cyclopropane-1,1-dicarboxamide |
| 140 | 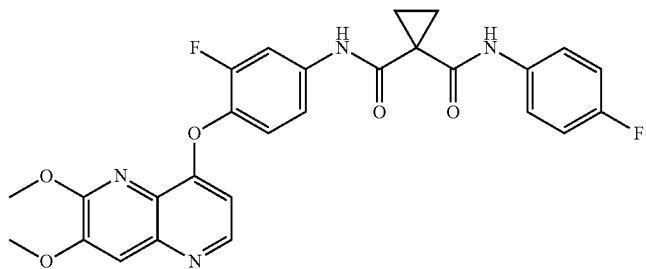 | 1-N'-[4-[(6,7-dimethoxy-1,5-naphthyridin-4-yl)oxy]-3-fluorophenyl]-1-N-(4-fluorophenyl)cyclopropane-1,1-dicarboxamide |
| 141 | 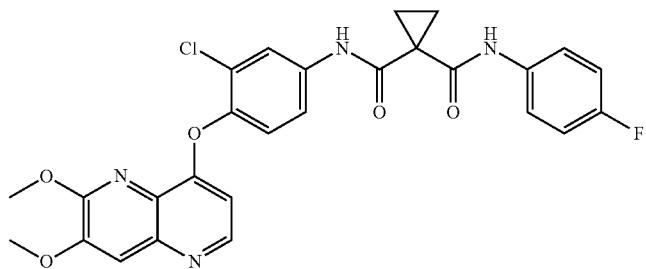 [SMILES: COc1cc2nccc(Oc3ccc(NC(=O)C4(C(=O)Nc5ccc(F)cc5)CC4)cc3Cl)c2nc1OC] | 1-N'-[3-chloro-4-[(6,7-dimethoxy-1,5-naphthyridin-4-yl)oxy]phenyl]-1-N-(4-fluorophenyl)cyclopropane-1,1-dicarboxamide |
| 142 | 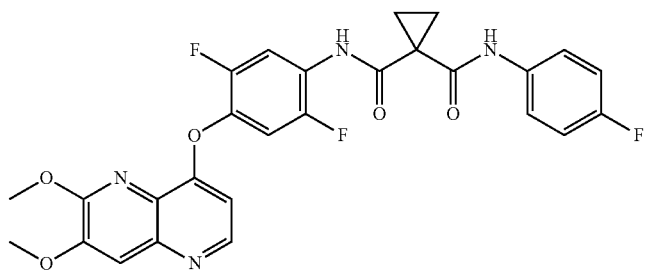 [SMILES: COc1cc2nccc(Oc3cc(F)c(NC(=O)C4(C(=O)Nc5ccc(F)cc5)CC4)cc3F)c2nc1OC] | 1-N'-[4-[(6,7-dimethoxy-1,5-naphthyridin-4-yl)oxy]-2,5-difluorophenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 149 | 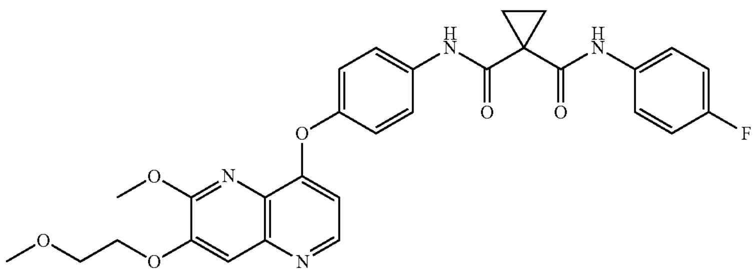 [SMILES: COCCOc1cc2nccc(Oc3ccc(NC(=O)C4(C(=O)Nc5ccc(F)cc5)CC4)cc3)c2nc1OC] | 1-N'-(4-fluorophenyl)-1-N-[4-[[6-methoxy-7-(2-methoxyethoxy)-1,5-naphthyridin-4-yl]oxy]phenyl]cyclopropane-1,1-dicarboxamide |
| 150 | 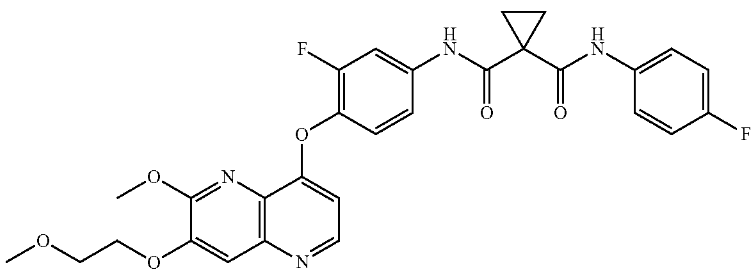 [SMILES: COCCOc1cc2nccc(Oc3ccc(NC(=O)C4(C(=O)Nc5ccc(F)cc5)CC4)cc3F)c2nc1OC] | 1-N'-[3-fluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 151 | 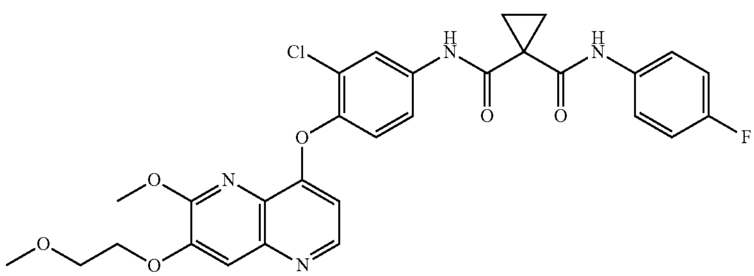 [SMILES: COCCOc1cc2nccc(Oc3ccc(NC(=O)C4(C(=O)Nc5ccc(F)cc5)CC4)cc3Cl)c2nc1OC] | 1-N'-[3-chloro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 152 | 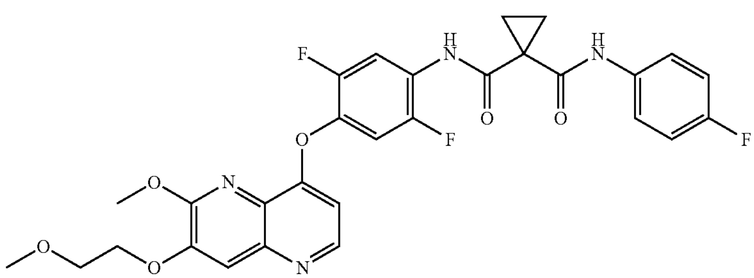 [SMILES: COCCOc1cc2nccc(Oc3cc(F)c(NC(=O)C4(C(=O)Nc5ccc(F)cc5)CC4)cc3F)c2nc1OC] | 1-N'-[2,5-difluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 153 | 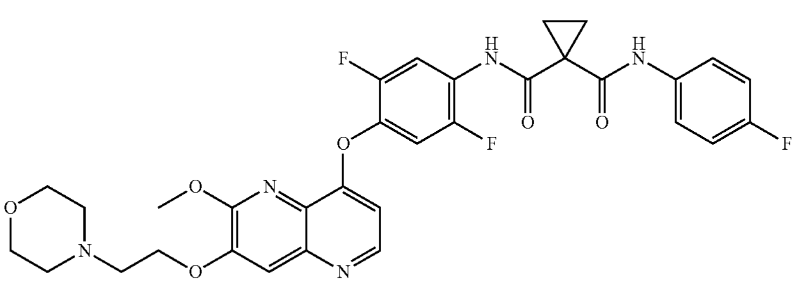 [SMILES: COc1nc2c(Oc3cc(F)c(NC(=O)C4(C(=O)Nc5ccc(F)cc5)CC4)cc3F)ccnc2cc1OCCN1CCOCC1] | 1-N'-[2,5-difluoro-4-[[6-methoxy-7-(2-morpholin-4-ylethoxy)-1,5-naphthyridin-4-yl]oxy]phenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 157 | 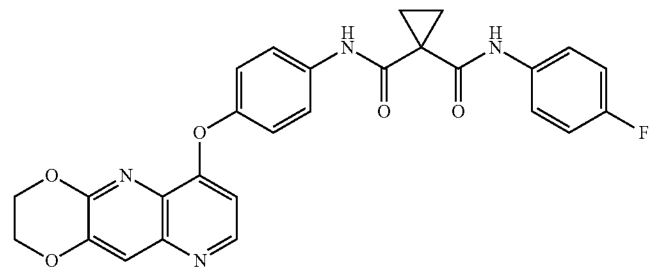 [SMILES: O=C(Nc1ccc(F)cc1)C1(C(=O)Nc2ccc(Oc3ccnc4cc5c(nc34)OCCO5)cc2)CC1] | 1-N-[4-(2,3-dihydro-[1,4]dioxino[2,3-b][1,5]naphthyridin-6-yloxy)phenyl]-1-N'-(4-fluorophenyl)cyclopropane-1,1-dicarboxamide |
| 158 | 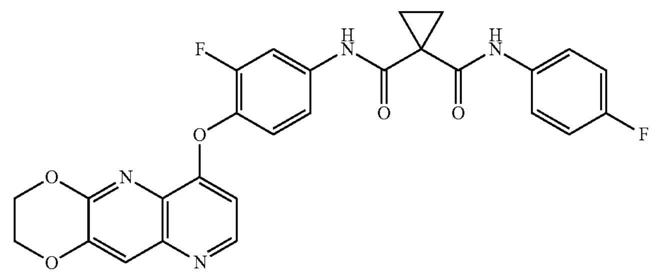 | 1-N'-[4-(2,3-dihydro-[1,4]dioxino[2,3-b][1,5]naphthyridin-6-yloxy)-3-fluorophenyl]-1-N-(4-fluorophenyl)cyclopropane-1,1-dicarboxamide |
| 159 | 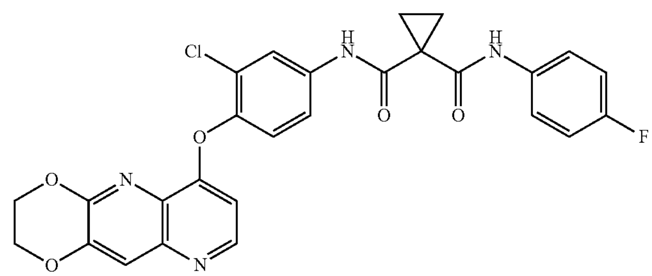 [SMILES: O=C(Nc1ccc(F)cc1)C1(C(=O)Nc2ccc(Oc3ccnc4cc5c(nc34)OCCO5)c(Cl)c2)CC1] | 1-N'-[3-chloro-4-(2,3-dihydro-[1,4]dioxino[2,3-b][1,5]naphthyridin-6-yloxy)phenyl]-1-N-(4-fluorophenyl)cyclopropane-1,1-dicarboxamide |
| 164 | 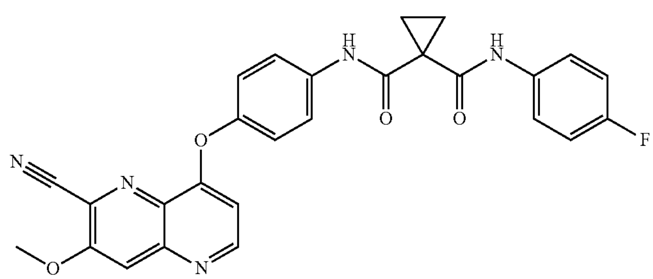 | 1-N-[4-[(6-cyano-7-methoxy-1,5-naphthyridin-4-yl)oxy]phenyl]-1-N'-(4-fluorophenyl)cyclopropane-1,1-dicarboxamide |
| 165 | 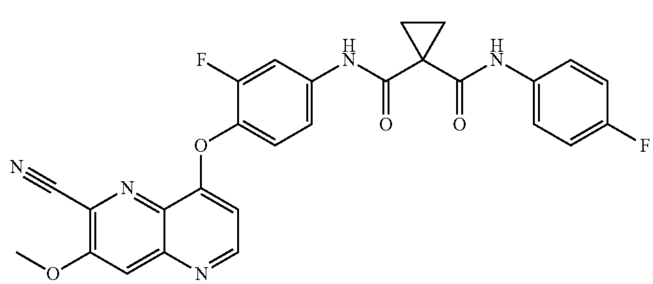 [SMILES: COc1cc2nccc(Oc3ccc(NC(=O)C4(C(=O)Nc5ccc(F)cc5)CC4)cc3F)c2nc1C#N] | 1-N'-[4-[(6-cyano-7-methoxy-1,5-naphthyridin-4-yl)oxy]-3-fluorophenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 166 | 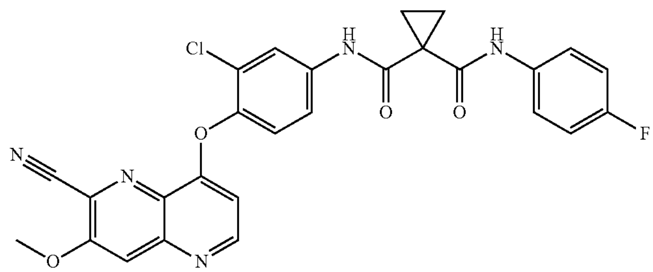 [SMILES: COc1cc2nccc(Oc3ccc(NC(=O)C4(C(=O)Nc5ccc(F)cc5)CC4)cc3Cl)c2nc1C#N] | 1-N'-[3-chloro-4-[(6-cyano-7-methoxy-1,5-naphthyridin-4-yl)oxy]phenyl]-1-N-(4-fluorophenyl)cyclopropane-1,1-dicarboxamide |
| 167 | 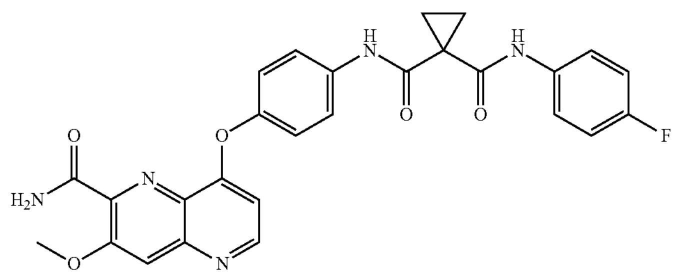 [SMILES: COc1cc2nccc(Oc3ccc(NC(=O)C4(C(=O)Nc5ccc(F)cc5)CC4)cc3)c2nc1C(N)=O] | 1-N-[4-[(6-carbamoyl-7-methoxy-1,5-naphthyridin-4-yl)oxy]phenyl]-1-N'-(4-fluorophenyl)cyclopropane-1,1-dicarboxamide |
| 168 | 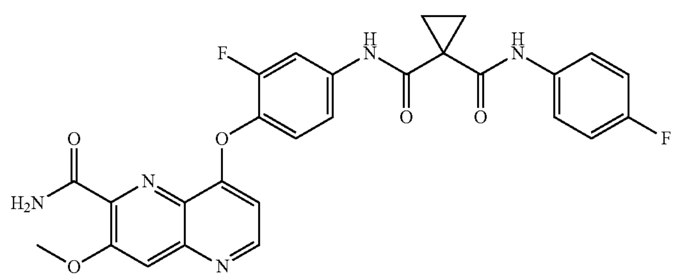 [SMILES: COc1cc2nccc(Oc3ccc(NC(=O)C4(C(=O)Nc5ccc(F)cc5)CC4)cc3F)c2nc1C(N)=O] | 1-N'-[4-[(6-carbamoyl-7-methoxy-1,5-naphthyridin-4-yl)oxy]-3-fluorophenyl]-1-N-(4-fluorophenyl)cyclopropane-1,1-dicarboxamide |
| 169 | 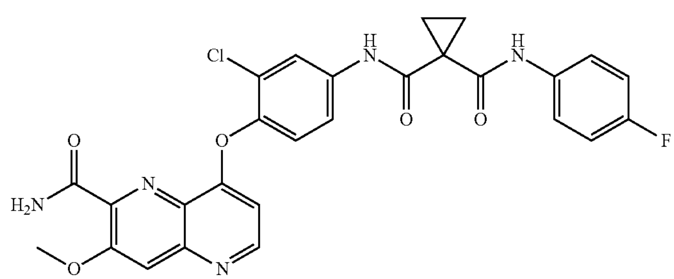 [SMILES: COc1cc2nccc(Oc3ccc(NC(=O)C4(C(=O)Nc5ccc(F)cc5)CC4)cc3Cl)c2nc1C(N)=O] | 1-N'-[4-[(6-carbamoyl-7-methoxy-1,5-naphthyridin-4-yl)oxy]-3-chlorophenyl]-1-N-(4-fluorophenyl)cyclopropane-1,1-dicarboxamide |
| 172 | 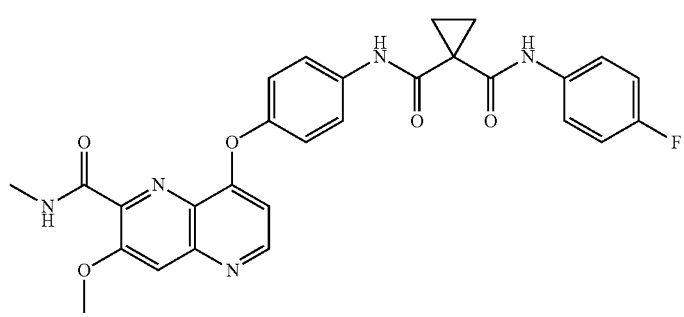 [SMILES: CNC(=O)c1nc2c(Oc3ccc(NC(=O)C4(C(=O)Nc5ccc(F)cc5)CC4)cc3)ccnc2cc1OC] | 1-N'-(4-fluorophenyl)-1-N-[4-[[7-methoxy-6-(methylcarbamoyl)-1,5-naphthyridin-4-yl]oxy]phenyl]cyclopropane-1,1-dicarboxamide |

TABLE 1-continued

Compounds of Formula I'

| Comp. | Structure | IUPAC Name |
|---|---|---|
| 173 | 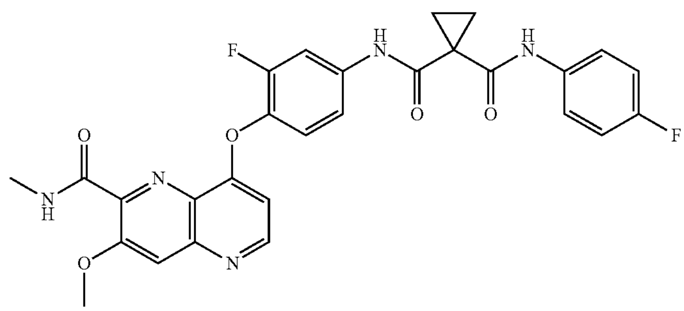 [SMILES: CNC(=O)c1nc2c(Oc3ccc(NC(=O)C4(C(=O)Nc5ccc(F)cc5)CC4)cc3F)ccnc2cc1OC] | 1-N'-[3-fluoro-4-[[7-methoxy-6-(methylcarbamoyl)-1,5-naphthyridin-4-yl]oxy]phenyl]-1-N-(4-fluorophenyl)cyclopropane-1,1-dicarboxamide |
| 174 | 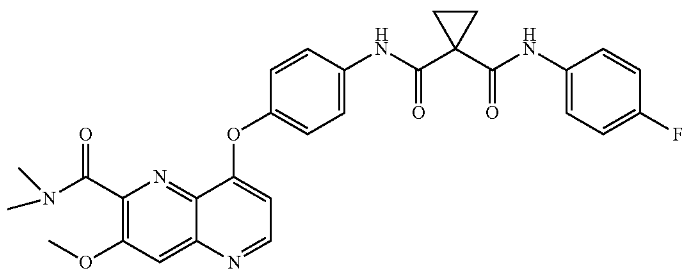 [SMILES: COc1cc2nccc(Oc3ccc(NC(=O)C4(C(=O)Nc5ccc(F)cc5)CC4)cc3)c2nc1C(=O)N(C)C] | 1-N-[4-[[6-(dimethylcarbamoyl)-7-methoxy-1,5-naphthyridin-4-yl]oxy]phenyl]-1-N'-(4-fluorophenyl)cyclopropane-1,1-dicarboxamide |
| 176 | 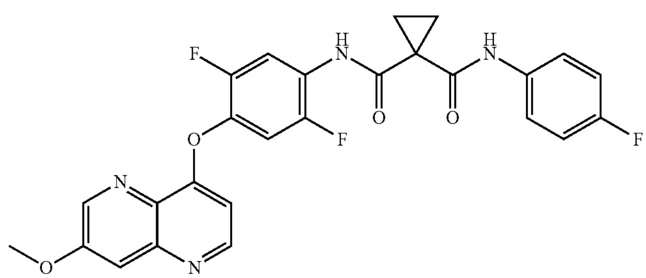 [SMILES: COc1cnc2c(Oc3cc(F)c(NC(=O)C4(C(=O)Nc5ccc(F)cc5)CC4)cc3F)ccnc2c1] | 1-N'-[2,5-difluoro-4-[(7-methoxy-1,5-naphthyridin-4-yl)oxy]phenyl]-1-N-(4-fluorophenyl)cyclopropane-1,1-dicarboxamide |
| 181 | 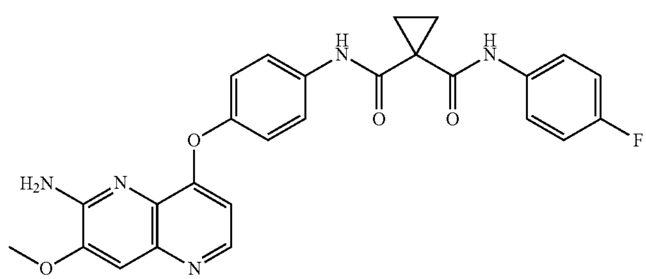 [SMILES: COc1cc2nccc(Oc3ccc(NC(=O)C4(C(=O)Nc5ccc(F)cc5)CC4)cc3)c2nc1N] | 1-N-[4-[(6-amino-7-methoxy-1,5-naphthyridin-4-yl)oxy]phenyl]-1-N'-(4-fluorophenyl)cyclopropane-1,1-dicarboxamide |
| 182 | 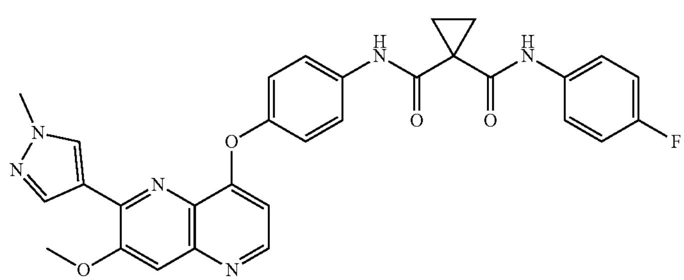 [SMILES: COc1cc2nccc(Oc3ccc(NC(=O)C4(C(=O)Nc5ccc(F)cc5)CC4)cc3)c2nc1-c1cnn(C)c1] | 1-N'-(4-fluorophenyl)-1-N-[4-[[7-methoxy-6-(1-methylpyrazol-4-yl)-1,5-naphthyridin-4-yl]oxy]phenyl]cyclopropane-1,1-dicarboxamide |

TABLE 1-continued

Compounds of Formula I'

| Comp. | Structure | IUPAC Name |
|---|---|---|
| 183 | 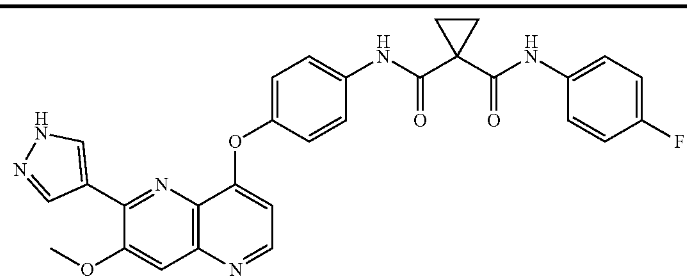 | 1-N'-(4-fluorophenyl)-1-N-[4-[[7-methoxy-6-(1H-pyrazol-4-yl)-1,5-naphthyridin-4-yl]oxy]phenyl]cyclopropane-1,1-dicarboxamide |
| 184 | 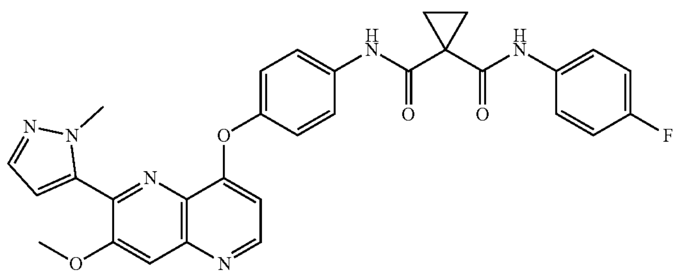 [SMILES: COc1cc2nccc(Oc3ccc(NC(=O)C4(C(=O)Nc5ccc(F)cc5)CC4)cc3)c2nc1-c1ccnn1C] | 1-N'-(4-fluorophenyl)-1-N-[4-[[7-methoxy-6-(2-methyl-pyrazol-3-yl)-1,5-naphthyridin-4-yl]oxy]phenyl]cyclo-propane-1,1-dicarboxamide |
| 189 | 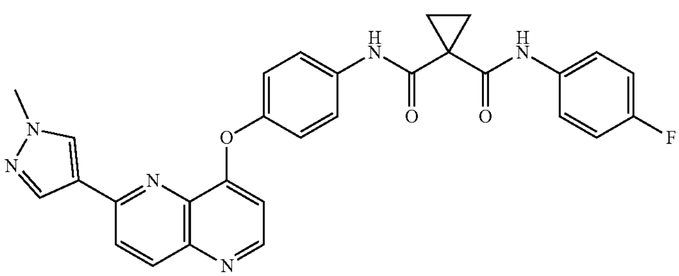 [SMILES: Cn1cc(-c2ccc3nccc(Oc4ccc(NC(=O)C5(C(=O)Nc6ccc(F)cc6)CC5)cc4)c3n2)cn1] | 1-N'-(4-fluorophenyl)-1-N-[4-[[6-(1-methylpyrazol-4-yl)-1,5-naphthyridin-4-yl]oxy]phenyl]cyclo-propane-1,1-dicarboxamide |

In one embodiment, the compound of Formula I' is a compound of Formula I:

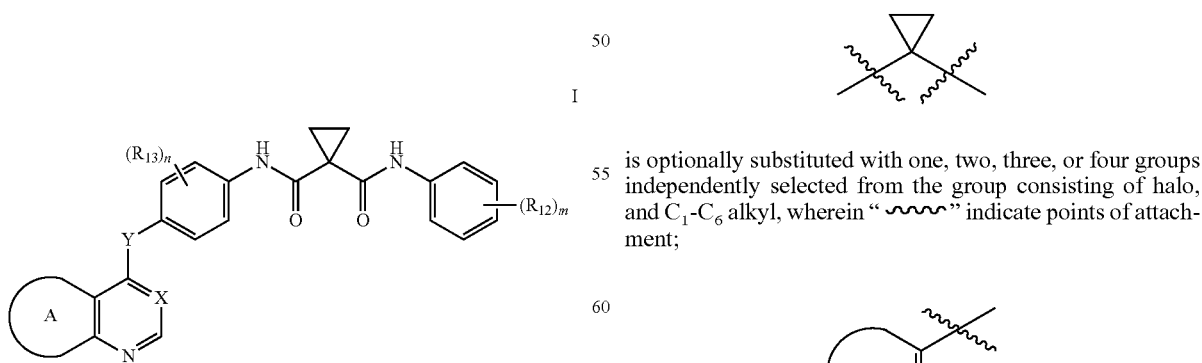

I wherein:
X is selected from N and C—H;
Y is O, S, SO, SO$_2$, NH, or N—(C$_1$-C$_6$ alkyl);
R$_{13}$ is selected from —H, halo, —CN, and optionally substituted C$_{1-6}$ alkyl;
R$_{12}$ is —H or halo;

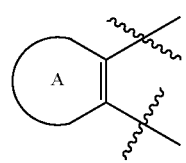

is optionally substituted with one, two, three, or four groups independently selected from the group consisting of halo, and C$_1$-C$_6$ alkyl, wherein "〜〜〜" indicate points of attachment;

is selected from the group consisting of

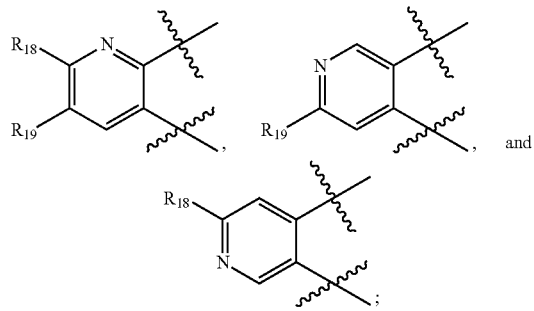

wherein $R_{18}$ and $R_{19}$ are selected from the group consisting of H, halo, —CN, optionally substituted $C_1$-$C_6$ alkyl, C(O)$NR_5R_6$, optionally substituted 5 or 6-membered heteroaryl, and optionally substituted $C_1$-$C_6$ alkoxy; or
when

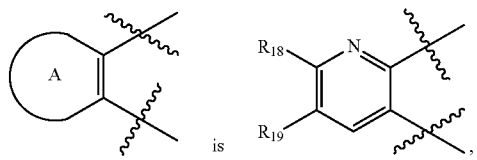

$R_{18}$ and $R_{19}$ can be joined together to form a 5 or 6-membered optionally substituted cycloalkyl or heterocycloalkyl;

$R_5$ and $R_6$ are selected from the group consisting of H, optionally substituted $C_{1-6}$ alkyl, or $R_5$ and $R_6$ taken together with the nitrogen to which they are attached to form a 5- or 6-membered optionally substituted heterocycle; and m and n are each independently 1 or 2;
provided that when

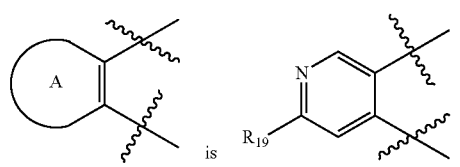

and X is C—H, $R_{19}$ is not optionally substituted $C_1$-$C_6$ alkyl, halo, or optionally substituted $C_1$-$C_6$ alkoxy.

In one embodiment, $R_{19}$ is selected from the group consisting of optionally substituted $C_1$-$C_6$ alkoxy and —CN. In a further embodiment, the $C_1$-$C_6$ alkoxy is optionally substituted with alkoxy or heterocycloalkyl.

In some embodiments,

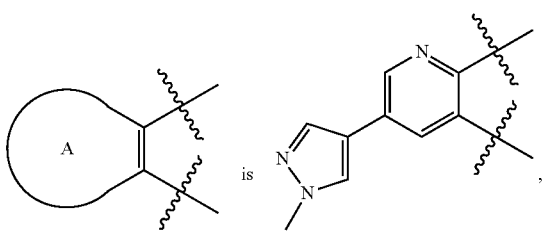

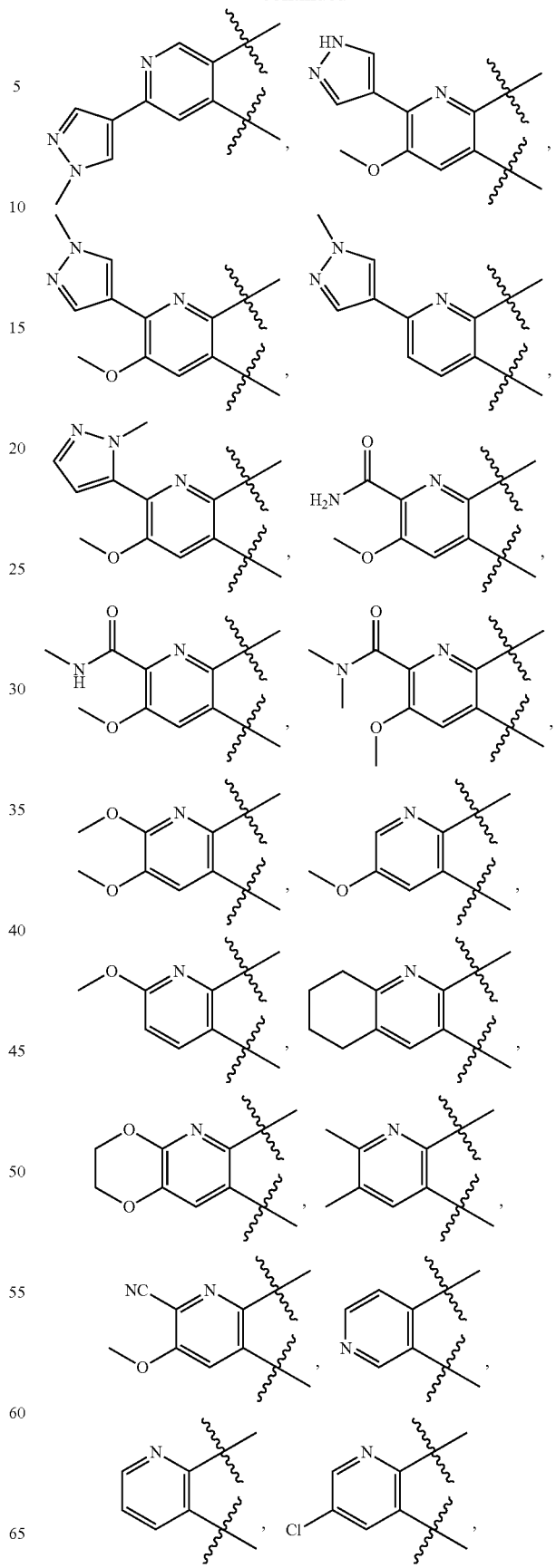

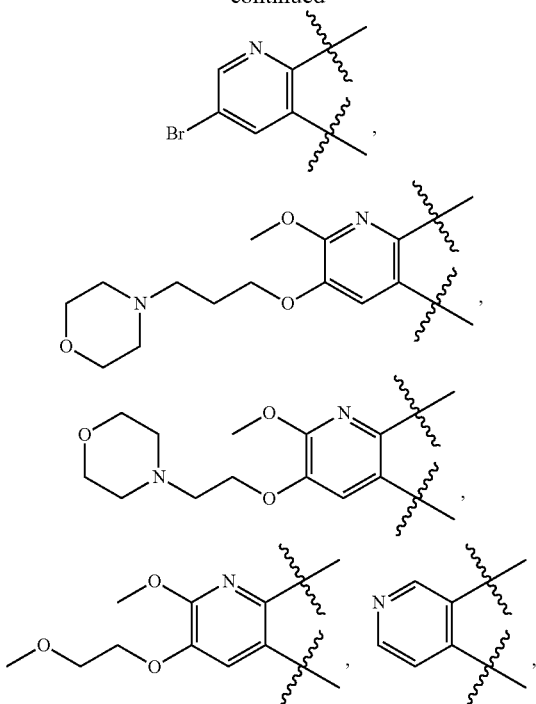
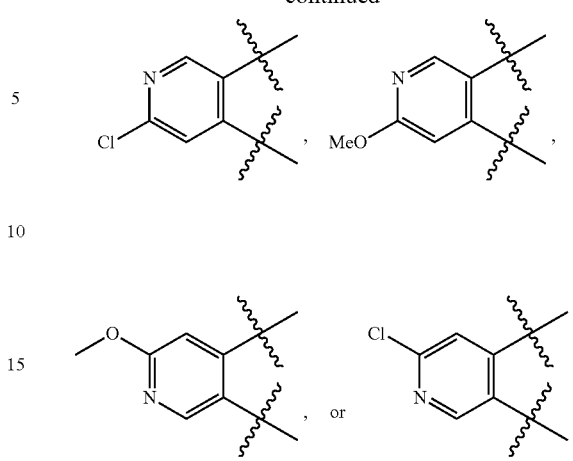

In one embodiment, X is N.

In another embodiment, $R_{13}$ is H.

In one embodiment, the compound of Formula I, or a pharmaceutically acceptable salt thereof, is selected from the compounds listed in Table 2, or a pharmaceutically acceptable salt thereof.

TABLE 2

Compounds of Formula I

| Comp. | Structure | IUPAC Name |
|---|---|---|
| 7 | 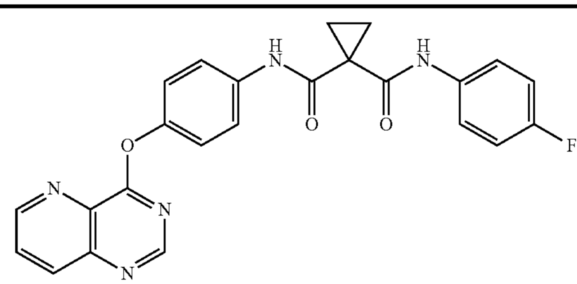 | 1-N'-(4-fluorophenyl)-1-N-(4-pyrido[3,2-d]pyrimidin-4-yloxyphenyl)cyclopropane-1,1-dicarboxamide |
| 12 | 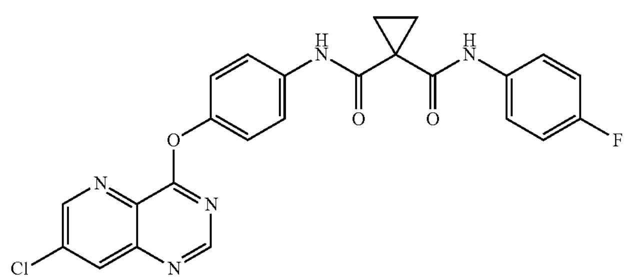 | 1-N-[4-(7-chloropyrido[3,2-d]pyrimidin-4-yl)oxyphenyl]-1-N'-(4-fluorophenyl)cyclopropane-1,1-dicarboxamide |
| 13 | 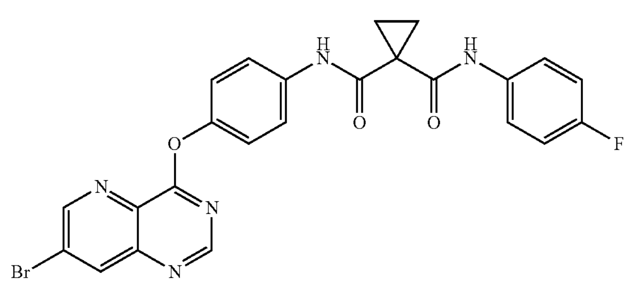 [SMILES: O=C(Nc1ccc(F)cc1)C1(C(=O)Nc2ccc(Oc3ncnc4cc(Cl)cnc34)cc2)CC1] | 1-N-[4-(7-bromopyrido[3,2-d]pyrimidin-4-yl)oxyphenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 16 | 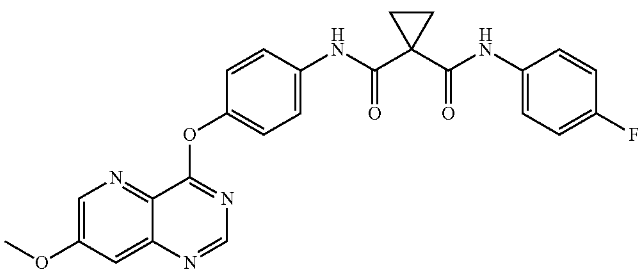 [SMILES: COc1cnc2c(Oc3ccc(NC(=O)C4(C(=O)Nc5ccc(F)cc5)CC4)cc3)ncnc2c1] | 1-N'-(4-fluorophenyl)-1-N-[4-(7-methoxypyrido[3,2-d]pyrimidin-4-yl)oxyphenyl]cyclopropane-1,1-dicarboxamide |
| 19 | 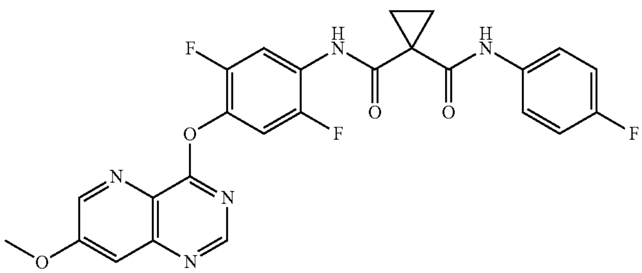 [SMILES: COc1cnc2c(Oc3cc(F)c(NC(=O)C4(C(=O)Nc5ccc(F)cc5)CC4)cc3F)ncnc2c1] | 1-N'-[2,5-difluoro-4-(7-methoxypyrido[3,2-d]pyrimidin-4-yl)oxyphenyl]-1-N-(4-fluorophenyl)cyclopropane-1,1-dicarboxamide |
| 28 | 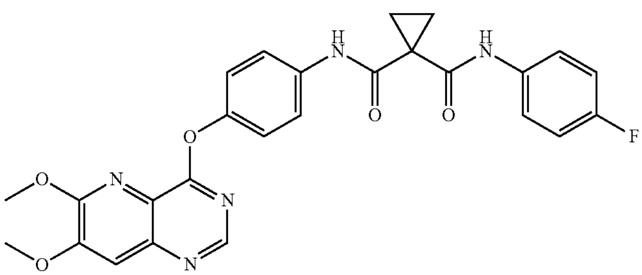 [SMILES: COc1cc2ncnc(Oc3ccc(NC(=O)C4(C(=O)Nc5ccc(F)cc5)CC4)cc3)c2nc1OC] | 1-N-[4-(6,7-dimethoxypyrido[3,2-d]pyrimidin-4-yl)oxyphenyl]-1-N'-(4-fluorophenyl)cyclopropane-1,1-dicarboxamide |
| 29 | 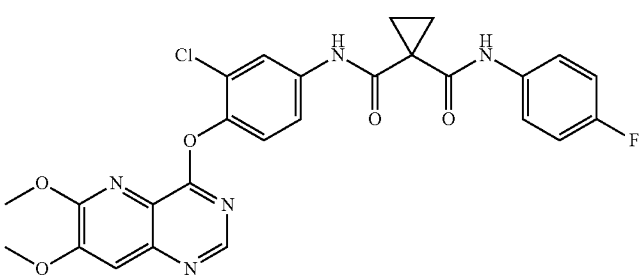 [SMILES: COc1cc2ncnc(Oc3ccc(NC(=O)C4(C(=O)Nc5ccc(F)cc5)CC4)cc3Cl)c2nc1OC] | 1-N'-[3-chloro-4-(6,7-dimethoxypyrido[3,2-d]pyrimidin-4-yl)oxyphenyl]-1-N-(4-fluorophenyl)cyclopropane-1,1-dicarboxamide |
| 30 | 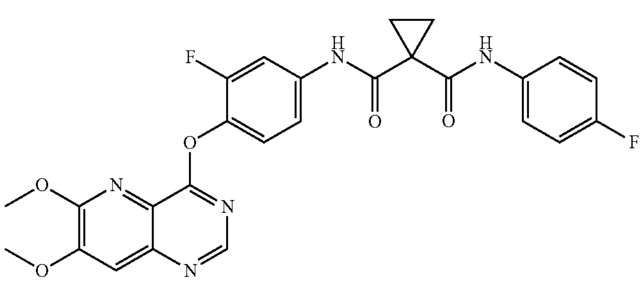 [SMILES: COc1cc2ncnc(Oc3ccc(NC(=O)C4(C(=O)Nc5ccc(F)cc5)CC4)cc3F)c2nc1OC] | 1-N'-[4-(6,7-dimethoxypyrido[3,2-d]pyrimidin-4-yl)oxy-3-fluorophenyl]-1-N-(4-fluorophenyl)cyclopropane-1,1-dicarboxamide |

TABLE 2-continued

Compounds of Formula I

| Comp. | Structure | IUPAC Name |
|---|---|---|
| 31 | 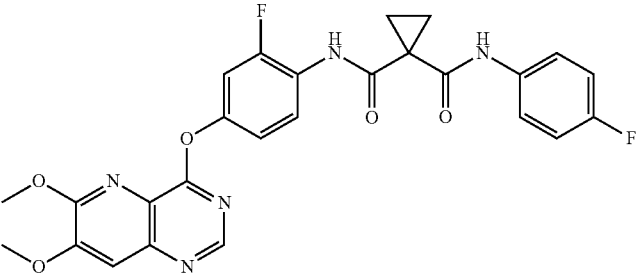 [SMILES: COc1cc2ncnc(Oc3ccc(NC(=O)C4(C(=O)Nc5ccc(F)cc5)CC4)c(F)c3)c2nc1OC] | 1-N'-[4-(6,7-dimethoxypyrido[3,2-d]pyrimidin-4-yl)oxy-2-fluorophenyl]-1-N-(4-fluorophenyl)cyclopropane-1,1-dicarboxamide |
| 32 | 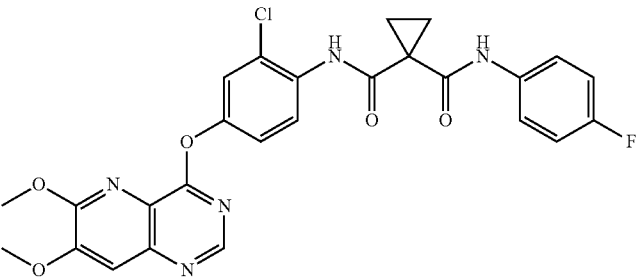 [SMILES: COc1cc2ncnc(Oc3ccc(NC(=O)C4(C(=O)Nc5ccc(F)cc5)CC4)c(Cl)c3)c2nc1OC] | 1-N'-[2-chloro-4-(6,7-dimethoxypyrido[3,2-d]pyrimidin-4-yl)oxyphenyl]-1-N-(4-fluorophenyl)cyclopropane-1,1-dicarboxamide |
| 33 | 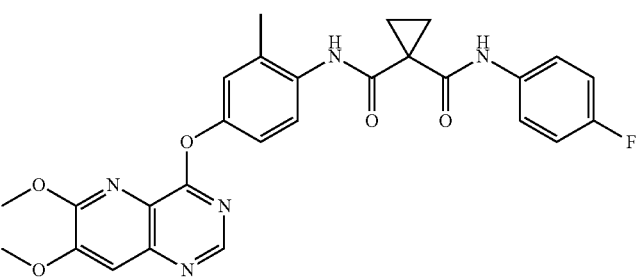 [SMILES: COc1cc2ncnc(Oc3ccc(NC(=O)C4(C(=O)Nc5ccc(F)cc5)CC4)c(C)c3)c2nc1OC] | 1-N'-[4-(6,7-dimethoxypyrido[3,2-d]pyrimidin-4-yl)oxy-2-methylphenyl]-1-N-(4-fluorophenyl)cyclopropane-1,1-dicarboxamide |
| 34 | 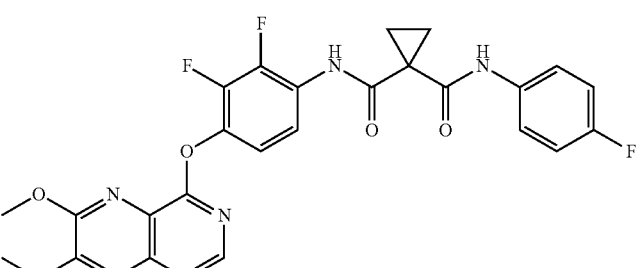 | 1-N'-[4-(6,7-dimethoxypyrido[3,2-d]pyrimidin-4-yl)oxy-2,3-difluorophenyl]-1-N-(4-fluorophenyl)cyclopropane-1,1-dicarboxamide |
| 35 | 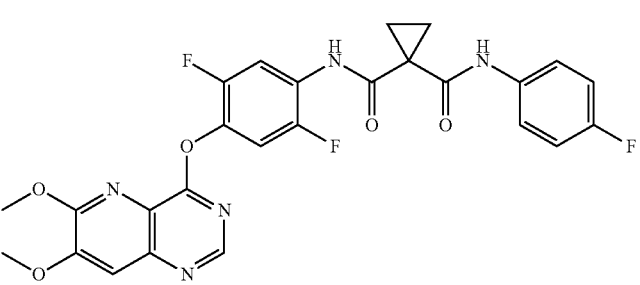 [SMILES: COc1cc2ncnc(Oc3cc(F)c(NC(=O)C4(C(=O)Nc5ccc(F)cc5)CC4)cc3F)c2nc1OC] | 1-N'-[4-(6,7-dimethoxypyrido[3,2-d]pyrimidin-4-yl)oxy-2,5-difluorophenyl]-1-N-(4-fluorophenyl)cyclopropane-1,1-dicarboxamide |

TABLE 2-continued

Compounds of Formula I

| Comp. | Structure | IUPAC Name |
|---|---|---|
| 43 | 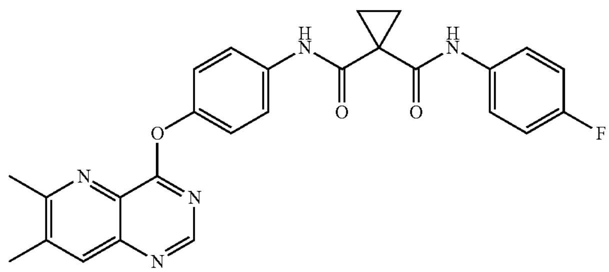 [SMILES: Cc1cc2ncnc(Oc3ccc(NC(=O)C4(C(=O)Nc5ccc(F)cc5)CC4)cc3)c2nc1C] | 1-N-[4-(6,7-dimethylpyrido[3,2-d]pyrimidin-4-yl)oxyphenyl]-1-N'-(4-fluorophenyl)cyclopropane-1,1-dicarboxamide |
| 52 | 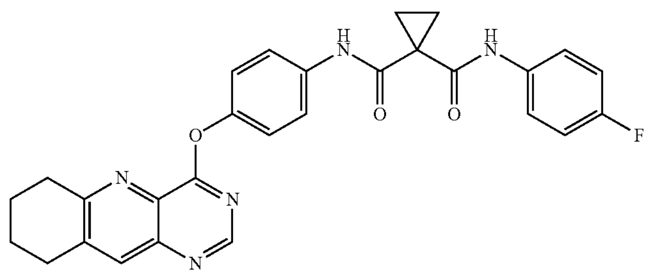 [SMILES: O=C(Nc1ccc(F)cc1)C1(C(=O)Nc2ccc(Oc3ncnc4cc5c(nc34)CCCC5)cc2)CC1] | 1-N'-(4-fluorophenyl)-1-N-[4-(6,7,8,9-tetrahydropyrimido[5,4-b]quinolin-4-yloxy)phenyl]cyclopropane-1,1-dicarboxamide |
| 57 | 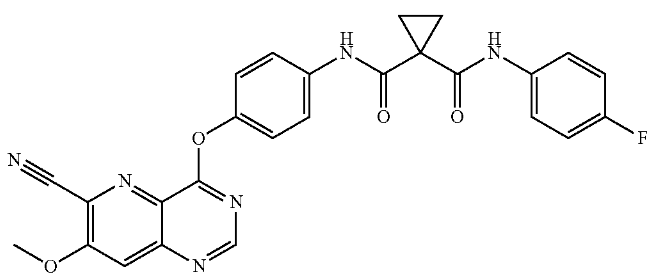 | 1-N-[4-(6-cyano-7-methoxypyrido[3,2-d]pyrimidin-4-yl)oxyphenyl]-1-N'-(4-fluorophenyl)cyclopropane-1,1-dicarboxamide |
| 65 | 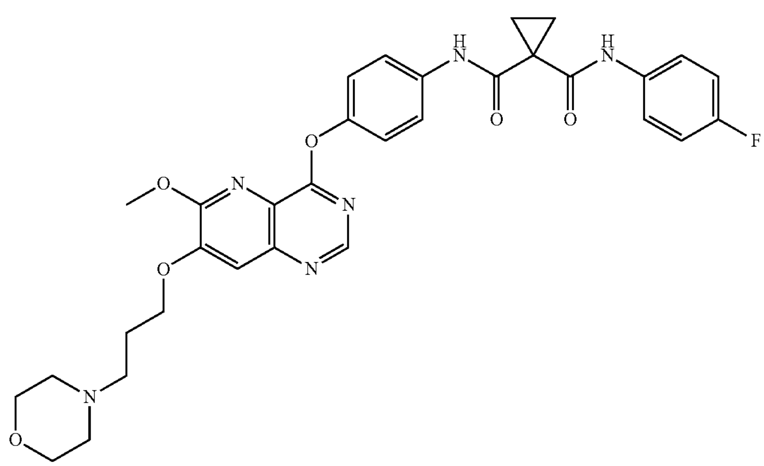 [SMILES: COc1nc2c(Oc3ccc(NC(=O)C4(C(=O)Nc5ccc(F)cc5)CC4)cc3)ncnc2cc1OCCCN1CCOCC1] | 1-N'-(4-fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide |

TABLE 2-continued

Compounds of Formula I

| Comp. | Structure | IUPAC Name |
|---|---|---|
| 66 | 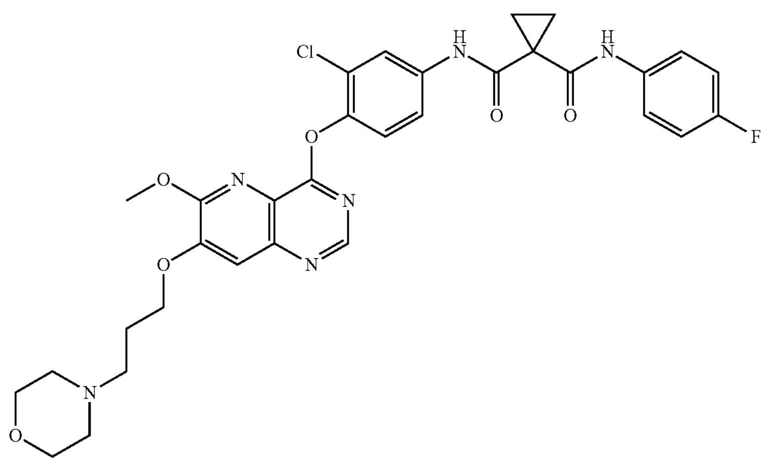 | 1-N'-[3-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 67 | 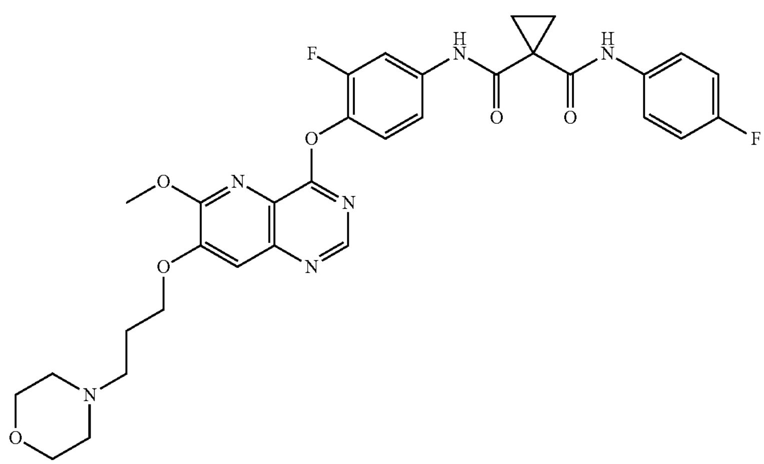 | 1-N'-[3-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 68 | 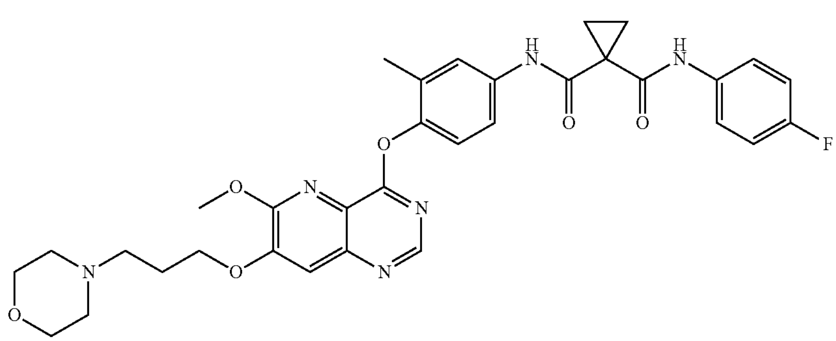 [SMILES: COc1nc2c(Oc3ccc(NC(=O)C4(C(=O)Nc5ccc(F)cc5)CC4)cc3C)ncnc2cc1OCCCN1CCOCC1] | 1-N-(4-fluorophenyl)-1-N'-[4-[6-methoxy-7-(3-morpholin-4-ylpropoxy)pyrido[3,2-d]pyrimidin-4-yl]oxy-3-methylphenyl]cyclopropane-1,1-dicarboxamide |

TABLE 2-continued

Compounds of Formula I

| Comp. | Structure | IUPAC Name |
|---|---|---|
| 69 | 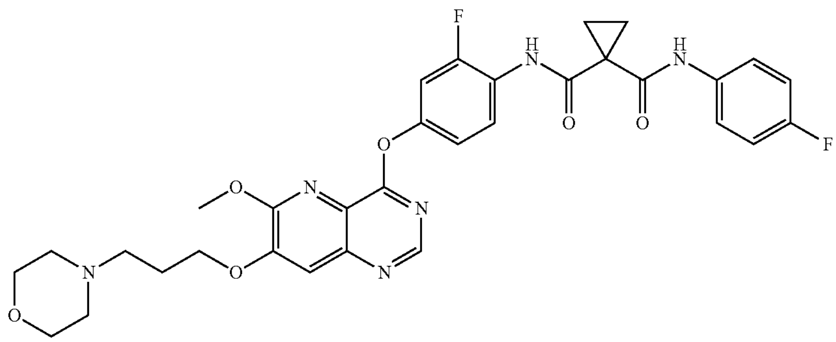 [SMILES: COc1nc2c(Oc3ccc(NC(=O)C4(C(=O)Nc5ccc(F)cc5)CC4)c(F)c3)ncnc2cc1OCCCN1CCOCC1] | 1-N'-[2-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 70 | 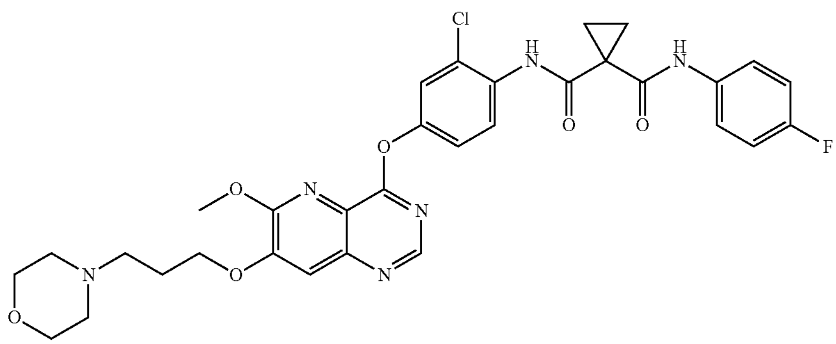 | 1-N'-[2-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 71 | 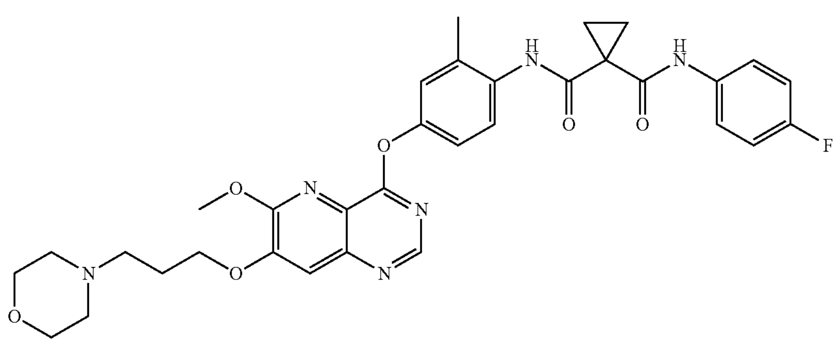 [SMILES: COc1nc2c(Oc3ccc(NC(=O)C4(C(=O)Nc5ccc(F)cc5)CC4)c(C)c3)ncnc2cc1OCCCN1CCOCC1] | 1-N-(4-fluorophenyl)-1-N'-[4-[6-methoxy-7-(3-morpholin-4-ylpropoxy)pyrido[3,2-d]pyrimidin-4-yl]oxy-2-methylphenyl]cyclopropane-1,1-dicarboxamide |
| 72 | 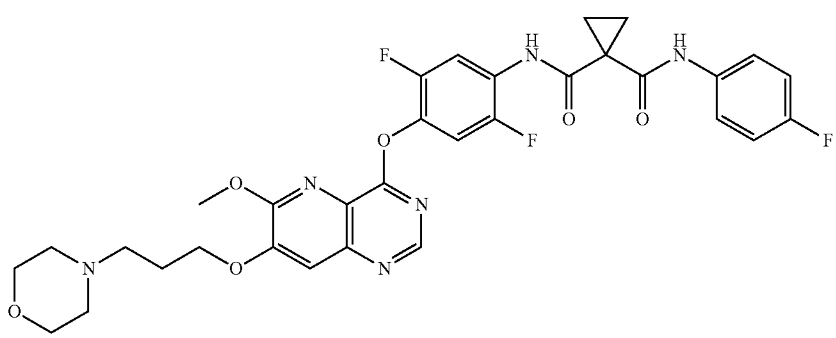 [SMILES: COc1nc2c(Oc3cc(F)c(NC(=O)C4(C(=O)Nc5ccc(F)cc5)CC4)cc3F)ncnc2cc1OCCCN1CCOCC1] | 1-N'-[2,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |

TABLE 2-continued

Compounds of Formula I

| Comp. | Structure | IUPAC Name |
|---|---|---|
| 73 | 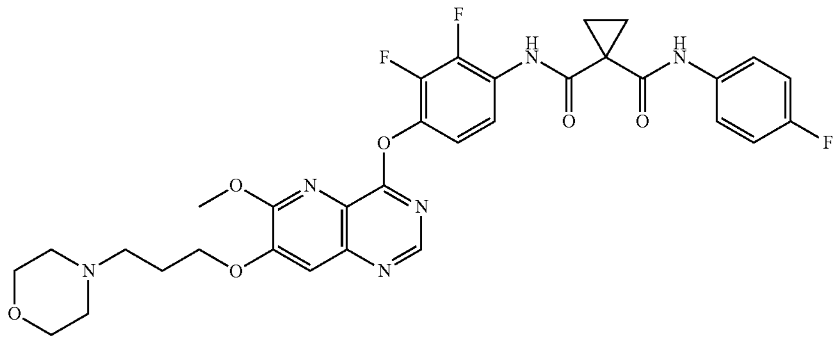 [SMILES: COc1nc2c(Oc3ccc(NC(=O)C4(C(=O)Nc5ccc(F)cc5)CC4)c(F)c3F)ncnc2cc1OCCCN1CCOCC1] | 1-N'-[2,3-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 74 | 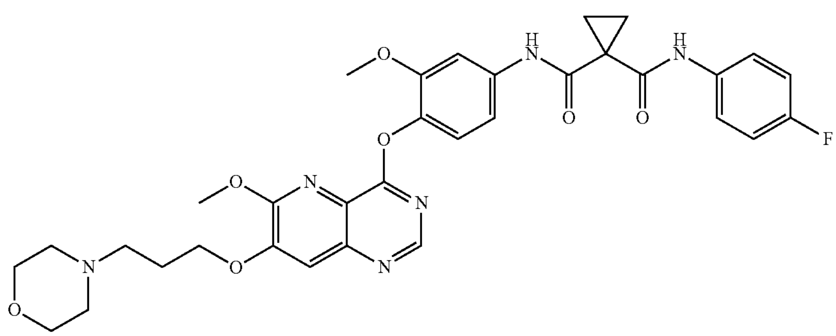 [SMILES: COc1cc(NC(=O)C2(C(=O)Nc3ccc(F)cc3)CC2)ccc1Oc1ncnc2cc(OCCCN3CCOCC3)c(OC)nc12] | 1-N-(4-fluorophenyl)-1-N'-[3-methoxy-4-[6-methoxy-7-(3-morpholin-4-ylpropoxy)pyrido[3,2-d]pyrimidin-4-yl]oxyphenyl]cyclopropane-1,1-dicarboxamide |
| 75 | 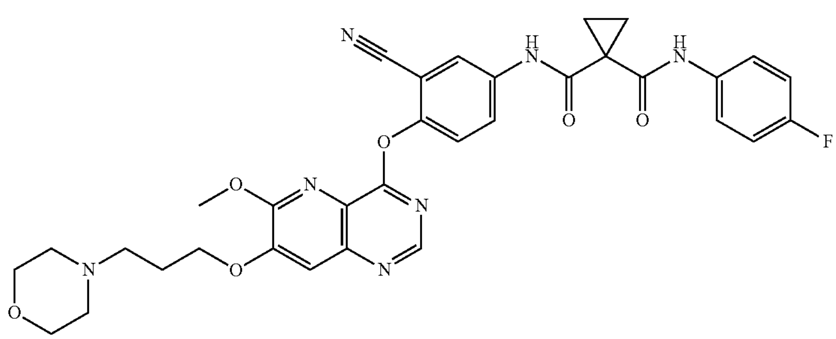 [SMILES: COc1nc2c(Oc3ccc(NC(=O)C4(C(=O)Nc5ccc(F)cc5)CC4)cc3C#N)ncnc2cc1OCCCN1CCOCC1] | 1-N'-[3-cyano-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 76 | 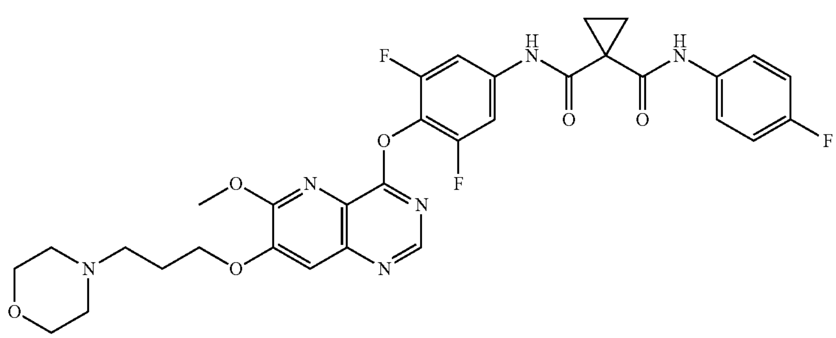 [SMILES: COc1nc2c(Oc3c(F)cc(NC(=O)C4(C(=O)Nc5ccc(F)cc5)CC4)cc3F)ncnc2cc1OCCCN1CCOCC1] | 1-N'-[3,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |

TABLE 2-continued

Compounds of Formula I

| Comp. | Structure | IUPAC Name |
|---|---|---|
| 78 | 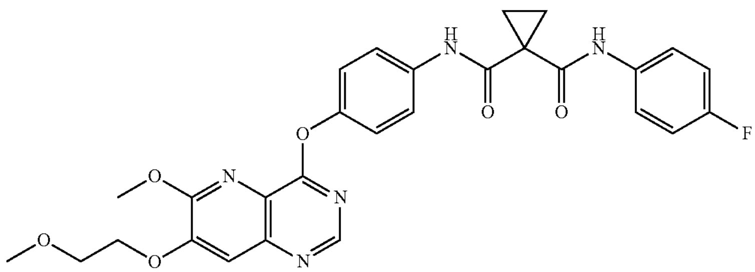 | 1-N'-(4-fluorophenyl)-1-N-[4-[6-methoxy-7-(2-methoxyethoxy)pyrido[3,2-d]pyrimidin-4-yl]oxyphenyl]cyclopropane-1,1-dicarboxamide |
| 79 | 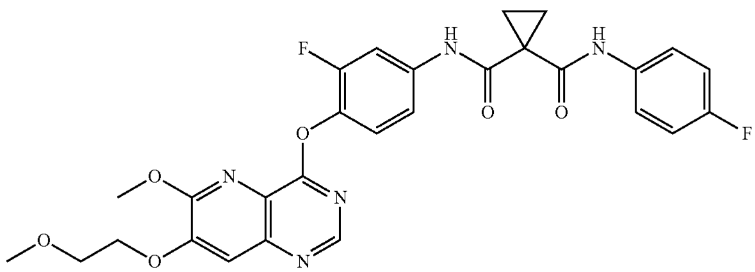 [SMILES: COCCOc1cc2ncnc(Oc3ccc(NC(=O)C4(C(=O)Nc5ccc(F)cc5)CC4)cc3F)c2nc1OC] | 1-N'-[3-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 80 | 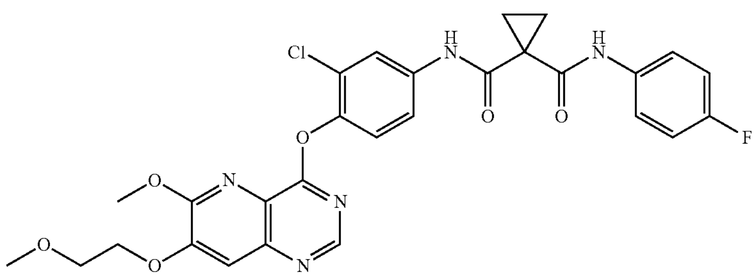 [SMILES: COCCOc1cc2ncnc(Oc3ccc(NC(=O)C4(C(=O)Nc5ccc(F)cc5)CC4)cc3Cl)c2nc1OC] | 1-N'-[3-chloro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 81 | 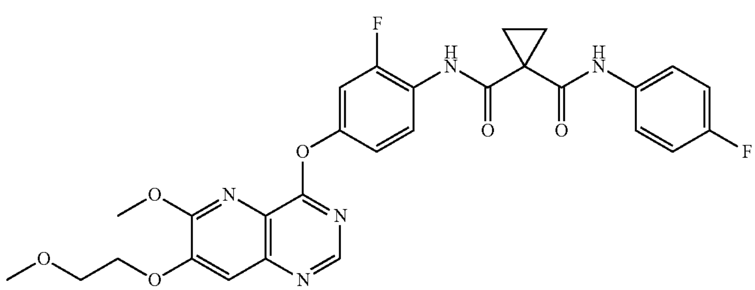 [SMILES: COCCOc1cc2ncnc(Oc3ccc(NC(=O)C4(C(=O)Nc5ccc(F)cc5)CC4)c(F)c3)c2nc1OC] | 1-N'-[2-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 82 | 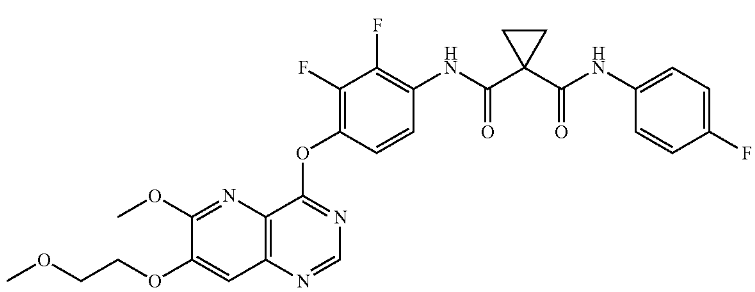 [SMILES: COCCOc1cc2ncnc(Oc3ccc(NC(=O)C4(C(=O)Nc5ccc(F)cc5)CC4)c(F)c3F)c2nc1OC] | 1-N'-[2,3-difluoro-4-[6-methoxy-7-(2-methoxyethoxy)pyrido[3,2-d]pyridmidin-4-yl]oxyphenyl]-1-N-(4-fluorophenyl)cyclopropane-1,1-dicarboxamide |

TABLE 2-continued

Compounds of Formula I

| Comp. | Structure | IUPAC Name |
|---|---|---|
| 83 | 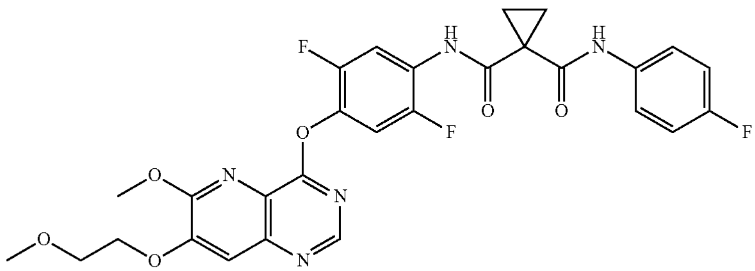 [SMILES: COCCOc1cc2ncnc(Oc3cc(F)c(NC(=O)C4(C(=O)Nc5ccc(F)cc5)CC4)cc3F)c2nc1OC] | 1-N'-[2,5-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 85 | 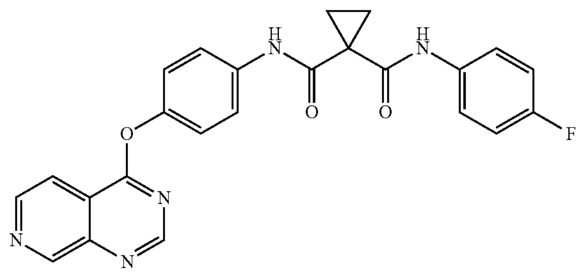 [SMILES: O=C(Nc1ccc(F)cc1)C1(C(=O)Nc2ccc(Oc3ncnc4cnccc34)cc2)CC1] | 1-N'-(4-fluorophenyl)-1-N-(4-pyrido[3,4-d]pyrimidin-4-yloxyphenyl)cyclopropane-1,1-dicarboxamide |
| 88 | 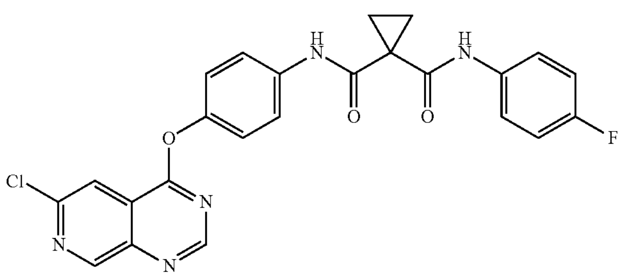 [SMILES: O=C(Nc1ccc(F)cc1)C1(C(=O)Nc2ccc(Oc3ncnc4cnc(Cl)cc34)cc2)CC1] | 1-N-[4-(6-chloropyrido[3,4-d]pyrimidin-4-yl)oxyphenyl]-1-N'-(4-fluorophenyl)cyclopropane-1,1-dicarboxamide |
| 91 | 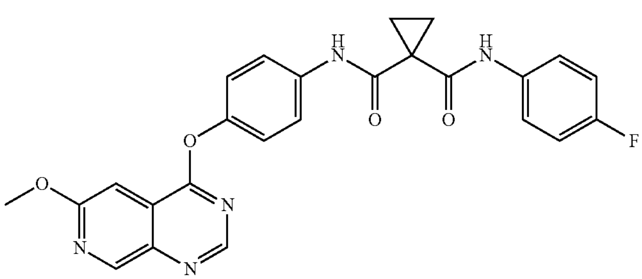 [SMILES: COc1cc2c(Oc3ccc(NC(=O)C4(C(=O)Nc5ccc(F)cc5)CC4)cc3)ncnc2cn1] | 1-N'-(4-fluorophenyl)-1-N-[4-(6-methoxypyrido[3,4-d]pyrimidin-4-yl)oxyphenyl]cyclopropane-1,1-dicarboxamide |
| 95 | 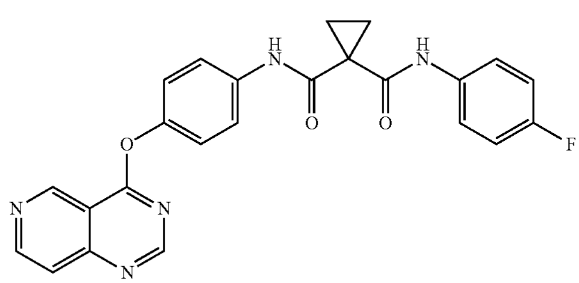 [SMILES: O=C(Nc1ccc(F)cc1)C1(C(=O)Nc2ccc(Oc3ncnc4ccncc34)cc2)CC1] | 1-N'-(4-fluorophenyl)-1-N-(4-pyrido[4,3-d]pyrimidin-4-yloxyphenyl)cyclopropane-1,1-dicarboxamide |

TABLE 2-continued

Compounds of Formula I

| Comp. | Structure | IUPAC Name |
|---|---|---|
| 101 | 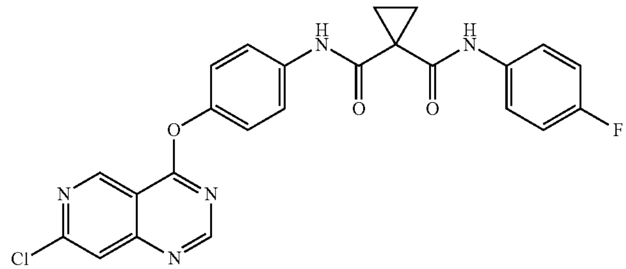 [SMILES: O=C(Nc1ccc(F)cc1)C1(C(=O)Nc2ccc(Oc3ncnc4cc(Cl)ncc34)cc2)CC1] | 1-N-[4-(7-chloropyrido[4,3-d]pyrimidin-4-yl)oxyphenyl]-1-N'-(4-fluorophenyl)cyclopropane-1,1-dicarboxamide |
| 104 | 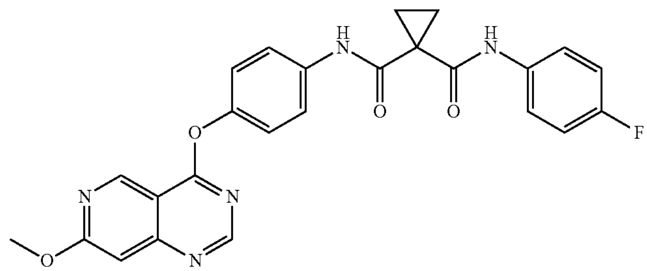 [SMILES: COc1cc2ncnc(Oc3ccc(NC(=O)C4(C(=O)Nc5ccc(F)cc5)CC4)cc3)c2cn1] | 1-N'-(4-fluorophenyl)-1-N-[4-(7-methoxypyrido[4,3-d]pyrimidin-4-yl)oxyphenyl]cyclopropane-1,1-dicarboxamide |
| 129 | 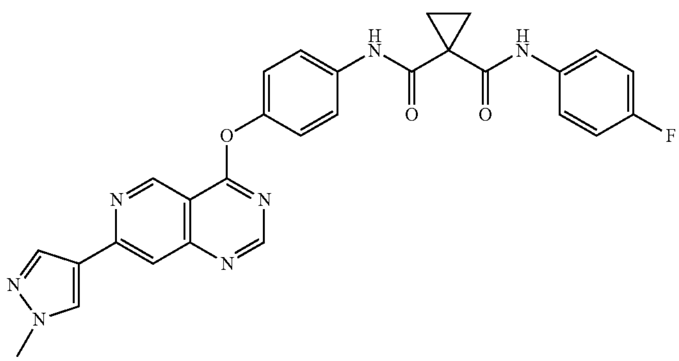 [SMILES: Cn1cc(-c2cc3ncnc(Oc4ccc(NC(=O)C5(C(=O)Nc6ccc(F)cc6)CC5)cc4)c3cn2)cn1] | 1-N'-(4-fluorophenyl)-1-N-[4-[7-(1-methylpyrazol-4-yl)pyrido[3,2-d]pyrimidin-4-yl]oxyphenyl]cyclopropane-1,1-dicarboxamide |
| 130 | 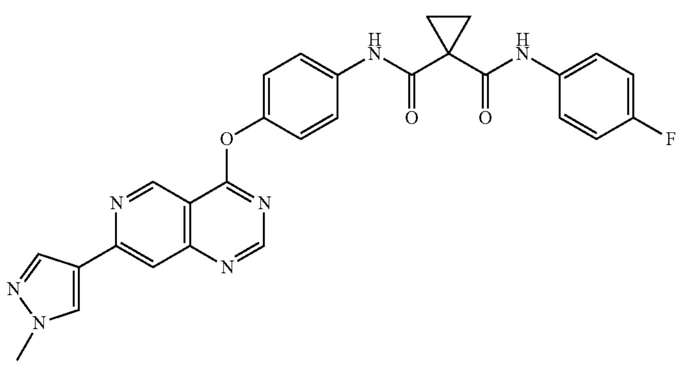 [SMILES: Cn1cc(-c2cc3ncnc(Oc4ccc(NC(=O)C5(C(=O)Nc6ccc(F)cc6)CC5)cc4)c3cn2)cn1] | 1-N'-(4-fluorophenyl)-1-N-[4-[7-(1-methylpyrazol-4-yl)pyrido[4,3-d]pyrimidin-4-yl]oxyphenyl]cyclopropane-1,1-dicarboxamide |
| 139 | 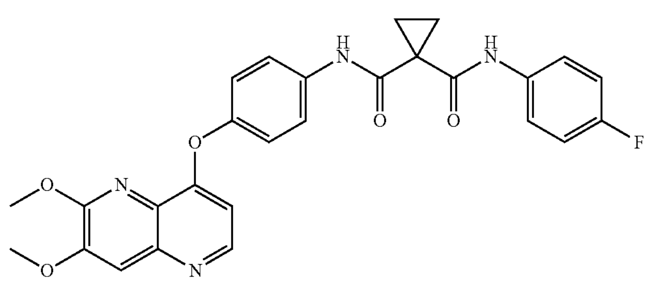 [SMILES: COc1cc2nccc(Oc3ccc(NC(=O)C4(C(=O)Nc5ccc(F)cc5)CC4)cc3)c2nc1OC] | 1-N-[4-[(6,7-dimethoxy-1,5-naphthyridin-4-yl)oxy]phenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 140 | 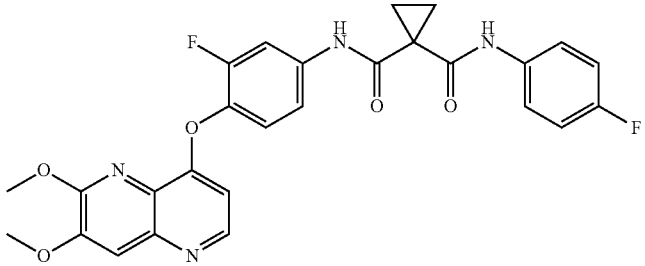 | 1-N'-[4-[(6,7-dimethoxy-1,5-naphthyridin-4-yl)oxy]-3-fluorophenyl]-1-N-(4-fluorophenyl)cyclopropane-1,1-dicarboxamide |
| 141 | 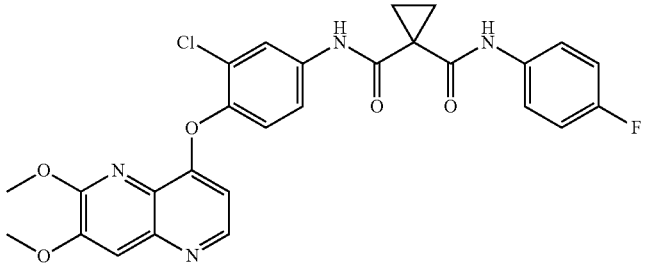 [SMILES: COc1cc2nccc(Oc3ccc(NC(=O)C4(C(=O)Nc5ccc(F)cc5)CC4)cc3Cl)c2nc1OC] | 1-N'-[3-chloro-4-[(6,7-dimethoxy-1,5-naphthyridin-4-yl)oxy]phenyl]-1-N-(4-fluorophenyl)cyclopropane-1,1-dicarboxamide |
| 142 | 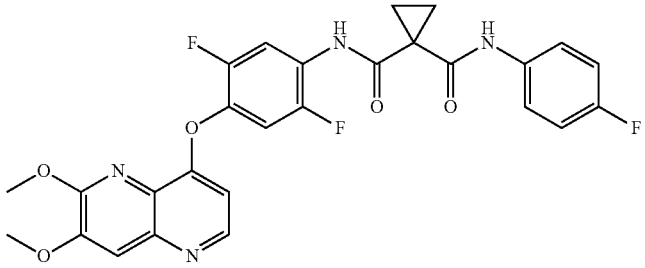 [SMILES: COc1cc2nccc(Oc3cc(F)c(NC(=O)C4(C(=O)Nc5ccc(F)cc5)CC4)cc3F)c2nc1OC] | 1-N'-[4-[(6,7-dimethoxy-1,5-naphthyridin-4-yl)oxy]-2,5-difluorophenyl]-1-N-(4-fluorophenyl)cyclopropane-1,1-dicarboxamide |
| 149 | 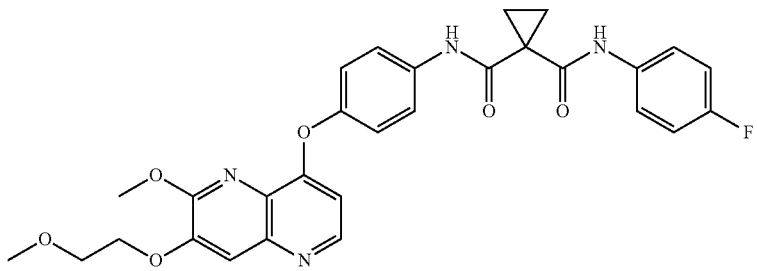 [SMILES: COCCOc1cc2nccc(Oc3ccc(NC(=O)C4(C(=O)Nc5ccc(F)cc5)CC4)cc3)c2nc1OC] | 1-N'-(4-fluorophenyl)-1-N-[4-[[6-methoxy-7-(2-methoxyethoxy)-1,5-naphthyridin-4-yl]oxy]phenyl]cyclopropane-1,1-dicarboxamide |
| 150 | 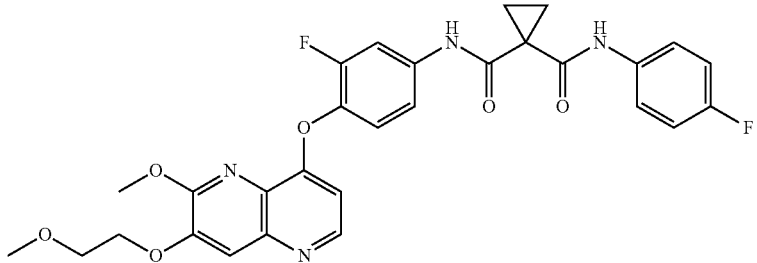 | 1-N'-[3-fluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |

TABLE 2-continued

Compounds of Formula I

| Comp. | Structure | IUPAC Name |
|---|---|---|
| 151 | 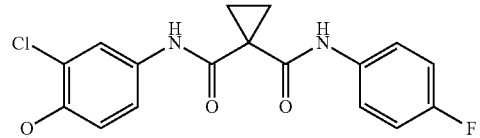 | 1-N'-[3-chloro-4-[[6-methoxy-7-(2-methoxyethoxy)-1,5-naphthyridin-4-yl]oxy]phneyl]-1-N-(4-fluorophenyl)cyclopropane-1,1-dicarboxamide |
| 152 | 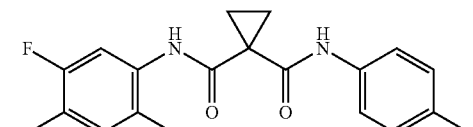 | 1-N'-[2,5-difluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 153 | 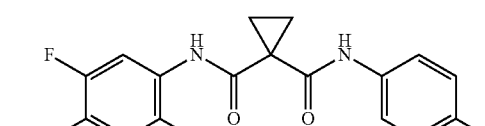 | 1-N'-[2,5-difluoro-4-[[6-7-(2-morpholin-4-ylethoxy)-1,5-naphthyridin-4-yl]oxy]phenyl]-1-N-(4-fluorophenyl)cyclopropane-1,1-dicarboxamide |
| 157 | 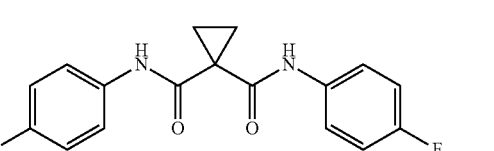 | 1-N-[4-(2,3-dihydro-[1,4]dioxino[2,3-b][1,5]naphthyridin-6-yloxy)phenyl]-1-N'-(4-fluorophenyl)cyclopropane-1,1-dicarboxamide |
| 158 | 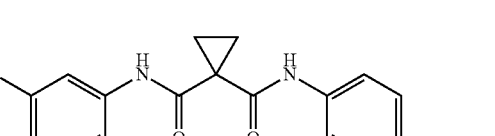 | 1-N'-[4-(2,3-dihydro-[1,4]dioxino[2,3-b][1,5]naphthyridin-6-yloxy)-3-fluorophenyl]-1-N-(4-fluorophenyl)cyclopropane-1,1-dicarboxamide |

TABLE 2-continued

Compounds of Formula I

| Comp. | Structure | IUPAC Name |
|---|---|---|
| 159 | 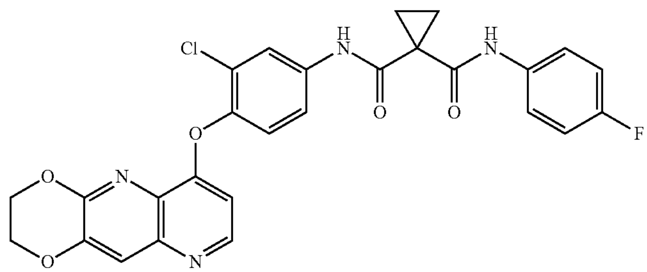 | 1-N'-[3-chloro-4-(2,3-dihydro-[1,4]dioxino[2,3-b][1,5]naphthyridin-6-yloxy)phenyl]-1-N-(4-fluorophenyl)cyclopropane-1,1-dicarboxamide |
| 164 | 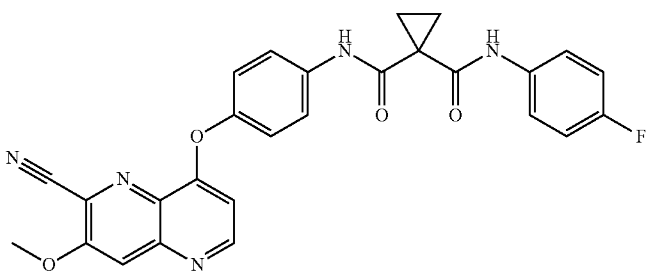 [SMILES: COc1cc2nccc(Oc3ccc(NC(=O)C4(C(=O)Nc5ccc(F)cc5)CC4)cc3)c2nc1C#N] | 1-N-[4-[(6-cyano-7-methoxy-1,5-naphthyridin-4-yl)oxy]phenyl]-1-N'-(4-fluorophenyl)cyclopropane-1,1-dicarboxamide |
| 165 | 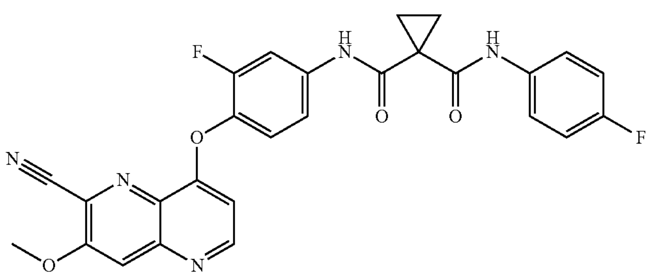 [SMILES: COc1cc2nccc(Oc3ccc(NC(=O)C4(C(=O)Nc5ccc(F)cc5)CC4)cc3F)c2nc1C#N] | 1-N'-[4-[(6-cyano-7-methoxy-1,5-naphthyridin-4-yl)oxy]-3-fluorophenyl]-1-N-(4-fluorophenyl)cyclopropane-1,1-dicarboxamide |
| 166 | 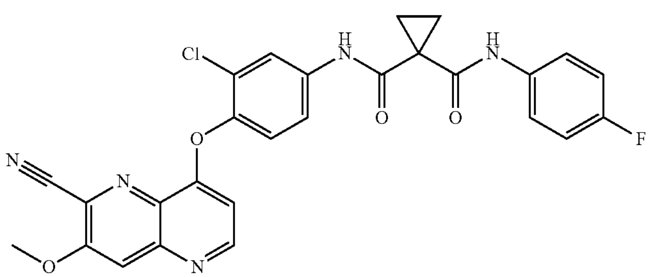 [SMILES: COc1cc2nccc(Oc3ccc(NC(=O)C4(C(=O)Nc5ccc(F)cc5)CC4)cc3Cl)c2nc1C#N] | 1-N'-[3-chloro-4-[(6-cyano-7-methoxy-1,5-naphthyridin-4-yl)oxy]phenyl]-1-N-(4-fluorophenyl)cyclopropane-1,1-dicarboxamide |
| 167 | 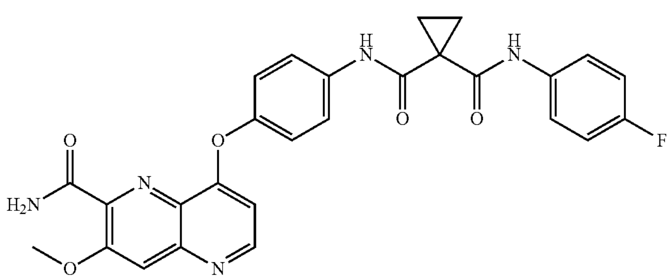 [SMILES: COc1cc2nccc(Oc3ccc(NC(=O)C4(C(=O)Nc5ccc(F)cc5)CC4)cc3)c2nc1C(N)=O] | 1-N-[4-[(6-carbamoyl-7-methoxy-1,5-naphthyridin-4-yl)oxy]phenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 168 | 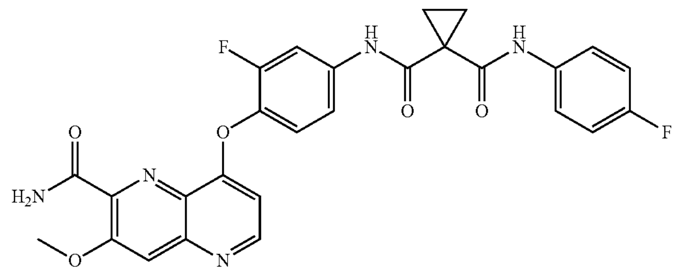 [SMILES: COc1cc2nccc(Oc3ccc(NC(=O)C4(C(=O)Nc5ccc(F)cc5)CC4)cc3F)c2nc1C(N)=O] | 1-N'-[4-[(6-carbamoyl-7-methoxy-1,5-naphthyridin-4-yl)oxy]-3-fluorophenyl]-1-N-(4-fluorophenyl)cyclopropane-1,1-dicarboxamide |
| 169 | 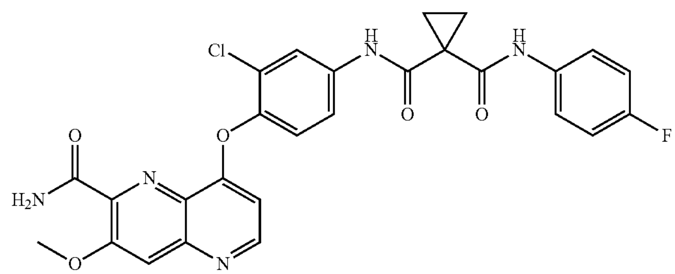 [SMILES: COc1cc2nccc(Oc3ccc(NC(=O)C4(C(=O)Nc5ccc(F)cc5)CC4)cc3Cl)c2nc1C(N)=O] | 1-N'-[4-[(6-carbamoyl-7-methoxy-1,5-naphthyridin-4-yl)oxy]-3-chlorophenyl]-1-N-(4-fluorophenyl)cyclopropane-1,1-dicarboxamide |
| 172 | 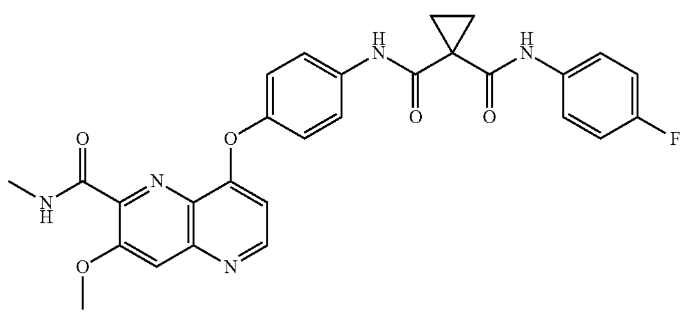 [SMILES: CNC(=O)c1nc2c(Oc3ccc(NC(=O)C4(C(=O)Nc5ccc(F)cc5)CC4)cc3)ccnc2cc1OC] | 1-N'-(4-fluorophenyl)-1-N-[4-[[7-methoxy-6-(methylcarbamoyl)-1,5-naphthyridin-4-yl]oxy]phenyl]cyclopropane-1,1-dicarboxamide |
| 173 | 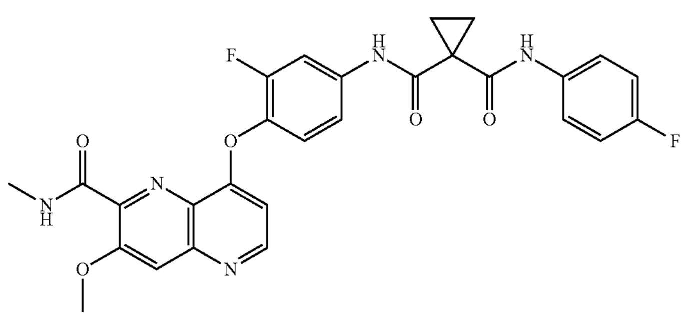 [SMILES: CNC(=O)c1nc2c(Oc3ccc(NC(=O)C4(C(=O)Nc5ccc(F)cc5)CC4)cc3F)ccnc2cc1OC] | 1-N'-[3-fluoro-4-[[7-methoxy-6-(methylcarbamoyl)-1,5-naphthyridin-4-yl]oxy]phenyl]-1-N-(4-fluorophenyl)cyclopropane-1,1-dicarboxamide |
| 174 | 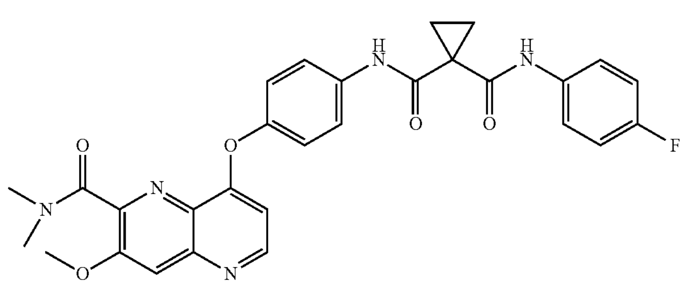 [SMILES: COc1cc2nccc(Oc3ccc(NC(=O)C4(C(=O)Nc5ccc(F)cc5)CC4)cc3)c2nc1C(=O)N(C)C] | 1-N-[4-[[6-(dimethylcarbamoyl)-7-methoxy-1,5-naphthyridin-4-yl]oxy]phenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 176 | 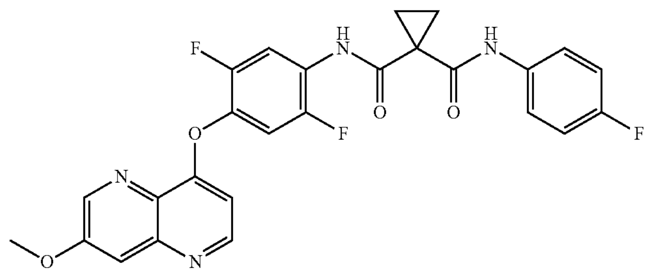 [SMILES: COc1cnc2c(Oc3cc(F)c(NC(=O)C4(C(=O)Nc5ccc(F)cc5)CC4)cc3F)ccnc2c1] | 1-N'-[2,5-difluoro-4-[(7-methoxy-1,5-naphthyridin-4-yl)oxy]phenyl]-1-N-(4-fluorophenyl)cyclopropane-1,1-dicarboxamide |
| 181 | 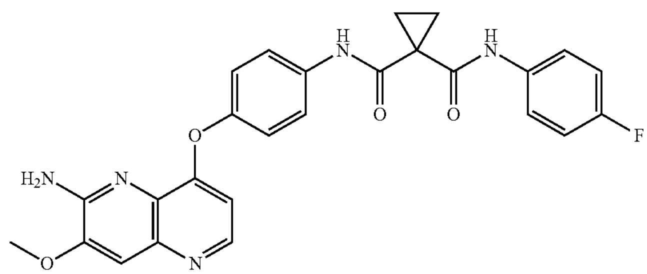 [SMILES: COc1cc2nccc(Oc3ccc(NC(=O)C4(C(=O)Nc5ccc(F)cc5)CC4)cc3)c2nc1N] | 1-N-[4-[(6-amino-7-methoxy-1,5-naphthyridin-4-yl)oxy]phenyl]-1-N'-(4-fluorophenyl)cyclopropane-1,1-dicarboxamide |
| 182 | 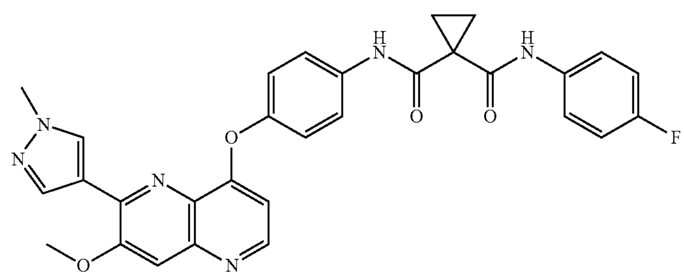 [SMILES: COc1cc2nccc(Oc3ccc(NC(=O)C4(C(=O)Nc5ccc(F)cc5)CC4)cc3)c2nc1-c1cnn(C)c1] | 1-N'-(4-fluorophenyl)-1-N-[4-[[7-methoxy-6-(1-methylpyrazol-4-yl)-1,5-naphthyridin-4-yl]oxy]phenyl]cyclopropane-1,1-dicarboxamide |
| 183 | 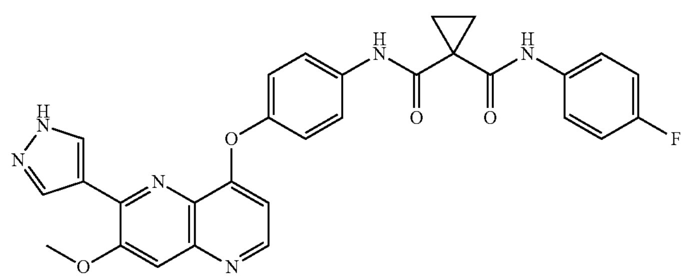 [SMILES: COc1cc2nccc(Oc3ccc(NC(=O)C4(C(=O)Nc5ccc(F)cc5)CC4)cc3)c2nc1-c1cn[nH]c1] | 1-N'-(4-fluorophenyl)-1-N-[4-[[7-methoxy-6-(1H-pyrazol-4-yl)-1,5-naphthyridin-4-yl]oxy]phenyl]cyclopropane-1,1-dicarboxamide |
| 184 | 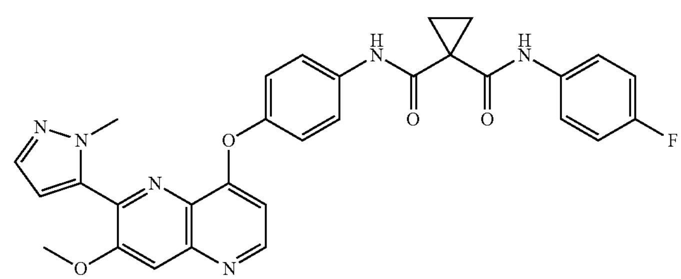 [SMILES: COc1cc2nccc(Oc3ccc(NC(=O)C4(C(=O)Nc5ccc(F)cc5)CC4)cc3)c2nc1-c1ccnn1C] | 1-N'-(4-fluorophenyl)-1-N-[4-[[7-methoxy-6-(2-methylpyrazol-3-yl)-1,5-naphthyridin-4-yl]oxy]phenyl]cyclopropane-1,1-dicarboxamide |

TABLE 2-continued

Compounds of Formula I

| Comp. | Structure | IUPAC Name |
|---|---|---|
| 189 | 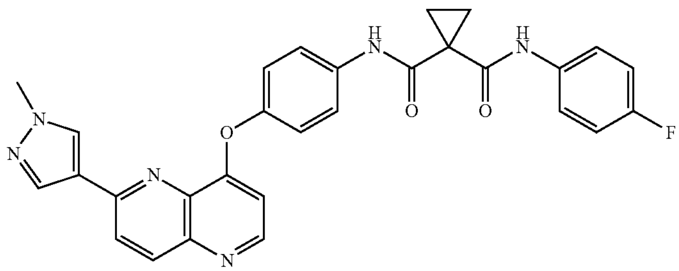 [SMILES: Cn1cc(-c2ccc3nccc(Oc4ccc(NC(=O)C5(C(=O)Nc6ccc(F)cc6)CC5)cc4)c3n2)cn1] | 1-N'-(4-fluorophenyl)-1-N-[4-[[6-(1-methylpyrazol-4-yl)-1,5-naphthyridin-4-yl]oxy]phenyl]cyclopropane-1,1-dicarboxamide |

In one embodiment, the compound of Formula I' is a compound of Formula II:

II or a pharmaceutically acceptable salt thereof, wherein:
$R_{16}$ is selected from the group consisting of —CN and —CO—NR$_5$R$_6$;
$R_{17}$ is selected from H and optionally substituted $C_1$-$C_6$ alkoxy;
$R_{13}$ is selected from the group consisting of —H, halo, —CN, or optionally substituted $C_{1-6}$ alkyl;
$R_{12}$ is —H or halo;

is optionally substituted with one, two, three, or four groups independently selected from the group consisting of halo, and $C_1$-$C_6$ alkyl, wherein "∼∼∼" indicate points of attachment;
$R_5$ and $R_6$ are each independently selected from the group consisting of H, optionally substituted $C_1$-$C_6$ alkyl, optionally substituted $C_3$-$C_6$ heterocycloalkyl, and optionally substituted $C_1$-$C_6$ cycloalkyl;
Y is O, S, SO, SO$_2$, NH, or N—($C_1$-$C_6$ alkyl); and
m and n are each independently 1 or 2.

In one embodiment, $R_{17}$ is H.
In another embodiment, is not substituted.

In another embodiment, $R_{12}$ is halo.
In a further embodiment, $R_{12}$ is para fluoro.
In one embodiment, $R_{16}$ is —CN or —CO—NR$_5$R$_6$.
In a further embodiment, $R_{16}$ is —CO—NH$_2$.
In one embodiment, $R_{16}$ and $R_{17}$ are joined together, with the atoms to which they are attached, to form a 5- or 6-membered optionally substituted heterocycloalkyl.
In one embodiment, Y is O.
In some embodiments, is

,

,

,

,

,

119

-continued

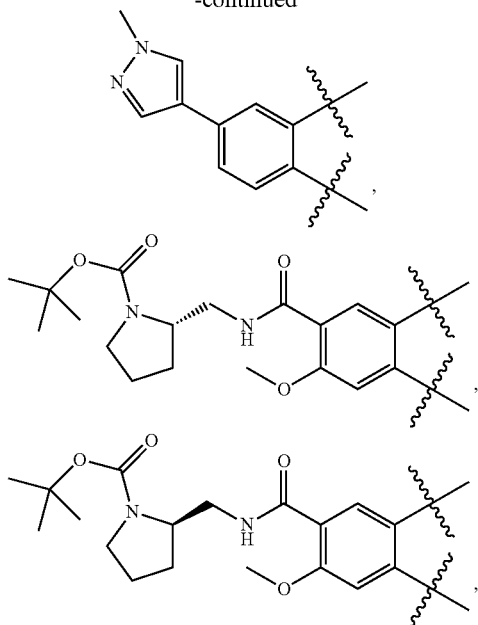

120

-continued

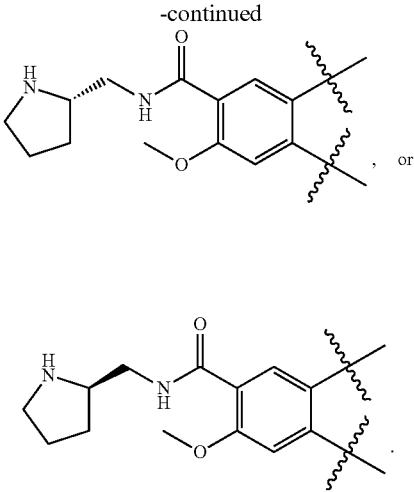

In one embodiment, the compound of Formula II, or a pharmaceutically acceptable salt thereof, is selected from the compounds listed in Table 3, or a pharmaceutically acceptable salt thereof.

TABLE 3

Compounds of Formula II

| Comp. | Structure | IUPAC Name |
|---|---|---|
| 106 | 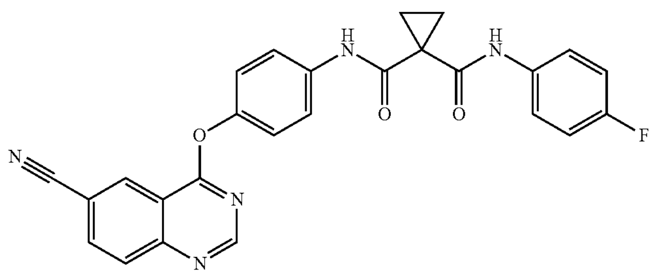 [SMILES: N#Cc1ccc2ncnc(Oc3ccc(NC(=O)C4(C(=O)Nc5ccc(F)cc5)CC4)cc3)c2c1] | 1-N-[4-(6-cyanoquinazolin-4-yl)oxyphenyl]-1-N'-(4-fluorophenyl)cyclopropane-1,1-dicarboxamide |
| 115 | 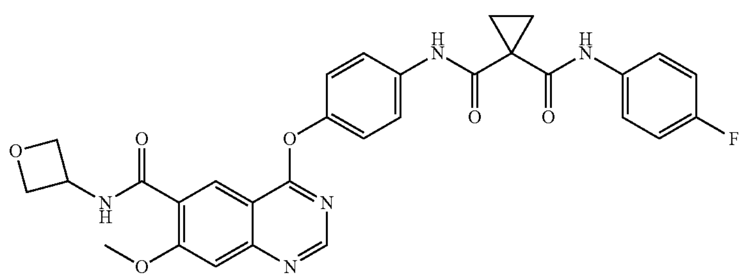 [SMILES: COc1cc2ncnc(Oc3ccc(NC(=O)C4(C(=O)Nc5ccc(F)cc5)CC4)cc3)c2cc1C(=O)NC1COC1] | 1-N'-(4-fluorophenyl)-1-N-[4-[7-methoxy-6-(oxetan-3-ylcarbamoyl)quinazolin-4-yl]oxyphenyl]cyclopropane-1,1-dicarboxamide |
| 116 | 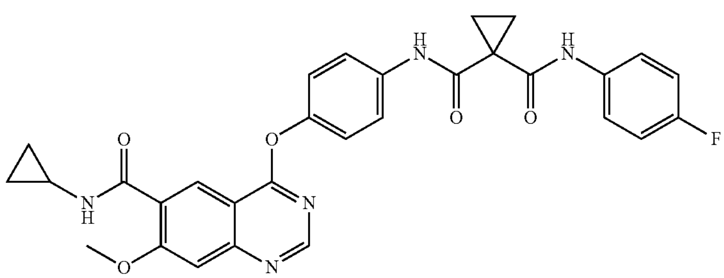 [SMILES: COc1cc2ncnc(Oc3ccc(NC(=O)C4(C(=O)Nc5ccc(F)cc5)CC4)cc3)c2cc1C(=O)NC1CC1] | 1-N-[4-[6-(cyclopropylcarbamoyl)-7-methoxyquinazolin-4-yl]oxyphenyl]-1-N'-(4-fluorophenyl)cyclopropane-1,1-dicarboxamide |

TABLE 3-continued

Compounds of Formula II

| Comp. | Structure | IUPAC Name |
|---|---|---|
| 117 | 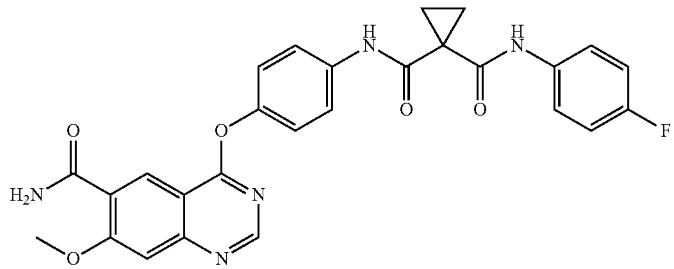 [SMILES: COc1cc2ncnc(Oc3ccc(NC(=O)C4(C(=O)Nc5ccc(F)cc5)CC4)cc3)c2cc1C(N)=O] | 1-N-[4-(6-carbamoyl-7-methoxyquinazolin-4-yl)oxyphenyl]-1-N'-(4-fluorophenyl)cyclopropane-1,1-dicarboxamide |
| 118 | 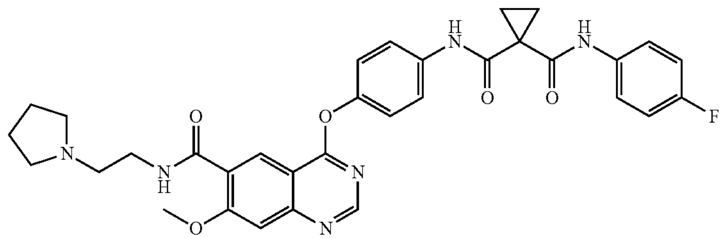 [SMILES: COc1cc2ncnc(Oc3ccc(NC(=O)C4(C(=O)Nc5ccc(F)cc5)CC4)cc3)c2cc1C(=O)NCCN1CCCC1] | 1-N'-(4-fluorophenyl)-1-N-[4-[7-methoxy-6-(2-pyrrolidin-1-ylethylcarbamoyl)quinazolin-4-yl]oxyphenyl]cyclopropane-1,1-dicarboxamide |
| 119 | 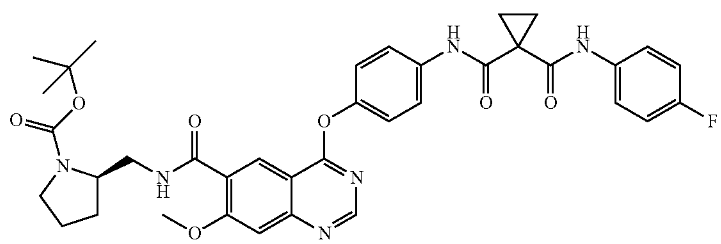 [SMILES: COc1cc2ncnc(Oc3ccc(NC(=O)C4(C(=O)Nc5ccc(F)cc5)CC4)cc3)c2cc1C(=O)NC[C@H]1CCCN1C(=O)OC(C)(C)C] | tert-butyl (2R)-2-[[[4-[4-[[1-[(4-fluorophenyl)carbamoyl]cyclopropanecarbonyl]amino]phenoxy]-7-methoxyquinazoline-6-carbonyl]amino]methyl]pyrrolidine-1-carboxylate |
| 120 | 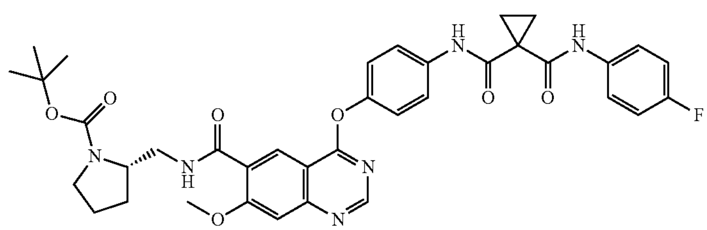 [SMILES: COc1cc2ncnc(Oc3ccc(NC(=O)C4(C(=O)Nc5ccc(F)cc5)CC4)cc3)c2cc1C(=O)NC[C@@H]1CCCN1C(=O)OC(C)(C)C] | tert-butyl (2S)-2-[[[4-[4-[[1-[(4-fluorophenyl)carbamoyl]cyclopropanecarbonyl]amino]phenoxy]-7-methoxyquinazoline-6-carbonyl]amino]methyl]pyrrolidine-1-carboxylate |
| 121 | 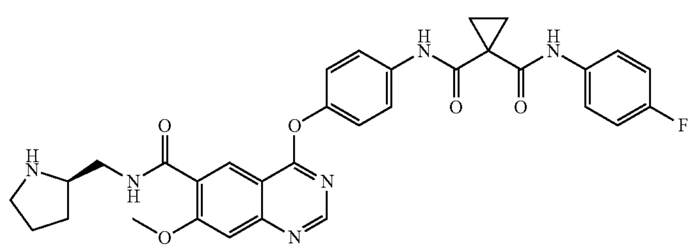 [SMILES: COc1cc2ncnc(Oc3ccc(NC(=O)C4(C(=O)Nc5ccc(F)cc5)CC4)cc3)c2cc1C(=O)NC[C@H]1CCCN1] | 1-N'-(4-fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide |
| 122 | 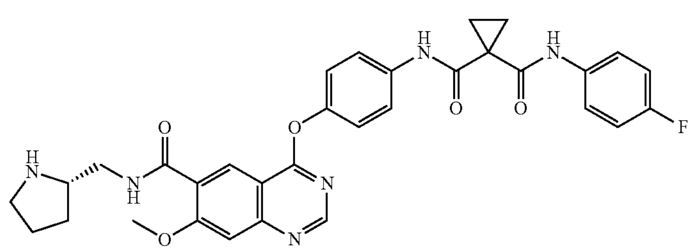 [SMILES: COc1cc2ncnc(Oc3ccc(NC(=O)C4(C(=O)Nc5ccc(F)cc5)CC4)cc3)c2cc1C(=O)NC[C@@H]1CCCN1] | 1-N'-(4-fluorophenyl)-1-N-[4-[7-methoxy-6-[[(2S)-pyrrolidin-2-yl]methylcarbamoyl]quinazolin-4-yl]oxyphenyl]cyclopropane-1,1-dicarboxamide |

TABLE 3-continued

Compounds of Formula II

| Comp. | Structure | IUPAC Name |
|---|---|---|
| 126 | 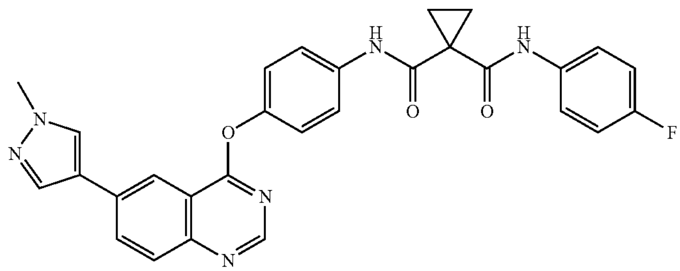 [SMILES: Cn1cc(-c2ccc3ncnc(Oc4ccc(NC(=O)C5(C(=O)Nc6ccc(F)cc6)CC5)cc4)c3c2)cn1] | 1-N'-(4-fluorophenyl)-1-N-[4-[6-(1-methylpyrazol-4-yl)quinazolin-4-yl]oxyphenyl]cyclopropane-1,1-dicarboxamide |

In one aspect, the invention includes a pharmaceutical composition comprising a compound described herein, and a pharmaceutically acceptable carrier or excipient.

In another aspect, the invention includes a method of treating a disease, disorder, or syndrome mediated at least in part by modulating in vivo activity of a protein kinase, comprising administering to a subject in need thereof a therapeutically effective amount of a compound described herein, or a pharmaceutical composition thereof.

General Administration

Administration of the compounds of the invention, or their pharmaceutically acceptable salts, in pure form or in an appropriate pharmaceutical composition, can be carried out via any of the accepted modes of administration or agents for serving similar utilities.

Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as, for example, tablets, suppositories, pills, soft elastic and hard gelatin capsules, powders, solutions, suspensions, aerosols, and the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, and the like. Compositions of the invention may be used in combination with anticancer or other agents that are generally administered to a patient being treated for cancer. Adjuvants include preserving, wetting, suspending, sweetening, flavoring, perfuming, emulsifying, and dispensing agents.

Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate, and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, and the like.

Compositions suitable for parenteral injection may comprise physiologically acceptable sterile aqueous or nonaqueous solutions, dispersions, suspensions or emulsions, and sterile powders for reconstitution into sterile injectable solutions or dispersions.

Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, and the like, a compound(s) of the invention, or a pharmaceutically acceptable salt thereof, and optional pharmaceutical adjuvants in a carrier, such as, for example, water, saline, aqueous dextrose, glycerol, ethanol, and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, and dimethylformamide; oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol, and sorbitan esters, microcrystalline cellulose, aluminum metahydroxide, bentonite, agar-agar, and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol, or a suppository wax, which are solid at ordinary temperatures but liquid at body temperature and therefore melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound (s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability, and length of action of the compound, the age, body weight, general health, sex, diet, mode, and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Combination Therapy

A compound as disclosed herein can be administered as a single therapy or in combination ("co-administered") with one or more additional therapies for the treatment of a disease or disorder, for instance a disease or disorder associated with hyper-proliferation such as cancer. Therapies that may be used in combination with a compound disclosed herein include: (i) surgery; (ii) radiotherapy (for example, gamma radiation, neutron beam radiotherapy, electron beam radiotherapy, proton therapy, brachytherapy, and systemic radioactive isotopes); (iii) endocrine therapy; (iv) adjuvant therapy, immunotherapy, CAR T-cell therapy; and (v) other chemotherapeutic agents.

The term "co-administered" ("co-administering") refers to either simultaneous administration, or any manner of separate sequential administration, of a compound of Formula I' or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents for cancer treatment can be found, for instance, at https://www.cancer.gov/about-cancer/treatment/drugs (last visited Jan. 22, 2019) and in publically available sources such as Cancer Principles and Practice of Oncology by V. T. Devita and S. Hellman (editors), $11^{th}$ edition (2018), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound as disclosed herein or a pharmaceutically acceptable salt thereof and at least one immunotherapy. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN™ (Trastuzumab) (Genentech, Calif) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3epitope) IgG antibody (ImClone System); IMC-C225 which is a chimeric anti-EGFR IgG antibody (ImClone System); VITAXIN™ which is a humanized anti-alpha V beta 3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 ($C_5$) antibody (Alexion Pharm); D2E7 is a humanized anti-TNF-alpha antibody (CAT/BASF); CDP870 is a humanized anti-TNF-alpha. Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-alpha. IgG4 antibody (Celltech); LDP-02 is a humanized anti-alpha4 beta7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-beta$_2$ antibody (Cambridge Ab Tech). Others are provided in later paragraphs.

Immunotherapies that can be used in combination with a compound as disclosed herein include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

In various embodiments, an immunological therapy or an immunological therapeutic agent can include, one or more of the following: an adoptive cell transfer, an angiogenesis inhibitor, Bacillus Calmette-Guerin therapy, biochemotherapy, a cancer vaccine, a chimeric antigen receptor (CAR) T-cell therapy, a cytokine therapy, gene therapy, an immune checkpoint modulator, an immunoconjugate, a radioconjugate, an oncolytic virus therapy, or a targeted drug therapy. The function or at least one of the functions of the immunological therapy or immunological therapeutic agent, collectively referred to herein as an "immunotherapeutic agent".

The present disclosure provides a method for preventing, treating, reducing, inhibiting or controlling a neoplasia, a tumor or a cancer in a subject in need thereof, involving administering a therapeutically effective amount of a combination comprising a compound of Formula I' and an immunotherapeutic agent. In one non-limiting embodiment, the method comprises administering a therapeutically effective amount of a combination comprising a compound of Formula I' in combination with an immunotherapeutic agent. In various embodiments, the combination provides a cooperative effect, an additive effect, or a synergistic effect in reducing the number of cancer cells when treated with the combination as compared to each treatment alone. In some embodiments, administration of a therapeutically effective amount of a combination comprising a compound of Formula I' and an immunotherapeutic agent, results in synergistic anti-tumor activity and/or antitumor activity that is more potent than the additive effect of administration of a compound of Formula I' or immunotherapeutic agent alone.

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

The present disclosure provides a combination of a compound of Formula I' and an immunotherapeutic agent. These exemplified combinations can be used to treat a subject with a cancer. In various embodiments, immunotherapeutic agents that find utility in the present compositions, formulations, and methods can include one or more agents or therapies, including: an adoptive cell transfer, an angiogenesis inhibitor, Bacillus Calmette-Guerin therapy, biochemotherapy, a cancer vaccine, a chimeric antigen receptor (CAR) T-cell therapy, a cytokine therapy, gene therapy, an immune checkpoint modulator, for example an immune checkpoint inhibitor, an immunoconjugate, a radioconjugate, an oncolytic virus therapy, or a targeted drug therapy.

In certain embodiments of the present disclosure, a therapeutically effective combination comprises a compound of Formula I' and an immunotherapeutic agent. In various related embodiments, the compound of Formula I' enhances the activity of the immunotherapeutic agent.

In certain embodiments of each of the aforementioned aspects, as well as other aspects and embodiments described elsewhere herein, the immunotherapeutic agent enhances the activity of the compound of Formula I'.

In certain embodiments of each of the aforementioned aspects, as well as other aspects and embodiments described elsewhere herein, the compound of Formula I' and the immunotherapeutic agent act synergistically. In various embodiments described herein, an exemplary immunotherapeutic agent is an immune cell (e.g. T-cell, dendritic cell, a natural killer cell and the like) modulator chosen from an agonist or an activator of a costimulatory molecule, wherein the modulator is a monoclonal antibody, a bispecific antibody comprising one or more immune checkpoint antigen binding moieties, a trispecific antibody, or an immune cell-engaging multivalent antibody/fusion protein/construct known in the art). In some embodiments, the immunotherapeutic agent can be an antibody that modulates a costimulatory molecule, bind to an antigen on the surface of an immune cell, or a cancer cell.

In each of these different embodiments, the antibody modulator can be a monoclonal antibody, a polyclonal antibody, a bispecific antibody, a trispecific or multispecific format antibody, a fusion protein, or a fragment thereof, for example, a Diabody, a Single-chain (sc)-diabody (scFv)2, a Miniantibody, a Minibody, a Barnase-barstar, a scFv-Fc, a sc(Fab)2, a Trimeric antibody construct, a Triabody antibody construct, a Trimerbody antibody construct, a Tribody antibody constuct, a Collabody antibody construct, a (scFv-TNFa)3, or a F(ab)3/DNL antibody construct.

In certain embodiments of each of the aforementioned aspects, as well as other aspects and embodiments described elsewhere herein, the immunotherapeutic agent is an agent that modulates immune responses, for example, a checkpoint inhibitor or a checkpoint agonist. In some embodiments, the immunotherapeutic agent is an agent that enhances anti-tumor immune responses. In some embodiments, the immunotherapeutic agent is an agent that increases cell-mediated immunity. In some embodiments, the immunotherapeutic agent is an agent that increases T-cell activity. In some embodiments, the immunotherapeutic agent is an agent that increases cytolytic T-cell (CTL) activity. In some embodiments, the immunotherapeutic agent is an antibody modulator that targets PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4, TGF beta, OX40, 41BB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art. In some embodiments, the immunotherapeutic agent is an agent that increases natural killer (NK) cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent or therapy that inhibits Treg activity. In some embodiments, the immunotherapeutic agent is an agent that inhibits the activity of inhibitory immune checkpoint receptors. In some embodiments, the combination of the present disclosure comprises a compound of Formula I' and an immunotherapeutic agent, wherein the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a modulator of SIRP-alpha activity, a modulator of TIGIT activity, a modulator of VSIG8 activity, a modulator of BTLA activity, a modulator of SIGLEC7 activity, a modulator of SIGLEC9 activity, a modulator of ICOS activity, a modulator of B7H3 activity, a modulator of B7H4 activity, a modulator of FAS activity, a modulator of BTNL2 activity, a cytokine, a chemokine, an interferon, an interleukin, a lymphokine, a member of the tumor necrosis factor (TNF) family, or an immunostimulatory oligonucleotide. In some embodiments, the immunotherapeutic agent is an immune checkpoint modulator (e.g., an immune checkpoint inhibitor e.g. an inhibitor of PD-1 activity, a modulator of PD-L1 activity, a modulator of PD-L2 activity, a modulator of CTLA-4, or a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule).

In one embodiment, the immunomodulator is an inhibitor of PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, for example, a monoclonal antibody, a bispecific antibody comprising one or more immune checkpoint antigen binding moieties, a trispecific antibody, or an immune cell-engaging multivalent antibody/fusion protein/construct known in the art that binds to the inhibitory molecule; e.g., an antibody or fragment thereof (also referred to herein as "an antibody molecule") that binds to PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4, TGF beta, or a combination thereof.

In some embodiments, where the combination comprises a compound of Formula I' and an immunotherapeutic agent, wherein the immunotherapeutic agent is a monoclonal antibody or a bispecific antibody. For example, the monoclonal or bispecific antibody may specifically bind a member of the c-Met pathway and/or an immune checkpoint modulator (e.g., the bispecific antibody binds to both a hepatocyte growth factor receptor (HGFR) and an immune checkpoint modulator described herein, such as an antibody that binds PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2 or CD27). In particular embodiments, the bispecific antibody specifically binds a human HGFR protein and one of PD-1, PD-L1, and CTLA-4.

In some embodiments, the immunotherapeutic agent is a cytokine, for example, a chemokine, an interferon, an interleukin, lymphokine, or a member of the tumor necrosis factor family. In some embodiments, the cytokine is IL-2, IL15, or interferon-gamma.

In some embodiments of any of the above aspects or those described elsewhere herein, the cancer is selected from the group consisting of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, glioblastoma multiforme, cervical cancer, stomach cancer, bladder cancer, head and neck cancer, and hepatoma.

In some embodiments of any of the above aspects or those described elsewhere herein, the subject's cancer or tumor does not respond to immune checkpoint inhibition (e.g., to any immune checkpoint inhibitor described herein, such as a PD-1 antagonist or PD-L1 antagonist) or the subject's cancer or tumor has progressed following an initial response to immune checkpoint inhibition (e.g., to any immune checkpoint inhibitor described herein, such as a PD-1 antagonist or PD-L1 antagonist).

In some embodiments of any of the above aspects or those described elsewhere herein, the subject is a human.

A checkpoint inhibitor can be any molecule, agent, treatment and/or method of inhibiting an immune checkpoint, and/or promoting an inhibitor of an immune checkpoint, e.g., by promoting an intrinsic immune checkpoint inhibitor; inhibiting a transcription factor involved in the expression of an immune checkpoint; and/or by acting in concert with some additional extrinsic factor. For example, a checkpoint inhibitor could include a treatment that inhibits transcription factors involved the expression of immune checkpoint genes, or promotes the expression of transcription factors for tumor-suppressor genes, e.g., BACH2 (Luan et al., (2016). Transcription Factors and Checkpoint Inhibitor Expression with Age: Markers of Immunosenescence. Blood, 128(22), 5983). Moreover, a checkpoint inhibitor can inhibit the transcription of immune checkpoint genes; the modification and/or processing of immune checkpoint mRNA; the translation of immune checkpoint proteins; and/or molecules involved in immunity or the immune checkpoint pathway, e.g., PD-1 transcription factors such as HIF-1, STAT3, NF-κB, and AP-1, or the activation of common oncogenic pathways such as JAK/STAT, RAS/ERK, or PI3K/AKT/mTOR (Zerdes et al., Genetic, transcriptional and post-translational regulation of the programmed death protein ligand 1 in cancer: biology and clinical correlations, Oncogenevolume 37, pages 4639-4661 (2018), the disclosure of which is incorporated herein by reference in its entirety).

Checkpoint inhibitors can include treatments, molecules, agents, and/or methods that regulate immune checkpoints at the transcriptional level, e.g., using the RNA-interference pathway co-suppression, and/or post-transcriptional gene silencing (PTGS) (e.g., microRNAs, miRNA; silencing-RNA, small-interfering-RNA, or short-interfering-RNA (siRNA). Transcriptional regulation of checkpoint molecules has been shown to involve mir-16, which has been shown to target the 3'UTR of the checkpoint mRNAs CD80, CD274 (PD-L1) and CD40 (Leibowitz et al., Post-transcriptional regulation of immune checkpoint genes by mir-16 in melanoma, Annals of Oncology (2017) 28; v428-v448). Mir-33a has also been shown to be involved in regulating the expression of PD-1 in cases of lung adenocarcinoma (Boldini et al., Role of microRNA-33a in regulating the expression of PD-1 in lung adenocarcinoma, Cancer Cell Int. 2017; 17: 105, the disclosure of which is incorporated herein by reference in its entirety).

T-cell-specific aptamer-siRNA chimeras have been suggested as a highly specific method of inhibiting molecules in the immune checkpoint pathway (Hossain et al., The aptamer-siRNA conjugates: reprogramming T cells for cancer therapy, Ther. Deliv. 2015 January; 6(1): 1-4, the disclosure of which is incorporated herein by reference in its entirety).

Alternatively, members of the immune checkpoint pathway can be inhibited using treatments that affect associated pathways, e.g., metabolism. For example, oversupplying the glycolytic intermediate pyruvate in mitochondria from CAD macrophages promoted expression of PD-L1 via induction of the bone morphogenetic protein 4/phosphorylated SMAD1/5/IFN regulatory factor 1 (BMP4/p-SMAD1/5/IRF1) signaling pathway.

Accordingly, implementing treatments that modulate the metabolic pathway can result in subsequent modulation of the immunoinhibitory PD-1/PD-L1 checkpoint pathway (Watanabe et al., Pyruvate controls the checkpoint inhibitor PD-L1 and suppresses T cell immunity, J Clin Invest. 2017 Jun. 30; 127(7): 2725-2738).

Checkpoint immunity can be regulated via oncolytic viruses that selectively replicate within tumor cells and induce acute immune responses in the tumor-microenvironment, i.e., by acting as genetic vectors that carry specific agents (e.g., antibodies, miRNA, siRNA, and the like) to cancer cells and effecting their oncolysis and secretion of cytokines and chemokines to synergize with immune checkpoint inhibition (Shi et al., Cancer Immunotherapy: A Focus on the Regulation of Immune Checkpoints, Int J Mol Sci. 2018 May; 19(5): 1389). Currently, there are clinical trials underway that utilize the following viruses as checkpoint inhibitors: poliovirus, measles virus, adenoviruses, poxviruses, herpes simplex virus (HSV), coxsackieviruses, reovirus, Newcastle disease virus (NDV), T-VEC (a herpes virus encoded with GM-CSF (granulocyte-macrophage colony stimulating factor)), and H101 (Shi et al., supra).

Checkpoint inhibitors can operate at the translational level of checkpoint immunity. The translation of mRNA into protein represents a key event in the regulation of gene expression, thus inhibition of immune checkpoint translation is a method in which the immune checkpoint pathway can be inhibited.

Inhibition of the immune checkpoint pathway can occur at any stage of the immune checkpoint translational process. For example, drugs, molecules, agents, treatments, and/or methods can inhibit the initiation process (whereby the 40S ribosomal subunit is recruited to the 5' end of the mRNA and scans the 5'UTR of the mRNA toward its 3' end. Inhibition can occur by targeting the anticodon of the initiator methionyl-transfer RNA (tRNA) (Met-tRNAi), its base-pairing with the start codon, or the recruitment of the 60S subunit to begin elongation and sequential addition of amino acids in the translation of immune-checkpoint-specific genes. Alternatively, a checkpoint inhibitor can inhibit checkpoints at the translational level by preventing the formation of the ternary complex (TC), i.e., eukaryotic initiation factor (eIF)2 (or one or more of its α, β, and γ subunits); GTP; and Met-tRNAi.

Checkpoint inhibition can occur via destabilization of eIF2α by precluding its phosphorylation via protein kinase R (PKR), PERK, GCN2, or HRI, or by precluding TCs from associating with the 40S ribosome and/or other initiation factors, thus preventing the preinitiation complex (PIC) from forming; inhibiting the eIF4F complex and/or its cap-binding protein eIF4E, the scaffolding protein eIF4G, or eIF4A helicase. Methods discussing the translational control of cancer are discussed in Truitt et al., New frontiers in translational control of the cancer genome, Nat Rev Cancer. 2016 Apr. 26; 16(5): 288-304, the disclosure of which is incorporated herein by reference in its entirety.

Checkpoint inhibitors can also include treatments, molecules, agents, and/or methods that regulate immune checkpoints at the cellular and/or protein level, e.g., by inhibiting an immune checkpoint receptor. Inhibition of checkpoints can occur via the use of antibodies, antibody fragments, antigen-binding fragments, small-molecules, and/or other drugs, agents, treatments, and/or methods.

Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response ('block' the immune response) against tumor tissues. In contrast to the majority of anti-cancer agents, checkpoint inhibitors do not target tumor cells directly, but rather target lymphocyte receptors or their ligands in order to enhance the endogenous antitumor activity of the immune system. (Pardoll, 2012, Nature Reviews Cancer 12:252-264).

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of antibody (Ab), ipilimumab (YERVOY®), that binds to and inhibits CTLA-4 for the treatment of patients with advanced melanoma (Hodi et al. (2010) N Engl J Med 363:711-23) and the development of antibodies such as nivolumab and pembrolizumab (formerly lambrolizumab; USAN Council Statement (2013) Pembrolizumab: Statement on a nonproprietary name adopted by the USAN Council (ZZ-165), Nov. 27, 2013) that bind specifically to the Programmed Death-1 (PD-1) receptor and block the inhibitory PD-1/PD-1 ligand pathway (Topalian et al. (2012a) N Engl J Med 366:2443-54; Topalian et al. (2012b) Curr Opin Immunol 24:207-12; Topalian et al. (2014) J Clin Oncol 32(10):1020-30; Hamid et al. (2013) N Engl J Med 369:134-144; Hamid and Carvajal (2013) Expert Opin Biol Ther 13(6):847-61; McDermott and Atkins (2013) Cancer Med 2(5):662-73).

PD-1 is a key immune checkpoint receptor expressed by activated T and B cells and mediates immunosuppression. Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. (2014) In vitro characterization of the anti-PD-1 antibody nivolumab, BMS-936558, and in vivo toxicology in non-human primates. Nivolumab has been approved for the treatment of patients with unresectable or metastatic melanoma and disease progression following ipilimumab and, if BRAF V600 mutation positive, a BRAF inhibitor and for the treatment of squamous non-small cell lung cancer.

Recent data suggest a secondary mechanism of anti-CTLA-4 antibodies, which could occur within the tumor itself. CTLA-4 has been found to be expressed in tumors at higher levels on regulatory T-cells (also referred to herein as "Treg cells") as compared with intra-tumoral effector T-cells (also referred to herein as "Teff cells"), resulting in the hypothesis of anti-CTLA-4 preferentially impacting the Treg cell. "Therapeutic use of anti-CTLA-4 antibodies", Christian U. Blank and Alexander Enk, International Immunology, Vol. 27, No. 1, pp. 3-10. A recent study of a PD-1 and CTLA-4 combination show that the combination blockade of the CTLA-4 and PD-1 pathways also cooperates to increase the ratio of Teff cells to both regulatory T-cells and MDSCs, thereby reducing suppression and promoting inflammation in the tumor microenvironment. "Combination of CTLA-4 and PD-1 blockade expands infiltrating T-cells and reduces regulatory T and myeloid cells within B16 melanoma tumors", Curran et al., PNAS|Mar. 2, 2010; vol. 107 (no. 9); pp. 4275-4280, the disclosure of which is incorporated herein by reference in its entirety. The combination of a checkpoint inhibitor and another therapeutic agent(s) may enhance or prolong anti-tumor response of the checkpoint inhibitor and/or effects of the therapeutic agent. In this regard, WO 2015/069770 discloses a combination treatment based on activating the adaptive immune response, in particular the combination of CTLA-4 and PD-1 inhibitors, for the treatment of cancer. The disclosure of WO 2015/069770 is incorporated by reference in its entirety in the disclosure of this application.

One mechanism by which the checkpoint blockade anti-CTLA-4 antibodies mediate anti-tumor effect is by decreasing regulatory T-cells. Due to the distinct mechanism of action of anti-CTLA-4 antibodies, they can successfully combine with the anti-PD1 checkpoint blockade antibodies which work to release the suppressive signaling conferred to effector T-cells. Dual blockade with these antibodies combine to improve anti-tumor response both preclinically (Proc Natl Acad Sci USA 2010, 107, 4275-4280) and in the clinic (N Engl J Med 2013, 369, 122-133; N Engl J Med 2015, 372, 2006-2017).

CTLA-4 attenuates the early activation of naïve and memory T cells through interactions with its ligands B7-1 (CD80) and B7-2 (CD86) (FIG. 1A). PD-1 is an receptor expressed on the surface of activated mature T cells, activated NK cells, B cells, monocytes and multiple normal tissues and plays a crucial role in the maintenance of peripheral tolerance [20-21]. In contrast to CTLA-4, PD-1 acts via interactions with its ligands PD-L1 (also known as B7-H1 or CD274) and is involved mainly in T cell activity modulation in peripheral tissues as well as providing a major immune resistance mechanism within the tumor microenvironment.

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, or an immunostimulatory oligonucleotide. In some embodiments, the immune checkpoint modulator, i.e. is an inhibitor or antagonist, or is an activator or agonist, for example, a CD28 modulator, a 4-1BB modulator, an OX40 modulator, a CD27 modulator, a CD80 modulator, a CD86 modulator, a CD40 modulator, or a GITR modulator, a Lag-3 modulator, a 41BB modulator, a LIGHT modulator, a CD40 modulator, a GITR modulator, a TGF-beta modulator, a TIM-3 modulator, a SIRP-alpha modulator, a TIGIT modulator, a VSIG8 modulator, a BTLA modulator, a SIGLEC7 modulator, a SIGLEC9 modulator, a ICOS modulator, a B7H3 modulator, a B7H4 modulator, a FAS modulator, and/or a BTNL2 modulator. In some embodiments, the immunotherapeutic agent is an immune checkpoint modulator as described above (e.g., an immune checkpoint modulator antibody, which can be in the form of a monoclonal antibody, a bispecific antibody comprising one or more immune checkpoint antigen binding moieties, a trispecific antibody, or an immune cell-engaging multivalent antibody/fusion protein/construct known in the art).

Combination treatments with immune checkpoint inhibitor immunotherapeutic agent may include antibodies that specifically target immune system checkpoints such as CTLA4, PD1 and PD-L1 are one of the most promising new avenues of immunotherapy for cancer and other diseases. Additional checkpoint targets, such as TIM-3, LAG-3, various B-7 ligands, CHK 1 and CHK2 kinases, BTLA, A2aR, and others, are also under investigation. Currently, three checkpoint inhibitors have received rapid approval from the U.S. Food and Drug Administration for cancer treatment, including ipilimumab (Yervoy@), a CTLA-4 inhibitor, and pembrolizumab (Keytruda®) and nivolumab (Opdivo®), both PD-1 inhibitors. In addition, several checkpoint inhibitor agents are in clinical trials.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., Int Immunol., 2007; 19: 813-824). The interaction of PD-1 with its ligands, PD-L1 and PD-L2, which are expressed on antigen-presenting cells (APCs) and dendritic cells (DCs), transmits negative regulatory stimuli to down-modulate the activated T cell immune response. Blockade of PD-1 suppresses this negative signal and amplifies T cell responses.

Numerous studies indicate that the cancer microenvironment manipulates the PD-L1-/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. First, and most importantly, this pathway is involved in negative regulation of immune responses of activated T effector cells, found in the periphery. Second, PD-L1 is up-regulated in cancer microenvironments, while PD-1 is also up-regulated on activated tumor infiltrating T cells, thus possibly potentiating a vicious cycle of inhibition. Third, this pathway is intricately involved in both innate and adaptive immune regulation through bi-directional signaling. These factors make the PD-1/PD-L1 complex a central point through which cancer can manipulate immune responses and promote its own progression.

CTLA-4 (also known as Cytotoxic T-lymphocyte-associated protein 4, CTLA4, CTLA-4, CD152, cluster of differentiation 152; ALPS5, CD, CELIAC3, GRD4, GSE, and IDDM12). CTLA-4 is a ~24.6-kDa single-pass type I membrane protein that plays an inhibitory role in T-cell function. CTLA-4 was originally identified by differential screening of a murine cytolytic T cell cDNA library, See Brunet et al., A new member of the immunoglobulin superfamily—CTLA-4, Nature. 1987 Jul. 16-22; 328(6127):267-70. CTLA- has been shown to interact with the b7 family ligands CD80 (also known as Cluster of differentiation 80, and B7-1); and CD86 (also known as Cluster of Differentiation 86 or B7-2). See Linsley et al., CTLA-4 is a second receptor for the B cell activation antigen B7, J Exp Med. 1991 Sep. 1; 174(3):561-9. Sequence comparison between the human CTLA-4 DNA encoding region, and that of CD28, reveals significant homology between both sequences, with the greatest similarity between juxtamembrane and cytoplasmic regions; accordingly, CTLA-4 is implicated in abrogating/reducing T-cell activity, and opposes the activity of CD28. CTLA-4 deficient mice have been shown to exhibit massive lymphoproliferation. Chambers et al., Lymphoproliferation in CTLA-4-deficient mice is mediated by costimulation-dependent activation of CD4+ T cells, Immunity. 1997 December; 7(6):885-95. It has been reported that CTLA-4 blockade augments T-cell responses both in vitro and in vivo, enhances an induced autoimmune disease, and exacerbates antitumor immunity. (See Luhder, J. Exp. Med. 1998; 187:427-432; Walunas et al., Immunity. 1994; 1:405-413; Kearney, J. Immunol. 1995; 155:1032-1036); Leach, Science 1996; 271:1734-1736). CTLA-4 has also been reported as having alternative and/or additional impact on the initial character of the T-cell immune response (Chambers, Curr. Opin. Immunol. 1997; 9:396-404; Bluestone, J. Immunol. 1997; 158:1989-1993; Thompson, Immunity 1997; 7:445-450).

The first immune-checkpoint inhibitor to be tested in a clinical trial was ipilimumab (Yervoy, Bristol-Myers Squibb), an CTLA-4 mAb. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAb is a powerful checkpoint inhibitor which removes "the break" from both naive and antigen-experienced cells. Therapy enhances the antitumor function of CD8+ T cells, increases the ratio of CD8+ T cells to Foxp3+ T regulatory cells, and inhibits the suppressive function of T regulatory cells. The major drawback to anti-CTLA-4 mAb therapy is the generation of autoimmune toxicities due to on-target effects of an over-exuberant immune system which has lost the ability to turn itself down. It has been reported that up to 25% of patients treated with ipilimumab developed serious grade 3-4 adverse events/autoimmune-type side effects including dermatitis, enterocolitis, hepatitis, endocrinopathies (including hypophysitis, thyroiditis, and adrenalitis), arthritis, uveitis, nephritis, and aseptic meningitis. In contrast to the anti-CTLA-4 experience, anti-PD-1 therapy appears to be better-tolerated and induces a relatively lower rate of autoimmune-type side effects.

In some embodiments, the immunotherapeutic agent is an agent that inhibits the activity of PD-1. In some embodiments, the immunotherapeutic agent is an agent that inhibits the activity of PD-L1 and/or PD-L2. In some embodiments, the immunotherapeutic agent is an agent that inhibits the activity of CTLA-4. In some embodiments, the immunotherapeutic agent is an agent that inhibits the activity of CD80 and/or CD86. In some embodiments, the immunotherapeutic agent is an agent that inhibits the activity of TIGIT. In some embodiments, the immunotherapeutic agent is an agent that inhibits the activity of KIR. In some embodiments, the immunotherapeutic agent is an agent that enhances or stimulates the activity of activating immune checkpoint receptors.

In some of the embodiments of the methods described herein, the immunotherapeutic agent is a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, or an IDO1 antagonist.

In some embodiments, the PD-1 antagonist is an antibody that specifically binds PD-1. In some embodiments, the antibody that binds PD-1 is pembrolizumab (KEYTRUDA®, MK-3475; Merck), pidilizumab (CT-011; Curetech Ltd.), nivolumab (OPDIVO®, BMS-936558, MDX-1106; Bristol Myer Squibb), MEDI0680 (AMP-514; AstraZenenca/MedImmune), REGN2810 (Regeneron Pharmaceuticals), BGB-A317 (BeiGene Ltd.), PDR-001 (Novartis), or STI-A1110 (Sorrento Therapeutics). In some embodiments, the antibody that binds PD-1 is described in PCT Publication WO 2014/179664, for example, an antibody identified as APE2058, APE1922, APE1923, APE1924, APE 1950, or APE1963 (Anaptysbio), or an antibody containing the CDR regions of any of these antibodies. In other embodiments, the PD-1 antagonist is a fusion protein that includes the extracellular domain of PD-L1 or PD-L2, for example, AMP-224 (AstraZeneca/MedImmune). In other embodiments, the PD-1 antagonist is a peptide inhibitor, for example, AUNP-12 (Aurigene).

In some embodiments, the PD-L1 antagonist is an antibody that specifically binds PD-L1. In some embodiments, the antibody that binds PD-L1 is atezolizumab (RG7446, MPDL3280A; Genentech), MEDI4736 (AstraZeneca/MedImmune), BMS-936559 (MDX-1105; Bristol Myers Squibb), avelumab (MSB0010718C; Merck KGaA), KD033 (Kadmon), the antibody portion of KD033, or STI-A1014 (Sorrento Therapeutics). In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies, the disclosure of which is incorporated herein by reference in its entirety.

In some embodiments, the CTLA-4 antagonist is an antibody that specifically binds CTLA-4. In some embodiments, the antibody that binds CTLA-4 is ipilimumab (YERVOY®; Bristol Myer Squibb) or tremelimumab (CP-675, 206; Pfizer). In some embodiments, the CTLA-4 antagonist a CTLA-4 fusion protein or soluble CTLA-4 receptor, for example, KARR-102 (Kahr Medical Ltd.).

In some embodiments, the LAG3 antagonist is an antibody that specifically binds LAG3. In some embodiments, the antibody that binds LAG3 is IMP701 (Prima BioMed), PIP731 (Prima BioMed/GlaxoSmithKline), BMS-986016 (Bristol Myer Squibb), LAG525 (Novartis), and GSK2831781 (GlaxoSmithKline). In some embodiments, the LAG3 antagonist includes a soluble LAG3 receptor, for example, IMP321 (Prima BioMed).

In some embodiments, the KIR antagonist is an antibody that specifically binds KTR. In some embodiments, the antibody that binds KIR is lirilumab (Bristol Myer Squibb/Innate Pharma).

In some embodiments, the immunotherapeutic agent used in the combinations disclosed herein (e.g., in combination with a compound of Formula I') is an activator or agonist of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In some embodiments, the OX40 agonist includes OX40 ligand, or an OX40-binding portion thereof. For example, the OX40 agonist may be MEDI6383 (AstraZeneca). In some embodiments, the OX40 agonist is an antibody that specifically binds OX40. In some embodiments, the antibody that binds OX40 is MEDI6469 (AstraZeneca/MedImmune), MEDI0562 (AstraZeneca/MedImmune), or MOXR0916 (RG7888; Genentech). In some embodiments, the OX40 agonist is a vector (e.g., an expression vector or virus, such as an adenovirus) capable of expressing OX40 ligand. In some embodiments the OX40-expressing vector is Delta-24-RGDOX (DNAtrix) or DNX2401 (DNAtrix).

In some embodiments, the 4-1BB (CD137) agonist is a binding molecule, such as an anticalin. In some embodiments, the anticalin is PRS-343 (Pieris AG). In some embodiments, the 4-1BB agonist is an antibody that specifically binds 4-1BB. In some embodiments, antibody that binds 4-1BB is PF-2566 (PF-05082566; Pfizer) or urelumab (BMS-663513; Bristol Myer Squibb).

In some embodiments, the CD27 agonist is an antibody that specifically binds CD27. In some embodiments, the antibody that binds CD27 is varlilumab (CDX-1127; Celldex).

In some embodiments, the GITR agonist comprises GITR ligand or a GITR-binding portion thereof. In some embodiments, the GITR agonist is an antibody that specifically binds GITR. In some embodiments, the antibody that binds GITR is TRX518 (GITR, Inc.), MK-4166 (Merck), or INBRX-110 (Five Prime Therapeutics/Inhibrx).

TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and TIM-3.

LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

PD-1 pathway blockade can be combined with vaccines or other a compound of Formula I' antibodies for improved therapeutic efficacy (Hirano, F. et al, Cancer Res., 65(3): 1089-1096 (2005); Li, B. et al, Clin. Cancer Res., 15: 1507-1509 (2009); and Curran, M. A. et al, Proc. Natl. Acad. Set, 107(9):4275-4280 (2010)).

In some embodiments, immunotherapeutic agents useful in the compositions and methods described herein may include a monoclonal antibody, a bispecific antibody comprising one or more immune checkpoint antigen binding moieties, a trispecific antibody, or an immune cell-engaging multivalent antibody/fusion protein/construct known in the art that target specifically both PD-1 and ligand PD-L1.

PD-1 (also known as Programmed Death 1, CD279, PDCD1) is a cell surface receptor with a critical role in regulating the balance between stimulatory and inhibitory signals in the immune system and maintaining peripheral tolerance (Ishida, Y et al. 1992 EMBO J. 11 3887; Kier, Mary E et al. 2008 Annu Rev Immunol 26 677-704; Okazaki, Taku et al. 2007 International Immunology 19 813-824). PD-1 is an inhibitory member of the immunoglobulin super-family with homology to CD28. The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Expression of PD-1 is inducible on T cells, B cells, natural killer (NK) cells and monocytes, for example upon lymphocyte activation via T cell receptor (TCR) or B cell receptor (BCR) signalling (Kier, Mary E et al. 2008 Annu Rev Immunol 26 677-704; Agata, Y et al 1996 Int Immunol 8 765-72). PD-1 is a receptor for the ligands CD80, CD86, PD-L1 (B7-H1, CD274) and PD-L2 (B7-DC, CD273), which are cell surface expressed members of the B7 family (Freeman, Gordon et al. 2000 J Exp Med 192 1027; Latchman, Y et al. 2001 Nat Immunol 2 261). Upon ligand engagement, PD-1 recruits phosphatases such as SUP-1 and SHP-2 to its intracellular tyrosine motifs which subsequently dephosphorylate effector molecules activated by TCR or BCR signalling (Chemnitz, J et al. 2004 J Immunol 173 945-954; Riley, James L 2009 Immunological Reviews 229 114-125) In this way, PD-1 transduces inhibitory signals into T and B cells only when it is engaged simultaneously with the TCR or BCR.

PD-1 has been demonstrated to down-regulate effector T cell responses via both cell-intrinsic and cell-extrinsic functional mechanisms. Inhibitory signaling through PD-1 induces a state of unresponsiveness in T cells, resulting in the cells being unable to clonally expand or produce optimal levels of effector cytokines. PD-1 may also induce apoptosis in T cells via its ability to inhibit survival signals from co-stimulation, which leads to reduced expression of key anti-apoptotic molecules such as Bcl-XL (Kier, Mary E et al. 2008 Annu Rev Immunol 26 677-704). In addition to these direct effects, recent publications have implicated PD-1 as being involved in the suppression of effector cells by promoting the induction and maintenance of regulatory T cells (TREG). For example, PD-L1 expressed on dendritic cells was shown to act in synergy with TGF-β to promote the induction of CD4+ FoxP3+TREG with enhanced suppressor function (Francisco, Loise M et al. 2009 J Exp Med 206 3015-3029).

TIM-3 (also known as T-cell immunoglobulin and mucin-domain containing-3, TIM-3, Hepatitis A virus cellular receptor 2, HAVCR2, HAVcr-2, KIM-3, TIMD-3, TIMD3, Tim-3, and CD366) is a ~33.4-kDa single-pass type I membrane protein involved in immune responses (Sanchez-Fueyo et al., Tim-3 inhibits T helper type 1-mediated auto- and alloimmune responses and promotes immunological tolerance, Nat. Immunol. 4:1093-1101(2003)).

TIM-3 is selectively expressed on Th1-cells, and phagocytic cells (e.g., macrophages and dendritic cells). The use of siRNA or a blocking antibody to reduce the expression of human resulted in increased secretion of interferon γ (IFN-γ) from CD4 positive T-cells, implicating the inhibitory role of TIM-3 in human T cells. Analysis of clinical samples from autoimmune disease patients showed no expression of TIM-3 in CD4 positive cells. In particular, expression level of TIM-3 is lower and secretion of IFN-γ is higher in T cell clones derived from the cerebrospinal fluid of patients with multiple sclerosis than those in clones derived from normal healthy persons (Koguchi K et al., J Exp Med. 203:1413-8. (2006)).

TIM-3 is the receptor for the ligands Galectin-9, which is a member of galectin family, molecules ubiquitously expressed on a variety of cell types and which binds β-galactoside; Phospatidyl serine (PtdSer) (DeKryff et al., T cell/transmembrane, Ig, and mucin-3 allelic variants differentially recognize phosphatidylserine and mediate phagocytosis of apoptotic cells, J Immunol. 2010 Feb. 15; 184(4): 1918-30); High Mobility Group Protein 1 (also known as HMGB1, HMG1, HMG3, SBP-1, HMG-1, and high mobility group box 1) Chiba et al., Tumor-infiltrating DCs suppress nucleic acid-mediated innate immune responses through interactions between the receptor TIM-3 and the alarmin HMGB1, Nat Immunol. 2012 September; 13(9): 832-42); and Carcinoembryonic Antigen Related Cell Adhesion Molecule 1 (also known as CEACAM1, BGP, BGP1, BGPI, carcinoembryonic antigen related cell adhesion molecule 1) (Huang et al., CEACAM1 regulates TIM-3-mediated tolerance and exhaustion, Nature. 2015 Jan. 15; 517 (7534):386-90).

BTLA (also known as B- and T-lymphocyte attenuator, BTLA1, CD272, and B and T lymphocyte associated) is a ~27.3-kDa single-pass type I membrane protein involved in lymphocyte inhibition during immune response. BTLA is constitutively expressed in both B and T cells. BTLA interacts with HVEM (herpes virus-entry mediator), a member of the tumor-necrosis factor receptor (TNFR) family (Gonzalez et al., Proc. Natl. Acad. Sci. USA, 2005, 102: 1116-21). The interaction of BTLA, which belongs to the CD28 family of the immunoglobulin superfamily, and HVEM, a costimulatory tumor-necrosis factor (TNF) receptor (TNFR), is unique in that it defines a cross talk between these two families of receptors. BTLA contains a membrane proximal immunoreceptor tyrosine-based inhibitory motif (ITIM) and membrane distal immunoreceptor tyrosine-based switch motif (ITSM). Disruption of either the ITIM or ITSM abrogated the ability of BTLA to recruit either SHP1 or SHP2, suggesting that BTLA recruits SHP1 and SHP2 in a manner distinct from PD-1 and both tyrosine motifs are required to block T cell activation. The BTLA cytoplasmic tail also contains a third conserved tyrosine-containing motif within the cytoplasmic domain, similar in sequence to a Grb-2 recruitment site (YXN). Also, a phosphorylated peptide containing this BTLA N-terminal tyrosine motif can interact with GRB2 and the p85 subunit of PI3K in vitro, although the functional effects of this interaction remain unexplored in vivo (Gavrieli et al., Bioochem. Biophysi Res Commun, 2003, 312, 1236-43). BTLA is the receptor for the ligands PTPN6/SHP-1; PTPN11/SHP-2; TNFRSF14/HVEM; and B7H4.

VISTA (also known as V-domain Ig suppressor of T cell activation VSIR, B7-H5, B7H5, GI24, PP2135, SISP1, DDlalpha, VISTA, C10orf54, chromosome 10 open reading frame 54, PD-1H, and V-set immunoregulatory receptor) is a ~33.9-kDa single-pass type I membrane protein involved in T-cell inhibitory response, embryonic stem cells differentiation via BMP4 signaling inhibition, and MMP14-mediated MMP2 activation (Yoon et al., Control of signaling-mediated clearance of apoptotic cells by the tumor suppressor p53, Science. 2015 Jul. 31; 349(6247): 1261669). VISTA interacts with the ligand VSIG-3 (Wang et al., VSIG-3 as a ligand of VISTA inhibits human T-cell function, Immunology. 2019 January; 156(1):74-85)

LAG-3 (also known as Lymphocyte-activation gene 3, LAG3, CD223, and lymphocyte activating 3) is a ~57.4-kDa single-pass type I membrane protein involved in lymphocyte activation that also binds to HLA class-II antigens. LAG-3 is a member of the immunoglobulin supergene family, and is expressed on activated T cells (Huard et al., 1994, Immunogenetics 39:213), NK cells (Triebel et al., 1990, J. Exp. Med. 171:1393-1405), regulatory T cells (Huang et al., 2004, Immunity 21:503-513; Camisaschi et al., 2010, J Immunol. 184:6545-6551; Gagliani et al., 2013, Nat Med 19:739-746), and plasmacytoid dendritic cells (DCs) (Workman et al., 2009, J Immunol 182:1885-1891). LAG-3 is a membrane protein encoded by a gene located on chromosome 12, and is structurally and genetically related to CD4. Similar to CD4, LAG-3 can interact with MHC class II molecules on the cell surface (Baixeras et al., 1992, J. Exp. Med. 176:327-337; Huard et al., 1996, Eur. J. Immunol. 26:1180-1186). It has been suggested that the direct binding of LAG-3 to MHC class II plays a role in down-regulating antigen-dependent stimulation of CD4+T lymphocytes (Huard et al., 1994, Eur. J. Immunol. 24:3216-3221) and LAG-3 blockade has also been shown to reinvigorate CD8+ lymphocytes in both tumor or self-antigen (Gross et al., 2007, J Clin Invest. 117:3383-3392) and viral models (Blackburn et al., 2009, Nat. Immunol. 10:29-37). Further, the intra-cytoplasmic region of LAG-3 can interact with LAP (LAG-3-associated protein), which is a signal transduction molecule involved in the downregulation of the CD3/TCR activation pathway (Iouzalen et al., 2001, Eur. J. Immunol. 31:2885-2891). Moreover, CD4+CD25+ regulatory T cells (Treg) have been shown to express LAG-3 upon activation, which contributes to the suppressor activity of Treg cells (Huang, C. et al., 2004, Immunity 21:503-513).

LAG-3 can also negatively regulate T cell homeostasis by Treg cells in both T cell-dependent and independent mechanisms (Workman, C. J. and Vignali, D. A., 2005, J. Immunol. 174:688-695).

LAG-3 has been shown to interact with MHC class II molecules (Huard et al., CD4/major histocompatibility complex class II interaction analyzed with CD4- and lymphocyte activation gene-3 (LAG-3)-Ig fusion proteins, Eur J Immunol. 1995 September; 25(9):2718-21).

Additionally, several kinases are known to be checkpoint inhibitors. For example, CHEK-1, CHEK-2, and A2aR.

CHEK-1 (also known as CHK 1 kinase, CHK1, and checkpoint kinase 1) is a ~54.4-kDa serine/threonine-protein kinase that is involved with checkpoint-mediated cell cycle arrest, and the activation of DNA repair in response to the DNA damage and/or unreplicated DNA.

CHEK-2 (also known as CHK2 kinase, CDS1, CHK2, HuCds1, LFS2, PP1425, RAD53, hCds1, and checkpoint kinase 2) is a ~60.9-kDa. serine/threonine-protein kinase involved in checkpoint-mediated cell cycle arrest, DNA-repair activation, and double-strand break-mediated apoptosis.

A2aR (also known as adenosine A2A receptor, ADORA2A, adenosine A2a receptor, A2aR, ADORA2, and RDC8) is a ~44.7-kDa multi-pass membrane receptor for adenosine and other ligands.

In various embodiments, the immunotherapeutic agent can comprise an antibody or an antigen binding fragment thereof. Within this definition, immune checkpoint inhibitors include bispecific antibodies and immune cell-engaging multivalent antibody/fusion protein/constructs known in the art. In some embodiments, immunotherapeutic agents which comprise bispecific antibodies may include bispecific antibodies that are bivalent and bind either the same epitope of the immune checkpoint molecule, two different epitopes of the same immune checkpoint molecule or different epitopes of two different immune checkpoints.

Persons of ordinary skill in the art can implement several bispecific antibody formats known in the field to target one or more of CTLA4, PD1, PD-L1 TIM-3, LAG-3, various B-7 ligands, B7H3, B7H4, CHK 1 and CHK2 kinases, BTLA, A2aR, OX40, 41BB, LIGHT, CD40, GITR, TGF-beta, SIRP-alpha, TIGIT, VSIG8, SIGLEC7, SIGLEC9, ICOS, FAS, BTNL2 and other for use in the combination described herein.

In various embodiments, the immunotherapeutic agent can include am immune cell-engaging multivalent antibody/fusion protein/construct.

In an embodiment of the disclosure, the checkpoint inhibitor, in combination with a compound of Formula I', is used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression.

In a further embodiment of the disclosure, there is provided a combination therapy for treating cancer, comprising a compound of Formula I' and blockade of checkpoint inhibitors with the potential to elicit potent and durable immune responses with enhanced therapeutic benefit and more manageable toxicity.

In a further embodiment of the disclosure, there is provided a combination therapy for treating cancer, comprising a compound of Formula I' and an immune checkpoint inhibitor. In an embodiment of the disclosure is provided a method for treating cancer and/or preventing the establishment of metastases by employing a checkpoint inhibitor which act synergistically with a compound of Formula I'.

In further embodiments, methods of the disclosure include, one or more of the following: 1) reducing or inhibiting growth, proliferation, mobility or invasiveness of a tumor or cancer cells that potentially or do develop metastases, 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established, 4) reducing or inhibiting formation or establishment of additional metastasis after the metastasis has been formed or established, 5) prolonged overall survival, 6) prolonged progression free survival, or 7) disease stabilization.

In an embodiment of the disclosure, administration of the immunotherapeutic agent, in combination therapy with a compound of Formula I', provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumor or cancer, or metastasis, i e., a therapeutic benefit or a beneficial effect.

A therapeutic benefit or beneficial effect is any objective or subjective, transient, temporary, or long-term improvement in the condition or pathology, or a reduction in onset, severity, duration or frequency of adverse symptom associated with or caused by cell proliferation or a cellular hyperproliferative disorder such as a neoplasia, tumor or cancer, or metastasis. It may lead to improved survival. A satisfactory clinical endpoint of a treatment method in accordance with the disclosure is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumor or cancer, or metastasis. A therapeutic benefit or improvement therefore may be, but is not limited to destruction of target proliferating cells (e.g., neoplasia, tumor or cancer, or metastasis) or ablation of one or more, most or all pathologies, adverse symptoms or complications associated with or caused by cell proliferation or the cellular hyperproliferative disorder such as a neoplasia, tumor or cancer, or metastasis. However, a therapeutic benefit or improvement need not be a cure or complete destruction of all target proliferating cells (e.g., neoplasia, tumor or cancer, or metastasis) or ablation of all pathologies, adverse symptoms or complications associated with or caused by cell proliferation or the cellular hyperproliferative disorder such as a neoplasia, tumor or cancer, or metastasis. For example, partial destruction of a tumor or cancer cell mass, or a stabilization of the tumor or cancer mass, size or cell numbers by inhibiting progression or worsening of the tumor or cancer, can reduce mortality and prolong lifespan even if only for a few days, weeks or months, even though a portion or the bulk of the tumor or cancer mass, size or cells remain.

Specific non-limiting examples of therapeutic benefit include a reduction in neoplasia, tumor or cancer, or metastasis volume (size or cell mass) or numbers of cells, inhibiting or preventing an increase in neoplasia, tumor or cancer volume (e.g., stabilizing), slowing or inhibiting neoplasia, tumor or cancer progression, worsening or metastasis, or inhibiting neoplasia, tumor or cancer proliferation, growth or metastasis.

In an embodiment of the disclosure, administration of the immunotherapeutic agent, in combination therapy with a compound of Formula I', provides a detectable or measurable improvement or overall response according to the irRC (as derived from time-point response assessments and based on tumor burden), including one of more of the following: (i) irCR—complete disappearance of all lesions, whether measurable or not, and no new lesions (confirmation by a repeat, consecutive assessment no less than 4 weeks from the date first documented), (ii) irPR—decrease in tumor burden .gtoreq.50% relative to baseline (confirmed by a consecutive assessment at least 4 weeks after first documentation).

Optionally, any method described herein may not take effect immediately. For example, treatment may be followed by an increase in the neoplasia, tumor or cancer cell numbers or mass, but over time eventual stabilization or reduction in tumor cell mass, size or numbers of cells in a given subject may subsequently occur.

Additional adverse symptoms and complications associated with neoplasia, tumor, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of adverse symptom or complication associated with or caused by a cellular hyperproliferative disorder, an improvement in the subjects quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In additional embodiment, a method prolongs or extends lifespan (survival) of the subject. In a further embodiment, a method improves the quality of life of the subject.

In one embodiment, administration of the immunotherapeutic agent, in combination therapy with a compound of Formula I', results in a clinically relevant improvement in one or more markers of disease status and progression selected from one or more of the following: (i): overall survival, (ii): progression-free survival, (iii): overall response rate, (iv): reduction in metastatic disease, (v): circulating levels of tumor antigens such as carbohydrate antigen 19.9 (CA19.9) and carcinembryonic antigen (CEA) or others depending on tumor, (vii) nutritional status (weight, appetite, serum albumin), (viii): pain control or analgesic use, (ix): CRP/albumin ratio.

Treatment with a compound of Formula I' in combination with an immunotherapeutic agent gives rise to more complex immunity including not only the development of innate immunity and type-1 immunity, but also immunoregulation which more efficiently restores appropriate immune functions.

In various exemplary methods, a checkpoint inhibitor antibody (monoclonal or polyclonal, bispecific, trispecific, or an immune cell-engaging multivalent antibody/fusion protein/construct) directed to a checkpoint molecule of interest (e.g., PD-1) may be sequenced and the polynucleotide sequence may then be cloned into a vector for expression or propagation. The sequence encoding the antibody or antigen-binding fragment thereof of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, methods for producing the recombinant antibodies can include the steps of culturing a host cell containing isolated nucleic acid(s) encoding the antibodies of the present disclosure. Methods for culturing a host cell containing isolated nucleic acid(s) encoding the antibodies of the present disclosure can be done in a variety of ways, depending on the nature of the antibody. In some embodiments, in the case where the antibodies of the disclosure are full length traditional antibodies, for example, a heavy chain variable region and a light chain variable region under conditions such that an antibody is produced and can be isolated.

In general, nucleic acids are provided that encode the antibodies or antigen-binding fragments thereof of the present disclosure. Such polynucleotides encode for both the variable and constant regions of each of the heavy and light chains, although other combinations are also contemplated by the present disclosure. The present disclosure also contemplates oligonucleotide fragments derived from the disclosed polynucleotides and nucleic acid sequences complementary to these polynucleotides.

The polynucleotides can be in the form of RNA, DNA, cDNA, genomic DNA, nucleic acid analogs, and synthetic DNA. The DNA may be double-stranded or single-stranded, and if single stranded, may be the coding (sense) strand or non-coding (anti-sense) strand. The coding sequence that encodes the polypeptide may be identical to the coding sequence or may be a different coding sequence, which sequence, as a result of the redundancy or degeneracy of the genetic code, encodes the same polypeptides.

In some embodiments, nucleic acid(s) encoding the antibodies of the present disclosure are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, and the like) or other components (selection genes, and the like), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, and the like.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, and the like), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, VA USA. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

Exemplary and illustrative recombinant methods for antibody molecular biology, expression, purification, and screening are described, for example, in Antibody Engineering, edited by Kontermann & Dubel, Springer, Heidelberg, 2001 and 2010 Hayhurst & Georgiou, 2001, Curr. Opin. Chem. Biol. 5:683-689; Maynard & Georgiou, 2000, Annu. Rev. Biomed.

Eng. 2:339-76; and Morrison, S. (1985) Science 229: 1202, the disclosures of which are incorporated herein by reference in their entireties.

In various embodiments, the polynucleotide sequence encoding the selected variable heavy and light chains may be used for genetic manipulation to humanize the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Immune checkpoint modulator antibodies of the present disclosure can be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or in yeast cells (e.g. *Pichia pastoris* or *Saccharomyces cerevisiae*. Methods for expressing antibodies recombinantly in plants or yeast have been disclosed. See, for example, Peeters, et al. Vaccine 19:2756, 2001; Lonberg, N. and D. Huszar Int. Rev. Immunol 13:65, 1995; and Horwitz, A. H. et al., Proc. Natl. Acad.

Sci. 85:8678-8682; the disclosures of which are hereby incorporated by reference in their entireties. Methods for making derivatives of antibodies, e.g., domain, single chain, and the like are known in the art.

Immunoassays and flow cytometry sorting techniques such as fluorescence activated cell sorting (FACS) can also be employed to isolate antibodies that are specific for checkpoint molecules.

In some embodiments, a polynucleotide comprises a sequence encoding the heavy chain and/or the light chain variable regions of the checkpoint inhibitor antibody or antigen-binding fragment thereof of the present disclosure. The sequence encoding the antibody or antigen-binding fragment thereof of interest may be maintained in a vector in a host cell and the host cell can then be expanded and frozen for future use. Vectors (including expression vectors) and host cells are further described herein.

The disclosure includes affinity matured checkpoint modulator antibodies. For example, affinity matured antibodies can be produced by procedures known in the art (Marks et al., 1992, Bio/Technology, 10:779-783; Barbas et al., 1994, Proc Nat. Acad. Sci. USA 91:3809-3813. One way of characterizing a CDR of an antibody and/or altering (such as improving) the binding affinity of a polypeptide, such as an antibody, termed "library scanning mutagenesis". An exemplary method for providing affinity matures antibodies and antigen-binding fragments can include replacing one or more amino acid positions in the CDR with two or more (such as 3, 4, 5, 6, 7, 8, 9, 10, 11, 12, 13, 14, 15, 16, 17, 18, 19, or 20) amino acids using art recognized methods. a library of clones are generated, each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a KD of about 10 nM or lower. The library of clones can then be recombinantly introduced into a selection construct using any method known in the art for selection, including phage display, yeast display, and ribosome display.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the KD of the antibody directed to a checkpoint molecule, to increase or decrease kon or to alter the binding specificity of the antibody. Techniques in site-directed mutagenesis are well-known in the art. See, e.g., Sambrook et al. and Ausubel et al.

Pharmaceutical compositions containing a compound of Formula I' according to the present disclosure will comprise an effective amount of a compound of Formula I', an immunotherapeutic agent, and/or both, typically dispersed in a pharmaceutically acceptable carrier. The phrases "pharmaceutically or pharmacologically acceptable" refers to molecular entities and compositions that do not produce adverse, allergic or other untoward reaction when administered to animal, such as, for example, a human, as appropriate. The preparation of an pharmaceutical composition that contains a compound of Formula I' will be known to those of skill in the art in light of the present disclosure, as exemplified by Remington's Pharmaceutical Sciences, 18th Ed. Mack Printing Company, 1990, Moreover, for animal (e.g., human) administration, it will be understood that preparations should meet sterility, pyrogenicity, general safety and purity standards. A specific example of a pharmacologically acceptable carrier for a combination compositions, containing a compound of Formula I' in admixture with an immunotherapeutic agent as described herein is borate buffer or sterile saline solution (0.9% NaCl).

Formulations of the an immunotherapeutic agent, for example an immune checkpoint modulator antibody used in accordance with the present disclosure can be prepared for storage by mixing an antibody having the desired degree of purity with optional pharmaceutically acceptable carriers, excipients or stabilizers as amply described and illustrated in Remington's Pharmaceutical Sciences 16th edition, Osol, A. Ed. [1980], in the form of lyophilized formulations or aqueous solutions and/or suspensions. Acceptable carriers, excipients, buffers or stabilizers are nontoxic to recipients at the dosages and concentrations employed, and include suitable aqueous and/or non-aqueous excipients that may be employed in the pharmaceutical compositions of the disclosure, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, buffers such as phosphate, citrate, and other organic acids. Antioxidants may be included, for example, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like; preservatives (such as octade-cyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues). Other exemplary pharmaceutically acceptable excipients may include polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In one illustrative embodiment, the pharmaceutical compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. In some embodiments, the checkpoint inhibitor antibodies or antigen-binding fragments thereof of the present disclosure are formulated for and can be lyophilized for storage and reconstituted in a suitable excipient prior to use according to art-known lyophilization and reconstitution techniques. In one exemplary pharmaceutical composition containing one or more checkpoint inhibitor antibodies or antigen-binding fragment thereof, the composition is formulated as a sterile, preservative-free solution of one or more checkpoint inhibitor antibodies or antigen-binding fragment thereof for intravenous or subcutaneous administration. The formulation can be supplied as either a single-use, prefilled pen, as a single-use, for example containing about 1 mL prefilled glass syringe, or as a single-use institutional use vial. Preferably, the pharmaceutical composition containing the checkpoint inhibitor antibody or antigen-binding fragment thereof is clear and colorless, with a pH of about 6.9-5.0, preferably a pH of 6.5-5.0, and even more preferably a pH ranging from about 6.0 to about 5.0. In various embodiments, the formulations comprising the pharmaceutical compositions can contain from about 500 mg to about 10 mg, or from about 400 mg to about 20 mg, or from about 300 mg to about 30 mg or from about 200 mg to about 50 mg of the checkpoint inhibitor antibody or antigen-binding fragment thereof per mL of solution when reconstituted and administered to the subject. Exemplary injection or infusion excipients can include mannitol, citric acid monohydrate, dibasic sodium phosphate dihydrate, monobasic sodium phosphate dihydrate, polysorbate 80, sodium chloride, sodium citrate and water for parenteral administration, for example, intravenously, intramuscularly, intraperitoneally, or subcutaneous administration.

In another exemplary embodiment, one or more immunotherapeutic agents, or an antigen-binding fragment thereof is formulated for intravenous or subcutaneous administration as a sterile aqueous solution containing 1-75 mg/mL, or more preferably, about 5-60 mg/mL, or yet more preferably, about 10-50 mg/mL, or even more preferably, about 10-40 mg/mL of antibody, with sodium acetate, polysorbate 80, and sodium chloride at a pH ranging from about 5 to 6. Preferably, the intravenous or subcutaneous formulation is a sterile aqueous solution containing 5, 10, 15, 20, 25, 30, 35, 40, 45, or 50 mg/mL of the immunotherapeutic agent, for example, an immune checkpoint inhibitor antibody or an antigen-binding fragment thereof, with 20 mM sodium acetate, 0.2 mg/mL polysorbate 80, and 140 mM sodium chloride at pH 5.5. Further, a solution comprising a checkpoint inhibitor antibody or an antigen-binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 5-500 mg of an immunotherapeutic agent or antigen-binding fragment thereof of the present disclosure, 10 mM histidine, 5% sucrose, and 0.01% polysorbate 80 at pH 5.8, with or without a compound of Formula I'. This composition may be provided as a lyophilized powder. When the powder is reconstituted at full volume, the composition retains the same formulation. Alternatively, the powder may be reconstituted at half volume, in which case the composition comprises 10-500 mg of an immunotherapeutic agent or antigen-binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the immunotherapeutic agent formulation. For example, from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof, may be given as a bolus, and the rest of the antibody dose may be administered by intravenous injection. A predetermined dose of the immunotherapeutic agent, or antigen-binding fragment thereof, may be administered, for example, over a period of an hour to two hours to five hours.

In a further embodiment, part of the dose is administered by a subcutaneous injection and/or infusion in the form of a bolus and the rest by infusion of the immunotherapeutic agent formulation. In some exemplary doses, the immunotherapeutic agent formulation can be administered subcutaneously in a dose ranging from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof. In some embodiments the dose may be given as a bolus, and the rest of the immunotherapeutic agent dose may be administered by subcutaneous or intravenous injection. A predetermined dose of the immunotherapeutic agent, or antigen-binding fragment thereof, may be administered, for example, over a period of an hour to two hours to five hours.

The formulation herein may also contain more than one active compound as necessary for the particular indication being treated, preferably those with complementary activities that do not adversely affect each other. For example, it may be desirable to provide one or more immunotherapeutic agents with other specificities. Alternatively, or in addition, the composition may comprise an anti-inflammatory agent, a chemotherapeutic agent, a cytotoxic agent, a cytokine, a growth inhibitory agent and/or a small molecule antagonist.

Such molecules are suitably present in combination in amounts that are effective for the purpose intended.

The formulations to be used for in vivo administration should be sterile, or nearly so. This is readily accomplished by filtration through sterile filtration membranes.

In various embodiments, illustrative formulations of the pharmaceutical compositions described herein can be prepared using methods widely known in the field of pharmaceutical formulations. In general, such preparatory methods can include the step of bringing the active ingredient into association with a carrier or one or more other accessory ingredients, and then, if desirable, packaging the product into a desired single- or multi-dose unit.

In some embodiments, the composition comprising a compound of Formula I' can be also delivered in a vesicle, and the immunotherapeutic agent can be delivered in the same liposome formulation, or in a separate formulation that is compatible with the liposomal formulation containing the compound of Formula I', In some illustrative examples, a liposome containing one or more liposomal surface moieties for example, polyethylene glycol, antibodies and antibody fragments thereof that target a desired tumor surface antigen, receptor, growth factor, glycoprotein, glycolipid or neoantigen, which are selectively transported into specific cells or organs, thus enhance targeted drug delivery.

In another embodiment, a compound of Formula I' can be delivered in a vesicle, in particular a liposome (see Langer, Science 249:1527-1533 (1990); Treat et al., in LIPOSOMES IN THE THERAPY OF INFECTIOUS DISEASE AND CANCER, Lopez-Berestein and Fidler (eds.), Liss, N.Y., pp. 353-365 (1989); Lopez-Berestein, ibid., pp. 317-327; see generally ibid.).

In yet another embodiment, a compound of Formula I', or the composition containing the combination, or a composition containing the immunotherapeutic agent, can be delivered in a controlled release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, controlled release of the compound of Formula I' can comprise polymeric materials to provide sustained, intermediate, pulsatile, or alternate release (see MEDICAL APPLICATIONS OF CONTROLLED RELEASE, Langer and Wise (eds.), CRC Pres., Boca Raton, Fla. (1974); CONTROLLED DRUG BIO-AVAILABILITY, DRUG PRODUCT DESIGN AND PERFORMANCE, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351(1989); Howard et al., J. Neurosurg. 71:105 (1989)). Other controlled-release systems discussed in the review by Langer (Science 249:1527-1533 (1990)) can be used.

The optimum concentration of the active ingredient(s) in the chosen medium can be determined empirically, according to procedures well known to the skilled artisan, and will depend on the ultimate pharmaceutical formulation desired and the use to be employed.

The present disclosure also provides a pharmaceutical pack or kit comprising one or more containers filled with one or more of the ingredients of the pharmaceutical compositions of the disclosure, which at minimum will include a compound of Formula I' and one or more checkpoint inhibitor antibodies or antigen-binding fragment thereof as described herein. In other embodiments, the kit may contain one or more further containers providing a pharmaceutically acceptable excipient, for example a diluent. In one embodiment a kit may comprise at least one container, wherein the container can include a compound of Formula I', a checkpoint inhibitor antibody or an antigen-binding fragment thereof of the present disclosure. The kit may also include a set of instructions for preparing and administering the final pharmaceutical composition to the subject in need thereof, for the treatment of a checkpoint molecule-mediated disease or disorder.

Some embodiments of the present disclosure, the immunotherapeutic agent is a population of immune cells, which can be administered in combination with a compound of Formula I' to treat a subject with cancer. In some embodiments, the immunotherapeutic agent is a population of immune cells, such as leukocytes (nucleated white blood cells), comprising (e.g., expressing) a receptor that binds to an antigen of interest. A leukocyte of the present disclosure may be, for example, a neutrophil, eosinophil, basophil, lymphocyte or a monocyte. In some embodiments, a leukocyte is a lymphocyte. Examples of lymphocytes include T cells, B cells, Natural Killer (NK) cells or NKT cells. In some embodiments, a T-cell is a CD4+ Th (T helper) cell, a CD8+ cytotoxic T cell, a γδT cell or a regulatory (suppressor) T cell. In some embodiments, an immune cell is a dendritic cell.

Immune cells of the present disclosure, in some embodiments, are genetically engineered to express an antigen-binding receptor. A cell is considered "engineered" if it contains an engineered (exogenous) nucleic acid. Engineered nucleic acids of the present disclosure may be introduced into a cell by any known (e.g., conventional) method. For example, an engineered nucleic acid may be introduced into a cell by electroporation (see, e.g., Heiser W. C. Transcription Factor Protocols: Methods in Molecular Biology™ 2000; 130: 117-134), chemical (e.g., calcium phosphate or lipid), transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see, e.g., Schaffner W. Proc Natl Acad Sci USA. 1980 April; 77(4): 2163-7), microinjection of purified DNA directly into the nucleus of the cell (see, e.g., Capecchi M. R. Cell. 1980 November; 22(2 Pt 2): 479-88), or retrovirus transduction.

Some aspects of the present disclosure provide an "adoptive cell" approach, which involves isolating immune cells (e.g., T-cells) from a subject with cancer, genetically engineering the immune cells (e.g., to express an antigen-binding receptor, such as a chimeric antigen receptor), expanding the cells ex vivo, and then re-introducing the immune cells into the subject. This method results in a greater number of engineered immune cells in the subject relative to what could be achieved by conventional gene delivery and vaccination methods. In some embodiments, immune cells are isolated from a subject, expanded ex vivo without genetic modification, and then re-introduced into the subject.

Immune cells of the present disclosure comprise receptors that bind to antigens, such as an antigen encoded by an exogenously delivered nucleic acid, as provided herein. In some embodiments, a leukocyte is modified (e.g., genetically modified) to express a receptor that binds to an antigen. The receptor may be, in some embodiments, a naturally-occurring antigen receptor (normally expressed on the immune cell), recombinant antigen receptor (not normally expressed on the immune cell) or a chimeric antigen receptor (CAR). Naturally-occurring and recombinant antigen receptors encompassed by the present disclosure include T cell receptors, B cell receptors, NK cell receptors, NKT cell receptors and dendritic cell receptors. A "chimeric antigen receptor" refers to an artificial immune cell receptor that is engineered to recognize and bind to an antigen expressed by tumor cells. Generally, a CAR is designed for a T cell and is a chimera of a signaling domain of the T-cell receptor (TcR) complex and an antigen-recognizing domain (e.g., a single chain fragment (scFv) of an antibody) (Enblad et al., Human Gene Therapy. 2015; 26(8):498-505), the disclosure of which is incorporated herein by reference in its entirety.

In some embodiments, an antigen binding receptor is a chimeric antigen receptor (CAR). A T cell that expressed a CAR is referred to as a "CAR T cell." A CAR T cell receptor, in some embodiments, comprises a signaling domain of the T-cell receptor (TcR) complex and an antigen-recognizing domain (e.g., a single chain fragment (scFv) of an antibody) (Enblad et al., Human Gene Therapy. 2015; 26(8):498-505) the disclosure of which is incorporated herein by reference in its entirety.

There are four generations of CARs, each of which contains different components. First generation CARs join an antibody-derived scFv to the CD3zeta (zeta. or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TcR CD3-zeta chain. Third-generation costimulatory domains may include, e.g., a combination of CD3z, CD27, CD28, 4-1BB, ICOS, or OX40. CARs, in some embodiments, contain an ectodomain (e.g., CD3), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2):151-155) the disclosure of which is incorporated herein by reference in its entirety.

In some embodiments, the chimeric antigen receptor (CAR) is a T-cell redirected for universal cytokine killing (TRUCK), also known as a fourth generation CAR. TRUCKs are CAR-redirected T-cells used as vehicles to produce and release a transgenic cytokine that accumulates in the targeted tissue, e.g., a targeted tumor tissue. The transgenic cytokine is released upon CAR engagement of the target. TRUCK cells may deposit a variety of therapeutic cytokines in the target. This may result in therapeutic concentrations at the targeted site and avoid systemic toxicity.

CARs typically differ in their functional properties. The CD3zeta signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence.

Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the T-cell response. See, for example, Enblad et al., Human Gene Therapy. 2015; 26(8):498-505; Chmielewski and Hinrich, Expert Opinion on Biological Therapy. 2015; 15(8): 1145-1154 the disclosures of which are incorporated herein by reference in their entireties.

In some embodiments, an illustrative immunotherapeutic agent is a first generation chimeric antigen receptor CAR. In some embodiments, a chimeric antigen receptor is a third generation CAR. In some embodiments, a chimeric antigen receptor is a second generation CAR. In some embodiments, a chimeric antigen receptor is a third generation CAR. In some embodiments, the chimeric antigen receptor is a fourth generation CAR or a T-cell redirected for universal cytokine killing (TRUCK).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. In some embodiments, a "spacer" domain or "hinge" domain is located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR of the disclosure comprises an antigen binding domain, such as a single chain Fv (scFv) specific for a tumor antigen. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to an antigen on a tumor cell encoded by an engineered nucleic acid, as provided herein.

An antigen binding domain (e.g., an scFv) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on tumor cells. Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (Mabs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. Molecular Therapy Nucleic Acids 2013; 2:e105, incorporated herein by reference in its entirety). Thus, methods, in some embodiments, comprise delivering to a tumor a combination comprising a compound of Formula I' and an immunotherapeutic agent, wherein the immunotherapeutic agent is an engineered nucleic acid that encodes an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

In some embodiments, a CAR is an antigen-specific inhibitory CAR (iCAR), which may be used, for example, to avoid off-tumor toxicity (Fedorov, V D et al. Sci. Transl. Med. published online Dec. 11, 2013, incorporated herein by reference in its entirety). iCARs contain an antigen-specific inhibitory receptor, for example, to block nonspecific immunosuppression, which may result from extra tumor target expression. iCARs may be based, for example, on inhibitory molecules CTLA-4 or PD-1. In some embodiments, these iCARs block T cell responses from T cells activated by either their endogenous T cell receptor or an activating CAR. In some embodiments, this inhibiting effect is temporary.

In some embodiments, CARs may be used in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., Cytotherapy. 2003; 5(3): 211-226; Maude et al., Blood. 2015; 125(26): 4017-4023, each of which is incorporated herein by reference in their entireties).

According to other aspects of the disclosure, the tumor antigenic component in the vaccine of the invention is any natural or synthetic tumor-associated protein or peptide or combination of tumor-associated proteins and/or peptides or glycoproteins or glycopeptides. In still yet other aspects, the antigenic component can be patient-specific or common to many or most patients with a particular type of cancer. According to one aspect, the antigenic component consists of a cell lysate derived from tumor tissue removed from the patient being treated. In another aspect, the lysate can be engineered or synthesized from exosomes derived from tumor tissue. In yet another aspect, the antigenic component consists of a cell lysate derived from tumor tissue extracted from one or more unrelated individuals or from tumor-cell lines.

In various embodiments, an illustrative immunotherapeutic agent comprises one or more cancer vaccines, for use in combination with a compound of Formula I'. The tumor-associated antigen component of the vaccine may be manufactured by any of a variety of well-known techniques. For individual protein components, the antigenic protein is isolated from tumor tissue or a tumor-cell line by standard chromatographic means such as high-pressure liquid chromatography or affinity chromatography or, alternatively, it is synthesized by standard recombinant DNA technology in a suitable expression system, such as $E.\ coli$, yeast or plants. The tumor-associated antigenic protein is then purified from the expression system by standard chromatographic means. In the case of peptide antigenic components, these are generally prepared by standard automated synthesis. Proteins and peptides can be modified by addition of amino acids, lipids and other agents to improve their incorporation into the delivery system of the vaccine (such as a multilamellar liposome). For a tumor-associated antigenic component derived from the patient's own tumor, or tumors from other individuals, or cell lines, the tumor tissue, or a single cell suspension derived from the tumor tissue, is typically homogenized in a suitable buffer. The homogenate can also be fractionated, such as by centrifugation, to isolate particular cellular components such as cell membranes or soluble material. The tumor material can be used directly or tumor-associated antigens can be extracted for incorporation in the vaccine using a buffer containing a low concentration of a suitable agent such as a detergent. An example of a suitable detergent for extracting antigenic proteins from tumor tissue, tumor cells, and tumor-cell membranes is diheptanoyl phosphatidylcholine. Exosomes derived from tumor tissue or tumor cells, whether autologous or heterologous to the patient, can be used for the antigenic component for incorporation in the vaccine or as a starting material for extraction of tumor-associated antigens.

In some embodiments of the present disclosure, a cancer vaccine, wherein the cancer vaccine includes at least one tumor-associated antigen, at least one immunostimulant, and optionally, at least one cell-based immunotherapeutic agent. In some embodiments, the immunostimulant component in the cancer vaccine of the disclosure is any Biological Response Modifier (BRM) with the ability to enhance the therapeutic cancer vaccine's effectiveness to induce humoral and cellular immune responses against cancer cells in a patient. According to one aspect, the immunostimulant is a cytokine or combination of cytokines. Examples of such cytokines include the interferons, such as IFN-gamma, the interleukins, such as IL-2, IL-15 and IL-23, the colony stimulating factors, such as M-CSF and GM-CSF, and tumor necrosis factor. According to another aspect, the immunostimulant component of the disclosed cancer vaccine includes one or more adjuvant-type immunostimulatory agents such as APC Toll-like Receptor agonists or costimulatory/cell adhesion membrane proteins, with or without immunostimulatory cytokines. Examples of Toll-like Receptor agonists include lipid A and CpG, and costimulatory/adhesion proteins such as CD80, CD86, and ICAM-1.

In some embodiments, the immunostimulant is selected from the group consisting of IFN-gamma (IFN-γ), IL-2, IL-15, IL-23, M-CSF, GM-CSF, tumor necrosis factor, lipid A, CpG, CD80, CD86, and ICAM-1, or combinations thereof. According to other aspects, the cell-based immunotherapeutic agent is selected from the group consisting of dendritic cells, tumor-infiltrating T lymphocytes, chimeric antigen receptor-modified T effector cells directed to the patient's tumor type, B lymphocytes, natural killer cells, bone marrow cells, and any other cell of a patient's immune system, or combinations thereof. In one aspect, the cancer vaccine immunostimulant includes one or more cytokines, such as interleukin 2 (IL-2), GM-CSF, M-CSF, and interferon-gamma (IFN-γ), one or more Toll-like Receptor agonists and/or adjuvants, such as monophosphoryl lipid A, lipid A, muramyl dipeptide (MDP) lipid conjugate and double stranded RNA, or one or more costimulatory membrane proteins and/or cell adhesion proteins, such CD80, CD86 and ICAM-1, or any combination of the above. In one aspect, the cancer vaccine includes an immunostimulant that is a cytokine selected from the group consisting of interleukin 2 (IL-2), GM-CSF, M-CSF, and interferon-gamma (IFN-γ). In another aspect, the cancer vaccine includes an immunostimulant that is a Toll-like Receptor agonist and/or adjuvant selected from the group consisting of monophosphoryl lipid A, lipid A, and muramyl dipeptide (MDP) lipid conjugate and double stranded RNA. In yet another aspect, the cancer vaccine includes an immunostimulant that is a costimulatory membrane protein and/or cell adhesion protein selected from the group consisting of CD80, CD86, and ICAM-1.

In various embodiments, an immunotherapeutic agent can include a cancer vaccine, wherein the cancer vaccine incorporates any tumor antigen that can be potentially used to construct a fusion protein according to the invention and particularly the following:

(a) cancer-testis antigens including NY-ESO-1, SSX2, SCP1 as well as RAGE, BAGE, GAGE and MAGE family polypeptides, for example, GAGE-1, GAGE-2, MAGE-1 MAGE-2, MAGE-3, MAGE-4, MAGE-5, MAGE-6, and MAGE-12, which can be used, for example, to address melanoma, lung, head and neck, NSCLC, breast, gastrointestinal, and bladder tumors; (b) mutated antigens, including p53, associated with various solid tumors, e.g., colorectal, lung, head and neck cancer; p21/Ras associated with, e.g., melanoma, pancreatic cancer and colorectal cancer; CDK4, associated with, e.g., melanoma; MUM1 associated with, e.g., melanoma; caspase-8 associated with, e.g., head and neck cancer; CIA 0205 associated with, e.g., bladder cancer; HLA-A2-R1701, beta catenin associated with, e.g., melanoma; TCR associated with, e.g., T-cell non-Hodgkin lymphoma; BCR-abl associated with, e.g., chronic myelogenous leukemia; triosephosphate isomerase; KIA 0205; CDC-27, and LDLR-FUT; (c) over-expressed antigens, including, Galectin 4 associated with, e.g., colorectal cancer; Galectin 9 associated with, e.g., Hodgkin's disease; proteinase 3 associated with, e.g., chronic myelogenous leukemia; WT 1 associated with, e.g., various leukemias; carbonic anhydrase associated with, e.g., renal cancer; aldolase A associated with, e.g., lung cancer; PRAME associated with, e.g., melanoma; HER-2/neu associated with, e.g., breast, colon, lung and ovarian cancer; mammaglobin, alpha-fetoprotein associated with, e.g., hepatoma; KSA associated with, e.g., colorectal cancer; gastrin associated with, e.g., pancreatic and gastric cancer; telomerase catalytic protein, MUC-1 associated with, e.g., breast and ovarian cancer; G-250 associated with, e.g., renal cell carcinoma; p53 associated with, e.g., breast, colon cancer; and carcinoembryonic antigen associated with, e.g., breast cancer, lung cancer, and cancers of the gastrointestinal tract such as colorectal cancer; (d) shared antigens, including melanoma-melanocyte differentiation antigens such as MART-1/Melan A; gp100; MC1R; melanocyte-stimulating hormone receptor; tyrosinase; tyrosinase related protein-1/TRP1 and tyrosinase related protein-2/TRP2 associated with, e.g., melanoma; (e) prostate associated antigens including PAP, PSA, PSMA, PSH-P1, PSM-P1, PSM-P2, associated with e.g., prostate cancer; (f) immunoglobulin idiotypes associated with myeloma and B cell lymphomas. In certain embodiments, the one or more TAA can be selected from pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pl 80erbB-3, c-met, mn-23H1, TAG-72-4, CA 19-9, CA 72-4, CAM 17.1, NuMa, K-ras, pi 6, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY—CO-1, RCAS1, SDCCAG16, TA-90 (Mac-2 binding protein/cyclophilin C-associated protein), TAAL6, TAG72, TLP, TPS or any combinations thereof.

In some embodiments, cancer vaccines of the present disclosure for use in combination with a compound of Formula I' can include a tumor antigen comprising the entire amino acid sequence, a portion of it, or specific immunogenic epitopes of one of the following human proteins: TCTN1 (Gene ID: ENSG00000204852), TCTN2 (Gene ID: ENSG00000168778), TCTN3 (Gene ID: ENSG00000119977), HIGD2A (Gene ID: ENSG00000146066), HIGD2B (Gene ID: ENSG00000175202), C4ORF32 (Gene ID: ENSG00000174749), FAM62A (E-SYT1, Gene ID: ENSG00000139641), COLEC 11 (Gene ID: ENSG00000118004), FSTL5 (Gene ID: ENSG00000168843), FAM82A2 (Gene ID: ENSG00000137824), SCARA5 (Gene ID: ENSG00000168079), VSTM1 (Gene ID: ENSG00000189068), RNF5 (Gene ID: ENSG00000183574), UNQ6126 (Gene ID: gi|169216088), DPY19L3 (Gene ID: ENSG00000178904), SLC39A10 (gene ID: ENSG00000196950), GPR107 (Gene ID: ENSG00000148358), COL20A1 (Gene ID: ENSG00000101203), GLT25D2 (Gene ID: ENSG00000198756), SYTL3 (Gene ID: ENSG00000164674), DENND1B (Gene ID: ENSG00000162701), C6orf98 (Gene ID: EG: 387079), FAM69B (Gene ID: ENSG00000165716), EMID1 (Gene ID: OTTHUMG00000030824), KLRG2 (GENE ID: ENSG00000188883), ERMP1 (GENE ID: ENSG00000099219), VMO1 (Gene ID: ENSG00000182853), C9orf46 (Gene ID: ENSG00000107020), F1137107 (Gene ID: ENSG00000177990), YIPF2 (Gene ID: ENSG00000130733), TRYX3 (PRSS58, ENSG00000258223.2), C14orf135 (Gene ID: ENSG00000126773), ANGPTL7 (Gene ID: ENSG00000171819), TPCN2 (Gene ID: ENSG00000162341), C18orf19 (Gene ID: ENSG00000177150), OLFML1 (Gene ID: ENSG00000183801), LYPD4 (Gene ID: ENSG00000101203), MEGF8 (Gene ID: ENSG00000105429), F1142986 (Gene ID: ENSG00000196460), SLC46A1 (Gene ID: ENSG00000076351), FAM180A (Gene ID: ENSG00000189320), CRISP-3 (GENE ID: ENSG00000096006), or combinations thereof. These tumor antigens are disclosed in WO2010/086162, WO2010/086163, WO2011/051278, WO2011/051276, WO2011/051277, WO2011/051280, WO2011/051271, WO2011/135068, WO2014/198919, the content of which is herein incorporated by reference in their entireties.

In various embodiments, an illustrative immunotherapeutic agent may include an mRNA operable to encode any one or more of the aforementioned cancer antigens useful for synthesizing a cancer vaccine. In some illustrative embodiments, the mRNA based cancer vaccine may have one or more of the following properties: a) the mRNA encoding each cancer antigen is interspersed by cleavage sensitive sites; b) the mRNA encoding each cancer antigen is linked directly to one another without a linker; c) the mRNA encoding each cancer antigen is linked to one another with a single nucleotide linker; d) each cancer antigen comprises a 20-40 amino acids and includes a centrally located SNP mutation; e) at least 40% of the cancer antigens have a highest affinity for class I MHC molecules from the subject; f) at least 40% of the cancer antigens have a highest affinity for class II MHC molecules from the subject; g) at least 40% of the cancer antigens have a predicted binding affinity of IC>500 nM for HLA-A, HLA-B and/or DRB1; h) the mRNA encodes 1 to 15 cancer antigens; i) 10-60% of the cancer antigens have a binding affinity for class I MHC and 10-60% of the cancer antigens have a binding affinity for class II MHC; and/or j) the mRNA encoding the cancer antigens is arranged such that the cancer antigens are ordered to minimize pseudo-epitopes.

In various embodiments, the combination comprising a compound of Formula I' and a cancer vaccine immunotherapeutic agent as disclosed herein can be used to illicit an immune response in a subject against a cancer antigen. The method involves administering to the subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, in combination with administering a compound of Formula I' either in the same composition or a separate composition, administered at the same time, or sequentially dosed, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An "anti-antigenic polypeptide antibody" is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, and the like. In exemplary embodiments, a traditional vaccine is a vaccine that has achieved regulatory approval and/or is registered by a national drug regulatory body, for example the Food and Drug Administration (FDA) in the United States or the European Medicines Agency (EMA.)

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, RNA vaccine immunotherapeutic agents of the present disclosure (e.g., mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, and the like.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the invention, antigen-specific antibodies are measured in units of g/ml or are measured in units of IU/L (International Units per liter) or mIU/ml (milli International Units per ml). In exemplary embodiments of the invention, an efficacious vaccine produces >0.5 µg/mL, >0.1 µg/mL, >0.2 µg/mL, >0.35 µg/mL, >0.5 µg/mL, >1 µg/mL, >2 µg/mL, >5 µg/mL or >10 µg/mL. In exemplary embodiments of the invention, an efficacious vaccine produces >10 mIU/mL, >20 mIU/mL, >50 mIU/mL, >100 mIU/mL, >200 mIU/mL, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay. Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Immunotherapeutic agents comprising a nucleic acid vaccine comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 μg and 400 μg of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a tumor in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient.

In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

In some embodiments, an illustrative immunotherapeutic agent can include one or more interfering RNAs that can be administered in combination with a compound of Formula I'.

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi). Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

Antigens which can be targeted for synthesizing a corresponding antisense RNA molecule can include any antigen that is specific for one or more tumors, for example, antigens exemplified above with reference to cancer vaccines.

In some embodiments, a combination of an immunotherapeutic agent and a compound of Formula I' can include a bispecific antibody immunotherapeutic agent. The bispecific antibody can include a protein construct having a first antigen binding moiety and a second antigen binding site that binds to a cytotoxic immune cell. The first antigen binding site can bind to a tumor antigen that is specifically being treated with the combination of the present invention. For example, the first antigen binding moiety may bind to a non-limiting example of tumor antigens selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin αVβ3, Integrin α5β1, MUC1, ERBB2, ERBB3, MET, IGF1R, EPHA3, TRAILR1, TRAILR2, RANKL, FAP and Tenascin among others. In some embodiments, the first antigen binding moiety has specificity to a protein or a peptide that is overexpressed on a tumor cell as compared to a corresponding non-tumor cell. In some embodiments, the first antigen binding moiety has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor.

The second antigen-binding moiety is any molecule that specifically binds to an antigen or protein or polypeptide expressed on the surface of a cytotoxic immune cell (a CIK cell). Exemplary non-limiting antigens expressed on the surface of the cytotoxic immune cells suitable for use with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRαβ, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In some embodiments, the second antigen binding moiety binds to CD3 of the cytotoxic immune cell, e.g., CIK cell. In some embodiments, the second antigen binding moiety binds to CD56 of the cytotoxic immune cell. In some embodiments, the second antigen binding moiety binds to the Fc receptor of the cytotoxic immune cell. In some embodiments, the Fc region of the bispecific antibody binds to the Fc receptor of the cytotoxic immune cell. In some embodiments, a second antigen-binding moiety is any molecule that specifically binds to an antigen expressed on the surface of a cytotoxic immune cell (e.g., a CIK cell). The second antigen binding moiety is specific for an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells. The second antigen binding moiety specifically binds to an antigen expressed on the surface of a cytotoxic immune cell. Exemplary non-limiting antigens expressed on the surface of the cytotoxic immune cells suitable for modulation with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRαβ, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In other embodiments, the bispecific antibody modulator is an activator of a costimulatory molecule (e.g., an OX40 agonist). In one embodiment, the OX40 agonist is a bispecific antibody molecule to OX40 and another tumor antigen or a costimulatory antigen. The OX40 agonist can be administered alone, or in combination with other immunomodulators, e.g., in combination with an inhibitor (for example an antibody construct) of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CD5, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand. In some embodiments, the second antigen binding moiety binds to the Fc receptor on the cytotoxic immune cell, e.g., CIK cell.

In some embodiments, the bispecific antibody immunotherapeutic agent has specificities for a tumor antigen and a CIK cell, which brings the tumor antigen expressing tumor cell in close proximity of the CIK cell, leading to the elimination of the tumor cell through anti-tumor cytotoxicity of CK cell. In some embodiments, the bispecific antibody has specificity for a tumor antigen but does not have specificity for a CIK cell, however, the Fc region of the bispecific antibody can bind to the Fc receptor of the CIK cell, which in turn brings the tumor cell in close proximity of the CIK cell, leading to the elimination of the tumor cell through anti-tumor cytotoxicity of CIK cell. In some embodiments, the bispecific antibody has specificity for a CIK cell but does not have specificity for tumor cell, however, the Fc region of the bispecific antibody can bind to the Fc receptor of the tumor cell, which in turn brings the tumor cell in close proximity of the CIK cell, leading to the elimination of the tumor cell through anti-tumor cytotoxicity of CIK cell.

In some embodiments, a combination of an immunotherapeutic agent and a compound of Formula I' can include an immune cell-engaging multivalent antibody/fusion protein/construct immunotherapeutic agent. In various embodiments, an exemplary immunotherapeutic agent can include immune cell-engaging multivalent antibody/fusion protein/construct which may comprise a recombinant structure, for example, all engineered antibodies that do not imitate the original IgG structure. Here, different strategies to multimerize antibody fragments are utilized. For example, shortening the peptide linker between the V domains forces the scFv to self-associate into a dimer (diabody; 55 kDa).

Bispecific diabodies are formed by the noncovalent association of two VHA-VLB and VHB-VLA fragments expressed in the same cell. This leads to the formation of heterodimers with two different binding sites. Single-chain diabodies (sc-diabodies) are bispecific molecules where the VHA-VLB and VHB-VLA fragments are linked together by an additional third linker. Tandem-diabodies (Tandabs) are tetravalent bispecific antibodies generated by two scDiabodies.

Also included are the di-diabodies known in the art. This 130-kDa molecule is formed by the fusion of a diabody to the N-terminus of the CH3 domain of an IgG, resulting in an IgG-like structure. Further diabody derivatives are the triabody and the tetra-body, which fold into trimeric and tetrameric fragments by shortening the linker to <5 or 0-2 residues. Also exemplified are (scFv)$_2$ constructs known as 'bispecific T cell engager' (BITE). BITEs are bispecific single-chain antibodies consisting of two scFv antibody fragments, joined via a flexible linker, that are directed against a surface antigen on target cells and CD3 on T cells. Also exemplified are bivalent (Fab)$_2$ and trivalent (Fab)$_3$ antibody formats. Also exemplified are minibodies and trimerbodies generated from scFvs. Exemplary constructs useful to target tumor antigens as can include one or more of: Diabody, Single-chain (sc)-diabody (scFv)2, Miniantibody, Minibody, Barnase-barstar, scFv-Fc, sc(Fab)2, Trimeric antibody constructs, Triabody antibody constructs, Trimerbody antibody constructs, Tribody antibody constucts, Collabody antibody constructs, (scFv-TNFa)3, F(ab) 3/DNL. In each of these exemplified constructs, at least one binding moiety may bind to an antigen or protein or polypeptide expressed on the surface of a cytotoxic immune cell, and at least one binding moiety will bind specifically to an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells.

In some embodiments, a combination of an immunotherapeutic agent and a compound of Formula I' can include a radioconjugate immunotherapeutic agent.

In various embodiments, a radioconjugate is a small molecule or large molecule (herein referred to as a "cell targeting agent"), for example and polypeptide, an antibody or an antibody fragment thereof, that is coupled to or otherwise affixed to a radionuclide, or a plurality of radionuclides, such that the binding of the radioconjugate to its target (a protein or molecule on or in a cancer cell), will lead to the death or morbidity of said cancer cell. In various embodiments, the radioconjugate can be a cell targeting agent labelled with a radionuclide, or the cell targeting agent may be coupled or otherwise affixed to a particle, or microparticle, or nanoparticle containing a plurality of radionuclides, wherein the radionuclides are the same or different. Methods for synthesizing radioconjugates are known in the art, and may include the class of immunoglobulin or antigen binding parts thereof, that are conjugated to a toxic radionuclide.

In some embodiments, the molecule that binds to the cancer cell can be known as a "cell targeting agent". As used herein, an exemplary cell targeting agent can allow the drug-containing nanoparticles or radionuclide to target the specific types of cells of interest.

Examples of cell targeting agents include, but are not limited to, small molecules (e.g., folate, adenosine, purine) and large molecule (e.g., peptide or antibody) that bind to or target a tumor associated antigen. Examples of tumor associated antigens include, but are not limited to, adenosine receptors, alpha v beta 3, aminopeptidase P, alpha fetoprotein, cancer antigen 125, carcinoembryonic antigen, cCaveolin-1, chemokine receptors, clusterin, oncofetal antigens, CD20, epithelial tumor antigen, melanoma associated antigen, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyosinase, and tyrosine kinases. In some embodiments, the cell targeting agent is folate or a folate derivative that binds specifically to folate receptors (FRs). In some embodiments, the cell targeting agent is an antibody, a bispecific antibody, a trispecific antibody or an antigen binding construct thereof, that specifically binds to a cancer antigen selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin αVβ3, Integrin α5β1, MUC1, ERBB2, ERBB3, MET, IGF1R, EPHA3, TRAILR1, TRAILR2, RANKL, FAP and Tenascin among others.

The use of folate as a targeting agent in the radioconjugate also allow both tumor cells and regulatory T (Treg) cells to be targeted for destruction. It is well accepted that high numbers of Treg cells suppress tumor immunity. Specifically, Treg cells suppress (foreign and self) reactive T cells without killing them through contact-dependent or cytokine (e.g., IL-10, TGF-.beta., and the like.) secretion. FR4 is selectively upregulated on Treg cells. It has been shown that antibody blockade of FR4 depleted Treg cells and provoked tumor immunity in tumor-bearing mice. Thus, folate-coated PBM nanoparticles carrying a cytotoxic agent would take FR-expressing cells for their destruction, which would both directly (i.e., BrCa cell) and indirectly (i.e., breast tumor associated and peripheral Treg cells) inhibit tumor progression.

In another further embodiment, the targeting agent is an antibody or peptide, or immune cell-engaging multivalent antibody/fusion protein/constructs capable of binding tumor associated antigens consisting of but not limited to: adenosine receptors, alpha v beta 3, aminopeptidase P, alpha fetoprotein, cancer antigen 125, carcinoembryonic antigen, caveolin-1, chemokine receptors, clusterin, oncofetal antigens, CD20, Human Growth Factor Receptor (HGFR), epithelial tumor antigen, melanoma associated antigen, MUC1, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyrosinase, tyrosine kinases, and the like.

In one embodiment, the treatment method includes the co-administration of a compound as disclosed herein or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agents" include chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478; alkylating agents such as thiotepa and CYTOXAN®; cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5 alpha-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma 11 and calicheamicin omega 11 (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Ore.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexet; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX®; and (ix) pharmaceutically acceptable salts, acids and derivatives of any of the above.

Chemotherapeutic agents also include antibodies, as described above, including alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nivolumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-8744695, Wyeth Research and Abbott Laboratories) which is a recombinant exclusively human-sequence, full-length IgG.sub.1 .lamda. antibody genetically modified to recognize interleukin-12 p40 protein.

Chemotherapeutic agents also include "tyrosine kinase inhibitors" including the EGFR inhibitors; small molecule HER2 tyrosine kinase inhibitor such as Mubritonib (TAK165, Takeda); CP-724.714, (Axon Medchem BV, an oral selective inhibitor of the ErbB2 receptor tyrosine kinase); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase 1 inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; antisense molecules (e.g. those that bind to HER-encoding nucleic acid); quinoxalines (U.S. Pat. No. 5,804,396); tryphostins (U.S. Pat. No. 5,804,396); Affinitac (ISIS 3521; Isis/Lilly); PKI166 (Novartis); Semaxinib (Pfizer); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca). Tyrosine kinase inhibitors also include Erlotinib (Tarceva®), Gefitinib (Iressa®), Dasatinib (Sprycel®), Nilotinib (Tasigna®), Crizotinib (Xalkori®), Ruxolitinib (Jakafi®), Vemurafenib (Zelboraf®), Vandetanib (Caprelsa®), Pazopanib (Votrient®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, veliparib, vismodegib, volasertib, cobimetinib (Cotellic®), and others.

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF alpha) blockers such as etanercept (Enbrel), infliximab (Remicade), adalimumab (1-Iumira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTal/132 blockers such as Anti-lymphotoxin alpha (LTa); miscellaneous investigational agents such as thioplatin, PS-341, phenylbutyrate, ET-18-OCH$_3$, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE) pixantrone; farnesyltransferase inhibitors such as lonafamib (SCH 6636, SARA-SAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include Poly ADP ribose polymerase (PARP) inhibitors: olaparib (Lynparza®), rucaprib (Rubraca®) niraparib (Zejula®), talzoparib (Talzenna®).

Effective combinations of compounds of Formula I' or any formulas as described herein with other agents may be identified through preclinical and clinical testing of the combinations, and will depend on many factors, including disease type and stage of development, overall health of the patient, toxicities and side effects of the agents, and the like.

In some embodiments, compounds as disclosed herein may be used in combination therapy with any of the kinase inhibitors disclosed herein for the treatement of diseases such as cancer. Exemplary kinase inhibitors include imatinib, baricitinib gefitinib, erlotinib, sorafenib, dasatinib, sunitinib, lapatinib, nilotinib, pirfenidone, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORy) modulators, a CK1 inhbitor, a CK1-α inhibitor, a Wnt pathway inhibitor (e.g., SST-215), or a mineralocorticoid receptor inhibitor, (e.g., esaxerenone or XL-550) for the treatment of a disease disclosed herein such as cancer.

In some embodiments, for treatement of cancer, compounds as disclosed herein may be used in combination with inhibitors of PD-1 or inhibitors of PD-L1, e.g., an anti-PD-1 monoclonal antibody or an anti-PD-L1 monoclonal antibody, for example, nivolumab (Opdivo), pembrolizumab (Keytruda, MK-3475), atezolizumab, avelumab, AMP-224, AMP-514, PDR001, durvalumab, pidilizumab (CT-011), CK-301, BMS 936559, and MPDL3280A; CTLA-4 inhibitors, e.g., an anti-CTLA-4 antibody, for example, ipilimumab (Yervoy) and tremelimumab; and phosphatidylserine inhbitiors, for example, bavituximab (PGN401); antibodies to cytokines (IL-10, TGF-β, and the like.); other anti-cancer agents such as cemiplimab.

In some embodiments, a compound as described herein can be used in combination with a vaccination protocol for the treatment of cancer. In some embodiments, a compound as described herein can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa.*

In some embodiments, compounds as disclosed herein may be used in combination with inhibitors of PARP, for example, olaparib (Lynparza®), rucaprib (Rubraca®), niraparib (Zejula®), talzoparib (Talzenna®).

The amount of both the compound disclosed herein or salt thereof and the additional one or more additional therapeutic agent (in those compositions which comprise an additional therapeutic agent as described above) that may be combined with carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-10,000 µg/kg body weight/day of the additional therapeutic agent can be administered.

Labeled Compounds and Assay Methods

Another aspect of the present invention relates to labeled compounds of the invention (radio-labeled, fluorescent-labeled, and the like.) that would be useful not only in imaging techniques but also in assays, both in vitro and in vivo, for localizing and quantitating TAM kinases in tissue samples, including human, and for identifying TAM kinase ligands by inhibition binding of a labeled compound. Accordingly, the present invention includes TAM kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The radionuclide that is incorporated in the instant radio-labeled compounds will depend on the specific application of that radio-labeled compound. For example, for in vitro metalloprotease labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br, or $^{77}$Br will generally be most useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S, and $^{82}$Br.

The present invention can further include synthetic methods for incorporating radio-isotopes into compounds of the invention. Synthetic methods for incorporating radio-isotopes into organic compounds are well known in the art, and a person of ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a TAM by monitoring its concentration variation when contacting with the TAM kinases, through tracking of the labeling. For example, a test compound (labeled) can be evaluated for its ability to reduce binding of another compound which is known to bind to a TAM kinase (i.e., standard compound). Accordingly, the ability of a test compound to compete with the standard compound for binding to the TAM kinase directly correlates to its binding affinity. Conversely, in some other screening assays, the standard compound is labeled, and test compounds are unlabeled. Accordingly, the concentration of the labeled standard compound is monitored in order to evaluate the competition between the standard compound and the test compound, and the relative binding affinity of the test compound is thus ascertained.

Synthesis

Compounds of this invention can be made by the synthetic procedures described below. The starting materials and reagents used in preparing these compounds are either available from commercial suppliers such as Sigma Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4$^{th}$ Edition); and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure and over a temperature range from about −78° C. to about 150° C., more preferably from about 0° C. to about 125° C., and most preferably at about room (or ambient) temperature, e.g., about 20° C. Unless otherwise stated (as in the case of a hydrogenation), all reactions are performed under an atmosphere of nitrogen.

The compounds disclosed and claimed herein have asymmetric carbon atoms or quaternized nitrogen atoms in their structure and may be prepared through the syntheses described herein as single stereoisomers, racemates, or mixtures of enantiomers and diastereomers. The compounds may also exist as geometric isomers. All such single stereoisomers, racemates, and geometric isomers, and mixtures thereof are intended to be within the scope of this invention.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereomeric salts or complexes which may be separated, for example, by crystallization; via formation of diastereomeric derivatives which may be separated, for example, by crystallization; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomers may be synthesized by asymmetric synthesis using optically active reagents, substrates, catalysts, or solvents, or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The methods of the present invention may be carried out as semi-continuous or continuous processes, more preferably as continuous processes.

The present invention as described above unless indicated otherwise may be carried out in the presence of a solvent or a mixture of two or more solvents. In particular the solvent is an aqueous or an organic solvent such as the ether-like solvent (e.g. tetrahydrofuran, methyltetrahydrofuran, diisopropyl ether, t-butylmethyl ether, or dibutyl ether), aliphatic hydrocarbon solvent (e.g. hexane, heptane, or pentane), saturated alicyclic hydrocarbon solvent (e.g. cyclohexane or cyclopentane), or aromatic solvent (e.g. toluene, o-, m-, or p-xylene, or t-butyl-benzene) or mixture thereof.

The starting materials and reagents, which do not have their synthetic route explicitly disclosed herein, are generally available from commercial sources or are readily prepared using methods well known to the person skilled in the art.

Processes

In one aspect, the invention provides a process for making a compound of Formula I':

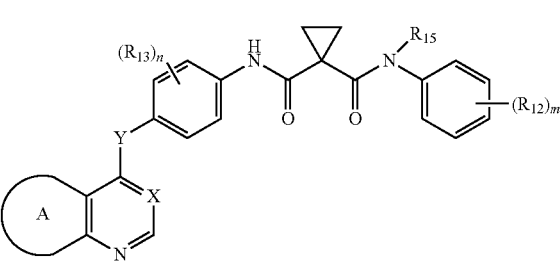

or a pharmaceutically acceptable salt thereof, comprising:
reacting a compound of Formula X:

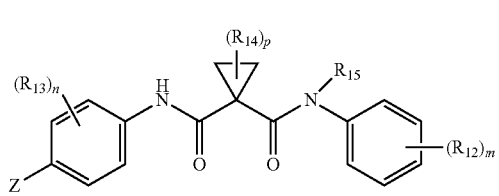

with a compound of Formula XI:

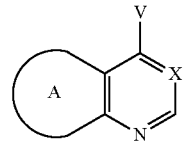

wherein

Ring A, Y, X, $R_{12}$, $R_{13}$, $R_{14}$, and $R_{15}$ are defined herein;

Z is selected from the group consisting of $NH_2$, SH, and OH; and

V is a leaving group.

In another aspect, the invention provides a process for making a compound of Formula I':

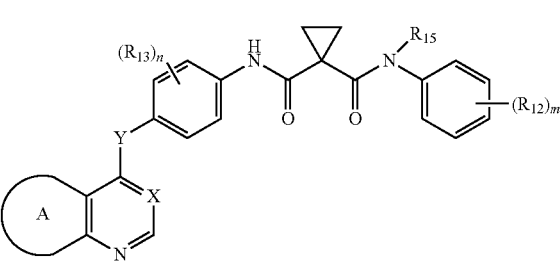

or a pharmaceutically acceptable salt thereof, comprising:
reacting a compound of formula XII:

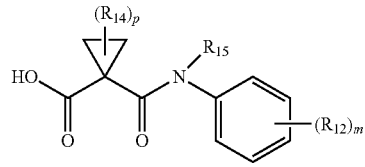

with a compound of formula XIII:

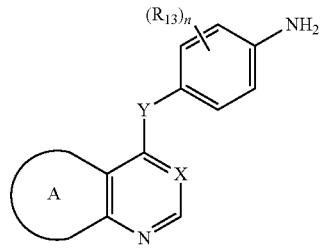

wherein

Ring A, Y, X, $R_{12}$, $R_{13}$, $R_{14}$, and $R_{15}$ are defined herein.

In one embodiment of this aspect, the invention provides making a compound of Formula XIII':

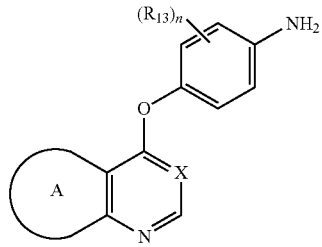
XIII' comprising reacting a compound of Formula XIV:

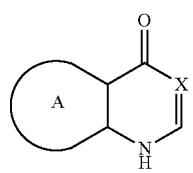
XIV with a compound of Formula XV:

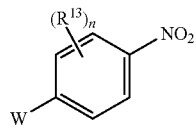
XV to form a compound of Formula XVI:

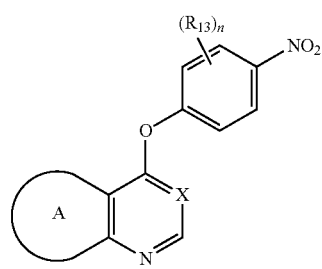
XVI and reducing the compound of Formula XVI to form a compound of Formula XIII.

The following examples are provided for the purpose of further illustration and are not intended to limit the scope of the claimed invention.

EXAMPLES

General Experimental Procedures:

The following general procedures are examples of synthesizing compounds of the present invention. One of ordinary skill in the art understands that the general procedures may be adapted to make other compounds of Formula I.

General Procedure A

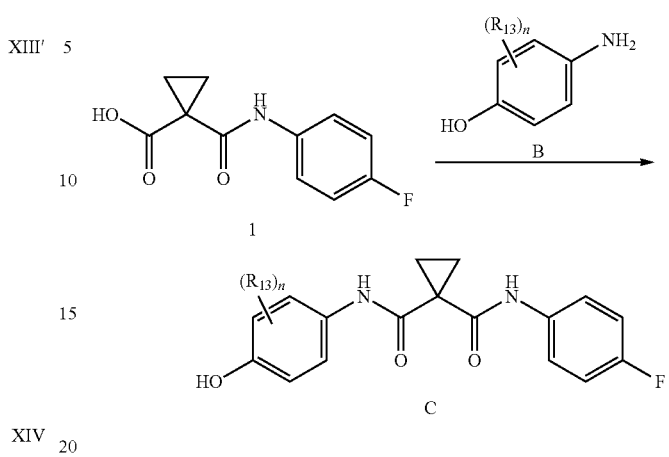

Carboxylic acid compound 1 can be converted to a compound of Formula C by coupling to an intermediate of Formula B using known coupling reagents, such as EDCI, DCC, HATU, BOP, and the like. The reaction can take place in the presence of a base such as, triethylamine, DIEA, pyridine, and the like. The coupling reaction can also take place in the presence of a solvent such as DMF, DMA, DCM, THF, and the like.

General Procedure B

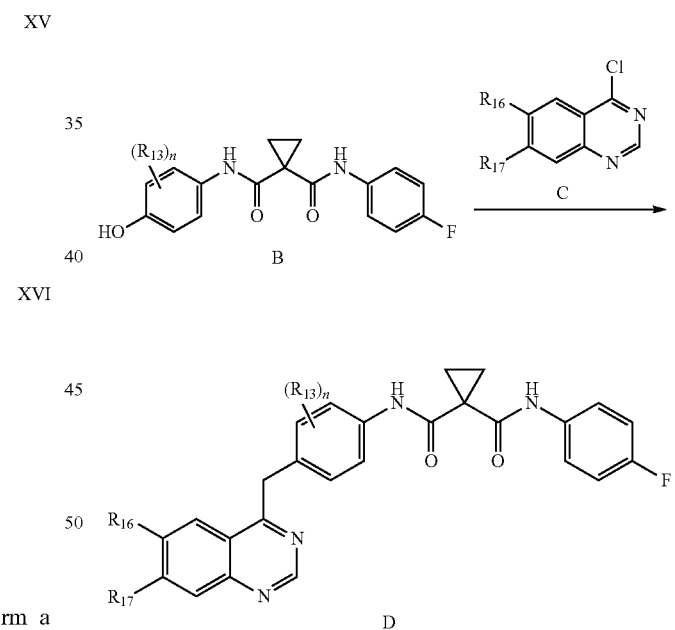

A compound of Formula B can be converted to a compound of Formula D by reacting with a compound of Formula C in the presence of a strong base, such as potassium t-butoxide or potassium carbonate, in a polar organic solvent, such as DMSO or DMF. A compound of Formula B can also be converted to a compound of Formula D by reaction with a compound of Formula C under transition metal coupling conditions. Exemplary conditions include a palladium coupling agent, such as Pd(OAc)$_2$ in the presence of 1) TrixiePhos and anisole, or 2) Xphos, K$_3$PO$_4$, toluene, and N-methyl-2-pyrrolidine (NMP).

General Procedure C

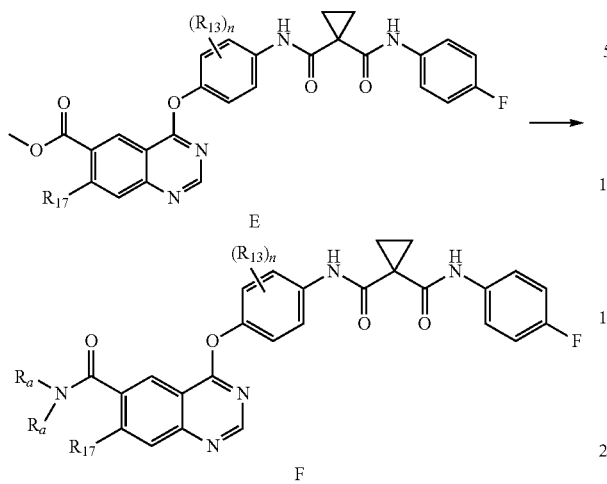

Esters of Formula E can be converted to the corresponding amide compounds of Formula F by first hydrolyzing to the corresponding carboxylic acid and then coupling with an amine of the Formula $NH(R_a)_2$, wherein each $R_a$ can be the same or different, or wherein both $R_a$ substituents, together with the nitrogen to which they are attached, form a cyclic structure. The hydrolysis step can be performed with a hydroxide base, such as sodium or lithium hydroxide in a polar solvent such as water, methanol, THF, DMF, DMSO, or any combination thereof. The coupling step can be performed using known coupling reagents, such as EDCI, DCC, HATU, BOP, and the like, in the presence of a base such as, triethylamine, DIEA, pyridine, and the like, and in the presence of a solvent such as DMF, DMA, DCM, THF, and the like.

General Procedure D

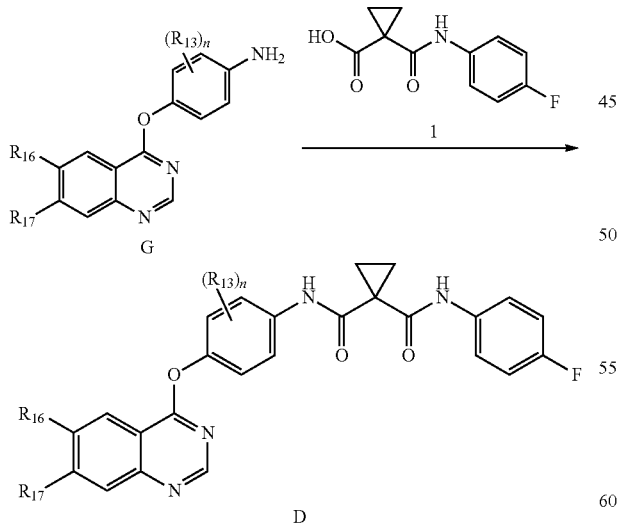

A compound of Formula G can be converted to a compound of Formula D by 1) direct coupling with Compound 1 or 2) activation of the carboxylic acid moiety of Compound 1, followed by nucleophilic substitution with a compound of Formula G. The coupling route can be performed using known coupling reagents, such as EDCI, DCC, HATU, BOP, and the like, in the presence of a base such as, triethylamine, DIEA, pyridine, and the like, and in the presence of a solvent such as DMF, DMA, DCM, THF, and the like. Activation of the carboxylic acid moiety of Compound 1 can be accomplished by first esterification of the carboxylic acid of Compound 1 with a phenolic compound such as pentafluorophenol or para-nitrophenol using means known to one having skill in the art, to form the corresponding phenolate. Second, nucleophilic substitution of the activated Compound 1 with a compound of Formula G will provide the compound of Formula D.

General Procedure E

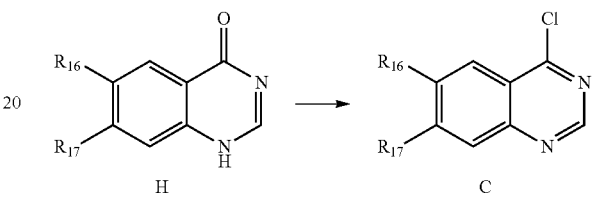

A compound of Formula H can be converted to a compound of Formula C by exposure to chloridating reagent such as oxalyl chloride, $SOCl_2$, and $POCl_3$. The transformation can be performed in the presence of a solvent or under neat conditions.

General Procedure F

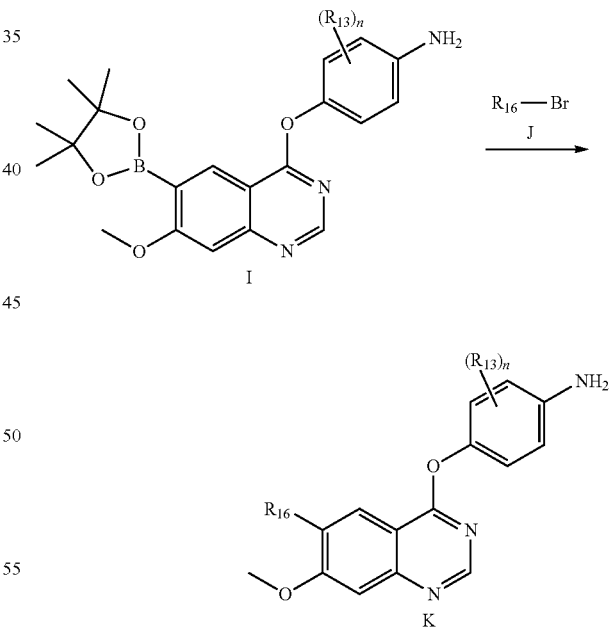

A compound of Formula I can be converted to a compound of Formula K using coupling chemistry. For example a compound of Formula I can be reacted with a compound of Formula J in the presence of a transition metal catalyst, such as bis(di-t-butyl(4-dimethylaminophenyl)phosphine) dichloropalladium(II) in a solvent, such as 1,4-dioxane, in the presence of a base, such as sodium carbonate, optionally under microwave irradiation.

General Procedure G

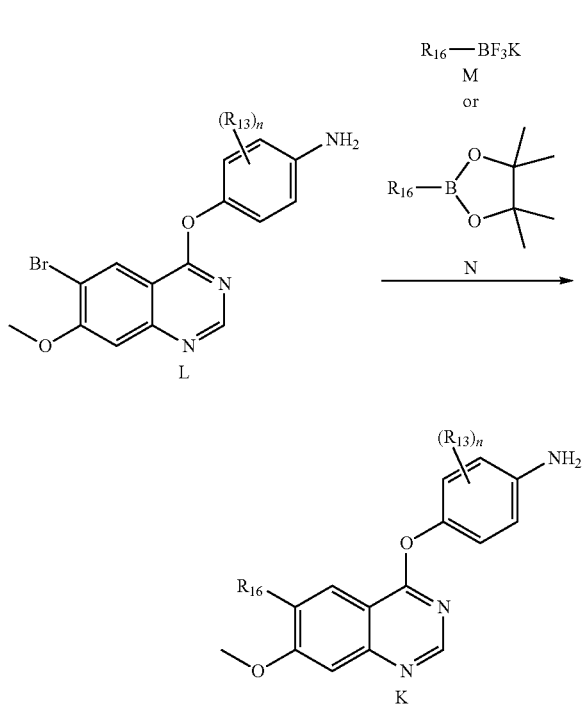

A compound of Formula L can be converted to a compound of Formula K using coupling chemistry, for example a compound of Formula I can be reacted with a compound of Formula M or N in the presence of a transition metal catalyst, such as bis(di-t-butyl(4-dimethylaminophenyl) phosphine)dichloropalladium(II) in a solvent, such as 1,4-dioxane, in the presence of a base, such as sodium carbonate, optionally under microwave irradiation.

General Procedure H

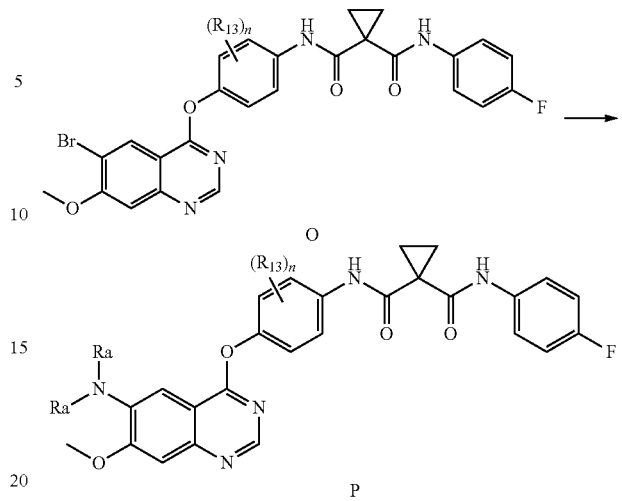

A compound of Formula O can be converted to the corresponding amine compounds of Formula P by coupling with an amine of the Formula $NH(R^a)_2$, wherein each $R^a$ can be the same or different, or wherein both $R^a$ substituents, together with the nitrogen to which they are attached, form a cyclic structure. The coupling step can be performed using a transition metal catalyst, such as bis(tri-t-butylphosphine) palladium(O), in the presence of a base, such as $K_3PO_4$, in a polar solvent, such as DMF, DMSO, or DMA.

General Procedure I

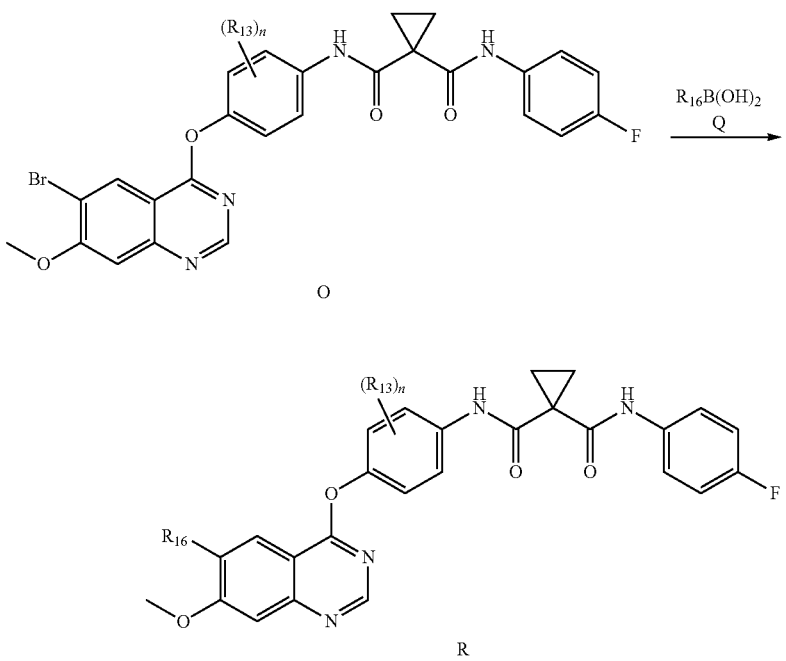

A compound of Formula O can also be converted to a compound of Formula R by coupling with a boronic acid compound of Formula Q in the presence of transition metal catalyst, such as bis(di-t-butyl(4-dimethylaminophenyl) phosphine)dichloropalladium(II), a base, such as sodium carbonate, and a solvent, such as 1,4-dioxane, optionally under microwave irradiation.

General Procedure J

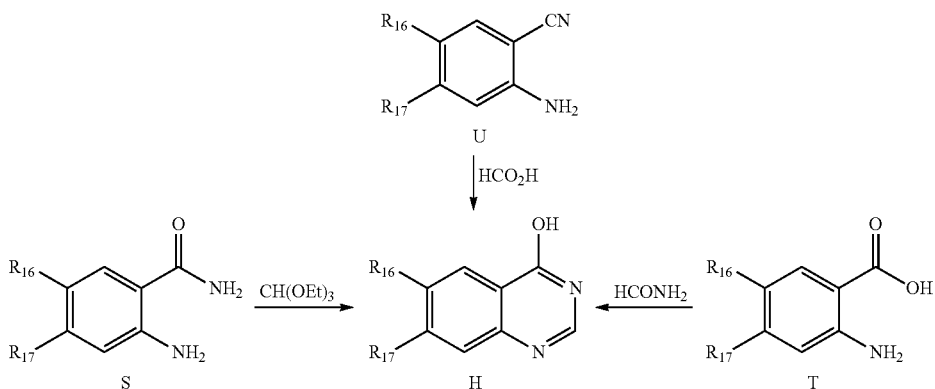

A compound of Formula H (shown here as the enol tautomer) can also be synthesized from a cyano compound of Formula U, an amide compound of Formula S, or a carboxylic acid compound of Formula T. A compound of Formula S is converted to Formula H in the presence of triethyl orthoformate under neat conditions at elevated temperatures, optionally under microwave irradiation. A compound of Formula T is converted to Formula H in the presence of formamide under neat conditions at elevated temperatures, optionally under microwave irradiation. A compound of Formula U is converted to Formula H in the presence of formic acid under neat conditions at elevated temperatures.

General Procedure K

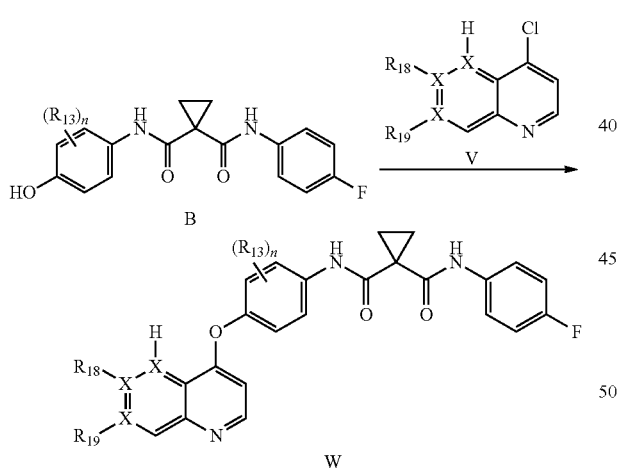

A compound of Formula B can be converted to a compound of Formula W by reacting with a compound of Formula V, wherein X is carbon or nitrogen and wherein $R_{18}$ and/or $R_{19}$ is absent when the X variable they are attached to is a nitrogen, in the presence of a strong base, such as potassium t-butoxide or potassium carbonate, in a polar organic solvent, such as DMSO or DMF. A compound of Formula B can also be converted to a compound of Formula W by reaction with a compound of Formula V under transition metal coupling conditions. Exemplary conditions include a palladium coupling agent, such as Pd(OAc)$_2$ in the presence of 1) TrixiePhos and anisole, or 2) Xphos, K$_3$PO$_4$, toluene, and N-methyl-2-pyrrolidine (NMP).

General Procedure L

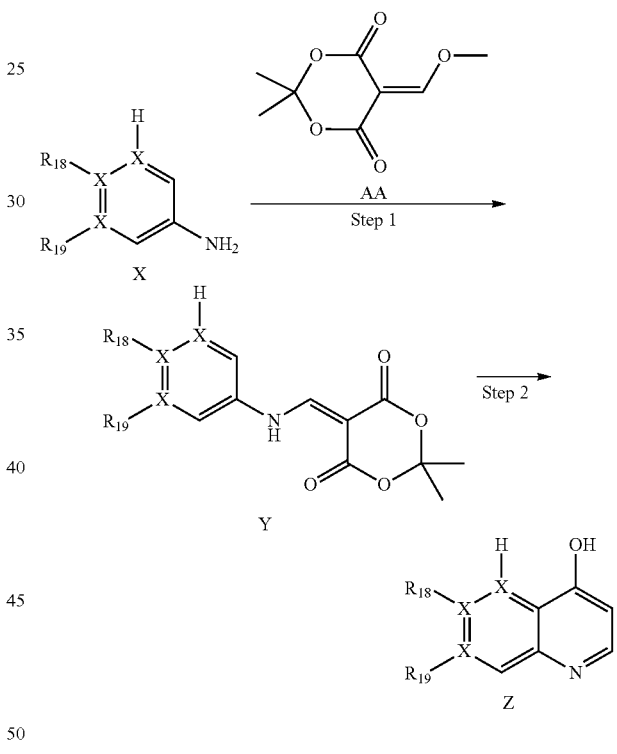

Step 1

A compound of Formula Y can be obtained by reacting a compound of Formula X, wherein the variable X is carbon or nitrogen and wherein $R_{18}$ and/or $R_{19}$ is absent when the X variable they are attached to is a nitrogen, with an acetal compound of Formula AA at elevated temperatures in a solvent such as trimethoxymethane or isopropanol. A compound of Formula AA can also be obtained in situ by first reacting 2,2-Dimethyl-1,3-dioxane-4,6-dione in trimethoxymethane prior to adding a compound of Formula X.

Step 2

A compound of Formula Z can be obtained via the intra-cyclization of a compound of Formula Y at elevated temperatures in a high-temperature solvent, such as diphenyl ether or dowtherm.

General Procedure M

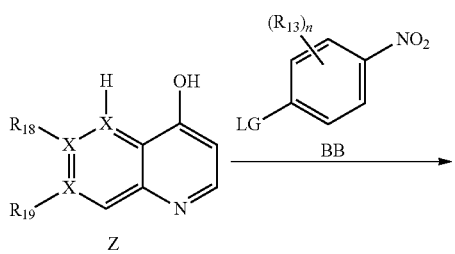
Z

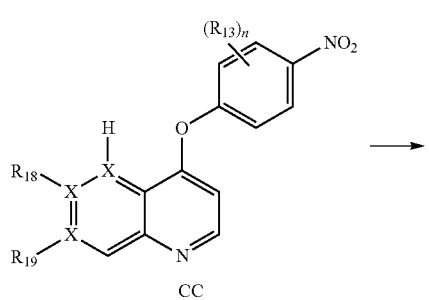
CC

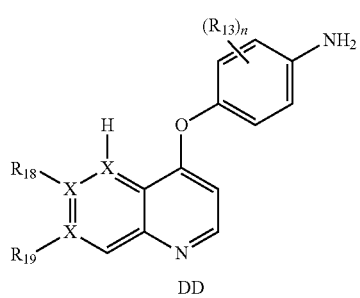
DD

Step 1

A compound of Formula Z, wherein X is carbon or nitrogen and wherein $R_{18}$ and/or $R_{19}$ is absent when the X variable they are attached to is a nitrogen, can be converted to a compound of Formula CC by reacting with a compound of Formula BB, wherein "LG" is a leaving group, in the presence of 1) cesium carbonate, or 2) silver oxide, in a solvent such as acetonitrile, DMF, DMSO, or DMA.

Step 2

The nitro moiety of a compound of Formula CC can be reduced to provide a compound of Formula DD using methods known to those skilled in the art, such as hydrogen gas in the presence of Pd/C or nickel metal, or by reduction with iron metal in the presence of $NH_4Cl$ in a solvent such as water, methanol, ethanol, or a combination thereof.

General Procedure N

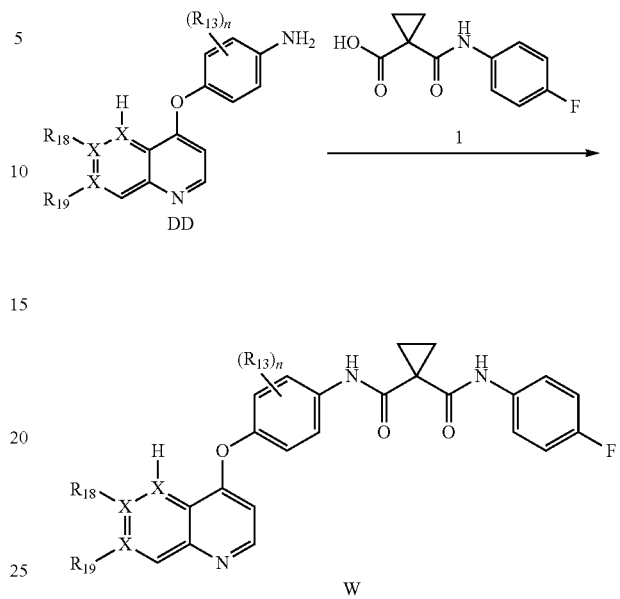
W

A compound of Formula DD, wherein X is carbon or nitrogen and wherein $R_{18}$ and/or $R_{19}$ is absent when the X variable they are attached to is a nitrogen, can be converted to a compound of Formula W by 1) direct coupling with Compound 1 or 2) activation of the carboxylic acid moiety of Compound 1, followed by nucleophilic substitution with a compound of Formula DD. The coupling route can be performed using known coupling reagents, such as EDCI, DCC, HATU, BOP, and the like, in the presence of a base such as, triethylamine, DIEA, pyridine, and the like, and in the presence of a solvent such as DMF, DMA, DCM, THF, and the like. Activation of the carboxylic acid moiety of Compound 1 can be accomplished by first esterification of the carboxylic acid of Compound 1 with a phenolic compound such as pentafluorophenol or para-nitrophenol using means known to one having skill in the art, to form the corresponding phenolate. Second, nucleophilic substitution of the activated Compound 1 with a compound of Formula DD will provide the compound of Formula W.

General Procedure O

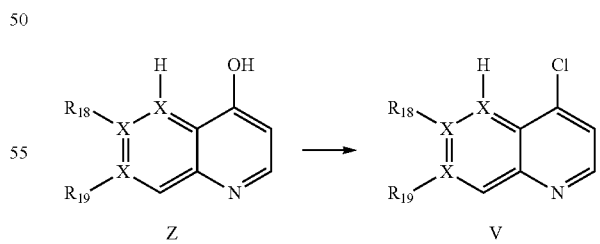

A compound of Formula Z, wherein X is carbon or nitrogen and wherein $R_{18}$ and/or $R_{19}$ is absent when the X variable they are attached to is a nitrogen, can be converted to a compound of Formula V by exposure to chloridating reagent such as oxalyl chloride, $SOCl_2$, and $POCl_3$. The transformation can be performed in the presence of a solvent or under neat conditions.

General Procedure P

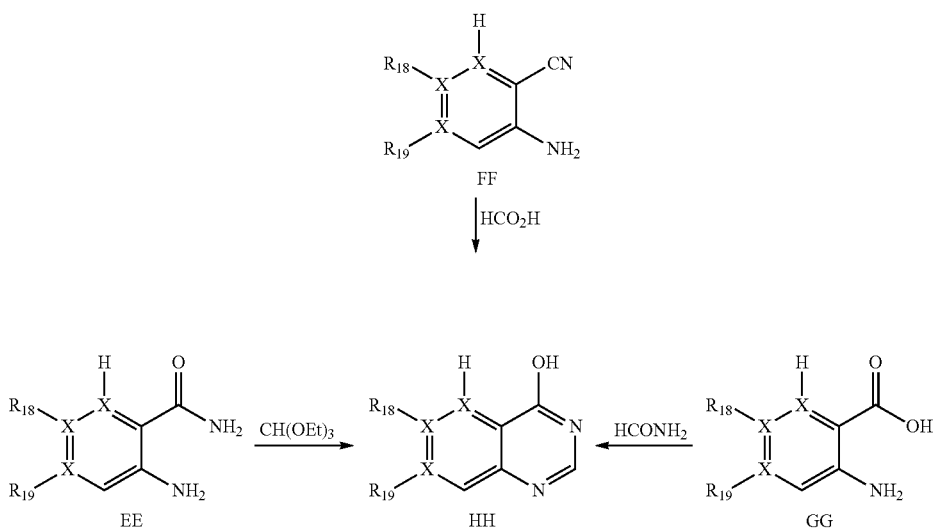

A compound of Formula HH, wherein X is carbon or nitrogen and wherein $R_{18}$ and/or $R_{19}$ is absent when the X variable they are attached to is a nitrogen, can be synthesized from a cyano compound of Formula FF, an amide compound of Formula EE, or a carboxylic acid compound of Formula GG. A compound of Formula EE is converted to Formula HH in the presence of triethyl orthoformate under neat conditions at elevated temperatures, optionally under microwave irradiation. A compound of Formula GG is converted to Formula HH in the presence of formamide under neat conditions at elevated temperatures, optionally under microwave irradiation. A compound of Formula FF is converted to Formula HH in the presence of formic acid under neat conditions at elevated temperatures.

General Procedure Q

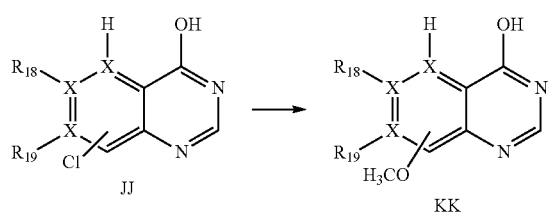

A compound of Formula JJ, wherein X is carbon or nitrogen and wherein $R_{18}$ and/or $R_{19}$ is absent when the X variable they are attached to is a nitrogen, can be converted to a compound of Formula KK by reacting with $NaOCH_3$ in a solvent, preferably anhydrous methanol, at elevated temperature, optionally under microwave irradiation.

The following specific examples are provided so that the invention can be further understood, and are not meant to limit the scope of the invention in any way.

SPECIFIC EXPERIMENTAL PROCEDURES

Example 1: N-(4-Fluorophenyl)-N-(4-hydroxyphenyl)cyclopropane-1,1-dicarboxamide (3)

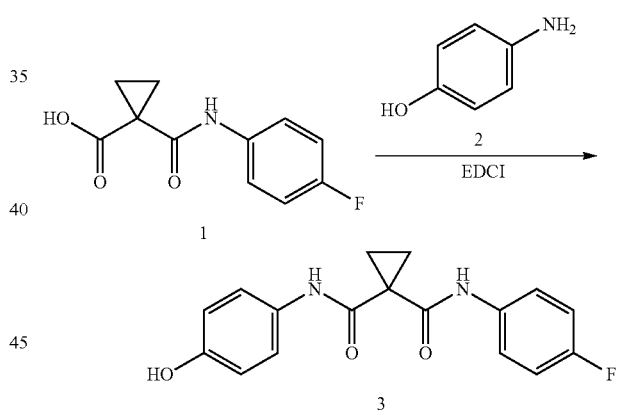

N-(4-Fluorophenyl)-N-(4-hydroxyphenyl)cyclopropane-1,1-dicarboxamide (3): To a solution of Compound 1 (10 g, 44.80 mmol, 1 eq.) and Compound 2 (5.87 g, 53.8 mmol, 1.2 eq.) in dimethyl acetamide (DMA) (60 mL) was added 3-(ethyliminomethyleneamino)-N,N-dimethyl-propan-1-amine hydrochloride (EDCI) (10.31 g, 53.8 mmol, 1.2 eq.). The mixture was stirred vigorously at 20° C. until the reaction was complete. The mixture was poured into aqueous (aq) saturated $NaHCO_3$ (400 mL) and extracted with EtOAc (4×100 mL). The combined organic phases were washed with aqueous saturated NaCl (100 mL), dried over anhydrous (anhyd) $Na_2SO_4$, and concentrated. Compound 3 (21 g, crude) (50% purity) was obtained. $^1H$ NMR (400 MHz, DMSO-$d_6$) δ 10.16 (br s, 1H), 9.72 (br s, 1H), 7.61 (dd, 2H), 7.34 (d, 2H), 7.13 (t, 2H) 6.68 (d, 2H), 1.42 (s, 4H); MS (EI) for $C_{17}H_{15}FN_2O_3$, found 314.9 (MH+).

Example 2: 1-N'-(4-Fluorophenyl)-1-N-(4-pyrido[3,2-d]pyrimidin-4-yloxyphenyl)cyclopropane-1,1-dicarboxamide (7)

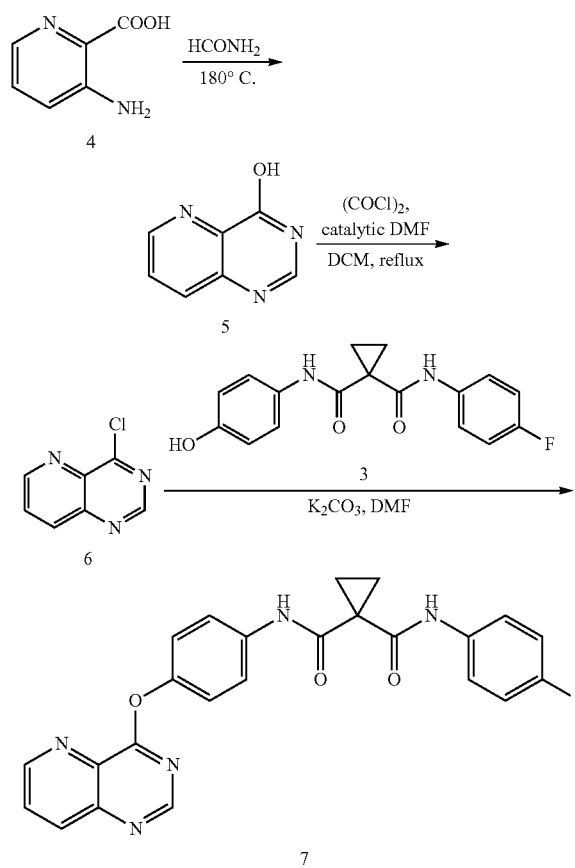

Example 3: 1-N-[4-(7-Chloropyrido[3,2-d]pyrimidin-4-yl)oxyphenyl]-1-N'-(4-fluorophenyl)cyclopropane-1,1-dicarboxamide (12)

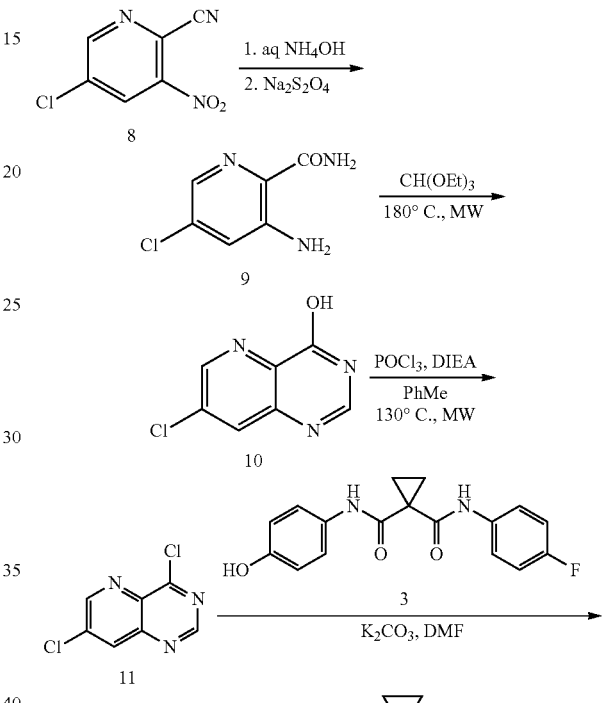

Pyrido[3,2-d]pyrimidin-4-ol (5): A mixture of Compound 4 (1.0 g, 7.2 mmol) in formamide (2.5 mL) was stirred at 140° C. for 1 hour, then at 170° C. for 1 hour and, finally at 180° C. for 1 hour. The reaction mixture was cooled to room temperature and water was added. The resulting suspension was filtered, and the solid was washed with water and suspended in MeOH. The suspension was filtered, and the solid was washed with DCM followed by hexanes and dried under vacuum to give Compound 5 as brown solid (280 mg, 26% yield). MS for $C_7H_5N_3O$, found 148 (MH+).

4-Chloropyrido[3,2-d]pyrimidine (6): To a mixture of Compound 5 (160 mg, 1.1 mmol) and DMF (1 drop) in dry DCM (2.0 mL) was added dropwise oxalyl chloride (0.24 mL, ~2.5 eq) and the resulting mixture refluxed overnight. The reaction mixture was evaporated, and the residue was treated with cold aq saturated $NaHCO_3$ (<10° C.) and then extracted with EtOAc (3×). The combined extracts were dried over anhydrous $Na_2SO_4$ and evaporated to give Compound 6 as brown solid (83 mg, ~90% purity, ~40% yield). This material was used without further purification in subsequent steps. MS for $C_7H_4ClN_3$, found 166 (MH+).

1-N'-(4-Fluorophenyl)-1-N-(4-pyrido[3,2-d]pyrimidin-4-yloxyphenyl)cyclopropane-1,1-dicarboxamide (7): A mixture of Compound 6 (39 mg, 0.24 mmol), Compound 3 (63 mg, 0.2 mmol) and $K_2CO_3$ (76 mg, 0.55 mmol) in DMF (1.0 mL) was stirred at 80° C. for 20 min. The reaction mixture was cooled to room temperature, and water was added. The resulting suspension was filtered and solid washed with water and dried under vacuum to give crude Compound 7 as a brown solid (89 mg, ~90% purity). Crude Compound 7 (80 mg) was subjected to chromatography on silica gel, eluted with 0-100% EtOAc in hexanes, to give pure Compound 7 as a white solid (70 mg, 79% yield). MS for $C_{24}H_{18}FN_5O_3$, found 444 (MH+).

3-Amino-5-chloropicolinamide (9): To Compound 8 (1.83 g, 10.0 mmol) in water (20 mL) was added 28% aq $NH_4OH$ (4.0 mL, 28.5 mmol), and the reaction was stirred at room temperature for 20 min. Sodium hydrosulfite (10.0 g, 85%, 57.3 mmol) was added, and the reaction mixture was stirred at room temperature for 90 min. The yellow precipitate was collected by vacuum filtration to give Compound 9 as yellow solid (0.77 g, 45% yield). MS for $C_6H_6ClN_3O$, found 172 (MH+).

7-Chloropyrido[3,2-d]pyrimidin-4-ol (10): A suspension of Compound 9 (220 mg, 1.27 mmol) in triethyl orthoformate (2.5 mL) was irradiated by microwave at 180° C. for 30 min. After cooling to room temperature, the brown precipitate was collected by vacuum filtration and washed with hexanes to give Compound 10 (220 mg, 95% yield). MS for $C_7H_4ClN_3O$, found 182 (MH+).

4,7-Dichloropyrido[3,2-d]pyrimidine (11): To a mixture of Compound 10 (90 mg, 0.5 mmol) in toluene (4 mL) was added DIEA (0.25 mL, 1.44 mmol) and phosphorus oxychloride (0.15 mL, 1.64 mmol), and the reaction was stirred at 130° C. under microwave irradiation for 1 hour. After cooling to room temperature, the reaction mixture was concentrated, and the resulting residue was subjected to chromatography on silica gel, eluted with 0-80% EtOAc in hexanes, to give Compound 11 as white crystals (71 mg, 71% yield). MS for $C_7H_3Cl_2N_3$, found 200 (MH+).

1-N-[4-(7-Chloropyrido[3,2-d]pyrimidin-4-yl)oxyphenyl]-1-N'-(4-fluorophenyl)cyclopropane-1,1-dicarboxamide (12): Compound 12 was made from Compound 11 in a manner analogous to the preparation of Compound 7 from Compound 6 in Step 3 of Example 2. MS for $C_{24}H_{17}ClFN_5O_3$, found 478 (MH+).

1-N-[4-(7-Bromopyrido[3,2-d]pyrimidin-4-yl)oxyphenyl]-1-N'-(4-fluorophenyl)cyclopropane-1,1-dicarboxamide (13). Compound 13 was prepared in a method analogous to Compound 12 in Example 3, starting the reaction sequence with 5-bromo-3-nitropicolinonitrile in place of Compound 8. MS for $C_{24}H_{17}BrFN_5O_3$, found 522 (MH+).

Example 4: 1-N'-(4-Fluorophenyl)-1-N-[4-(7-methoxypyrido[3,2-d]pyrimidin-4-yl)oxyphenyl]cyclopropane-1,1-dicarboxamide (16)

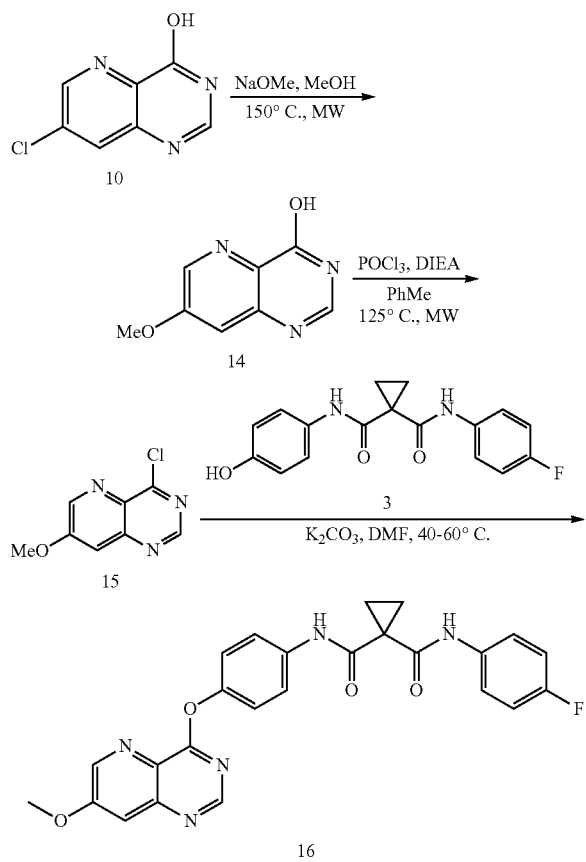

7-Methoxypyrido[3,2-d]pyrimidin-4-ol (14): A microwave vial was charged with Compound 10 (220 mg, 1.22 mmol) and a 1.0 M solution of sodium methoxide in methanol (6.5 mL, 6.5 mmol). The vial was capped and irradiated in a microwave reactor at 150° C. for 90 min. The reaction was neutralized with aq saturated $NH_4Cl$ (5 mL), concentrated, and diluted with cold water. The resulting precipitate was collected by vacuum filtration and dried in vacuo to provide Compound 14 as an off-white solid (183 mg, 85% yield). MS for $C_8H_7N_3O_2$, found 178 (MH+).

4-Chloro-7-methoxypyrido[3,2-d]pyrimidine (15): Compound 15 was made from Compound 14 in a manner analogous to the preparation of Compound 11 from Compound 10 in Step 3 of Example 3. MS for $C_8H_6ClN_3O$, found 196 (MH+).

—N'-(4-Fluorophenyl)-1-N-[4-(7-methoxypyrido[3,2-d]pyrimidin-4-yl)oxyphenyl]cyclopropane-1,1-dicarboxamide (16): Compound 16 was made from Compound 15 in a manner analogous to the preparation of Compound 7 from Compound 6 in Step 3 of Example 2. MS for $C_{25}H_{20}FN_5O_4$, found 474 (MH+).

Example 5: N-(2,5-Difluoro-4-hydroxyphenyl)-N-(4-fluorophenyl)cyclopropane-1,1-dicarboxamide (18)

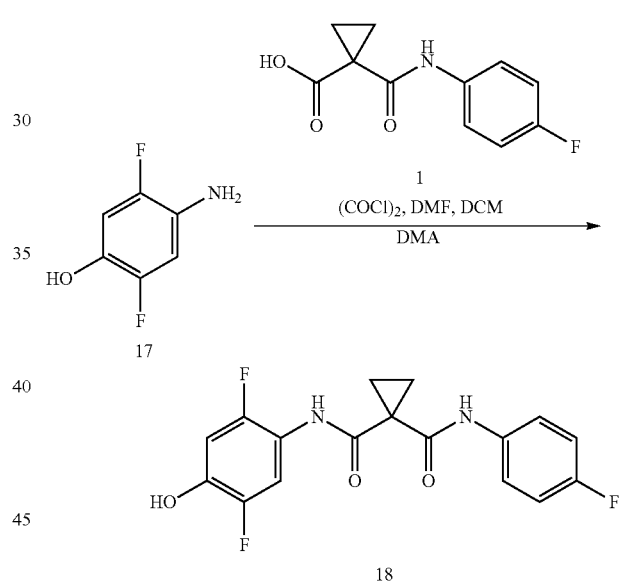

N-(2,5-Difluoro-4-hydroxyphenyl)-N-(4-fluorophenyl)cyclopropane-1,1-dicarboxamide (18): To a solution of Compound 1 (242.87 mg, 1.03 mmol, 1.5 eq) in DCM (10 mL) was added $(COCl)_2$ (157.45 mg, 1.24 mmol, 1.8 eq) and then DMF (68.91 umol, 5.30 uL, 0.1 eq). The mixture was stirred for 1 hour at 15° C. To the mixture was added a solution of Compound 17 (100 mg, 689.15 umol, 1.0 eq) in DMA (6 mL), and the resulting mixture was stirred for 1 hour at 15° C. The reaction was quenched with aq $NaHCO_3$ (50 mL), extracted with EtOAc (3×30 mL). The combined extracts were washed with aq saturated NaCl (2×100 mL), dried over anhydrous $Na_2SO_4$, and concentrated. The residue was purified by flash column chromatography on silica gel (0-10% MeOH in DCM) to give Compound 18 as a brown solid (180 mg, 67.1% yield). $^1$H NMR (400 MHz, DMSO-$d_6$) δ 10.32 (s, 1H), 10.22 (s, 1H), 9.97 (s, 1H), 7.66-7.54 (m, 3H), 7.16 (t, 2H), 6.83 (dd, 1H), 1.61-1.48 (m, 4H); MS for $C_{17}H_{13}F_3N_2O_3$, found 350.9 (MH+).

Example 6: 1-N'-[2,5-Difluoro-4-(7-methoxypyrido[3,2-d]pyrimidin-4-yl)oxyphenyl]-1-N-(4-fluorophenyl)cyclopropane-1,1-dicarboxamide (19)

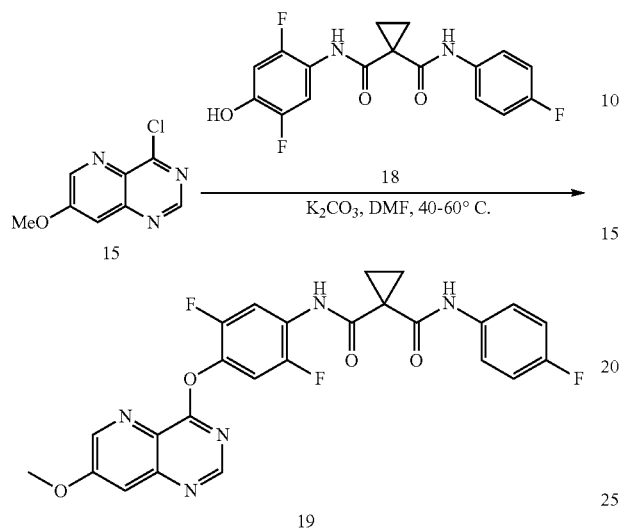

1-N'-[2,5-Difluoro-4-(7-methoxypyrido[3,2-d]pyrimidin-4-yl)oxyphenyl]-1-N-(4-fluorophenyl)cyclopropane-1,1-dicarboxamide (19): Compound 19 was made from Compound 15 in a manner analogous to the preparation of Compound 7 from Compound 6 in Step 3 of Example 2. MS for $C_{25}H_{18}F_3N_5O_4$, found 510 (MH+).

Example 7: 4-Chloro-6,7-dimethoxypyrido[3,2-d]pyrimidine (27)

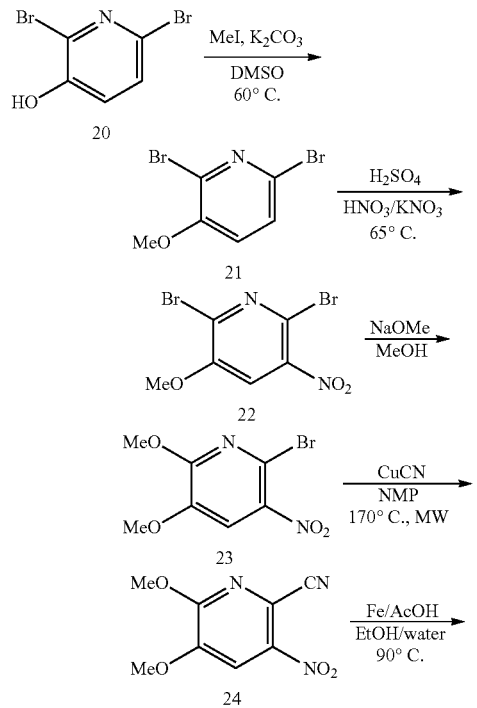

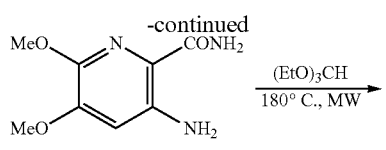

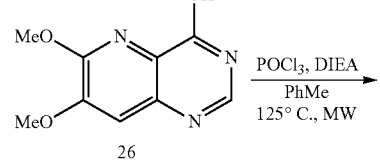

2,6-Dibromo-3-methoxypyridine (21): To a solution of Compound 20 (2.62 g, 10.4 mmol) in DMSO (4.5 mL) were added $K_2CO_3$ (1.35 g, 9.8 mmol) and methyl iodide (2.2 mL, 35.3 mmol), and the reaction mixture was stirred at 60° C. for 1 hour. The mixture was cooled to room temperature and poured into water (50 mL), and filtered. The resulting solids were washed with ice cold water and dried under vacuum to give Compound 21 (2.5 g, 90% yield). MS for $C_6H_5Br_2NO$, found 268 (MH+).

2,6-Dibromo-3-methoxy-5-nitropyridine (22): To conc $H_2SO_4$ (15 ml) at 0° C. were added nitric acid (67%, 4.0 mL) and $KNO_3$ (2.0 g) followed by Compound 21 (2.0 g, 7.5 mmol). The reaction mixture was stirred at 65° C. overnight, after which it was poured into crushed ice and neutralized carefully with solid $Na_2CO_3$, then extracted with EtOAc (2 times). The combined organic extracts were concentrated, and the resulting residue was purified by flash silica gel chromatography (0-80% of EtOAc in hexanes) to give Compound 22 (732 mg, 31% yield).

2-Bromo-5,6-dimethoxy-3-nitropyridine (23): To a solution of Compound 22 (200 mg, 0.64 mmol) in anhydrous MeOH (6 mL) was added NaOMe (46 mg, 0.85 mmol). The reaction mixture was stirred at room temperature for 1 hour and then concentrated under vacuum. The resulting residue was washed with water and filtered. The collected solids were washed with ice cold water and dried under vacuum to give Compound 23 (150 mg, 89% yield).

5,6-Dimethoxy-3-nitropicolinonitrile (24): A mixture of Compound 23 (150 mg, 0.57 mmol) and CuCN (170 mg, 1.90 mmol) in NMP (5 mL) was heated at 170° C. under microwave irradiation for 10 min and then cooled to room temperature. The reaction mixture was poured into ice water, and the resulting suspension was filtered, washed with water, and resuspended in hot EtOAc for 30 min. The resulting mixture was filtered through Celite®, and the filtrate was concentrated under vacuum to give Compound 24 which was used without further purification.

3-Amino-5,6-dimethoxypicolinamide (25): Compound 24 was mixed with Fe (130 mg, 2.0 mmol), AcOH (0.4 mL, 6.7 mmol), water (6 mL), and EtOH (14 mL). The mixture was stirred at 90° C. for 20 min and then cooled to room temperature. The pH was adjusted with aq 28% $NH_4OH$ until basic. The resulting mixture was filtered through Celite®. Volatile organics were removed from the filtrate under vacuum, and the resulting mixture was extracted with EtOAc (2 times). The combined EtOAc extracts were concentrated, and the resulting residue was purified by flash silica gel chromatography (0-100% EtOAc in hexanes) to give Compound 25 as an off-white solid (49 mg, 44% yield over 2 steps). MS for $C_8H_{11}N_3O_3$, found 198 (MH+).

6,7-Dimethoxypyrido[3,2-d]pyrimidin-4-ol (26): Compound 26 was made from Compound 25 in a manner analogous to the preparation of Compound 10 from Compound 9 in Step 2 of Example 3. MS for $C_9H_9N_3O_3$, found 208 (MH+).

6,7-Dimethoxypyrido[3,2-d]pyrimidin-4-ol (27): Compound 27 was made from Compound 26 in a manner analogous to the preparation of Compound 11 from Compound 10 in Step 3 of Example 3. MS for $C_9H_8ClN_3O_2$, found 226 (MH+).

Example 8: 1-N-[4-(6,7-dimethoxypyrido[3,2-d]pyrimidin-4-yl)oxyphenyl]-1-N'-(4-fluorophenyl)cyclopropane-1,1-dicarboxamide (28)

1-N-[4-(6,7-dimethoxypyrido[3,2-d]pyrimidin-4-yl)oxyphenyl]-1-N'-(4-fluorophenyl)cyclopropane-1,1-dicarboxamide (28): Compound 28 was made from Compound 27 in a manner analogous to the preparation of Compound 7 from Compound 6 in Step 3 of Example 2. MS for $C_{26}H_{22}FN_5O_5$, found 504 (MH+).

The following compounds were prepared from Compound 27 in a method analogous to Compound 28 in Example 8 using the appropriately substituted N-(4-fluorophenyl)-N-(4-hydroxyphenyl)cyclopropane-1,1-dicarboxamides which were synthesized using methods analogous to those used in Example 1 or Example 5.

1-N'-[3-Chloro-4-(6,7-dimethoxypyrido[3,2-d]pyrimidin-4-yl)oxyphenyl]-1-N-(4-fluorophenyl)cyclopropane-1,1-dicarboxamide (29): MS (EI) for $C_{26}H_{21}ClFN_5O_5$, found 538 (MH+).

1-N'-[4-(6,7-Dimethoxypyrido[3,2-d]pyrimidin-4-yl)oxy-3-fluorophenyl]-1-N-(4-fluorophenyl)cyclopropane-1,1-dicarboxamide (30): MS (EI) for $C_{26}H_{21}F_2N_5O_5$, found 522 (MH+).

1-N'-[4-(6,7-Dimethoxypyrido[3,2-d]pyrimidin-4-yl)oxy-2-fluorophenyl]-1-N-(4-fluorophenyl)cyclopropane-1,1-dicarboxamide (31): MS (EI) for $C_{26}H_{21}F_2N_5O_5$, found 522 (MH+).

1-N'-[2-Chloro-4-(6,7-dimethoxypyrido[3,2-d]pyrimidin-4-yl)oxyphenyl]-1-N-(4-fluorophenyl)cyclopropane-1,1-dicarboxamide (32): MS (EI) for $C_{26}H_{21}ClFN_5O_5$, found 538 (MH+).

1-N'-[4-(6,7-Dimethoxypyrido[3,2-d]pyrimidin-4-yl)oxy-2-methylphenyl]-1-N-(4-fluorophenyl)cyclopropane-1,1-dicarboxamide (33): MS (EI) for $C_{27}H_{24}FN_5O_5$, found 518 (MH+).

1-N'-[4-(6,7-Dimethoxypyrido[3,2-d]pyrimidin-4-yl)oxy-2,3-difluorophenyl]-1-N-(4-fluorophenyl)cyclopropane-1,1-dicarboxamide (34): MS (EI) for $C_{26}H_{20}F_3N_5O_5$, found 540 (MH+).

1-N'-[4-(6,7-Dimethoxypyrido[3,2-d]pyrimidin-4-yl)oxy-2,5-difluorophenyl]-1-N-(4-fluorophenyl)cyclopropane-1,1-dicarboxamide (35): MS (EI) for $C_{26}H_{20}F_3N_5O_5$, found 540 (MH+).

Example 9: 1-N-[4-(6,7-Dimethylpyrido[3,2-d]pyrimidin-4-yl)oxyphenyl]-1-N'-(4-fluorophenyl)cyclopropane-1,1-dicarboxamide (43)

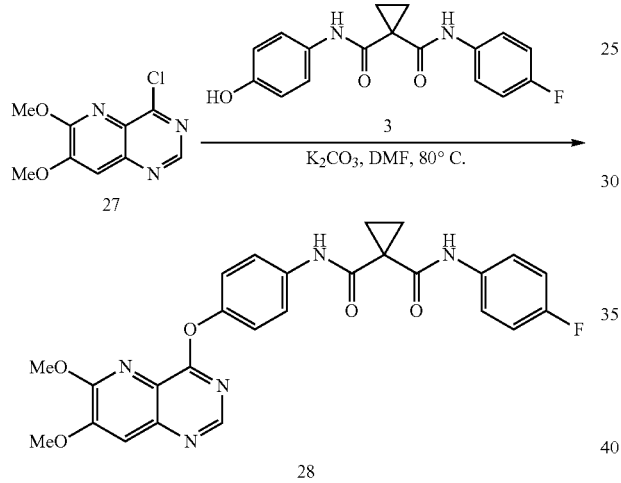

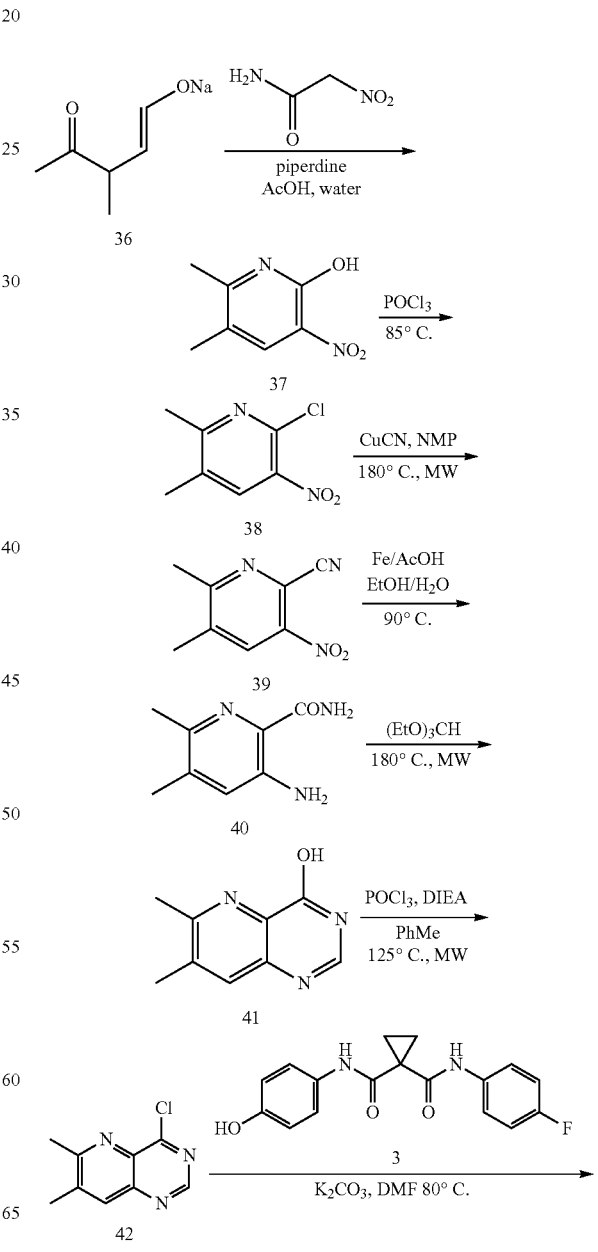

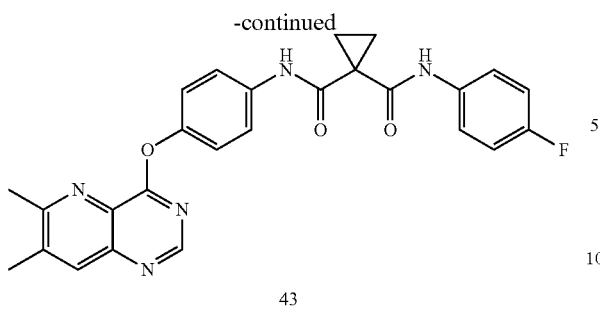

43

5,6-Dimethyl-3-nitropyridin-2-ol (37): Compound 37 was obtained from a modification of known procedures for producing 3-cyanopyridinones from the reaction of compounds like 36 with 2-cyanoacetamide (*J. Med. Chem.* 2005, 48(6), 1948-1964). The 2-cyanoacetamide was replaced with 2-nitroacetamide (1.7 g, 16.3 mmol) and reacted with Compound 36 (2.0 g, 14.7 mmol) to produce Compound 37 (780 mg, 32% yield). MS for $C_7H_8N_2O_3$, found 169 (MH+).

2-Chloro-5,6-dimethyl-3-nitropyridine (38): A mixture of Compound 37 (330 mg, 1.96 mmol) and $POCl_3$ (1.5 mL) was stirred at 85° C. for 4 hours. The mixture was concentrated under vacuum, treated with ice water, neutralized with aq saturated $NaHCO_3$, and extracted with EtOAc (3 times). The combined EtOAc extracts were concentrated, and the residue was subjected to plug filtration through silica gel, eluting with DCM to give Compound 38 (310 mg, 85% yield). MS for $C_7H_7ClN_2O_2$, found 187 (MH+).

5,6-dimethyl-3-nitropicolinonitrile (39): A mixture of Compound 38 (230 mg, 1.23 mmol) and CuCN (440 mg, 4.91 mmol) in NMP (8 mL) was heated at 180° C. under microwave irradiation for 60 min. EtOAc (40 mL) was added, and the resulting mixture was filtered. The filtrate was washed with water and concentrated under vacuum to give Compound 39, contaminated with NMP, which was used without further purification. MS for $C_8H_7N_3O_2$, found 178 (MH+).

3-Amino-5,6-dimethylpicolinamide (40): Crude Compound 39 was mixed with Fe (240 mg, 4.28 mmol), AcOH (1.0 mL, 16.7 mmol), water (5 mL), and EtOH (16 mL). The resulting mixture was stirred at 90° C. for 30 min and then cooled to room temperature. The pH was adjusted to basic with 28% aq $NH_4OH$, and the mixture was concentrated under vacuum to remove volatile organics. The resulting mixture was filtered through Celite®, and the filtrate was extracted with EtOAc (3 times). The combined EtOAc extracts were dried over anhydrous $Na_2SO_4$ and concentrated to give Compound 40, still contaminated with NMP from the previous reaction. MS for $C_8H_{11}N_3O$, found 166 (MH+).

6,7-Dimethylpyrido[3,2-d]pyrimidin-4-ol (41): Compound 41 was made from Compound 40 in a manner analogous to the preparation of Compound 10 from Compound 9 in Step 2 of Example 3. MS for $C_9H_9N_3O$, found 176 (MH+).

4 4-Chloro-6,7-dimethylpyrido[3,2-d]pyrimidine (42): Compound 42 was made from Compound 41 in a manner analogous to the preparation of Compound 11 from Compound 10 in Step 3 of Example 3. MS for $C_9H_8ClN_3$, found 194 (MH+).

1-N-[4-(6,7-Dimethylpyrido[3,2-d]pyrimidin-4-yl)oxyphenyl]-1-N'-(4-fluorophenyl)cyclopropane-1,1-dicarboxamide (43): Compound 43 was made from Compound 42 in a manner analogous to the preparation of Compound 7 from Compound 6 in Step 3 of Example 2. MS for $C_{26}H_{22}FN_5O_3$, found 472 (MH+).

Example 10: 1-N'-(4-Fluorophenyl)-1-N-[4-(6,7,8,9-tetrahydropyrimido[5,4-b]quinolin-4-yloxy)phenyl]cyclopropane-1,1-dicarboxamide (52)

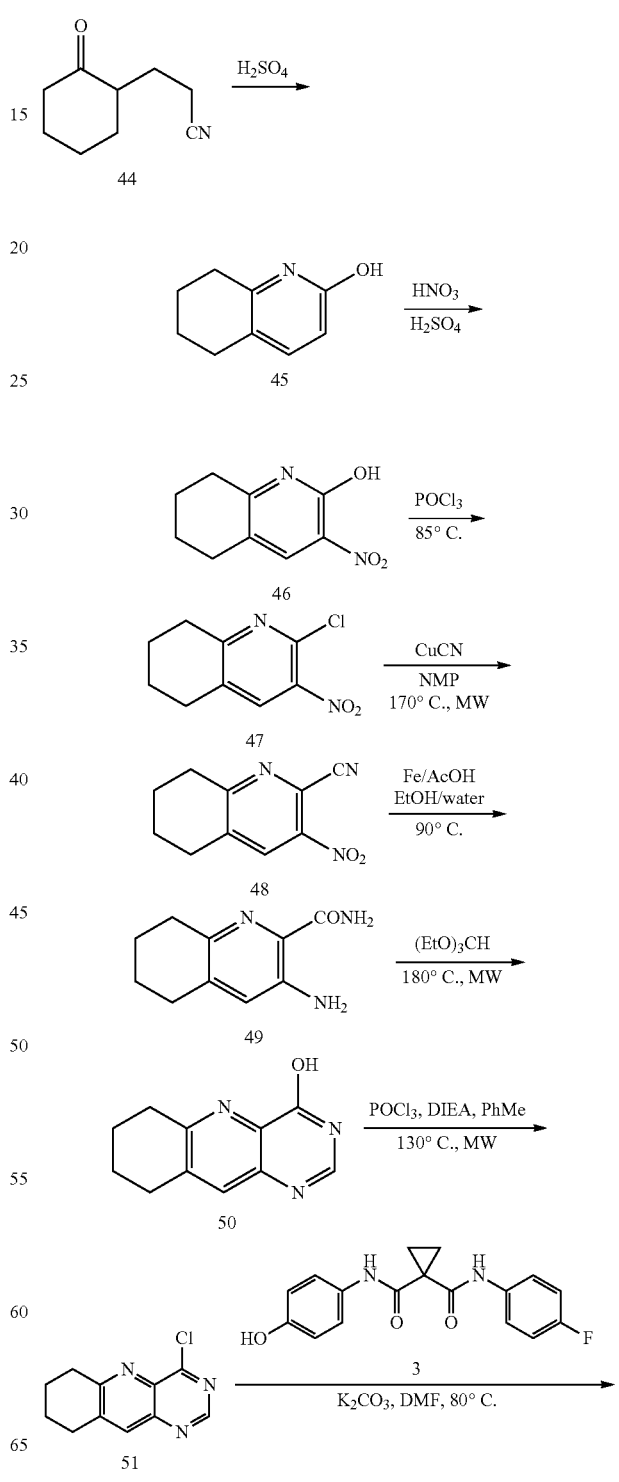

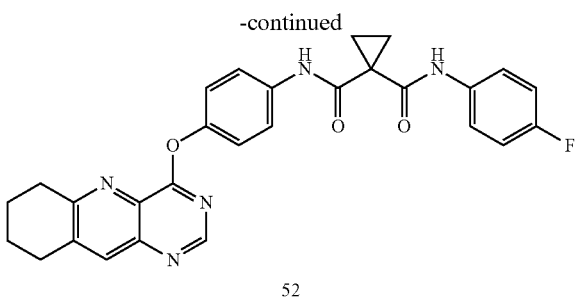

52

5,6,7,8-Tetrahydroquinolin-2-ol (45): Compound 44 (2.0 g, 13 mmol) was added dropwise to ice cold H$_2$SO$_4$ (12 mL), and the resulting mixture was stirred for 3 hours while warming to room temperature. The reaction was then poured over ice, neutralized with concentrated NH$_4$OH, and extracted with DCM (2 times). The combined organic layers were dried over anhydrous Na$_2$SO$_4$, filtered through Celite®, and concentrated to give Compound 45 as a white solid (1.04 g, 54% yield) which was used in subsequent steps without further purification. MS for C$_9$H$_{11}$NO, found 150 (MH+).

3-Nitro-5,6,7,8-tetrahydroquinolin-2-ol (46): Nitric acid (0.5 mL, 67%) was added slowly at 5° C. to a solution of Compound 45 (900 mg, 6.04 mmol) in H$_2$SO$_4$ (8 ml, 98%) while the temperature was kept below 15° C. The mixture was stirred at 5° C. for an additional 1 hour and then poured onto ice. The resulting precipitate was filtered off, washed with water, and dried to give Compound 46 (766 mg). The filtrate was extracted with DCM.

The combined organic extracts were dried over anhydrous MgSO$_4$ and concentrated to give an additional 280 mg of Compound 46 (89% yield total). MS for C$_9$H$_{10}$N$_2$O$_3$, found 195 (MH+).

2-Chloro-3-nitro-5,6,7,8-tetrahydroquinoline (47): POCl$_3$ (4 mL) was added to Compound 46 (766 mg, 3.95 mmol) and the mixture stirred at 85° C. overnight. After concentrating the reaction mixture, the resulting residue was partitioned between aq saturated NaHCO$_3$ and DCM. The organic layer was washed once with aq saturated NaCl, dried over anhydrous Na$_2$SO$_4$, and concentrated to give Compound 47, which was used directly in the next step without further purification. MS for C$_9$H$_9$ClN$_2$O$_2$, found 213 (MH+).

3-Nitro-5,6,7,8-tetrahydroquinoline-2-carbonitrile (48): A mixture of Compound 47 (106 mg, 0.5 mmol) and CuCN (90 mg, 1.0 mmol) in NMP (2.0 mL) was heated at 170° C. under microwave irradiation for 20 min. Another portion of CuCN (40 mg) was added, and irradiation continued for another 40 min. The resulting mixture was poured into ice water (20 mL) and extracted with EtOAc (2 times). The combined EtOAc extracts were dried over anhydrous Na$_2$SO$_4$ and concentrated to give Compound 48, which was used without further purification. MS for C$_{10}$H$_9$N$_3$O$_2$, found 204 (MH+).

3-Amino-5,6,7,8-tetrahydroquinoline-2-carboxamide (49): Crude Compound 48 was mixed with Fe (140 mg, 2.5 mmol), AcOH (0.4 mL, 6.7 mmol), water (6 mL), and EtOH (14 mL). The mixture was stirred at 90° C. for 20 min then cooled to room temperature. The pH of the resulting mixture was adjusted to basic with aq 28% NH$_4$OH. Volatile organic solvents were removed under vacuum. The resulting mixture was filtered through Celite®, and the filtrate was concentrated and then extracted with EtOAc (2 times). The combined EtOAc extracts were dried over anhydrous Na$_2$SO$_4$ and concentrated to give Compound 49 as a brown solid (83 mg, 87% yield over 2 steps). MS for C$_{10}$H$_{13}$N$_3$O, found 192 (MH+).

6,7,8,9-Tetrahydropyrimido[5,4-b]quinolin-4-ol (50): Compound 50 was made from Compound 49 in a manner analogous to the preparation of Compound 10 from Compound 9 in Step 2 of Example 3. MS for C$_{11}$H$_{11}$N$_3$O, found 202 (MH+).

4-Chloro-6,7,8,9-tetrahydropyrimido[5,4-b]quinoline (51): Compound 51 was made from Compound 50 in a manner analogous to the preparation of Compound 11 from Compound 10 in Step 3 of Example 3. MS for C$_{11}$H$_{10}$ClN$_3$, found 220 (MH+).

1-N'-(4-Fluorophenyl)-1-N-[4-(6,7,8,9-tetrahydropyrimido[5,4-b]quinolin-4-yloxy)phenyl]cyclopropane-1,1-dicarboxamide (52): Compound 52 was made from Compound 51 in a manner analogous to the preparation of Compound 7 from Compound 6 in Step 3 of Example 2. MS for C$_{28}$H$_{24}$FN$_5$O$_3$, found 498 (MH+).

Example 11: 1-N-[4-(6-Cyano-7-methoxypyrido[3,2-d]pyrimidin-4-yl)oxyphenyl]-1-N'-(4-fluorophenyl)cyclopropane-1,1-dicarboxamide (57)

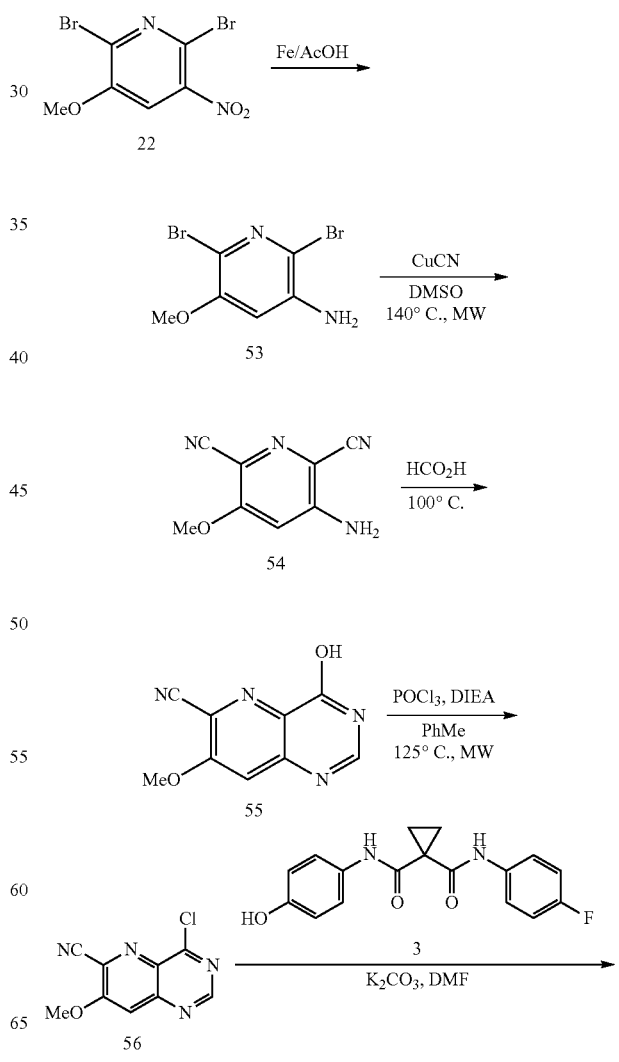

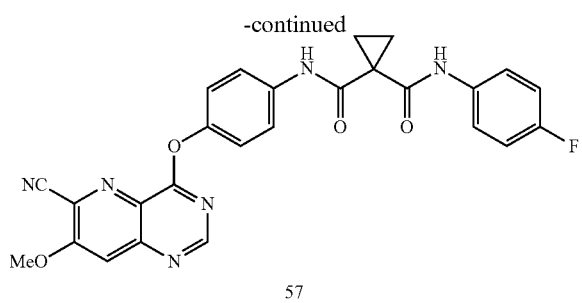

57

2,6-Dibromo-5-methoxypyridin-3-amine (53): To Compound 22 (360 mg, 1.15 mmol) was added AcOH (4 mL), followed by Fe powder (260 mg, 4.64 mmol). The reaction mixture was stirred at room temperature for 2 hours and then poured into ice water. The pH of the resulting mixture was adjusted to 7 with $Na_2CO_3$. The resulting solids were filtered and then washed with DCM. The filtrate was dried over anhyd $Na_2SO_4$ and concentrated to give crude Compound 53 (340 mg, ~100% yield). MS for $C_6H_6Br_2N_5O$, found 283 (MH+).

3-Amino-5-methoxypyridine-2,6-dicarbonitrile (54): A mixture of Compound 53 (270 mg, 0.96 mmol) and CuCN (260 mg, 2.89 mmol) in DMSO (4.5 mL) was heated at 140° C. under microwave irradiation for 60 min. EtOAc (40 mL) was added, and the resulting suspension was filtered. The EtOAc filtrate was washed with water and concentrated under vacuum. The resulting residue was purified by silica gel chromatography (0-100% EtOAc in DCM) to give Compound 54 (78 mg, 47% yield). MS for $C_8H_6N_4O$, found 173 (M-H).

4-Hydroxy-7-methoxypyrido[3,2-d]pyrimidine-6-carbonitrile (55): Compound 54 (70 mg, 0.40 mmol) in formic acid (1.2 mL, >95%) was stirred at 100-110° C. for 3 days and concentrated to a solid. The solid was washed with EtOAc and dried to give Compound 55 (52 mg, 64% yield). MS for $C_9H_6N_4O_2$, found 203 (MH+).

4-Chloro-7-methoxypyrido[3,2-d]pyrimidine-6-carbonitrile (56): Compound 56 was made from Compound 55 in a manner analogous to the preparation of Compound 11 from Compound 10 in Step 3 of Example 3. MS for $C_9H_5ClN_4O$, found 221 (MH+).

1-N-[4-(6-Cyano-7-methoxypyrido[3,2-d]pyrimidin-4-yl)oxyphenyl]-1-N'-(4-fluorophenyl)cyclopropane-1,1-dicarboxamide (57): Compound 57 was made from Compound 56 in a manner analogous to the preparation of Compound 7 from Compound 6 in Step 3 of Example 2. MS for $C_{26}H_{19}FN_6O_4$, found 499 (MH+).

Example 12: 4-(3-((4-Chloro-6-methoxypyrido[3,2-d]pyrimidin-7-yl)oxy)propyl)-morpholine (64)

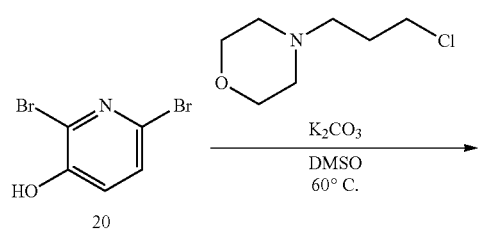

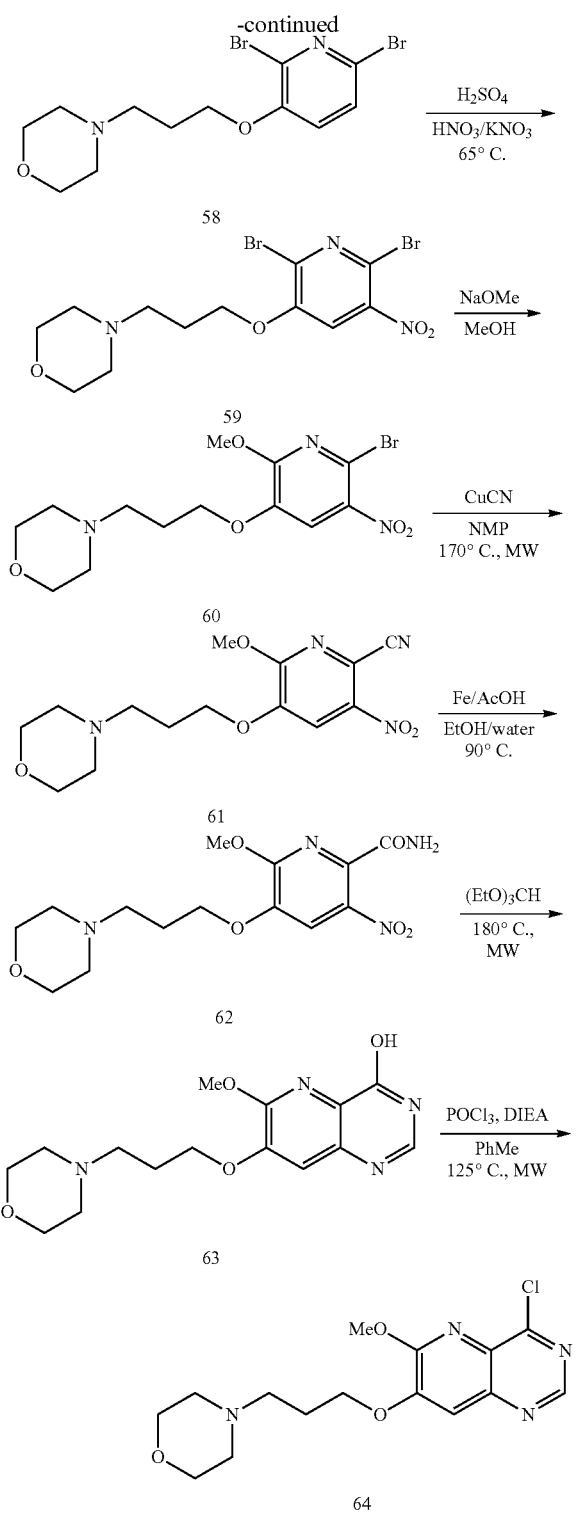

4-(3-((2,6-Dibromopyridin-3-yl)oxy)propyl)morpholine (58): Compound 58 was synthesized from Compound 20 in a manner analogous to that used to convert Compound 20 to Compound 21 in Step 1 of Example 7, replacing the MeI with 4-(3-chloropropyl)morpholine. MS (EI) for $C_{12}H_{16}Br_2N_2O_2$, found 379 (MH+).

4-(3-((2,6-Dibromo-5-nitropyridin-3-yl)oxy)propyl)morpholine (59): Compound 59 was synthesized from Compound 58 in a manner analogous to that used to convert Compound 21 to Compound 22 in Example 7.

4-(3-((6-Bromo-2-methoxy-5-nitropyridin-3-yl)oxy)propyl)morpholine (60): Compound 60 was synthesized from Compound 59 in a manner analogous to that used to convert Compound 22 to Compound 23 in Example 7.

6-Methoxy-5-(3-morpholinopropoxy)-3-nitropicolinonitrile (61): Compound 61 was synthesized from Compound 60 in a manner analogous to that used to convert Compound 23 to Compound 24 in Example 7.

6-Methoxy-5-(3-morpholinopropoxy)-3-nitropicolinamide (62): Compound 62 was synthesized from Compound 61 in a manner analogous to that used to convert Compound 24 to Compound 25 in Example 7. MS (EI) for $C_{14}H_{22}N_4O_4$, found 311 (MH+).

6-Methoxy-7-(3-morpholinopropoxy)pyrido[3,2-d]pyrimidin-4-ol (63): Compound 63 was made from Compound 62 in a manner analogous to the preparation of Compound 10 from Compound 9 in Step 2 of Example 3. MS (EI) for $C_{15}H_{20}N_4O_4$, found 321 (MH+).

4-(3-((4-Chloro-6-methoxypyrido[3,2-d]pyrimidin-7-yl)oxy)propyl)morpholine (64): Compound 64 was made from Compound 63 in a manner analogous to the preparation of Compound 11 from Compound 10 in Step 3 of Example 3. MS (EI) for $C_{15}H_{19}Cl_4O_3$, found 339 (MH+).

Example 13: 1-N'-(4-Fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide (65)

The following compounds were prepared from Compound 64 in a method analogous to Compound 65 in Example 13 using the appropriately substituted N-(4-fluorophenyl)-N-(4-hydroxyphenyl)cyclopropane-1,1-dicarboxamides which were synthesized using methods analogous to those used in Example 1 or Example 5:

1-N'-[3-Chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (66): MS (EI) for $C_{32}H_{32}ClFN_6O_6$, found 651 (MH+).

1-N'-[3-Fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (67): MS (EI) for $C_{32}H_{32}F_2N_6O_6$, found 635 (MH+).

1-N-(4-Fluorophenyl)-1-N'-[4-[6-methoxy-7-(3-morpholin-4-ylpropoxy)pyrido[3,2-d]pyrimidin-4-yl]oxy-3-methylphenyl]cyclopropane-1,1-dicarboxamide (68): $^1$H NMR (400 MHz, CDCl$_3$) δ 9.07 (s, 1H), 8.83 (s, 1H), 8.58 (s, 1H), 7.53 (d, 1H), 7.52-7.43 (m, 3H), 7.43 (s, 1H), 7.20 (d, 1H), 7.05 (t, 2H), 4.28 (t, 2H), 4.22 (s, 3H), 3.74 (t, 4H), 2.58 (t, 2H), 2.55-2.43 (m, 4H), 2.19 (s, 3H), 2.17-2.08 (m, 2H), 1.72-1.67 (m, 2H), 1.67-1.62 (m, 2H); MS (EI) for $C_{33}H_{35}FN_6O_6$, found 631.2 (MH+).

1-N'-[2-Fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (69): $^1$H NMR (400 MHz, CDCl$_3$) δ 9.16 (s, 1H), 8.97 (br s, 1H), 8.61 (s, 1H), 8.32 (t, 1H), 7.51 (dd, 2H), 7.43 (s, 1H), 7.18-7.09 (m, 2H), 7.05 (t, 2H), 4.28 (t, 2H), 4.21 (s, 3H), 3.74 (t, 4H), 2.58 (t, 2H), 2.54-2.45 (m, 4H), 2.18-2.09 (m, 2H), 1.79-

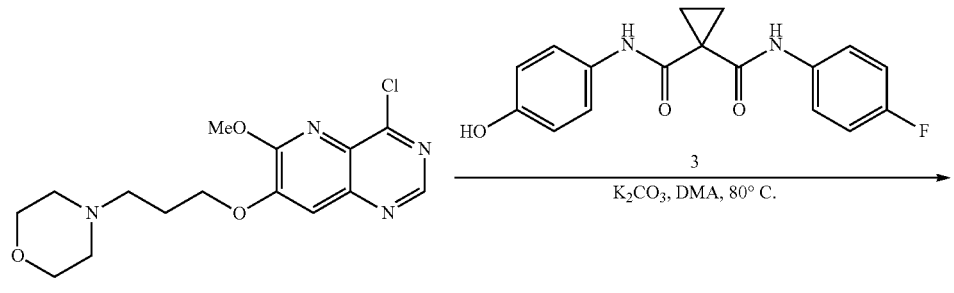

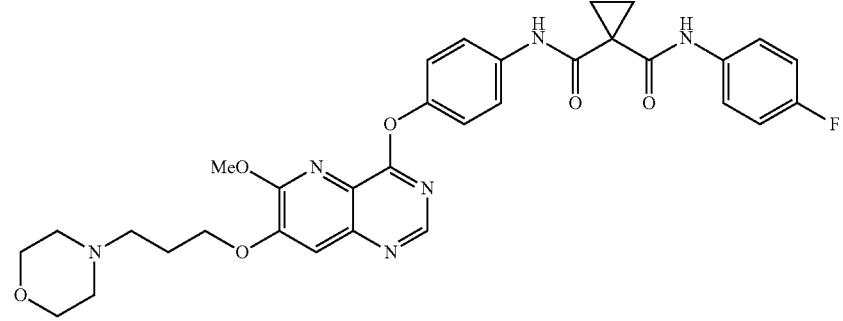

1-N'-(4-Fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide (65): Compound 65 was made from Compound 64 in a manner analogous to the preparation of Compound 7 from Compound 6 in Step 3 of Example 2. MS for $C_{32}H_{33}FN_6O_6$, found 617 (MH+).

1.73 (m, 2H), 1.72-1.66 (m, 2H); MS (EI) for $C_{32}H_{32}F_2N_6O_6$, found 635.1 (MH+).

1-N'-[2-Chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (70): $^1$H NMR (400 MHz, CDCl$_3$) δ 9.52 (s, 1H), 8.88 (s, 1H), 8.61 (s, 1H), 8.42 (d, 1H), 7.52 (dd, 2H), 7.43 (s, 1H), 7.40 (d, 1H), 7.25 (d, 1H), 7.05 (t, 2H), 4.29 (t, 2H), 4.21 (s, 3H), 3.77-3.69 (m, 4H), 2.58 (t, 2H), 2.55-2.42 (m, 4H), 2.20-2.06 (m, 2H), 1.86-1.78 (m, 2H), 1.71-1.63 (m, 2H); MS (EI) for $C_{32}H_{32}ClFN_6O_6$, found 651.1 (MH+).

1-N-(4-Fluorophenyl)-1-N'-[4-[6-methoxy-7-(3-morpholin-4-ylpropoxy)pyrido[3,2-d]pyrimidin-4-yl]oxy-2-methylphenyl]cyclopropane-1,1-dicarboxamide (71): $^1$H NMR (400 MHz, CDCl$_3$) δ 9.13 (s, 1H), 8.76 (s, 1H), 8.61 (s, 1H), 7.93 (d, 1H), 7.50 (dd, 2H), 7.42 (s, 1H), 7.18-7.12 (m, 2H), 7.05 (t, 2H), 4.28 (t, 2H), 4.22 (s, 3H), 3.74 (t, 4H), 2.58 (t, 2H), 2.55-2.42 (m, 4H), 2.35 (s, 3H), 2.18-2.09 (m, 2H), 1.76-1.71 (m, 2H), 1.71-1.67 (m, 2H); MS (EI) for $C_{33}H_{35}FN_6O_6$, found 631.2 (MH+).

1-N'-[2,5-Difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (72): MS (EI) for $C_{32}H_{31}F_3N_6O_6$, found 653 (MH+).

1-N'-[2,3-Difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (73): MS (EI) for $C_{32}H_{31}F_3N_6O_6$, found 653 (MH+).

1-N-(4-Fluorophenyl)-1-N'-[3-methoxy-4-[6-methoxy-7-(3-morpholin-4-ylpropoxy)pyrido[3,2-d]pyrimidin-4-yl]oxyphenyl]cyclopropane-1,1-dicarboxamide (74): $^1$H NMR (400 MHz, CDCl$_3$) δ 9.20 (s, 1H), 8.74 (s, 1H), 8.57 (s, 1H), 7.53 (d, 1H), 7.48 (dd, 2H), 7.42 (s, 1H), 7.21 (d, 1H), 7.10-7.02 (m, 3H), 4.28 (t, 2H), 4.23 (s, 3H), 3.77 (s, 3H), 3.74 (t, 4H), 2.57 (t, 2H), 2.54-2.44 (m, 4H), 2.17-2.08 (m, 2H), 1.74-1.68 (m, 2H), 1.66-1.62 (m, 2H); MS (EI) for $C_{33}H_{35}FN_6O_7$, found 647.2 (MH+).

1-N'-[3-Cyano-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (75): MS (EI) for $C_{33}H_{32}FN_7O_6$, found 642.2 (MH+).

1-N'-[3,5-Difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (76): $^1$H NMR (400 MHz, DMSO-d$_6$) δ 10.49 (s, 1H), 10.02 (s, 1H), 8.61 (s, 1H), 7.69 (s, 1H), 7.67-7.58 (m, 4H), 7.16 (t, 2H), 4.30 (t, 2H), 4.10 (s, 3H), 3.58 (t, 4H), 2.45 (t, 2H), 2.38 (s, 4H), 1.98 (quin, 2H), 1.46 (d, 4H); MS (EI) for $C_{32}H_{31}F_3N_6O_6$, found 653.1 (MH+).

Example 14: 1-N'-(4-Fluorophenyl)-1-N-[4-[6-methoxy-7-(2-methoxyethoxy)pyrido[3,2-d]pyrimidin-4-yl]oxyphenyl]cyclopropane-1,1-dicarboxamide (78)

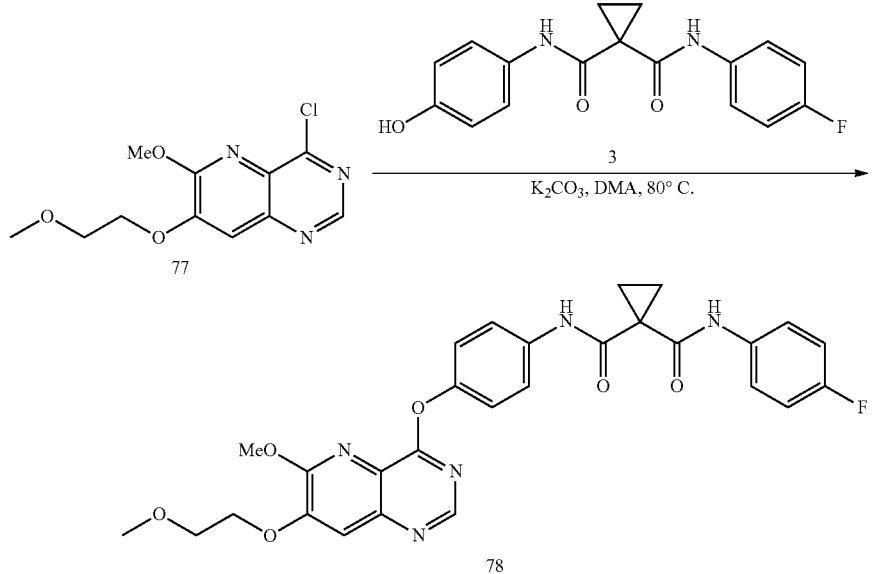

4-Chloro-6-methoxy-7-(2-methoxyethoxy)pyrido[3,2-d]pyrimidine (77): Compound 77 can be made following a similar sequence of steps to those used to make Compound 64 in Example 12, substituting 1-bromo-2-methoxyethane or 1-chloro-2-methoxyethane for the 4-(3-chloropropyl)morpholine used in the first step.

1-N'-(4-Fluorophenyl)-1-N-[4-[6-methoxy-7-(2-methoxyethoxy)pyrido[3,2-d]pyrimidin-4-yl]oxyphenyl]cyclopropane-1,1-dicarboxamide (78): Compound 78 was made from Compound 77 in a manner analogous to the preparation of Compound 7 from Compound 6 in Step 3 of Example 2. MS for $C_{28}H_{26}FN_5O_6$, found 548 (MH+).

The following compounds were prepared from Compound 77 in a method analogous to Compound 78 in Example 14 using the appropriately substituted N-(4-fluorophenyl)-N-(4-hydroxyphenyl)cyclopropane-1,1-dicarboxamides which were synthesized using methods analogous to those used in Example 1 or Example 5:

1-N'-[3-Fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (79): MS for $C_{28}H_{25}F_2N_5O_6$, found 566 (MH+).

1-N'-[3-Chloro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (80): MS for $C_{28}H_{25}ClFN_5O_6$, found 582 (MH+).

1-N'-[2-Fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (81): MS for $C_{28}H_{25}F_2N_5O_6$, found 566 (MH+).

1-N'-[2,3-Difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (82): MS for $C_{28}H_{24}F_3N_5O_6$, found 584 (MH+).

1-N'-[2,5-Difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (83): MS for $C_{28}H_{24}F_3N_5O_6$, found 584 (MH+).

Example 15: 1-N'-(4-Fluorophenyl)-1-N-(4-pyrido[3,4-d]pyrimidin-4-yloxyphenyl)cyclopropane-1,1-dicarboxamide (85)

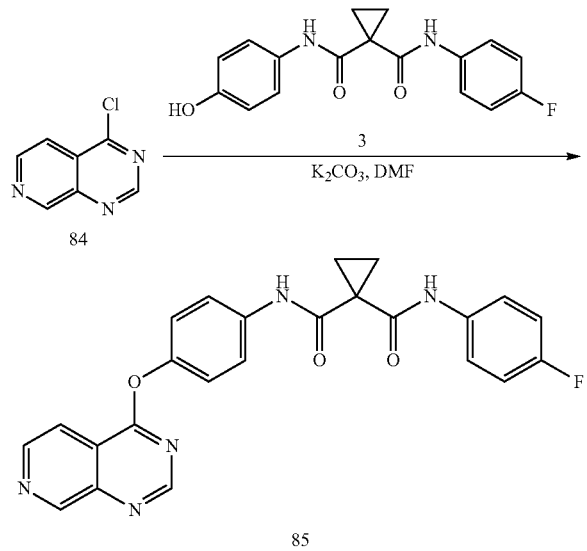

N-(4-Fluorophenyl)-N-(4-(pyrido[3,4-d]pyrimidin-4-yloxy)phenyl)cyclopropane-1,1-dicarboxamide (228): Compound 85 was made from Compound 84 in a manner analogous to the preparation of Compound 7 from Compound 6 in Step 3 of Example 2. $^1$H NMR (400 MHz, DMSO-d$_6$) δ 10.19 (br s, 1H), 10.08 (br s, 1H), 9.43 (s, 1H), 8.88 (s, 1H), 8.86 (d, 1H), 8.22 (d, 1H), 7.74 (d, 2H), 7.63-7.65 (m, 2H), 7.32 (d, 2H), 7.15 (d, 2H), 1.48 (s, 4H); MS for $C_{24}H_{18}FN_5O_3$, found 444.0 (MH+).

Example 16: 1-N-[4-(6-Chloropyrido[3,4-d]pyrimidin-4-yl)oxyphenyl]-1-N'-(4-fluorophenyl)cyclopropane-1,1-dicarboxamide (88)

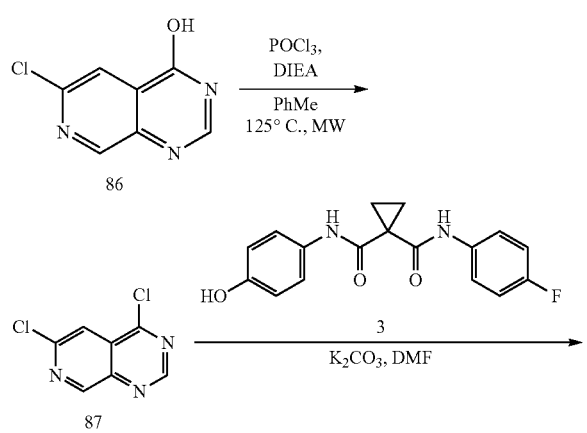

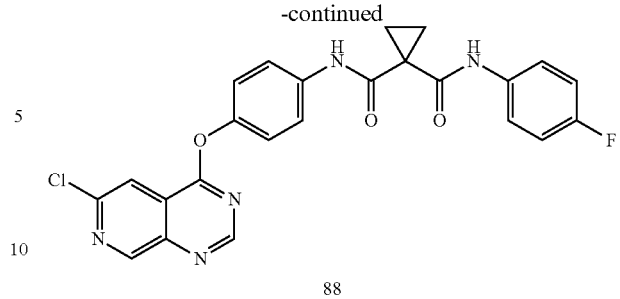

4,6-Dichloropyrido[3,4-d]pyrimidine (87): Compound 87 was made from Compound 86 in a manner analogous to the preparation of Compound 11 from Compound 10 in Step 3 of Example 3.

1-N-[4-(6-Chloropyrido[3,4-d]pyrimidin-4-yl)oxyphenyl]-1-N'-(4-fluorophenyl)cyclopropane-1,1-dicarboxamide (88): Compound 88 was made from Compound 87 in a manner analogous to the preparation of Compound 7 from Compound 6 in Step 3 of Example 2. MS for $C_{24}H_{17}ClFN_5O_3$, found 478 (MH+).

Example 17: 1-N'-(4-Fluorophenyl)-1-N-[4-(6-methoxypyrido[3,4-d]pyrimidin-4-yl)oxyphenyl]cyclopropane-1,1-dicarboxamide (91)

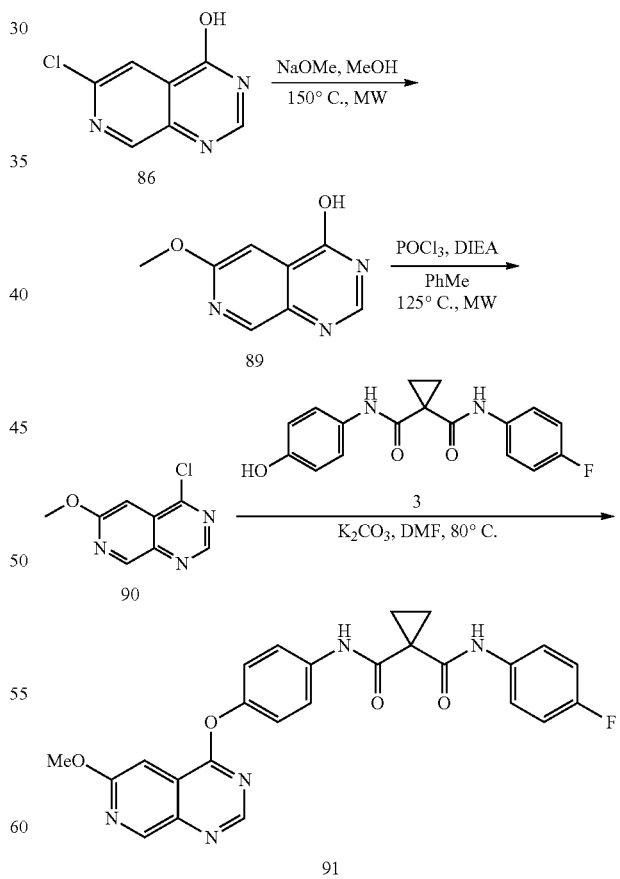

6-Methoxypyrido[3,4-d]pyrimidin-4-ol (89): Compound 89 was made from Compound 86 in a manner analogous to the preparation of Compound 14 from Compound 10 in Step 1 of Example 4.

4-Chloro-6-methoxypyrido[3,4-d]pyrimidine (90): Compound 90 was made from Compound 89 in a manner analogous to the preparation of Compound 11 from Compound 10 in Step 3 of Example 3.

1-N'-(4-Fluorophenyl)-1-N-[4-(6-methoxypyrido[3,4-d]pyrimidin-4-yl)oxyphenyl]cyclopropane-1,1-dicarboxamide (91): Compound 91 was made from Compound 90 in a manner analogous to the preparation of Compound 7 from Compound 6 in Step 3 of Example 2. MS for $C_{25}H_{20}FN_5O_4$, found 474 (MH+).

Example 18: 1-N'-(4-Fluorophenyl)-1-N-(4-pyrido[4,3-d]pyrimidin-4-yloxyphenyl)cyclopropane-1,1-dicarboxamide (95)

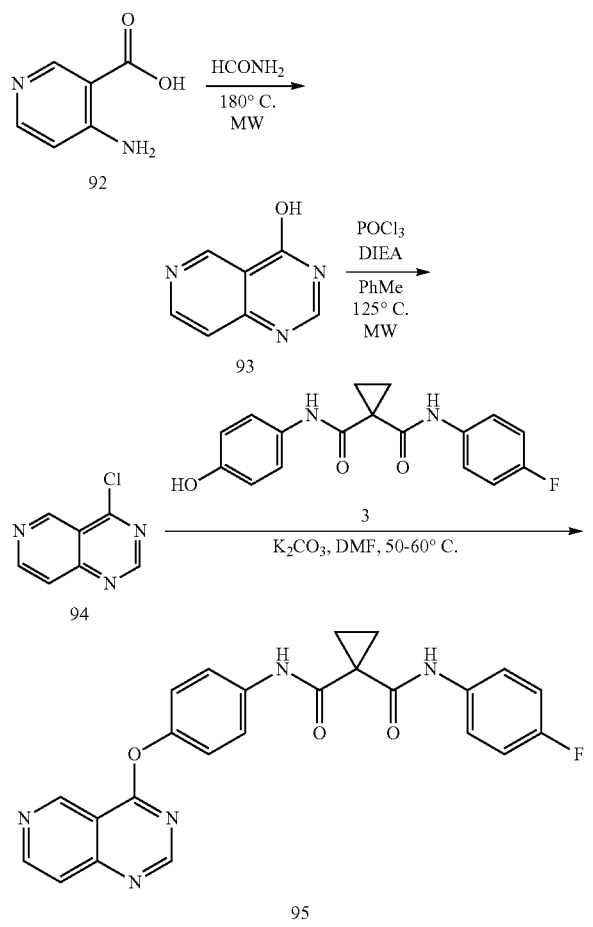

Example 19: 1-N-[4-(7-Chloropyrido[4,3-d]pyrimidin-4-yl)oxyphenyl]-1-N'-(4-fluorophenyl)cyclopropane-1,1-dicarboxamide (101)

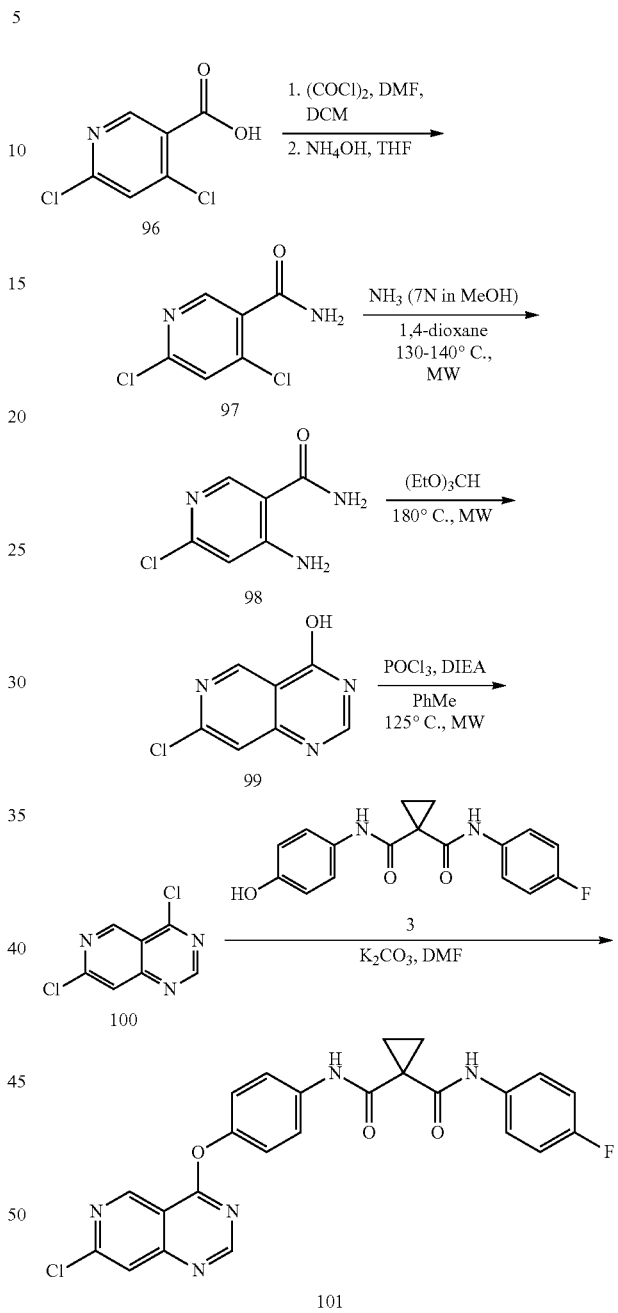

Pyrido[4,3-d]pyrimidin-4-ol (93): Compound 93 was made from Compound 92 in a manner analogous to the preparation of Compound 5 from Compound 4 in Step 1 of Example 2. MS for $C_7H_5N_3O$, found 148 (MH+).

4-Chloropyrido[4,3-d]pyrimidine (94): Compound 94 was made from Compound 93 in a manner analogous to the preparation of Compound 11 from Compound 10 in Step 3 of Example 3. MS for $C_7H_4ClN_3$, found 166 (MH+).

1-N'-(4-Fluorophenyl)-1-N-(4-pyrido[4,3-d]pyrimidin-4-yloxyphenyl)-cyclopropane-1,1-dicarboxamide (95): Compound 95 was made from Compound 94 in a manner analogous to the preparation of Compound 7 from Compound 6 in Step 3 of Example 2. MS for $C_{24}H_{18}FN_5O_3$, found 444 (MH+).

4,6-Dichloronicotinamide (97): To a suspension of Compound 96 (2.0 g, 10.4 mmol) in DCM (40 mL) cooled to 5° C. was added oxalyl chloride (3 mL, 33.8 mmol) followed by DMF (0.3 mL). The reaction was stirred at 0-5° C. for 2 hours and then allowed to warm to room temperature over 1.5 hours. The volatiles were removed in vacuo, and the crude residue was suspended in THF (40 mL) and then cooled to 0-5° C. To this stirred suspension was added concentrated NH₄OH (15 mL, 28%) dropwise, and the resulting reaction mixture was stirred at room temperature for 1 hour. The volatiles were removed under vacuum, and the crude residue was partitioned between EtOAc and water.

The aqueous phase was further extracted with EtOAc (2 times). The combined EtOAc phases were dried over anhydrous Na$_2$SO$_4$ and concentrated to give Compound 97 as a white solid (1.8 g, 91% yield).

4-Amino-6-chloronicotinamide (98): A mixture of Compound 97 (191 mg, 1.0 mmol) and NH$_3$ (7M in MeOH, 0.15 mL, 1.05 mmol) in 1,4-dioxane (3.5 mL) was heated at 130° C. under microwave irradiation for 1 hour. Additional NH$_3$ (7M in MeOH, 0.55 mL, 3.85 mmol) was added and microwave irradiation continued at 130° C. for an additional 1 hour.

One more aliquot of NH$_3$ (7M in MeOH, 0.50 mL, 3.75 mmol) was added, and microwave irradiation continued at 140° C. for 2 hours. The resulting reaction mixture was concentrated, and the residue was suspended in DCM. The resulting solids were filtered, washed with DCM, and dried to give Compound 98 (158 mg, 92% yield). MS for C$_6$H$_6$ClN$_3$O, found 172 (MH+).

7-Chloropyrido[4,3-d]pyrimidin-4-ol (99): Compound 99 was made from Compound 98 in a manner analogous to the preparation of Compound 10 from Compound 9 in Step 2 of Example 3. MS for C$_7$H$_4$ClN$_3$O, found 182 (MH+).

4,7-Dichloropyrido[4,3-d]pyrimidine (100): Compound 100 was made from Compound 99 in a manner analogous to the preparation of Compound 11 from Compound 10 in Step 3 of Example 3. MS for C$_7$H$_3$Cl$_2$N$_3$, found 200 (MH+).

1-N-[4-(7-Chloropyrido[4,3-d]pyrimidin-4-yl)oxyphenyl]-1-N'-(4-fluorophenyl)cyclopropane-1,1-dicarboxamide (101): Compound 101 was made from Compound 100 in a manner analogous to the preparation of Compound 7 from Compound 6 in Step 3 of Example 2. MS for C$_{24}$H$_{17}$ClFN$_5$O$_3$, found 478 (MH+).

Example 20: 1-N'-(4-Fluorophenyl)-1-N-[4-(7-methoxypyrido[4,3-d]pyrimidin-4-yl)oxyphenyl]cyclopropane-1,1-dicarboxamide (104)

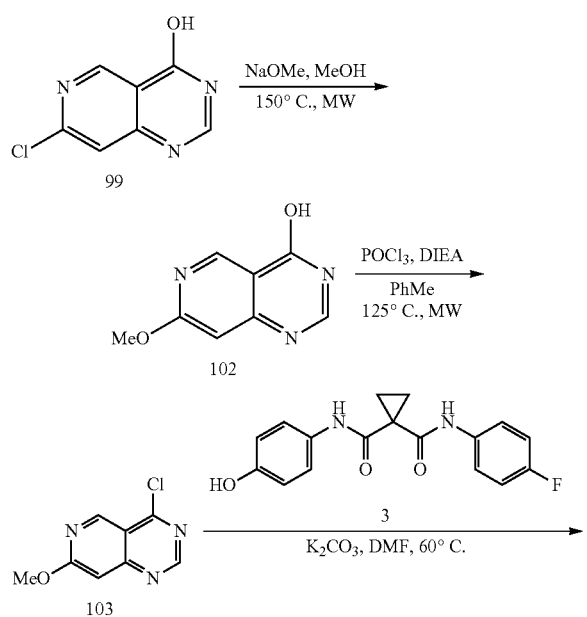

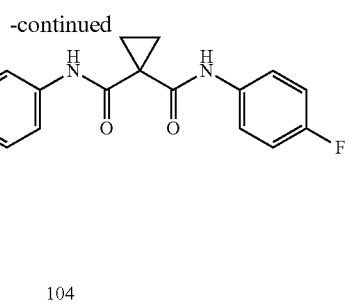

7-Methoxypyrido[4,3-d]pyrimidin-4-ol (102): Compound 102 was made from Compound 99 in a manner analogous to the preparation of Compound 14 from Compound 10 in Step 1 of Example 4. MS for C$_8$H$_7$N$_3$O$_2$, found 178 (MH+).

4-Chloro-7-methoxypyrido[4,3-d]pyrimidine (103): Compound 103 was made from Compound 102 in a manner analogous to the preparation of Compound 11 from Compound 10 in Step 3 of Example 3.

1-N'-(4-Fluorophenyl)-1-N-[4-(7-methoxypyrido[4,3-d]pyrimidin-4-yl)oxyphenyl]cyclopropane-1,1-dicarboxamide (104): Compound 104 was made from Compound 103 in a manner analogous to the preparation of Compound 7 from Compound 6 in Step 3 of Example 2. MS for C$_{25}$H$_{20}$FN$_5$O$_4$, found 474 (MH+).

Example 21: 1-N-[4-(6-Cyanoquinazolin-4-yl)oxyphenyl]-1-N'-(4-fluorophenyl)cyclopropane-1,1-dicarboxamide (106)

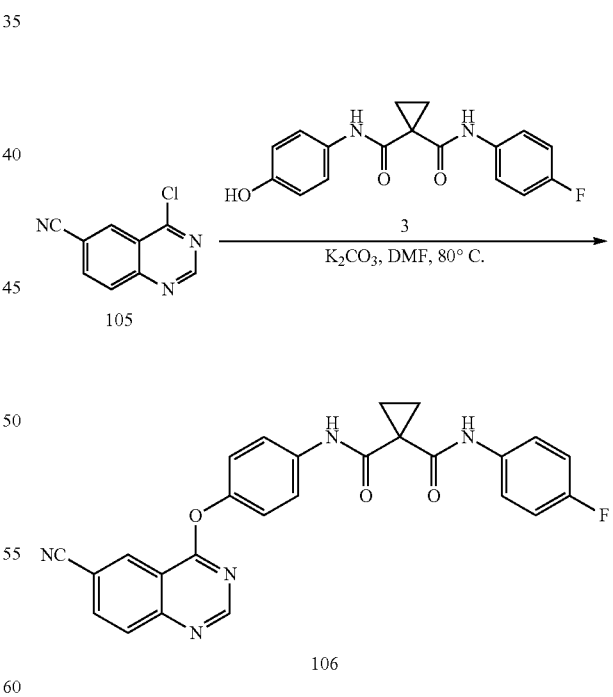

1-N-[4-(6-Cyanoquinazolin-4-yl)oxyphenyl]-1-N'-(4-fluorophenyl)cyclopropane-1,1-dicarboxamide (106): Compound 106 was made from Compound 105 in a manner analogous to the preparation of Compound 7 from Compound 6 in Step 3 of Example 2. MS for C$_{26}$H$_{18}$FN$_5$O$_3$, found 468 (MH+).

Example 22: 4-Chloro-7-methoxyquinazoline-6-carbonyl chloride (112)

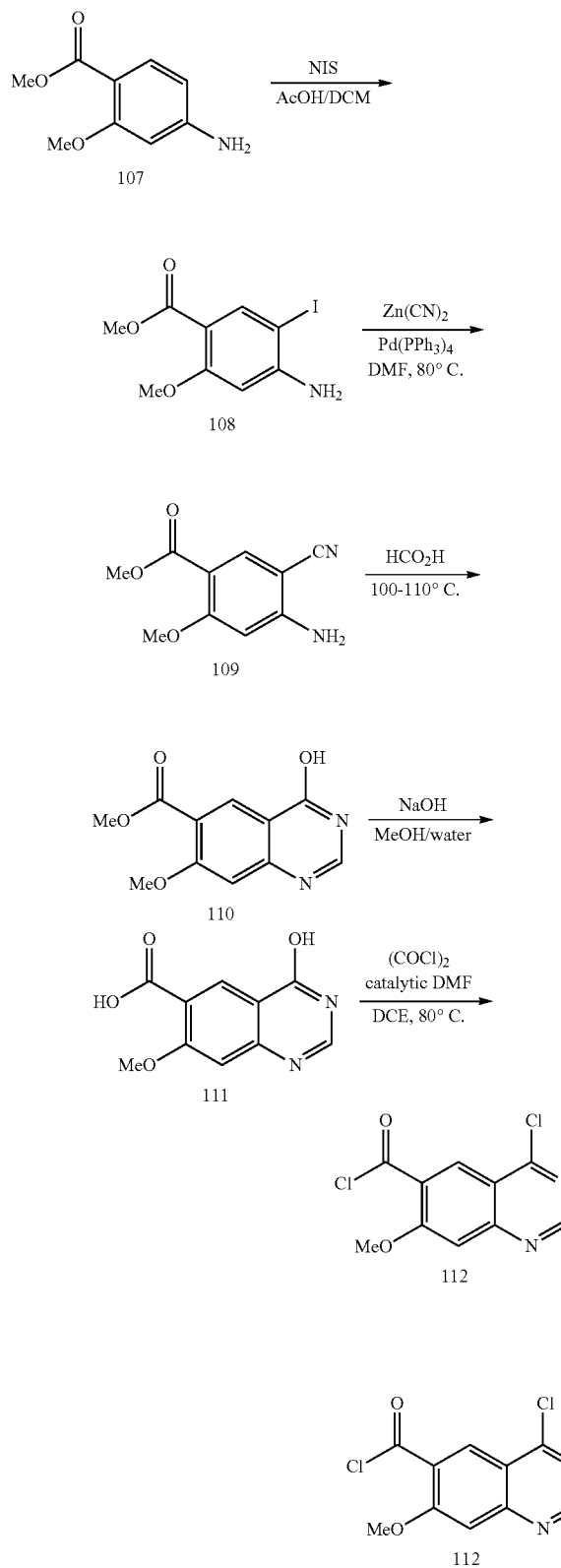

Methyl 4-amino-5-iodo-2-methoxybenzoate (108): At 0-5° C., N-iodosuccinimide (2.30 g, 10.2 mmol) was added to a suspension of Compound 107 (1.81 g, 10 mmol) in AcOH (25 mL) and DCM (12 mL). The mixture was stirred at 5° C. for 10 min, followed by stirring at room temperature for 3 hours. The mixture was concentrated, and the resulting residue was treated with aq saturated $NaHCO_3$ until pH 8 was achieved. The resulting suspension was filtered, and the resulting solids were washed with water followed by i-PrOH and hexanes and dried to give Compound 108 (2.72 g, 88% yield) which was used in the next step without further purification. MS for $C_9H_{10}INO_3$, found 308 (MH+).

Methyl 4-amino-5-cyano-2-methoxybenzoate (109): To a solution of Compound 108 (2.5 g, 8.1 mmol) and dicyanozinc (1.5 g, 12.8 mmol) in DMF (25 mL) under argon, was added $Pd(PPh_3)_4$ (1.0 g, 0.87 mmol) and the reaction mixture was stirred at 80° C. overnight. Water was added and the resulting suspension was filtered, washed with water, dried and then resuspended in EtOAc. The EtOAc suspension was stirred for 15 min, then filtered and dried to give Compound 109 as an off-white powder (1.5 g, 90% yield). MS for $C_{10}H_{10}N_2O_3$, found 207 (MH+).

Methyl 4-hydroxy-7-methoxyquinazoline-6-carboxylate (110): Compound 109 (1.5 g, crude from previous step) in formic acid (22 mL, >95%) was stirred at 100-110° C. for 1 day and filtered to remove the white solid. The filtrate was diluted with ether (100 mL), and the resulting suspension was filtered to give Compound 110 (1.01 g, 88% yield). MS for $C_{11}H_{10}N_2O_4$, found 235 (MH+).

4-Hydroxy-7-methoxyquinazoline-6-carboxylic acid (111): A mixture of Compound 110 (508 mg, 2.17 mmol) and NaOH (1.0 g, 25 mmol) in water (5 mL) and MeOH (5 mL) was stirred at room temperature for 1 hour, concentrated, and the pH adjusted to 3 with concd HCl. The resulting suspension was filtered, and the resulting solids were washed with water and dried to give Compound 111 (390 mg, 82% yield). MS for $C_{10}H_8N_2O_4$, found 221 (MH+).

4-Chloro-7-methoxyquinazoline-6-carbonyl chloride (112): To a mixture of Compound 111 (110 mg, 0.5 mmol) in 1,2-dichloroethane (5 mL) was added oxalyl chloride (0.6 mL, 7 mmol) followed by a catalytic amount of DMF. The reaction was stirred in a sealed tube at 80° C. for 3 hours and concentrated to give crude Compound 112 which was used directly in subsequent steps without further purification.

Example 23: 1-N'-(4-Fluorophenyl)-1-N-[4-[7-methoxy-6-(oxetan-3-ylcarbamoyl)quinazolin-4-yl]oxyphenyl]cyclopropane-1,1-dicarboxamide (115)

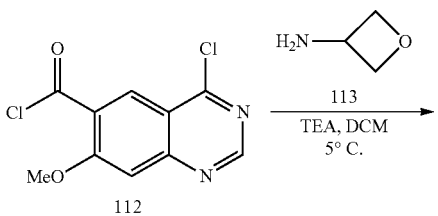

-continued

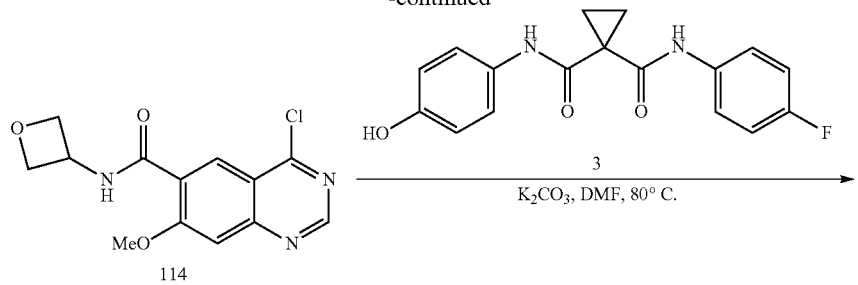

4-Chloro-7-methoxy-N-(oxetan-3-yl)quinazoline-6-carboxamide (114): Crude Compound 112 was dissolved in DCM (5 mL) and the solution was cooled to 5° C. To the solution was added TEA (0.2 mL, 1.44 mmol) followed by Compound 113 (40 mg, 0.55 mmol) dropwise. The resulting mixture was stirred at 5° C. for 30 min and then concentrated to give crude Compound 114 which was used in the next step without further purification. MS for $C_{13}H_{12}ClN_3O_3$, found 294 (MH+).

1-N'-(4-Fluorophenyl)-1-N-[4-[7-methoxy-6-(oxetan-3-ylcarbamoyl)quinazolin-4-yl]oxyphenyl]cyclopropane-1,1-dicarboxamide (115): Compound 115 was made from Compound 114 in a manner analogous to the preparation of Compound 7 from Compound 6 in Step 3 of Example 2. MS for $C_{30}H_{26}FN_5O_6$, found 572 (MH+).

The following compounds were prepared using a method analogous to that for Compound 115 in Example 23 by initially reacting Compound 112 with the appropriate amine followed by the coupling of that product to Compound 3 using an analogous method to the way Compound 6 was coupled to Compound 3 in Step 3 of Example 2:

1-N-[4-[6-(Cyclopropylcarbamoyl)-7-methoxyquinazolin-4-yl]oxyphenyl]-1-N'-(4-fluorophenyl)cyclopropane-1,1-dicarboxamide (116): Cyclopropylamine was used in place of Compound 113. MS for $C_{30}H_{26}FN_5O_5$, found 556 (MH+).

1-N-[4-(6-Carbamoyl-7-methoxyquinazolin-4-yl)oxyphenyl]-1-N'-(4-fluorophenyl)cyclopropane-1,1-dicarboxamide (117): Ammonia was used in place of Compound 113. MS for $C_{27}H_{22}FN_5O_5$, found 516 (MH+).

1-N'-(4-Fluorophenyl)-1-N-[4-[7-methoxy-6-(2-pyrrolidin-1-ylethylcarbamoyl)quinazolin-4-yl]oxyphenyl]cyclopropane-1,1-dicarboxamide (118): 2-(Pyrrolidin-1-yl)ethan-1-amine was used in place of Compound 113. MS for $C_{33}H_{33}FN_6O_5$, found 613 (MH+).

tert-Butyl (2R)-2-[[[4-[4-[[1-[(4-fluorophenyl)carbamoyl]cyclopropanecarbonyl]-amino]phenoxy]-7-methoxyquinazoline-6-carbonyl]amino]methyl]pyrrolidine-1-carboxylate (119): t-Butyl (R)-2-(aminomethyl)pyrrolidine-1-carboxylate was used in place of Compound 113. MS for $C_{37}H_{39}FN_6O_7$, found 699 (MH+).

tert-Butyl (2S)-2-[[[4-[4-[[1-[(4-fluorophenyl)carbamoyl]cyclopropanecarbonyl]-amino]phenoxy]-7-methoxyquinazoline-6-carbonyl]amino]methyl]pyrrolidine-1-carboxylate (120): t-Butyl (S)-2-(aminomethyl)pyrrolidine-1-carboxylate was used in place of Compound 113. MS for $C_{37}H_{39}FN_6O_7$, found 699 (MH+).

Example 24: 1-N'-(4-Fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide (121)

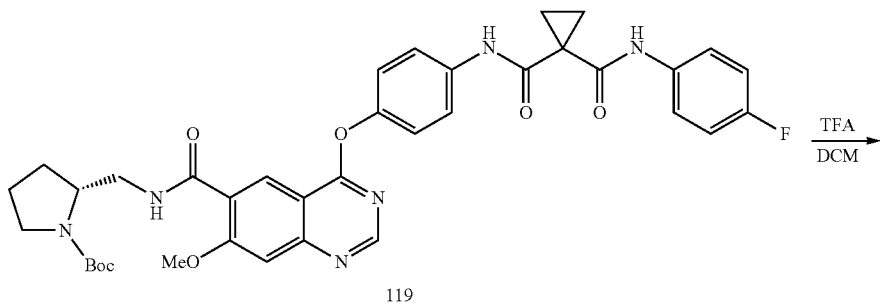

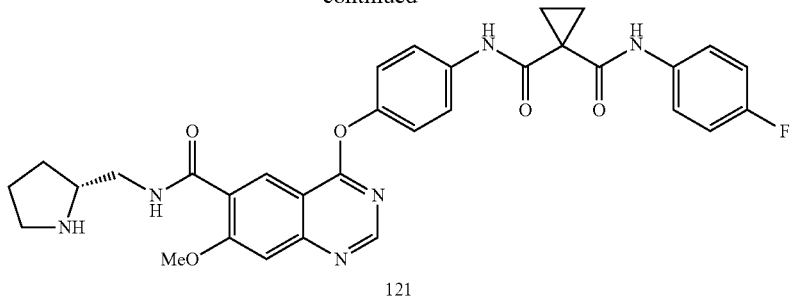

121

1-N'-(4-Fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide (121): Compound 121 was synthesized from Compound 119 using standard procedures for N-Boc deprotection using TFA in DCM at room temperature or slightly elevated temperatures. MS for $C_{32}H_{31}FN_6O_5$, found 599 (MH+).

The following compound was prepared from Compound 120 in a manner analogous to the method used to convert Compound 119 to Compound 121 in Example 24:

1-N'-(4-Fluorophenyl)-1-N-[4-[7-methoxy-6-[[(2S)-pyrrolidin-2-yl]methylcarbamoyl]quinazolin-4-yl]oxyphenyl]cyclopropane-1,1-dicarboxamide (122): MS for $C_{32}H_{31}FN_6O_5$, found 599 (MH+).

Example 25: 1-N'-(4-Fluorophenyl)-1-N-[4-[6-(1-methylpyrazol-4-yl)quinazolin-4-yl]oxyphenyl]cyclopropane-1,1-dicarboxamide (126)

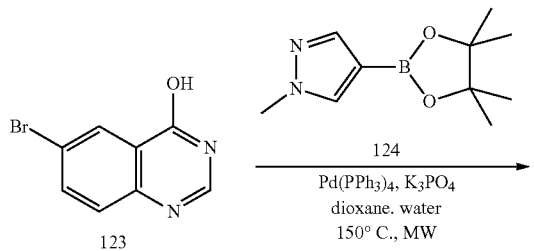

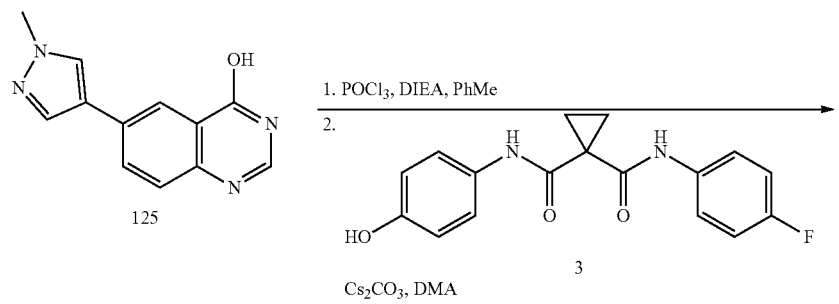

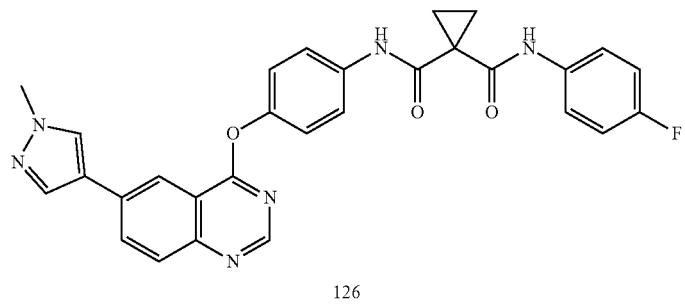

126

6-(1-Methyl-1H-pyrazol-4-yl)quinazolin-4-ol (125): In a microwave reaction tube were mixed commercially available Compound 123 (225 mg, 1.0 mmol), Compound 124 (270 mg, 1.3 mmol), K$_3$PO$_4$ (636 mg, 3.0 mmol), Pd(PPh$_3$)$_4$ (115 mg, 0.1 mmol), 1,4-dioxane (6 mL) and water (3 mL). The reaction mixture was irritated for 20 minutes at 150° C. After cooling, the mixture was diluted with EtOAc, The phases were separated, and the aqueous phase was extracted with 15% MeOH in EtOAc. Removal of the solvents gave crude Compound 125 (crude yield 225 mg) which was used in the next step without further purification.

1-N'-(4-Fluorophenyl)-1-N-[4-[6-(1-methylpyrazol-4-yl) quinazolin-4-yl]oxyphenyl]cyclopropane-1,1-dicarboxamide (126): To a mixture of crude Compound 125 (225 mg, 1.0 mmol) and DIEA (650 mg, 5 mmol) in PhMe (3 mL) was added POCl$_3$ (766 mg, 5.0 mmol). The mixture was stirred at 105° C. for 2 hour, then cooled to room temperature. The resulting mixture was concentrated, neutralized with cold saturated NaHCO$_3$, and extracted with EtOAc. The extracts were concentrated in vacuo. A mixture of the resulting residue (100 mg, 0.41 mmol), Compound 3 (128 mg, 0.41 mmol) and Cs$_2$CO$_3$ (267 mg, 0.82 mmol) in DMA (1.5 mL) was stirred at 60° C. for 10 hours and then cooled to room temperature. The mixture was diluted with water and extracted with EtOAc. The organic phase was concentrated, and the resulting residue was purified by flash column chromatography and prep HPLC to give Compound 126 (80 mg, 0.15% overall yield in three steps). MS (EI) for C$_{29}$H$_{23}$FN$_6$O$_3$, found: 523 (MH+).

Example 26: 1-N'-(4-Fluorophenyl)-1-N-[4-[7-(1-methylpyrazol-4-yl)pyrido[3,2-d]pyrimidin-4-yl]oxyphenyl]cyclopropane-1,1-dicarboxamide (129)

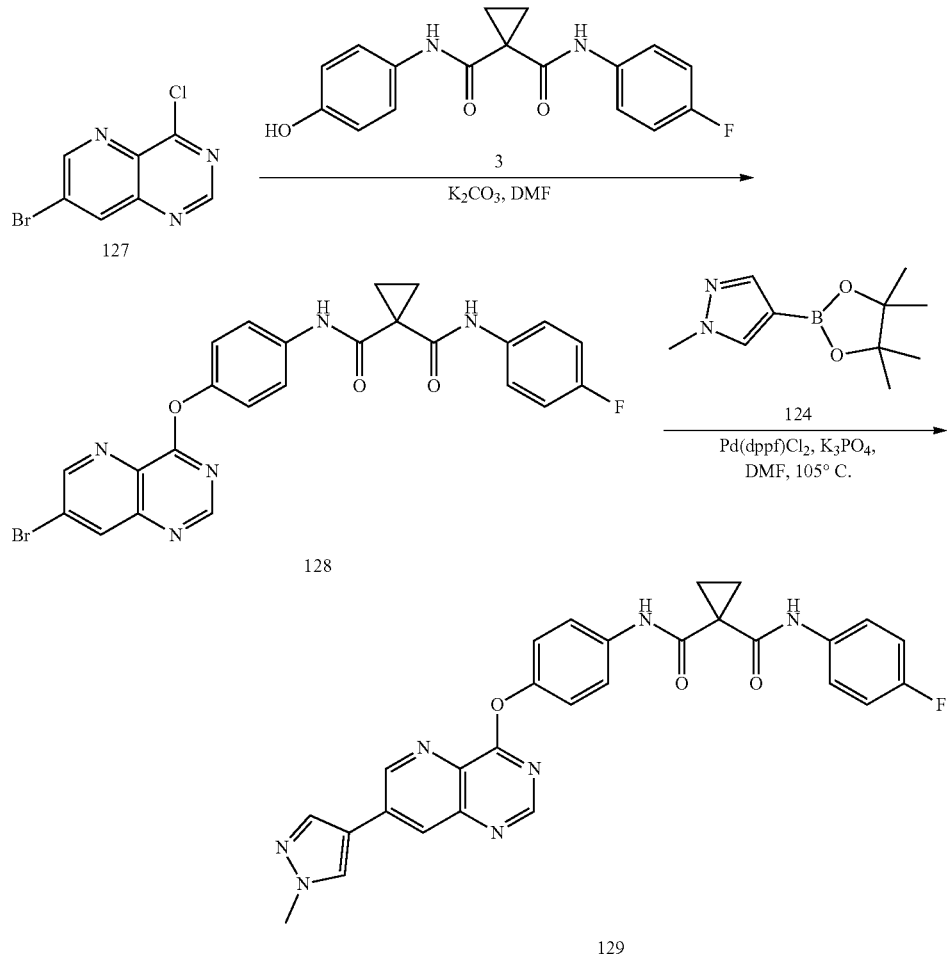

N-(4-((7-Bromopyrido[3,2-d]pyrimidin-4-yl)oxy)phenyl)-N-(4-fluorophenyl)cyclopropane-1,1-dicarboxamide (128): Compound 128 was made from Compound 127 in a manner analogous to the preparation of Compound 7 from Compound 6 in Step 3 of Example 2. $^1$H NMR (400 MHz, DMSO-d$_6$) δ 10.17 (br s, 1H), 10.07 (br s, 1H), 9.19 (d, 1H), 8.82-8.77 (m, 2H), 7.73 (d, 2H), 7.68-7.60 (m, 2H), 7.28 (d, 2H), 7.15 (t, 2H), 1.47 (s, 4H); MS for C$_{24}$H$_{17}$BrFN$_5$O$_3$, found 524.2 (MH+).

1-N'-(4-Fluorophenyl)-1-N-[4-[7-(1-methylpyrazol-4-yl) pyrido[3,2-d]pyrimidin-4-yl]oxyphenyl]cyclopropane-1,1-dicarboxamide (129): A mixture of Compound 128 (115 mg, 220.17 umol, 1 eq), Compound 124 (69 mg, 331.63 umol, 1.51 eq), K$_3$PO$_4$ (127 mg, 598.31 umol, 2.72 eq) and Pd(dppf)Cl$_2$ (10 mg, 13.67 umol, 6.21e-2 eq) in DMF (1 mL) was degassed and purged with nitrogen gas 3 times, after which the mixture was stirred at 105° C. for 16 hours under an atmosphere of nitrogen until complete. The mixture was cooled to room temperature and purified by combi-flash (Silica Flash Column, eluent of 50~100% ethyl acetate/petroleum ether gradient) to give Compound 129 as an off-white solid (64.0 mg, 55.5% yield). $^1$H NMR (400 MHz, CDCl$_3$) δ 9.20 (d, 1H), 9.08 (s, 1H), 8.93 (br s, 1H), 8.76 (s, 1H), 8.29 (d, 1H), 8.00 (s, 1H), 7.91 (s, 1H), 7.66 (d, 2H), 7.51-7.45 (m, 2H), 7.30 (d, 2H), 7.04 (t, 2H), 4.04 (s, 3H), 1.67 (s, 4H); MS for C$_{28}$H$_{22}$FN$_7$O$_3$, found 524.2 (MH+).

Example 27: 1-N'-(4-Fluorophenyl)-1-N-[4-[7-(1-methylpyrazol-4-yl)pyrido[4,3-d]pyrimidin-4-yl]oxyphenyl]cyclopropane-1,1-dicarboxamide (130)

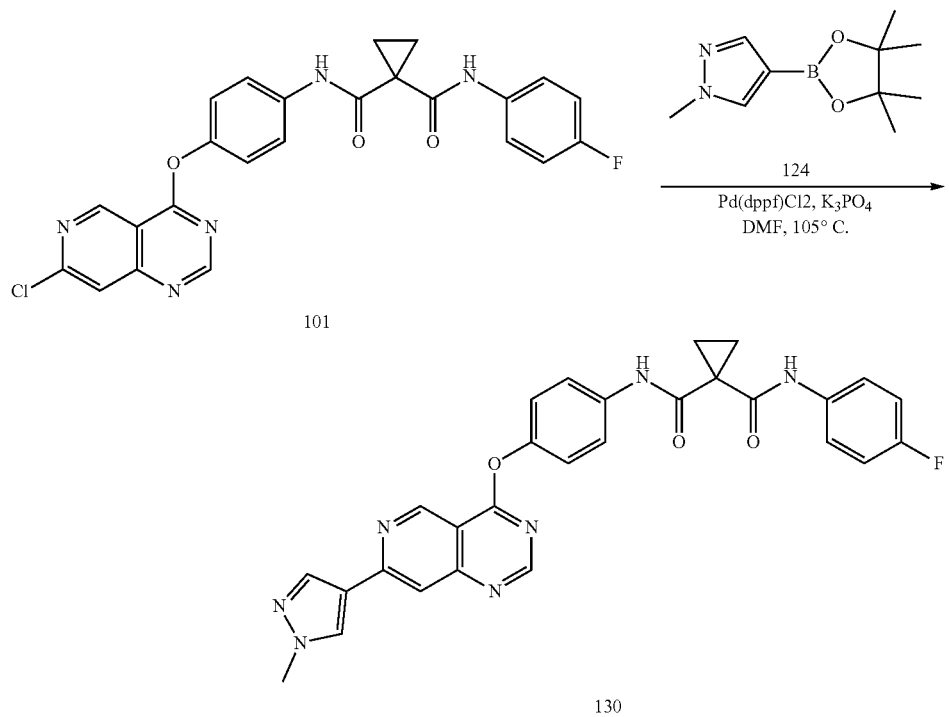

1-N'-(4-Fluorophenyl)-1-N-[4-[7-(1-methylpyrazol-4-yl)pyrido[4,3-d]pyrimidin-4-yl]oxyphenyl]cyclopropane-1,1-dicarboxamide (130): Compound 130 was made from Compound 101 in a manner analogous to the preparation of Compound 129 from Compound 128 in Step 2 of Example 26. MS for C$_{28}$H$_{22}$FN$_7$O$_3$, found 524.1 (MH+).

Example 28: 6,7-Dimethoxy-1,5-naphthyridin-4-ol (136)

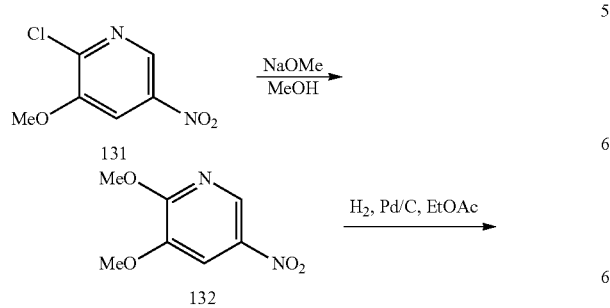

-continued

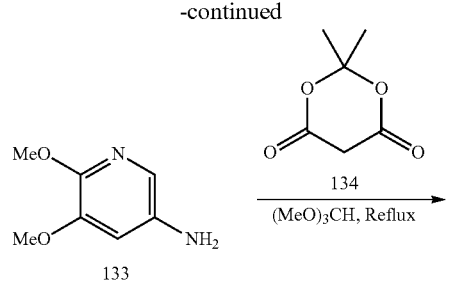

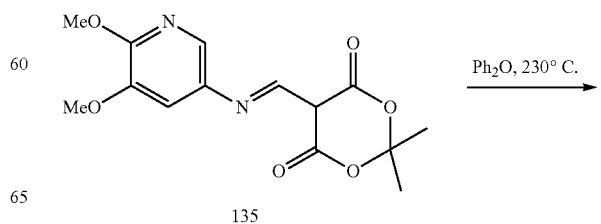

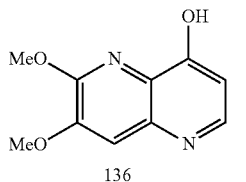

2,3-Dimethoxy-5-nitropyridine (132): Freshly cut sodium (0.6 g, 26 mmol) was added portionwise to MeOH (50 mL) and the mixture was stirred at room temperature until the sodium dissolved. Compound 131 (3.0 g, 15.9 mmol) was added, and the reaction mixture was stirred at room temperature for 1 hour. Water (100 mL) was added, and the mixture was filtered. The solids were washed with water and dried to give Compound 132 (2.78 g, 95% yield). MS for $C_7H_8N_2O_4$, found 185 (MH+).

2,3-Dimethoxy-5-nitropyridine (133): To a solution of Compound 132 (2.78 g, 15.1 mmol) in EtOAc (40 mL) under argon was added 10% Pd/C (53% water, 880 mg). The reaction mixture was stirred under one atmosphere of $H_2$ at room temperature overnight and then filtered through Celite®. The filtrate was concentrated under vacuum to provide crude Compound 133 as brown solid (2.31 g, 100% yield). MS for $C_7H_{10}N_2O_2$, found 155 (MH+).

5-(((5,6-Dimethoxypyridin-3-yl)imino)methyl)-2,2-dimethyl-1,3-dioxane-4,6-dione (135): A solution of triethyl orthoformate (12 mL) and Compound 134 (1.44 g, 10.0 mmol) was stirred at 106° C. for 2.5 hour, followed by the addition of Compound 133 (1.54 g, 10.0 mmol) while maintaining the same temperature. A precipitate appeared within several minutes. The heterogeneous mixture was heated at 105° C. for an additional 10 min, cooled to room temperature and filtered. The solids were washed with hexanes and dried to give crude Compound 135 (3.6 g). MS for $C_{14}H_{16}N_2O_6$, found 309 (MH+).

6,7-Dimethoxy-1,5-naphthyridin-4-ol (136): A solution of Compound 135 (1.55 g, 5.03 mmol) in diphenyl ether (12 mL) was heated at 250° C. for 30 min, and then cooled to room temperature. Diethyl ether was added, and the mixture was filtered to give crude Compound 136 as a brown solid (0.92 g, 89% yield). MS for $C_{10}H_{10}N_2O_3$, found 207 (MH+).

Example 29: 1-N-[4-[(6,7-Dimethoxy-1,5-naphthyridin-4-yl)oxy]phenyl]-1-N'-(4-fluorophenyl)cyclopropane-1,1-dicarboxamide (139)

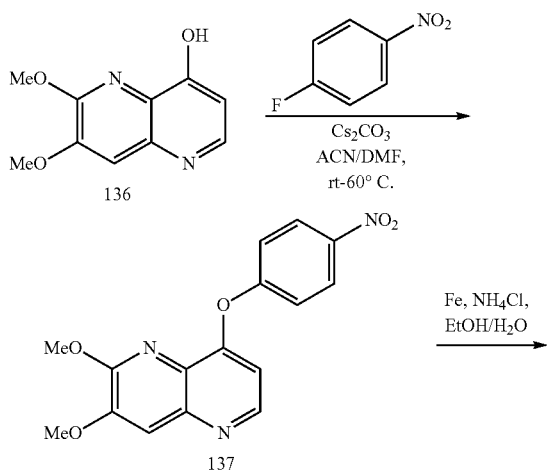

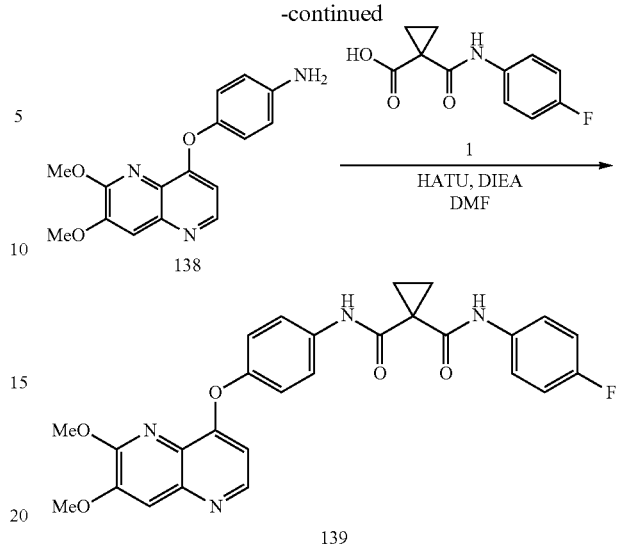

2,3-Dimethoxy-8-(4-nitrophenoxy)-1,5-naphthyridine (137): A mixture of Compound 136 (61 mg, 0.30 mmol), 1-fluoro-4-nitrobenzene (63 mg, 0.45 mmol), and $Cs_2CO_3$ (198 mg, 0.60 mmol) in acetonitrile (2 mL) was stirred at 60° C. until the reaction was complete. The reaction mixture was diluted with EtOAc (8 mL) and filtered. The filtrated was purified by silica gel column and eluted with 0-100% of EtOAc in hexanes to give Compound 137 (36 mg, 37% yield). MS for $C_{16}H_{13}N_3O_5$, found 328 (MH+).

4-((6,7-Dimethoxy-1,5-naphthyridin-4-yl)oxy)aniline (138): Compound 137 (36 mg, 0.11 mmol) was mixed with Fe (56 mg, 1.0 mmol), $NH_4Cl$ (108 mg, 2.0 mmol), water (1 mL), and EtOH (3 mL). The mixture was stirred at 85° C. for 60 min, cooled to room temperature, and filtered through Celite. The filtrate was concentrated, and the resulting residue was partitioned between saturated aq $NaHCO_3$ (2 mL) and EtOAc. The aqueous phase was further extracted with EtOAc (2×). The combined extract were dried over $Na_2SO_4$ and evaporated to give crude Compound 138 (30 mg, 91% yield). MS for $C_{16}H_{15}N_3O_3$, found 298 (MH+).

1-N-[4-[(6,7-Dimethoxy-1,5-naphthyridin-4-yl)oxy]phenyl]-1-N'-(4-fluorophenyl)cyclopropane-1,1-dicarboxamide (139): To a mixture of Compound 138 (30 mg, 0.1 mmol), Compound 1 (36 mg, 0.15 mmol), and DIEA (60 mg, 0.46 mmol) in DMF (1 mL) was added HATU (114 mg, 0.30 mmol), and the reaction was stirred at room temperature overnight. Saturated aq $NaHCO_3$ was added to precipitate the product, which was then filtered, washed with water, and subjected to HPLC purification to give Compound 139 (12 mg, 24% yield). MS for $C_{27}H_{23}FN_4O_5$, found 503 (MH+).

The following compounds were prepared using an analogous three step process to that used in the synthesis of Compound 139 in Example 29 by initially reacting Compound 136 with the appropriately substituted 1-fluoro-4-nitrobenzene. Lower temperatures (40° C.) were used for the first steps:

1-N'-[4-[(6,7-Dimethoxy-1,5-naphthyridin-4-yl)oxy]-3-fluorophenyl]-1-N-(4-fluorophenyl)cyclopropane-1,1-dicarboxamide (140): 1,2-Difluoro-4-nitrobenzene was used in place of 1-fluoro-4-nitrobenzene in step 1. MS (EI) for $C_{27}H_{22}F_2N_4O_5$, found 521 (MH+).

1-N'-[3-Chloro-4-[(6,7-dimethoxy-1,5-naphthyridin-4-yl)oxy]phenyl]-1-N-(4-fluorophenyl)cyclopropane-1,1-dicarboxamide (141): 2-Chloro-1-fluoro-4-nitrobenzene was used in place of 1-fluoro-4-nitrobenzene in step 1. MS (EI) for $C_{27}H_{22}ClFN_4O_5$, found 537 (MH+).

1-N'-[4-[(6,7-Dimethoxy-1,5-naphthyridin-4-yl)oxy]-2,5-difluorophenyl]-1-N-(4-fluorophenyl)cyclopropane-1,1-dicarboxamide (142): 1,2,5-Trifluoro-4-nitrobenzene was used in place of 1-fluoro-4-nitrobenzene in step 1. MS (EI) for $C_{27}H_{21}F_3N_4O_5$, found 539 (MH+).

Example 30: 1-N'-(4-Fluorophenyl)-1-N-[4-[[6-methoxy-7-(2-methoxyethoxy)-1,5-naphthyridin-4-yl]oxy]phenyl]cyclopropane-1,1-dicarboxamide (149)

$C_8H_9BrClNO_2$, found 268 (MH+)). This intermediate product (2.68 g, 10.0 mmol) was mixed with NaOMe (3.0 g, 55.5 mmol) in MeOH (40 mL) and heated at 70° C. overnight. The reaction mixture was concentrated to remove MeOH, and the resulting residue was partitioned between water and EtOAc. The EtOAc phase was washed with aq saturated NaCl, dried over $Na_2SO_4$, and evaporated to give crude Compound 144 as an oil containing some residual solvent (3.0 g). MS for $C_9H_{12}BrNO_3$, found 262/264 (MH+).

6-Methoxy-5-(2-methoxyethoxy)pyridin-3-amine (145): Compound 144 (3.0 g, crude) was mixed with diphenylmethanimine (3.6 g, 20 mmol), Pd(OAc)₂ (360 mg, 1.61 mmol), BINAP (1.3 g, 2.08 mmol) and NaO'Bu (1.6 g, 16.7

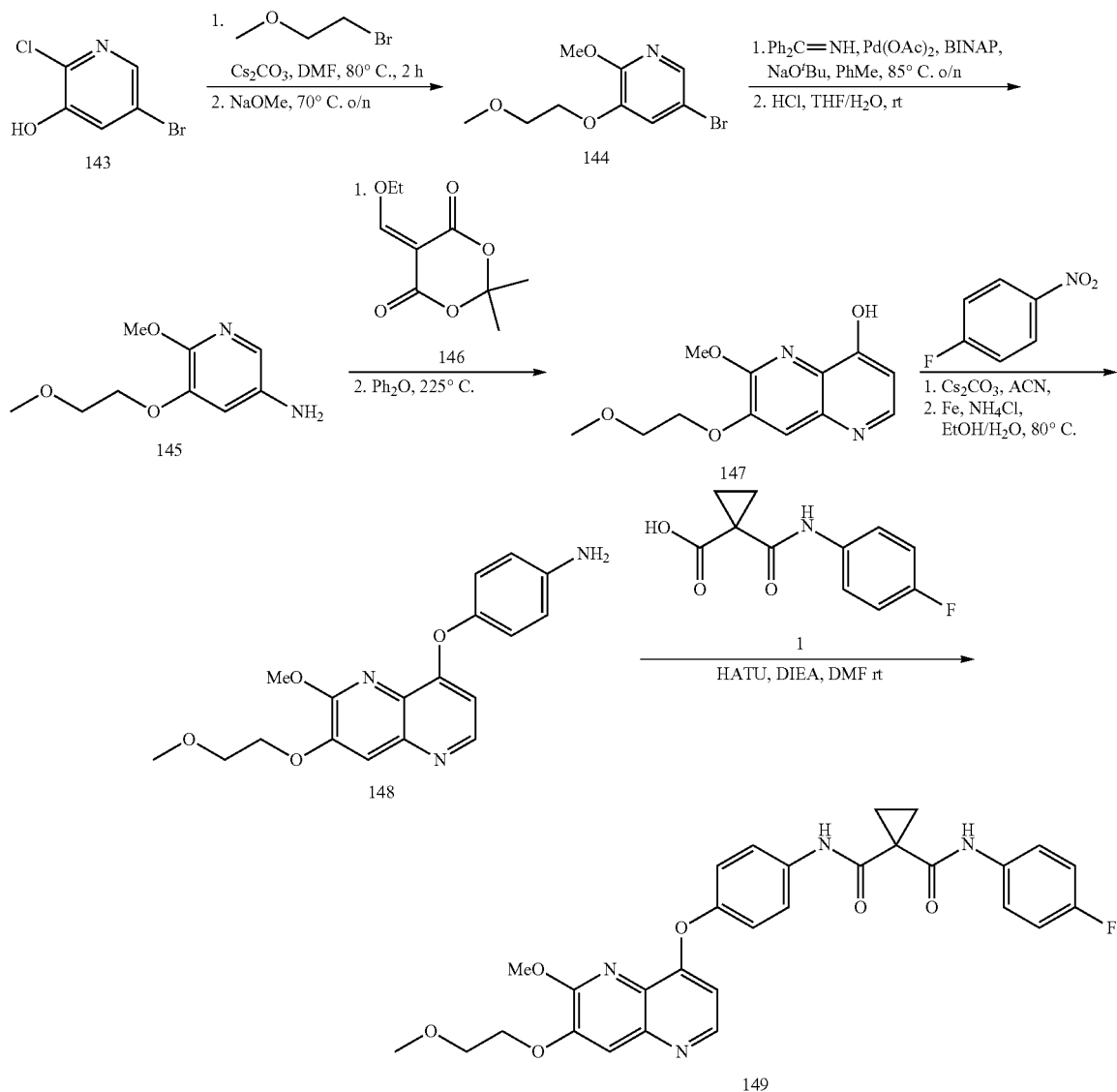

2,3-Dimethoxy-8-(4-nitrophenoxy)-1,5-naphthyridine (144): A mixture of Compound 143 (2.10 g, 10.0 mmol), 1-bromo-2-methoxyethane (1.50 g, 10.8 mmol), and $Cs_2CO_3$, (6.6 g, 20.2 mmol) in DMF was stirred at 80° C. for 2 hours, quenched with water, and extracted with EtOAc (2×), The combined extracts were washed with aq saturated NaCl, dried over $Na_2SO_4$, and evaporated to give the crude intermediate product as an off-white solid (2.68 g, MS for mmol) in toluene (60 mL). The resulting mixture was degassed with argon and stirred at 85° C. overnight. The reaction mixture was partitioned between water and EtOAc. The organic phase was separated and evaporated to dryness. To the residue was added THF (40 mL) and HCl (aq, 2M, 40 mL), and the resulting mixture was stirred at room temperature overnight. The pH of the reaction mixture was adjusted to pH10 with $NaHCO_3$ and extracted with EtOAc.

The extract was concentrated, and the resulting residue was subjected to chromatography on silica gel, eluted with 0-90% EtOAc in hexanes to afford Compound 145 as a brown oil (1.4 g, 71% yield from Compound 143). MS for $C_9H_{14}N_2O_3$, found 199 (MH+).

6,7-Dimethoxy-1,5-naphthyridin-4-yl)oxy)aniline (147): Compound 147 was made from Compound 145 and Compound 146 in a manner analogous to the preparation of Compound 136 from Compound 133 and Compound 134 in Steps 3 and 4 of Example 28. MS for $C_{12}H_{14}N_2O_4$, found 251 (MH+).

6,7-Dimethoxy-1,5-naphthyridin-4-yl)oxy)aniline (148): Compound 148 was made from Compound 147 in a manner analogous to the preparation of Compound 138 from Compound 136 in Steps 1 and 2 of Example 29.

1-N'-(4-Fluorophenyl)-1-N-[4-[[6-methoxy-7-(2-methoxyethoxy)-1,5-naphthyridin-4-yl]oxy]phenyl]cyclopropane-1,1-dicarboxamide (149): Compound 149 was made from Compound 148 in a manner analogous to the preparation of Compound 139 from Compound 138 in Step 3 of Example 29. MS for $C_{29}H_{27}FN_4O_6$, found 547 (MH+).

The following compounds were prepared using an analogous multi-step process to that used in the synthesis of Compound 149 in Example 30. For Compounds 150-152, Compound 147 was reacted with the appropriately substituted 1-fluoro-4-nitrobenzene. For Compound 153, 4-(2-bromoethyl)morpholine replaced the 1-bromo-2-methoxyethane in the first step:

1-N'-[3-Fluoro-4-[[6-methoxy-7-(2-methoxyethoxy)-1,5-naphthyridin-4-yl]oxy]phenyl]-1-N-(4-fluorophenyl)cyclopropane-1,1-dicarboxamide (150): 1,2-Difluoro-4-nitrobenzene was used in place of 1-fluoro-4-nitrobenzene. MS (EI) for $C_{29}H_{26}F_2N_4O_6$, found 565 (MH+).

1-N'-[3-Chloro-4-[[6-methoxy-7-(2-methoxyethoxy)-1,5-naphthyridin-4-yl]oxy]phenyl]-1-N-(4-fluorophenyl)cyclopropane-1,1-dicarboxamide (151): 2-Chloro-1-fluoro-4-nitrobenzene was used in place of 1-fluoro-4-nitrobenzene. MS (EI) for $C_{29}H_{26}ClFN_4O_6$, found 581 (MH+).

1-N'-[2,5-Difluoro-4-[[6-methoxy-7-(2-methoxyethoxy)-1,5-naphthyridin-4-yl]oxy]phenyl]-1-N-(4-fluorophenyl)cyclopropane-1,1-dicarboxamide (152): 1,2,5-Trifluoro-4-nitrobenzene was used in place of 1-fluoro-4-nitrobenzene. MS (EI) for $C_{29}H_{25}F_3N_4O_6$, found 583 (MH+).

1-N'-[2,5-Difluoro-4-[[6-methoxy-7-(2-morpholin-4-ylethoxy)-1,5-naphthyridin-4-yl]oxy]phenyl]-1-N-(4-fluorophenyl)cyclopropane-1,1-dicarboxamide (153): 1,2,5-Trifluoro-4-nitrobenzene was used in place of 1-fluoro-4-nitrobenzene. MS (EI) for $C_{32}H_{30}F_3N_5O_6$, found 638 (MH+).

Example 31: 1-N-[4-(2,3-Dihydro-[1,4]dioxino[2,3-b][1,5]naphthyridin-6-yloxy)phenyl]-1-N'-(4-fluorophenyl)cyclopropane-1,1-dicarboxamide (157)

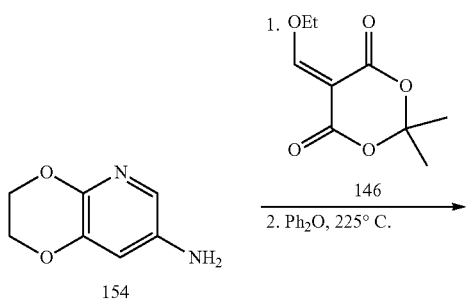

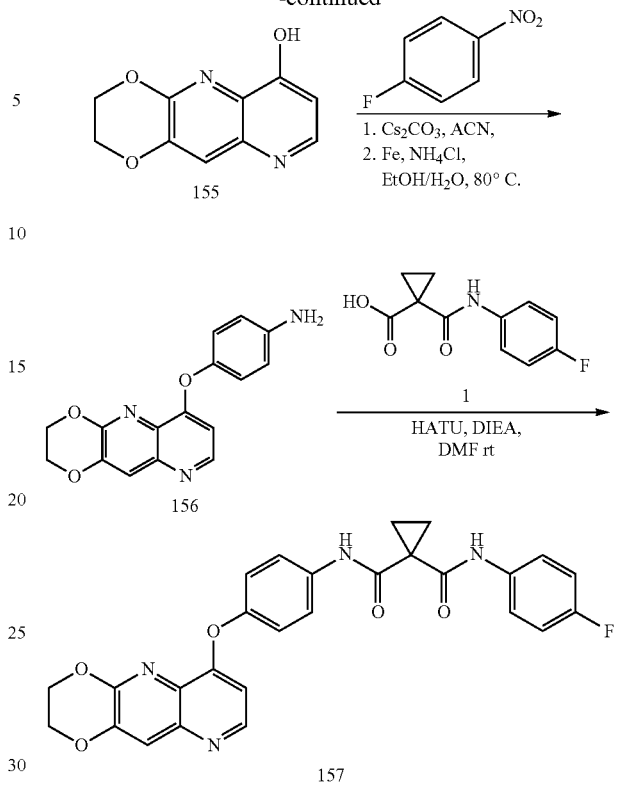

2,3-Dihydro-[1,4]dioxino[2,3-b][1,5]naphthyridin-6-ol (155): Compound 155 was made from Compound 154 and Compound 146 in a manner analogous to the preparation of Compound 136 from Compound 133 and Compound 134 in Steps 3 and 4 of Example 28. MS for $C_{10}H_8N_2O_3$, found 205 (MH+).

4-((2,3-Dihydro-[1,4]dioxino[2,3-b][1,5]naphthyridin-6-yl)oxy)aniline (156): Compound 156 was made from Compound 155 in a manner analogous to the preparation of Compound 138 from Compound 136 in Steps 1 and 2 of Example 29.

1-N-[4-(2,3-Dihydro-[1,4]dioxino[2,3-b][1,5]naphthyridin-6-yloxy)phenyl]-1-N'-(4-fluorophenyl)cyclopropane-1,1-dicarboxamide (157): Compound 157 was made from Compound 156 in a manner analogous to the preparation of Compound 139 from Compound 138 in Step 3 of Example 29. MS for $C_{27}H_{21}FN_4O_5$, found 501 (MH+).

The following compounds were prepared from Compound 155 using an analogous three step process to that used in the synthesis of Compound 139 from Compound 136 in Example 29 by initially reacting Compound 155 with the appropriately substituted 1-fluoro-4-nitrobenzene:

1-N'-[4-(2,3-dihydro-[1,4]dioxino[2,3-b][1,5]naphthyridin-6-yloxy)-3-fluorophenyl]-1-N-(4-fluorophenyl)cyclopropane-1,1-dicarboxamide (158): 1,2-Difluoro-4-nitrobenzene was used in place of 1-fluoro-4-nitrobenzene. MS (EI) for $C_{27}H_{20}F_2N_4O_5$, found 519 (MH+).

1-N'-[3-Chloro-4-(2,3-dihydro-[1,4]dioxino[2,3-b][1,5]naphthyridin-6-yloxy)phenyl]-1-N-(4-fluorophenyl)cyclopropane-1,1-dicarboxamide (159): 2-Chloro-1-fluoro-4-nitrobenzene was used in place of 1-fluoro-4-nitrobenzene. MS (EI) for $C_{27}H_{20}ClFN_4O_5$, found 535 (MH+).

Example 32: 1-N-[4-[(6-Cyano-7-methoxy-1,5-naphthyridin-4-yl)oxy]phenyl]-1-N'-(4-fluorophenyl)cyclopropane-1,1-dicarboxamide (164)

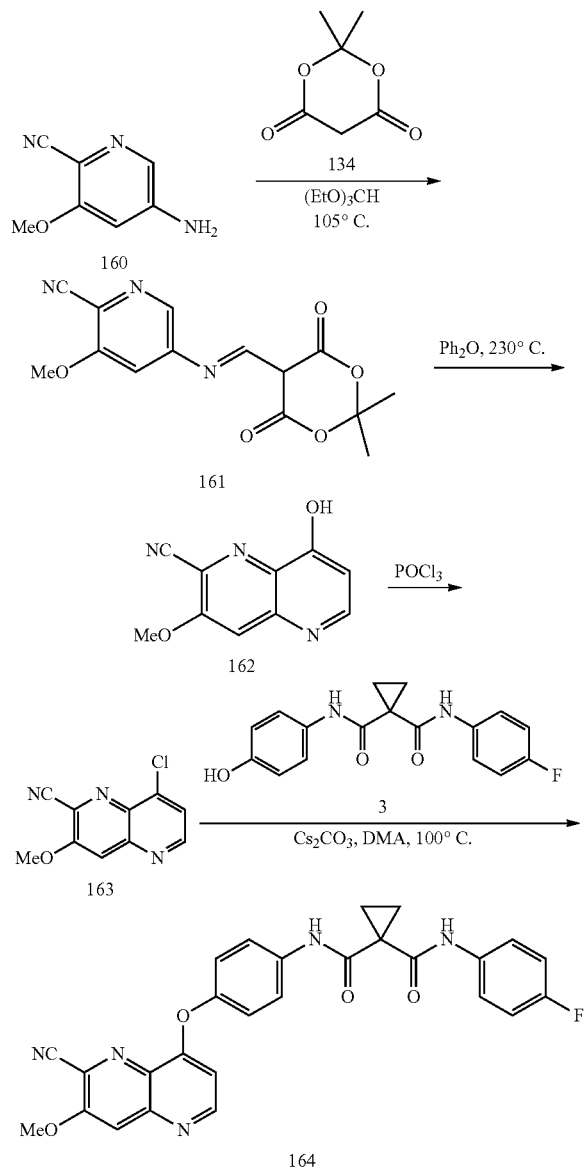

5-(((2,2-Dimethyl-4,6-dioxo-1,3-dioxan-5-yl)methylene)amino)-3-methoxypicolinonitrile (161): Compound 161 was made from Compound 160 and Compound 134 in a manner analogous to the preparation of Compound 135 from Compound 133 and Compound 134 in Step 3 of Example 28. MS (EI) for $C_{14}H_{13}N_3O_5$, found 304 (MH+).

8-Hydroxy-3-methoxy-1,5-naphthyridine-2-carbonitrile (162): Compound 162 was made from Compound 161 in a manner analogous to the preparation of Compound 136 from Compound 135 in Step 4 of Example 28. MS (EI) for $C_{10}H_7N_3O_2$, found 202 (MH+).

8-Chloro-3-methoxy-1,5-naphthyridine-2-carbonitrile (163): Compound 163 was made from Compound 162 in a manner analogous to the preparation of Compound 38 from Compound 37 in Step 2 of Example 9.

1-N-[4-[(6-Cyano-7-methoxy-1,5-naphthyridin-4-yl)oxy]phenyl]-1-N'-(4-fluorophenyl)cyclopropane-1,1-dicarboxamide (164): Compound 164 was made from Compound 163 and Compound 3 using a variation of the method used to prepare Compound 7 from Compound 6 in Step 3 of Example 2. $Cs_2CO_2$ in DMA was used in place of $K_2CO_3$ in DMF. MS (EI) for $C_{27}H_{20}FN_5O_4$, found 498 (MH+).

The following compounds were prepared from Compound 163 in a method analogous to the method used to make Compound 28 from Compound 27 in Example 8 using the appropriately substituted N-(4-fluorophenyl)-N-(4-hydroxyphenyl)cyclopropane-1,1-dicarboxamides which were synthesized using methods analogous to those used in Example 1 or Example 5:

1-N'-[4-[(6-Cyano-7-methoxy-1,5-naphthyridin-4-yl)oxy]-3-fluorophenyl]-1-N-(4-fluorophenyl)cyclopropane-1,1-dicarboxamide (165): MS (EI) for $C_{27}H_{19}F_2N_5O_4$, found 516 (MH+).

1-N'-[3-Chloro-4-[(6-cyano-7-methoxy-1,5-naphthyridin-4-yl)oxy]phenyl]-1-N-(4-fluorophenyl)cyclopropane-1,1-dicarboxamide (166): MS (EI) for $C_{27}H_{19}ClFN_5O_4$, found 532 (MH+).

Example 33: 1-N-[4-[(6-Carbamoyl-7-methoxy-1,5-naphthyridin-4-yl)oxy]phenyl]-1-N'-(4-fluorophenyl)cyclopropane-1,1-dicarboxamide (167)

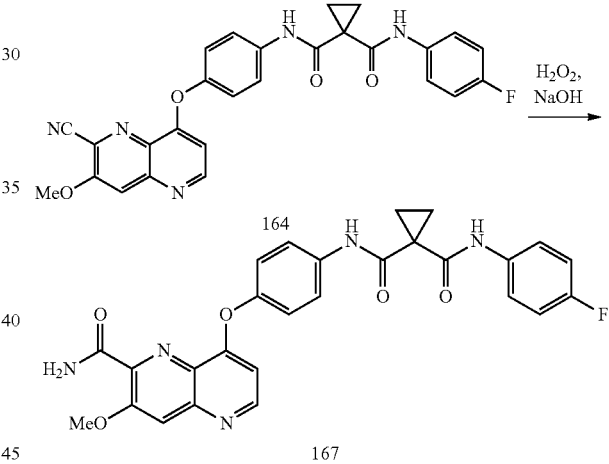

1-N-[4-[(6-Carbamoyl-7-methoxy-1,5-naphthyridin-4-yl)oxy]phenyl]-1-N'-(4-fluorophenyl)cyclopropane-1,1-dicarboxamide (167): To a mixture of compound 164 (17 mg, 0.034 mmol) and NaOH (aq, 50%, 0.2 mL) was added $H_2O_2$ (aq 30%, 1.0 mL). The mixture was stirred at room temperature for 5 min, quenched with saturated $NaHCO_3$, and extracted with EtOAc. The EtOAc extracts were concentrated in vacuo, and the resulting residue was purified by Flash silica gel chromatography (0-10% MeOH in DCM) to give Compound 167 (3 mg, 17% yield). MS (EI) for $C_{27}H_{22}FN_5O_5$, found 516 (MH+).

The following compounds were made using a method analogous to that used to make Compound 167 in Example 33:

1-N'-[4-[(6-Carbamoyl-7-methoxy-1,5-naphthyridin-4-yl)oxy]-3-fluorophenyl]-1-N-(4-fluorophenyl)cyclopropane-1,1-dicarboxamide (168): Using Compound 165 in place of Compound 164. MS (EI) for $C_{27}H_{21}F_2N_5O_5$, found 534 (MH+).

1-N'-[4-[(6-Carbamoyl-7-methoxy-1,5-naphthyridin-4-yl)oxy]-3-chlorophenyl]-1-N-(4-fluorophenyl)cyclopropane-1,1-dicarboxamide (169): Using Compound 166 in place of Compound 164. MS (EI) for $C_{27}H_{21}ClFN_5O_5$, found 550 (MH+).

Example 34: 1-N'-(4-Fluorophenyl)-1-N-[4-[[7-methoxy-6-(methylcarbamoyl)-1,5-naphthyridin-4-yl]oxy]phenyl]cyclopropane-1,1-dicarboxamide (172)

pound 28 from Compound 27 in Example 8 using the appropriately substituted N-(4-fluorophenyl)-N-(4-hydroxyphenyl)cyclopropane-1,1-dicarboxamide which were synthesized using a method analogous to that used in Example 1 or Example 5:

1-N'-[3-Fluoro-4-[[7-methoxy-6-(methylcarbamoyl)-1,5-naphthyridin-4-yl]oxy]phenyl]-1-N-(4-fluorophenyl)cyclopropane-1,1-dicarboxamide (173). MS (EI) for $C_{28}H_{23}F_2N_5O_5$, found 548 (MH+).

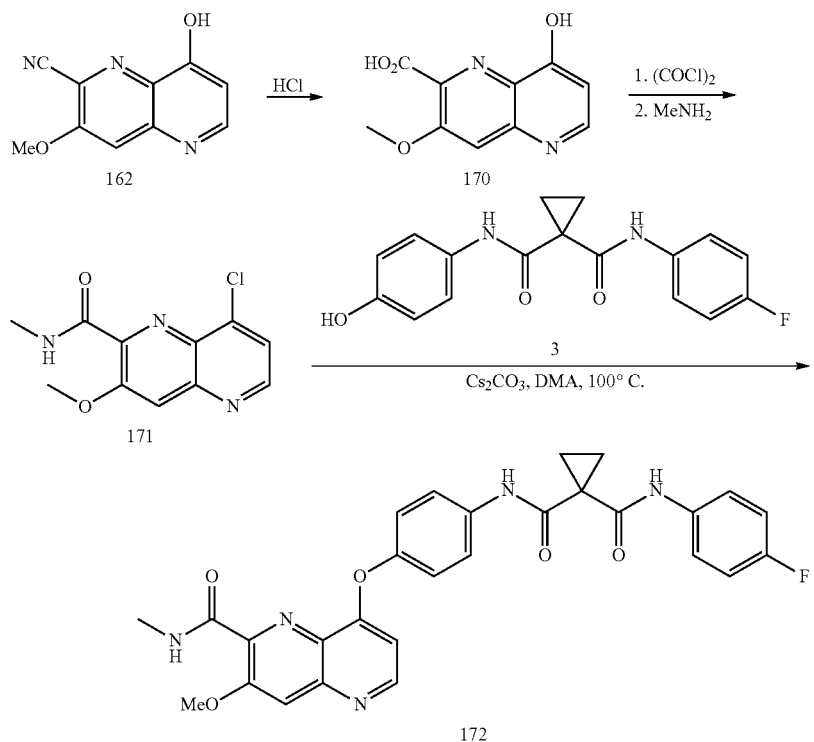

8-Hydroxy-3-methoxy-1,5-naphthyridine-2-carboxylic acid (170). Compound 162 (100 mg, 0.5 mmol) in concentrated HCl (36%) (2 mL) was stirred at 85° C. overnight. The resulting reaction mixture was concentrated to dryness to give crude Compound 170 which was used in subsequent reactions without further purification. MS (EI) for $C_{10}H_8N_2O_4$, found 221 (MH+).

8-Chloro-3-methoxy-N-methyl-1,5-naphthyridine-2-carboxamide (171). To crude Compound 170 was added DCE (3 mL) and (COCl)$_2$ (0.3 mL). The reaction mixture was refluxed for 2 hours and concentrated in vacuo, and the resulting residue was dissolved in DCM (5 mL). With efficient stirring at 0° C., TEA (0.8 mL) was added, followed by MeNH$_2$·HCl (120 mg). The mixture was stirred at room temperature for 30 min and concentrated to afford crude Compound 171. MS (EI) for $C_{11}H_{10}ClN_3O_2$, found 252 (MH+).

1-N'-(4-Fluorophenyl)-1-N-[4-[[7-methoxy-6-(methylcarbamoyl)-1,5-naphthyridin-4-yl]oxy]phenyl]cyclopropane-1,1-dicarboxamide (172): Compound 172 was made from Compound 171 and Compound 3 using a variation of the method used to prepare Compound 7 from Compound 6 in Step 3 of Example 2. Cs$_2$CO$_2$ in DMA was used in place of K$_2$CO$_3$ in DMF. MS (EI) for $C_{28}H_{24}FN_5O_5$, found 530 (MH+).

The following compound was prepared from Compound 171 in a method analogous to that used to produce Com- The following compound can be prepared from Compound 170 in a sequence of reactions similar to that followed in Example 34 to form Compound 172 from Compound 170, substituting dimethylamine for the MeNH$_2$·HCl in part 2 of step 2:

1-N-[4-[[6-(Dimethylcarbamoyl)-7-methoxy-1,5-naphthyridin-4-yl]oxy]phenyl]-1-N'-(4-fluorophenyl)cyclopropane-1,1-dicarboxamide (174). MS (EI) for $C_{29}H_{26}FN_5O_5$, found 544 (MH+).

Example 35: 1-N'-[2,5-Difluoro-4-[(7-methoxy-1,5-naphthyridin-4-yl)oxy]phenyl]-1-N-(4-fluorophenyl)cyclopropane-1,1-dicarboxamide (176)

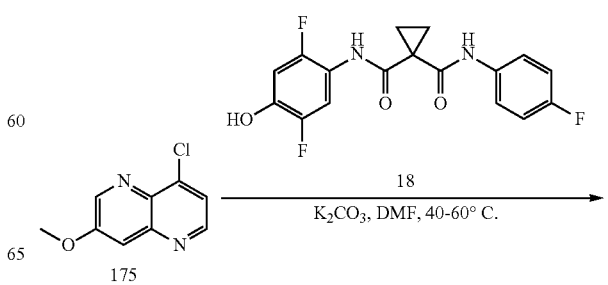

233
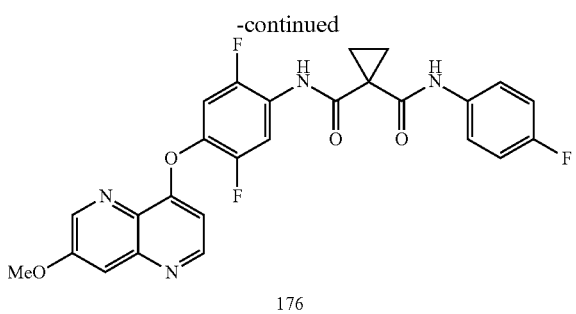
176
234
1-N'-[2,5-Difluoro-4-[(7-methoxy-1,5-naphthyridin-4-yl)oxy]phenyl]-1-N-(4-fluorophenyl)cyclopropane-1,1-dicarboxamide (176): Compound 176 was made from Compound 175 in a manner analogous to the preparation of Compound 7 from Compound 6 in Step 3 of Example 2. MS for $C_{26}H_{19}F_3N_4O_4$, found 509 (MH+).
Example 36: 1-N-[4-[(6-Amino-7-methoxy-1,5-naphthyridin-4-yl)oxy]phenyl]-1-N'-(4-fluorophenyl)cyclopropane-1,1-dicarboxamide (181)
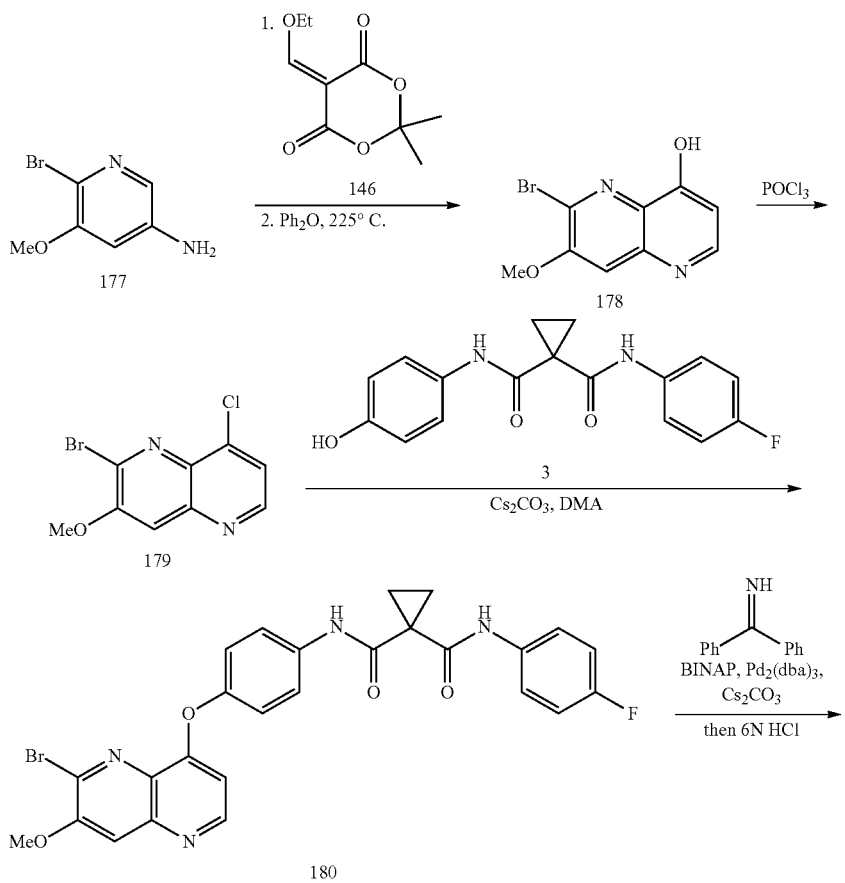
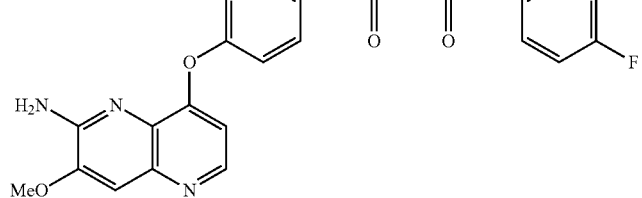
181

6-Bromo-7-methoxy-1,5-naphthyridin-4-ol (178): Compound 178 can be made from Compound 177 and Compound 146 in a manner analogous to the preparation of Compound 136 from Compound 133 and Compound 134 in Steps 3 and 4 of Example 28. MS for $C_9H_7BrN_2O_2$, found 255/257 (MH+).

2-Bromo-8-chloro-3-methoxy-1,5-naphthyridine (179): Compound 179 was made from Compound 178 in a manner analogous to the preparation of Compound 38 from Compound 37 in Step 2 of Example 9.

N-(4-((6-Bromo-7-methoxy-1,5-naphthyridin-4-yl)oxy)phenyl)-N-(4-fluorophenyl)cyclopropane-1,1-dicarboxamide (180): Compound 180 was made from Compound 179 and Compound 3 using a variation of the method used to prepare Compound 7 from Compound 6 in Step 3 of Example 2. $Cs_2CO_2$ in DMA was used in place of $K_2CO_3$ in DMF. MS (EI) for $C_{26}H_{20}BrFN_4O_4$, found 550 (MH+).

1-N-[4-[(6-Amino-7-methoxy-1,5-naphthyridin-4-yl)oxy]phenyl]-1-N'-(4-fluorophenyl)cyclopropane-1,1-dicarboxamide (181): A mixture of Compound 180 (50 mg, 0.091 mmol), diphenylmethanimine (181 mg, 1 mmol), $Pd_2(dba)_3$ (18 mg, 0.02 mmol), BINAP (12 mg, 0.02 mmol), and $Cs_2CO_3$ (49 mg, 0.16 mmol) in 1,4-dioxane (1.5 mL) was stirred at 120° C. for 6 hours. The mixture was cooled down to 20° C., diluted with EtOAc, and filtered. The filtrate was concentrated and purified by flash column chromatography and prep HPLC to give the Compound 181 as a solid (0.8 mg, 1.8% yield). MS (EI) for $C_{26}H_{22}FN_5O_4$, found 488 (MH+).

Example 37: 1-N'-(4-Fluorophenyl)-1-N-[4-[[7-methoxy-6-(1-methylpyrazol-4-yl)-1,5-naphthyridin-4-yl]oxy]phenyl]cyclopropane-1,1-dicarboxamide (182)

1-N'-(4-Fluorophenyl)-1-N-[4-[[7-methoxy-6-(1-methylpyrazol-4-yl)-1,5-naphthyridin-4-yl]oxy]phenyl]cyclopropane-1,1-dicarboxamide (182): To a microwave reaction tube were added Compound 180 (50 mg, 0.09 mmol), Compound 124 (31 mg, 0.15 mmol), $Na_2CO_3$ (32 mg, 0.3 mmol), Pd(Amphos)$Cl_2$ (10 mg, 0.014 mmol), 1,4-dioxane (3 mL), and water (0.6 mL). The reaction mixture was irritated for 10 minutes at 150° C. After cooling, the mixture was extracted with EtOAc, washed with aq saturated NaCl, and concentrated. The crude product was purified by prep HPLC to give Compound 182 (2 mg, 3.6%). MS (EI) for $C_{30}H_{25}FN_6O_4$, found 553 (MH+).

The following compounds were prepared from Compound 180 in a method analogous to Compound 182 in Example 37.

1-N'-(4-Fluorophenyl)-1-N-[4-[[7-methoxy-6-(1H-pyrazol-4-yl)-1,5-naphthyridin-4-yl]oxy]phenyl]cyclopropane-1,1-dicarboxamide (183): MS for $C_{29}H_{23}FN_6O_4$, found 539 (MH+).

1-N'-(4-Fluorophenyl)-1-N-[4-[[7-methoxy-6-(2-methylpyrazol-3-yl)-1,5-naphthyridin-4-yl]oxy]phenyl]cyclopropane-1,1-dicarboxamide (184): MS for $C_{30}H_{25}FN_6O_4$, found 553 (MH+).

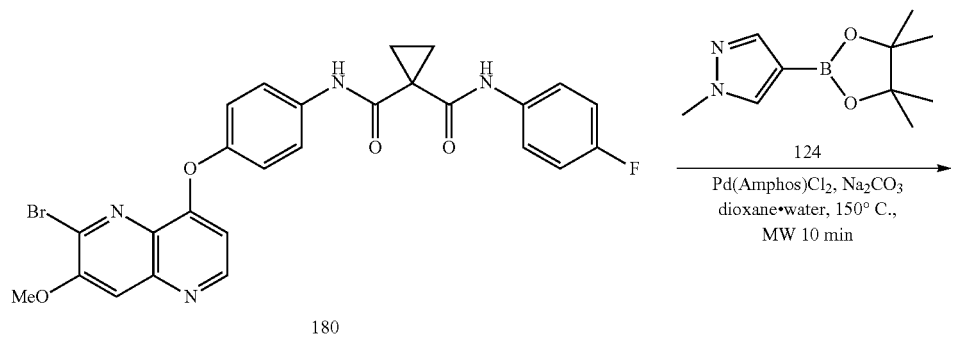

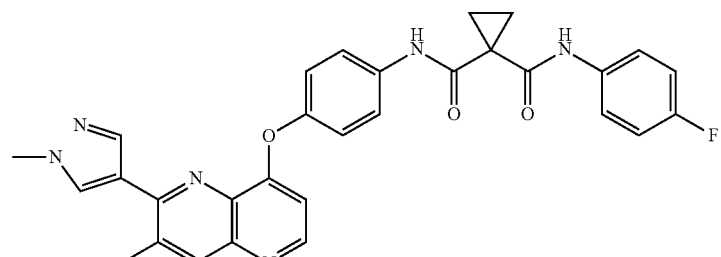

Example 38: 1-N'-(4-Fluorophenyl)-1-N-[4-[[6-(1-methylpyrazol-4-yl)-1,5-naphthyridin-4-yl]oxy]phenyl]cyclopropane-1,1-dicarboxamide (189)

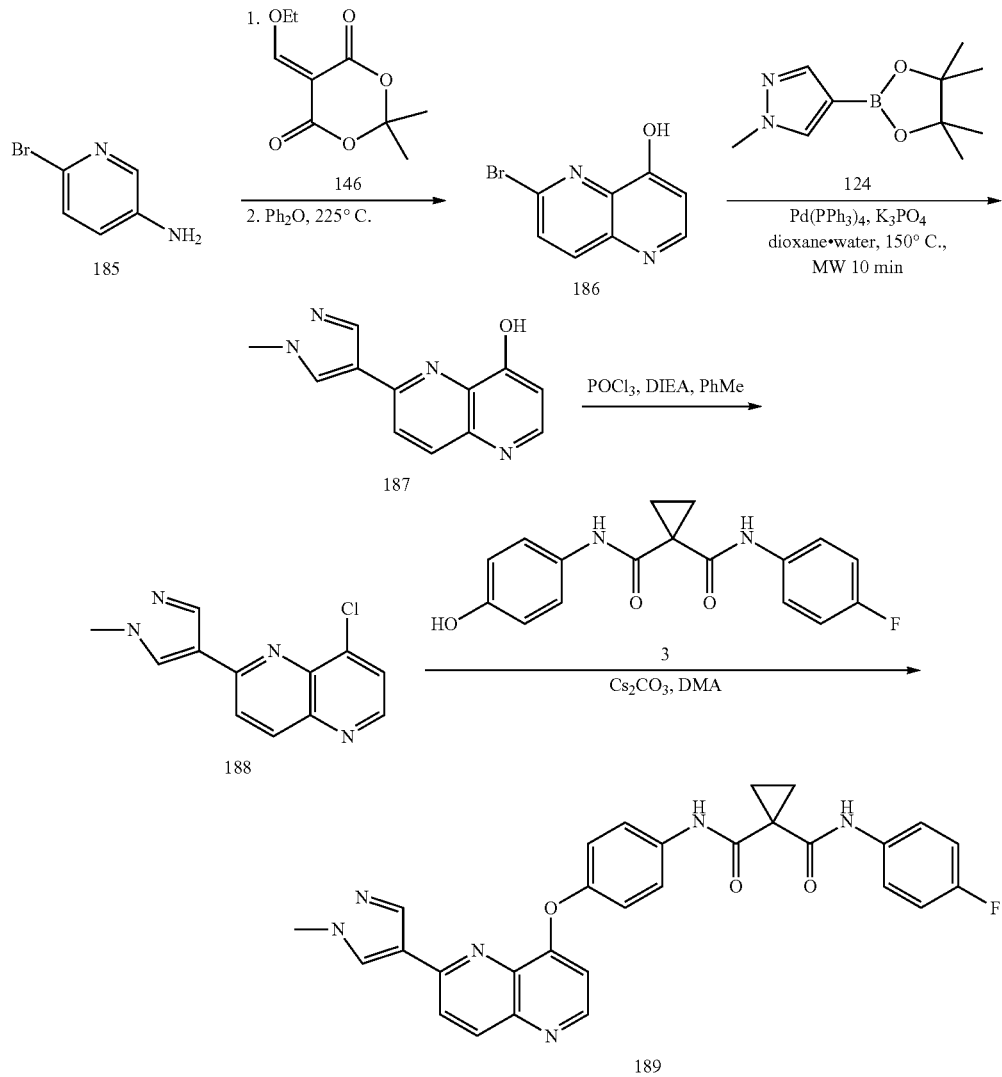

6-Bromo-1,5-naphthyridin-4-ol (186): Compound 186 can be made from Compound 185 and Compound 146 in a manner analogous to the preparation of Compound 136 from Compound 133 and Compound 134 in Steps 3 and 4 of Example 28.

6-(1-Methyl-1H-pyrazol-4-yl)-1,5-naphthyridin-4-ol (187): In a microwave reaction tube were mixed Compound 186 (225 mg, 1.0 mmol), Compound 124 (270 mg, 1.3 mmol), $K_3PO_4$ (636 mg, 3.0 mmol), $Pd(PPh_3)_4$ (115 mg, 0.1 mmol), 1,4-dioxane (7 mL), and water (3 mL). The reaction mixture was irritated for 20 minutes at 150° C. After cooling, the mixture was diluted with EtOAc. The phases were separated and the aqueous phase was further extracted with 15% MeOH in EtOAc. The solvents were removed from the combined organic phases to give crude Compound 187 (227 mg), which was used in the next step without further purification.

8-Chloro-2-(1-methyl-1H-pyrazol-4-yl)-1,5-naphthyridine (188): Compound 188 was made from Compound 187 in a manner analogous to the preparation of Compound 11 from Compound 10 in Step 3 of Example 3. The crude product (36 mg) was used in the next step without further purification.

1-N'-(4-Fluorophenyl)-1-N-[4-[[6-(1-methylpyrazol-4-yl)-1,5-naphthyridin-4-yl]oxy]phenyl]cyclopropane-1,1-dicarboxamide (189): Compound 189 (2 mg, 0.4% overall yield in 3 steps from Compound 186) was made from Compound 188 and Compound 3 using a variation of the method used to prepare Compound 7 from Compound 6 in Step 3 of Example 2. $Cs_2CO_2$ in DMA was used in place of $K_2CO_3$ in DMF. (EI) for $C_{29}H_{23}FN_6O_3$, found 523 (MH+).

BIOLOGICAL EXAMPLES

Kinase Assays

Kinase activity and compound inhibition were investigated using the $^{33}$P-Phosphoryl transfer radiometric kinase assay, performed using the KinaseProfiler™ service of Euro fins Pharma Discovery Services UK Limited. Dose-response experiments were performed using nine compound concentrations in a 96-well microtiter plate. For each assay, all compounds were prepared to a 50× final assay concentration (50 µM) in 100% DMSO, then diluted in a half-log series, with the final top concentration at 1 µM. This working stock of the compound was added to the assay well as the first component in the reaction, followed by the remaining components as detailed in the following assay protocols below. The positive control wells (100% kinase activity) contain all components of the reaction including 2% DMSO (control for solvent effects), except the compound of interest. Blank wells contain all components of the reaction, with the reference inhibitor, staurosporine. This reference compound was used to abolish kinase activity and generated the 0% kinase activity base-line. $IC_{50}$ values were calculated by nonlinear regression analysis using the sigmoidal dose-response (variable slope) curve fit on XLFit version 5.3 (ID Business Solutions).

Example A: Human AXL Kinase Assay

Human Axl (residues H473-A894 with Q764R, 161 nM) was incubated with 8 mM MOPS pH 7.0, 0.2 mM EDTA, 250 µM KKSRGDYMTMQIG, 10 mM magnesium acetate and 10 µM [γ-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example B: Human KDR Kinase Assay

Human KDR (residues K790-V1356, 55 nM) was incubated with 8 mM MOPS pH 7.0, 0.2 mM EDTA, 0.33 mg/mL myelin basic protein, 10 mM magnesium acetate, and 10 µM [γ-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example C: Human Mer Kinase Assay

Human Mer (residues R557-E882 with H628Q and R794A, 0.7 nM) was incubated with 8 mM MOPS pH 7.0, 0.2 mM EDTA, 30 mM NaCl, 250 µM GGMEDIYFEFMGGKKK, 10 mM magnesium acetate, and 10 µM [γ-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example D: Human Met Kinase Assay

Human Met (residues R974-S1390 with A1209G and V1290L, 3.4 nM) was incubated with 8 mM MOPS pH 7.0, 0.2 mM EDTA, 250 µM KKKGQEEEYVFIE, 1 mM sodium orthovanadate, 5 mM sodium-6-glycerophosphate, 10 mM magnesium acetate, and 10 µM [γ-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Activity data obtained for the Example compounds using the kinase assays in Examples A, C, and D is provided in Table 4 (A: $IC_{50} \leq 10$ nM; B: 10 nM $< IC50 \leq 100$ nM; C: 100 nM $< IC_{50} \leq 1000$ nM; D: $IC_{50} > 1000$ nM).

TABLE 4

Biological Activities of Selected Compounds

| Compound No. | IUPAC Name | Axl $IC_{50}$ (nM) | Mer $IC_{50}$ (nM) | c-Met $IC_{50}$ (nM) |
|---|---|---|---|---|
| 7 | 1-N'-(4-fluorophenyl)-1-N-(4-pyrido[3,2-d]pyrimidin-4-yloxyphenyl)cyclopropane-1,1-dicarboxamide | D | D | C |
| 12 | 1-N-[4-(7-chloropyrido[3,2-d]pyrimidin-4-yl)oxyphenyl]-1-N'-(4-fluorophenyl)cyclopropane-1,1-dicarboxamide | D | C | C |
| 13 | 1-N-[4-(7-bromopyrido[3,2-d]pyrimidin-4-yl)oxyphenyl]-1-N'-(4-fluorophenyl)cyclopropane-1,1-dicarboxamide | C | C | C |
| 16 | 1-N'-(4-fluorophenyl)-1-N-[4-(7-methoxypyrido[3,2-d]pyrimidin-4-yl)oxyphenyl]cyclopropane-1,1-dicarboxamide | C | C | B |
| 28 | 1-N-[4-(6,7-dimethoxypyrido[3,2-d]pyrimidin-4-yl)oxyphenyl]-1-N'-(4-fluorophenyl)cyclopropane-1,1-dicarboxamide | A | A | B |
| 29 | 1-N'-[3-chloro-4-(6,7-dimethoxypyrido[3,2-d]pyrimidin-4-yl)oxyphenyl]-1-N-(4-fluorophenyl)cyclopropane-1,1-dicarboxamide | B | A | A |
| 30 | 1-N'-[4-(6,7-dimethoxypyrido[3,2-d]pyrimidin-4-yl)oxy-3-fluorophenyl]-1-N-(4-fluorophenyl)cyclopropane-1,1-dicarboxamide | A | A | A |
| 43 | 1-N-[4-(6,7-dimethylpyrido[3,2-d]pyrimidin-4-yl)oxyphenyl]-1-N'-(4-fluorophenyl)cyclopropane-1,1-dicarboxamide | C | C | C |
| 52 | 1-N'-(4-fluorophenyl)-1-N-[4-(6,7,8,9-tetrahydropyrimido[5,4-b]quinolin-4-yloxy)phenyl]cyclopropane-1,1-dicarboxamide | C | C | C |
| 57 | 1-N-[4-(6-cyano-7-methoxypyrido[3,2-d]pyrimidin-4-yl)oxyphenyl]-1-N'-(4-fluorophenyl)cyclopropane-1,1-dicarboxamide | C | B | C |
| 65 | 1-N'-(4-fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide | B | A | B |
| 66 | 1-N'-[3-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide | A | A | A |

TABLE 4-continued

Biological Activities of Selected Compounds

| Compound No. | IUPAC Name | Axl IC$_{50}$ (nM) | Mer IC$_{50}$ (nM) | c-Met IC$_{50}$ (nM) |
|---|---|---|---|---|
| 67 | 1-N'-[3-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide | A | A | A |
| 85 | 1-N'-(4-fluorophenyl)-1-N-(4-pyrido[3,4-d]pyrimidin-4-yloxyphenyl)cyclopropane-1,1-dicarboxamide | C | C | C |
| 88 | 1-N-[4-(6-chloropyrido[3,4-d]pyrimidin-4-yl)oxyphenyl]-1-N'-(4-fluorophenyl)cyclopropane-1,1-dicarboxamide | C | C | D |
| 91 | 1-N'-(4-fluorophenyl)-1-N-[4-(6-methoxypyrido[3,4-d]pyrimidin-4-yl)oxyphenyl]cyclopropane-1,1-dicarboxamide | C | B | C |
| 95 | 1-N'-(4-fluorophenyl)-1-N-(4-pyrido[4,3-d]pyrimidin-4-yloxyphenyl)cyclopropane-1,1-dicarboxamide | C | C | C |
| 101 | 1-N-[4-(7-chloropyrido[4,3-d]pyrimidin-4-yl)oxyphenyl]-1-N'-(4-fluorophenyl)cyclopropane-1,1-dicarboxamide | C | C | C |
| 104 | 1-N'-(4-fluorophenyl)-1-N-[4-(7-methoxypyrido[4,3-d]pyrimidin-4-yl)oxyphenyl]cyclopropane-1,1-dicarboxamide | B | B | B |
| 106 | 1-N-[4-(6-cyanoquinazolin-4-yl)oxyphenyl]-1-N'-(4-fluorophenyl)cyclopropane-1,1-dicarboxamide | D | C | D |
| 115 | 1-N'-(4-fluorophenyl)-1-N-[4-[7-methoxy-6-(oxetan-3-ylcarbamoyl)quinazolin-4-yl]oxyphenyl]cyclopropane-1,1-dicarboxamide | B | B | B |
| 116 | 1-N-[4-[6-(cyclopropylcarbamoyl)-7-methoxyquinazolin-4-yl]oxyphenyl]-1-N'-(4-fluorophenyl)cyclopropane-1,1-dicarboxamide | B | B | B |
| 117 | 1-N-[4-(6-carbamoyl-7-methoxy-quinazolin-4-yl)oxyphenyl]-1-N'-(4-fluorophenyl)cyclopropane-1,1-dicarboxamide | B | A | B |
| 118 | 1-N'-(4-fluorophenyl)-1-N-[4-[7-methoxy-6-(2-pyrrolidin-1-ylethylcarbamoyl)quinazolin-4-yl]oxyphenyl]cyclopropane-1,1-dicarboxamide | B | A | B |
| 119 | tert-butyl (2R)-2-[[[4-[4-[[1-[(4-fluorophenyl)carbamoyl]cyclopropanecarbonyl]amino]phenoxy]-7-methoxyquinazoline-6-carbonyl]amino]methyl]pyrrolidine-1-carboxylate | B | B | C |
| 120 | tert-butyl (2S)-2-[[[4-[4-[[1-[(4-fluorophenyl)carbamoyl]cyclopropanecarbonyl]amino]phenoxy]-7-methoxyquinazoline-6-carbonyl]amino]methyl]pyrrolidine-1-carboxylate | B | B | C |
| 121 | 1-N'-(4-fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide | A | A | A |
| 122 | 1-N'-(4-fluorophenyl)-1-N-[4-[7-methoxy-6-[[(2S)-pyrrolidin-2-yl]methylcarbamoyl]quinazolin-4-yl]oxyphenyl]cyclopropane-1,1-dicarboxamide | A | A | B |
| 139 | 1-N-[4-[(6,7-dimethoxy-1,5-naphthyridin-4-yl)oxy]phenyl]-1-N'-(4-fluorophenyl)cyclopropane-1,1-dicarboxamide | A | A | A |
| 140 | 1-N'-[4-[(6,7-dimethoxy-1,5-naphthyridin-4-yl)oxy]-3-fluorophenyl]-1-N-(4-fluorophenyl)cyclopropane-1,1-dicarboxamide | A | A | A |
| 141 | 1-N'-[3-chloro-4-[(6,7-dimethoxy-1,5-naphthyridin-4-yl)oxy]phenyl]-1-N-(4-fluorophenyl)cyclopropane-1,1-dicarboxamide | B | A | A |

Example E: AXL Autophosphorylation ELISA in A-172 Cells

A-172 glioblastoma cells (ATCC #CRL-1620) were seeded at $2.5 \times 10^5$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). A-172 cells were incubated at 37° C., 5% $CO_2$ for 24 h and then starved for 24 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 1 μg/mL recombinant human Gas6 (R&D Systems #885-GSB-500) for 15 min, washed with cold PBS, and immediately lysed with 150 μL of cold 1×lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 μL/well added into the human phospho-AXL DuoSet IC ELISA (R&D Systems #DYC2228-2). Assay was performed according to manufacturer's instructions and sample phospho-AXL concentrations were extrapolated using human phospho-AXL control (R&D Systems #841645) as a standard. Positive control wells (100% activity) contained Gas6-stimulated, DMSO-treated cell lysates. Negative control wells (0% activity) contained Gas6-stimulated, reference inhibitor-treated cell lysates. IC$_{50}$ values were calculated by nonlinear regression analysis using a 4-parameter logistic curve fit in ActivityBase XE (IDBS).

Example F: Met Autophosphorylation ELISA in PC-3 Cells

PC-3 prostate cancer cells (ATCC #CRL-1435) were seeded at $4 \times 10^4$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). PC-3 cells were incubated at 37° C., 5% $CO_2$ for 24 h and then starved for 3 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human HGF (R&D Systems

294-HG-250) for 10 min, washed with cold PBS, and immediately lysed with 130 μL of cold 1×lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 100 μL/well added into the PathScan phospho-Met (panTyr) Sandwich ELISA (Cell Signaling Technology #7333). Assay was performed according to manufacturer's instructions. Positive control wells (100% activity) contained HGF-stimulated, DMSO-treated cell lysates. Negative control wells (0% activity) contained HGF-stimulated, reference inhibitor-treated cell lysates. $IC_{50}$ values were calculated by nonlinear regression analysis using a 4-parameter logistic curve fit in ActivityBase XE (IDBS).

Example G: KDR Autophosphorylation ELISA in HUVEC Cells

Human umbilical vein endothelial cells or HUVEC (Lonza #C2519A) were seeded at $2 \times 10^4$ cells/well onto 96-well plates (Corning #3904), in EGM-2 growth medium (Lonza #CC-3162) containing 1% Penicillin Streptomycin (Thermo Fisher #15140-122). HUVEC cells were incubated at 37° C., 5% $CO_2$ for 24 h and then starved for 24 h in serum-free EBM-2 basal medium (Lonza #CC-3156) containing 1% Penicillin Streptomycin. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human VEGF165 (R&D Systems #293-VE-500) for 5 min, washed with cold PBS, and immediately lysed with 130 μL of cold 1×lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 μL/well added into the human phospho-KDR DuoSet IC ELISA (R&D Systems #DYC1766-2). Assay was performed according to manufacturer's instructions and sample phospho-KDR concentrations were extrapolated using human phospho-KDR control (R&D Systems #841421) as a standard. Positive control wells (100% activity) contained VEGF165-stimulated, DMSO-treated cell lysates. Negative control wells (0% activity) contained non-stimulated cell lysates. $IC_{50}$ values were calculated by nonlinear regression analysis using a 4-parameter logistic curve fit in ActivityBase XE (IDBS).

Example H: Mer Autophosphorylation ELISA in Transient Transfected 293A Cells 293A cells (Thermo Fisher #R70507) were seeded at $1.5 \times 10^6$ cells/well onto 100 mm dish (Greiner #664169), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). 293A cells were incubated at 37° C., 5% $CO_2$ for 24 h and then transfected with 6 μg MERTK DNA (Genecopoeia #EX-Z8208-M02) using TransIT LT1 transfection reagent (Mirus-Bio #MIR2305). After 24 h incubation, the transfected 293A cells were seeded at $1 \times 10^5$ cells/well onto 96-well plates (Corning #3904) in DMEM growth medium overnight. Test compounds were serially diluted to produce an 8-point dose curve in fresh serum-free medium to a final concentration of 0.3% DMSO (vehicle) and added to the cells and incubated for 1 h. Cells were then immediately lysed with 150 μL of cold 1×lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 50 μL/well added into the human phospho-Mer DuoSet IC ELISA (R&D Systems #DYC2579-2). Assay was performed according to manufacturer's instructions and sample phospho-Mer concentrations were extrapolated using human phospho-Mer control (R&D Systems #841793) as a standard. Positive control wells (100% activity) contained DMSO-treated cell lysates. Negative control wells (0% activity) contained reference inhibitor-treated cell lysates. $IC_{50}$ values were calculated by nonlinear regression analysis using a 4-parameter logistic curve fit in ActivityBase XE (IDBS).

Compounds of the present disclosure, as exemplified herein, showed $IC_{50}$ values in the following ranges: A: $IC_{50} \leq 10$ nM; B: 10 nM $< IC_{50} \leq 100$ nM; C: 100 nM $< IC_{50} \leq 300$ nM; D: $IC_{50} > 300$ nM. "NT" means not tested.

Activity data obtained for the Example compounds using cell based kinase assays in Examples F, G, H and I is provided in Table 5.

TABLE 5

Cellular Activities of Selected Compounds

| Compound No. | Axl $IC_{50}$ (nM) | Mer $IC_{50}$ (nM) | c-Met $IC_{50}$ (nM) | KDR $IC_{50}$ (nM) |
|---|---|---|---|---|
| 7 | NT | NT | NT | NT |
| 12 | NT | NT | NT | NT |
| 13 | NT | NT | NT | NT |
| 16 | NT | NT | NT | NT |
| 19 | B | B | B | C |
| 28 | B | B | C | B |
| 29 | B | NT | B | A |
| 30 | A | A | B | A |
| 31 | A | B | B | B |
| 32 | B | NT | C | C |
| 33 | C | NT | D | C |
| 34 | A | A | B | B |
| 35 | A | A | A | B |
| 43 | NT | NT | NT | NT |
| 52 | NT | NT | NT | NT |
| 57 | NT | NT | NT | NT |
| 65 | A | B | B | A |
| 66 | A | NT | B | A |
| 67 | A | A | B | A |
| 68 | B | B | C | B |
| 69 | A | A | B | B |
| 70 | B | B | C | C |
| 71 | B | D | C | B |
| 72 | A | B | B | B |
| 73 | A | A | B | A |
| 74 | C | NT | D | B |
| 75 | B | B | B | B |
| 76 | A | A | B | B |
| 78 | B | NT | C | A |
| 79 | A | A | B | A |
| 80 | B | A | B | A |
| 81 | A | A | B | B |
| 82 | A | B | B | A |
| 83 | A | A | B | A |
| 85 | NT | NT | NT | NT |
| 88 | NT | NT | NT | NT |
| 91 | D | NT | D | D |

TABLE 5-continued

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 95 | NT | NT | NT | NT |
| 101 | NT | NT | NT | NT |
| 104 | D | NT | D | D |
| 106 | NT | NT | NT | NT |
| 115 | D | NT | C | B |
| 116 | C | NT | C | B |
| 117 | A | NT | C | B |
| 118 | B | B | C | C |
| 119 | C | NT | D | B |
| 120 | D | NT | D | C |
| 121 | B | NT | C | C |
| 122 | B | NT | C | D |
| 126 | C | NT | D | D |
| 129 | B | C | C | C |
| 130 | B | B | B | A |
| 139 | A | A | B | A |
| 140 | A | A | A | A |
| 141 | B | NT | A | A |
| 142 | A | NT | B | A |
| 149 | A | A | B | A |
| 150 | A | A | A | A |
| 151 | B | B | B | A |
| 152 | A | NT | B | A |
| 153 | A | NT | B | A |
| 157 | D | NT | D | D |
| 158 | D | NT | D | D |
| 159 | D | NT | C | D |
| 164 | C | NT | D | C |
| 165 | B | NT | C | C |
| 166 | C | NT | C | B |
| 167 | C | NT | D | D |
| 168 | D | NT | C | D |
| 169 | B | NT | B | B |
| 172 | C | NT | D | D |
| 173 | C | NT | C | C |
| 174 | D | NT | C | D |
| 176 | A | NT | B | C |
| 181 | NT | NT | NT | NT |
| 182 | NT | NT | NT | NT |
| 183 | D | NT | D | D |
| 184 | D | NT | D | D |
| 189 | NT | NT | NT | NT |

Example I: Pharmacokinetic Studies

Pharmacokinetic properties of select compounds as described herein were assessed in male Sprague-Dawley rats. The non-GLP study was designed to investigate the pharmacokinetics of chosen compounds in plasma following an intravenous or oral dose administration to male Sprague Dawley rats. Two groups of male Sprague-Dawley rats (three animals per group) received either an intravenous or oral (gavage) dose of compound at target dose levels of 3 mg/kg. Animals were observed for any clinically relevant abnormalities during dosing and at each sample collection period.

Animals in the PO group were fasted overnight prior to dose administration. Food was returned following the collection of the 4-hour blood sample. Water was not withheld.

Immediately prior to dosing, the body weight of each animal was recorded. Doses (rounded to the nearest 0.001 mL) were calculated based on the pretreatment body weight (kg) and a dose volume of 2.5 mL/kg for intravenous administration and 5 mL/kg for oral administration. Intravenous formulations were administered via a jugular vein cannula. Immediately after dosing, the cannula was flushed with saline and the line was tied off. The oral dose was administered via a ball-tipped feeding needle. Dosing syringe volumes for administration were second-person verified prior to dosing and that volume along with the results for the concentration verification analysis were used to calculate the actual dose administered. Dosing syringes were weighed immediately prior to and immediately after dosing each animal as a gravimetric check.

Serial blood samples (approximately 200 µL per sample) were collected from each animal at 0.083 (IV dosing only), 0.25, 0.5, 1, 2, 4, 6 (PO dosing only), 8, 24, 32, 48, and 72 hours after dosing. Blood samples were collected into tubes containing K$_2$EDTA via the non-dosing jugular-vein cannula (JVC), which was flushed with an approximately equal volume of saline following each collection.

Blood samples were stored on wet ice until processed to plasma by centrifugation (3500 rpm at 5° C. for 10 minutes) within 1 hour of collection. Plasma samples were transferred into matrix tubes and then stored in a −80° C. freezer.

Plasma samples and dose formulation samples were analyzed for the compounds of interest using liquid chromatography-tandem mass spectrometry (LC-MS/MS) methods. Pharmacokinetic parameter estimates were calculated from the individual animal plasma concentration-time data using the actual dose based on the analysis of the dosing formulations, nominal sampling times (all collections were within an acceptable range of target), and non-compartmental methods. The concentration-time data were analyzed to fit either an intravenous—bolus (IV) plasma analysis model (201) or extra-vascular (PO) dosing plasma analysis model (200) using the software WinNonlin Phoenix version 6.3 (Pharsight). The single-dose pharmacokinetic parameters assessed include, as appropriate: C$_{max}$ (observed peak or maximum concentration); T$_{max}$ (observed time of peak concentration); T$_{1/2}$ (terminal half-life); V$_z$ (volume of distribution based on the terminal phase); V$_{ss}$ (volume of distribution at steady state); AUC$_{INF}$ (area under the concentration-time curve computed from time zero to infinity); AUC$_{last}$ (area under the concentration-time curve computed from time zero to the time of the last quantifiable concentration); C$_0$ (back-extrapolated concentration at time zero); CL (total body clearance); Vz/F (volume of distribution for extravascular administration based on the terminal phase); CL/F (total body clearance for extravascular administration); F % (bioavailability); and MRT$_{last}$ (mean residence time).

Areas-under-the-plasma concentration-time curves (AUC) were estimated using the linear-log trapezoidal rule. The area through the time (T$_{last}$) of the last observable concentration (C$_{last}$) is reported as AUC$_{last}$. AUC extrapolated to infinity, (AUC$_{INF}$) was estimated by adding AUC$_{last}$ and the ratio of C$_{last}$/λ$_z$, where λ$_z$ is the terminal rate constant. Apparent terminal half-life (T$_{1/2}$) was calculated as ln(2)/λ$_z$ and determined using the slope of the log-linear terminal phase of the concentration-time curve, defined by a minimum of three plasma concentration-time points. Half-lives are reported if the correlation for the regression line, as measured by r squared, is ≥0.9 when rounded. After IV administration, volume of distribution (Vz) was calculated as Dose/λ$_z$*AUC$_{INF-obs}$, clearance (CL) was calculated as Dose/AUC$_{INF-obs}$ and volume of distribution at steady state (V$_{ss}$) was estimated as MRT$_{INF}$*CL. Mean residence time (MRT) from the time of dosing to the time of the last measurable concentration was calculated as AUMC$_{last}$/AUC$_{last}$. For model 200 the bioavailability (i.e. fraction of total dose that reaches the systemic circulation) cannot be calculated. Consequently, volume and clearance for this model is Vz/F or CL/F, respectively; where F is defined as bioavailability (i.e. fraction of total dose that reaches the systemic circulation; (Average $AUC_{last-po}$/Average $AUC_{last-iv}$)*[$Dose_{IV}$/$Dose_{PO}$]*100).

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

---

The invention claimed is:

1. A compound of Formula I':

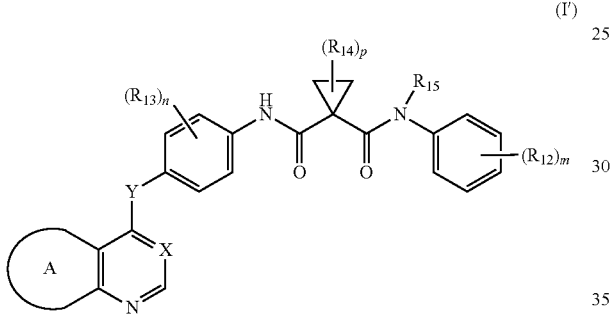

(I')

or a pharmaceutically acceptable salt thereof, wherein:

Y is O, S, SO, SO$_2$, NH, or —N(C$_{1-6}$ alkyl)-;

ring A is

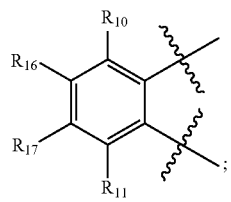

X is N;

R$_{16}$ is 5-14 membered heteroaryl, —CN, or —C(O)NR$^a$R$^a$, wherein the 5-14 membered heteroaryl is optionally substituted with 1, 2, 3, 4, or 5 substituents, and each substituent is independently selected from halo, (C$_1$-C$_6$) alkyl, —CN, —NO$_2$, phenyl, (C$_1$-C$_6$) alkoxy, or oxo, provided that when R$_{16}$ is 5-membered heteroaryl, then the 5-membered heteroaryl does not connect to the fused phenyl ring moiety through a ring nitrogen atom; and R$_{17}$ is —H or —OR$^a$ R$_{10}$ and R$_{11}$ are each independently —H, halo, (C$_1$-C$_6$) alkyl, (C$_1$-C$_6$) haloalkyl, or (C$_1$-C$_6$) haloalkoxy;

each R$_{13}$ is independently —H, halo, —OH, —CN, (C$_1$-C$_6$) alkyl, (C$_1$-C$_6$) alkoxy, (C$_1$-C$_6$) haloalkoxy, —NH$_2$, —NH(C$_1$-C$_6$)alkyl, —N(C$_1$-C$_6$ alkyl)$_2$, or (C$_3$-C$_6$) cycloalkyl;

each R$_{14}$ is independently —H, halo, or (C$_1$-C$_6$) alkyl;

R$_{15}$ is H;

each R$_{12}$ is independently —H or halo;

each R$^a$ is independently —H, (C$_1$-C$_6$) alkyl, (C$_3$-C$_{10}$) cycloalkyl, 4-14 membered heterocycloalkyl, or (4-14 membered heterocycloalkyl)-(C$_1$-C$_4$) alkylene-, wherein the (C$_1$-C$_6$) alkyl, (C$_3$-C$_{10}$) cycloalkyl, 4-14 membered heterocycloalkyl, and (4-14 membered heterocycloalkyl)-(C$_1$-C$_4$) alkylene- of R$^a$ are each optionally substituted with 1, 2, 3, 4, or 5 substituents, and each substituent is independently selected from (C$_1$-C$_6$) alkyl, (C$_1$-C$_6$) alkoxy, or —C(O)O(C$_1$-C$_4$) alkyl;

the subscript n is an integer of 1, 2, 3, or 4;

the subscript m is an integer of 1, 2, 3, 4, or 5; and the subscript p is an integer of 0, 1, 2, 3, or 4.

2. The compound of claim 1, or a pharmaceutically acceptable salt thereof, wherein R$_{16}$ is —CN, —C(O)NR$^a$R$^a$, or 5- to 6-membered heteroaryl, wherein the 5- to 6-membered heteroaryl is optionally substituted with 1, 2, or 3 (C$_1$-C$_6$) alkyl.

3. The compound of claim 1, or a pharmaceutically acceptable salt thereof, wherein R$_{17}$ is —H or —O(C$_1$-C$_6$) alkyl.

4. The compound of claim 1, or a pharmaceutically acceptable salt thereof, wherein R$_{16}$ is selected from CN, (oxetan-3-yloxy)carbamoyl, cyclopropylcarbamoyl, carbamoyl, 2-(pyrrolidin-1-yl)ethylcarbamoyl, 1-(t-butoxycarbonylpyrrolidin-2-yl)methylcarbamoyl, 1-(pyrrolidin-2-yl)methylcarbamoyl, dimethylcarbamoyl, methylcarbamoyl, 2-oxazolyl, pyrazol-3-yl, pyrazol-4-yl, 4-isoxazolyl, 3,5-dimethylisoxazol-4-yl, 1-methyl-pyrazol-4-yl, 2-methyl-pyrazol-3-yl, 2-ethyl-pyrazol-3-yl, 2-(2-hydroxyethyl)-pyrazol-3-yl, 2-(2,2,2-trifluoroethyl)-pyrazol-3-yl, 2-(2-fluoroethyl)-pyrazol-3-yl, 2-(2,2-difluoroethyl)-pyrazol-3-yl, 2-trifluoromethyl-pyrazol-3-yl, 2-difluoromethyl-pyrazol-3-yl, 1-methyl-imidazol-4-yl, 1-methyl-imidazol-2-yl, 1H-imidazol-2-yl, (2-hydroxyethoxy)carbamoyl, (2,2-dihydroxyethoxy)carbamoyl, (oxetan-3-yl)carbamoyl, methoxycarbamoyl, 1,3,4-oxadiazol-3-yl, or 1H-1,2,3-triazol-5-yl.

5. The compound of claim 1, or a pharmaceutically acceptable salt thereof, wherein R$_{16}$ is R$^a$NHC(O).

6. The compound of claim 1, or a pharmaceutically acceptable salt thereof, wherein R$_{10}$ and R$_{11}$ are each H.

7. The compound of claim 1, or a pharmaceutically acceptable salt thereof, wherein $R_{17}$ is H.

8. The compound of claim 1, or a pharmaceutically acceptable salt thereof, wherein $R_{12}$ is para fluoro.

9. The compound of claim 1, or a pharmaceutically acceptable salt thereof, wherein

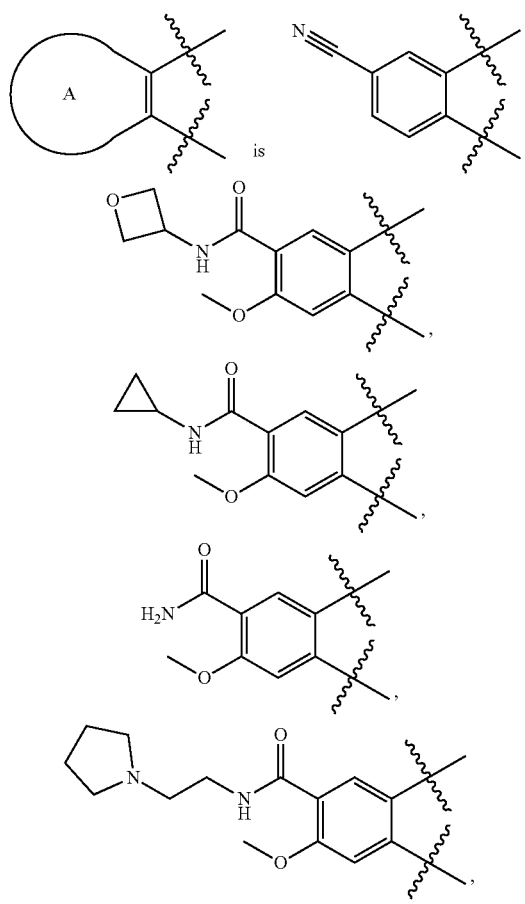

-continued

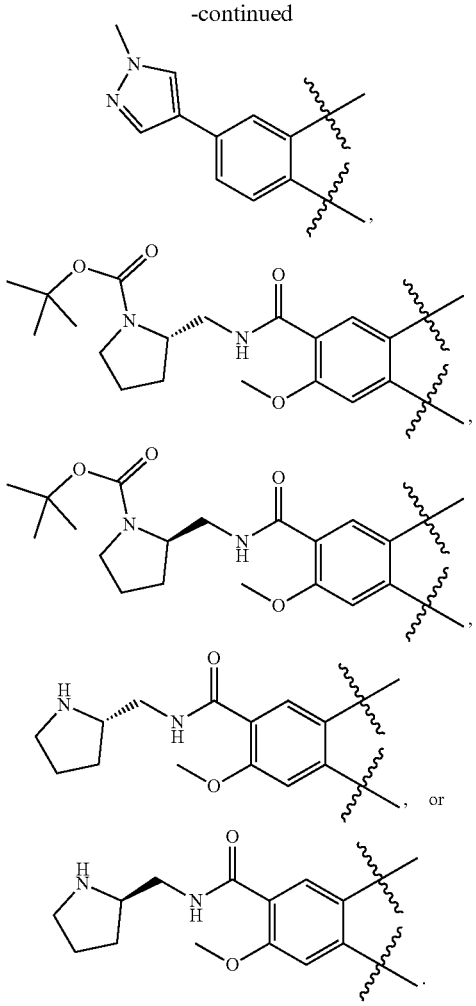

10. The compound of claim 1, or a pharmaceutically acceptable salt thereof, wherein Y is O.

11. The compound of claim 1, wherein the compound is selected from

TABLE 3

Compounds of Formula II

| Comp. | Structure | IUPAC Name |
|---|---|---|
| 106 | 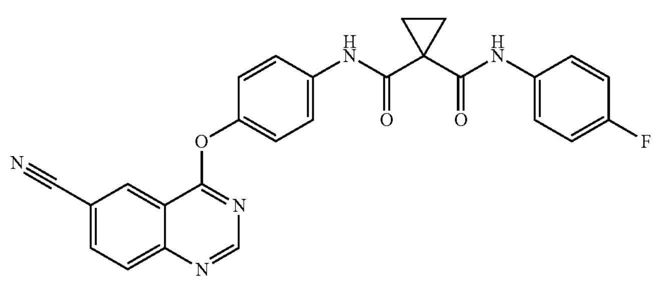 [SMILES: N#Cc1ccc2ncnc(Oc3ccc(NC(=O)C4(C(=O)Nc5ccc(F)cc5)CC4)cc3)c2c1] | 1-N-[4-(6-cyanoquinazolin-4-yl)oxyphenyl]-1-N'-(4-fluorophenyl)cyclopropane-1,1-dicarboxamide |

TABLE 3-continued

Compounds of Formula II

| Comp. | Structure | IUPAC Name |
|---|---|---|
| 115 | 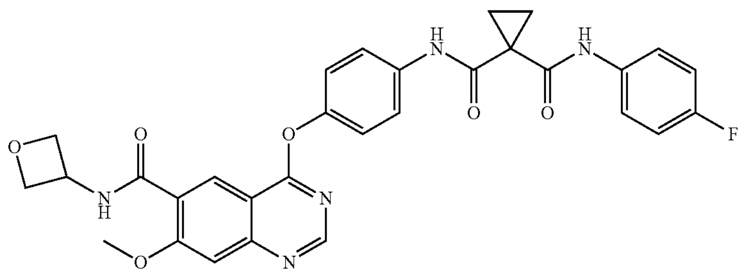 [SMILES: COc1cc2ncnc(Oc3ccc(NC(=O)C4(C(=O)Nc5ccc(F)cc5)CC4)cc3)c2cc1C(=O)NC1COC1] | 1-N'-(4-fluorophenyl)-1-N-[4-[7-methoxy-6-(oxetan-3-ylcarbamoyl)quinazolin-4-yl]oxyphenyl]cyclopropane-1,1-dicarboxamide |
| 116 | 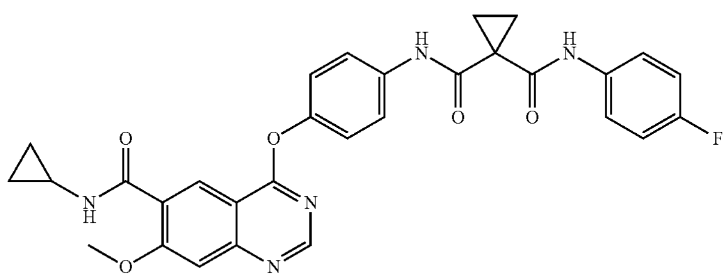 [SMILES: COc1cc2ncnc(Oc3ccc(NC(=O)C4(C(=O)Nc5ccc(F)cc5)CC4)cc3)c2cc1C(=O)NC1CC1] | 1-N-[4-[6-(cyclopropylcarbamoyl)-7-methoxyquinazolin-4-yl]oxyphenyl]-1-N'-(4-fluorophenyl)cyclopropane-1,1-dicarboxamide |
| 117 | 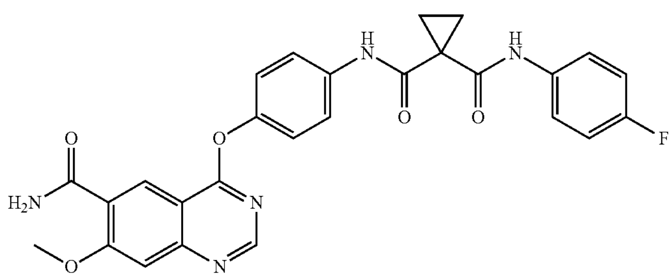 [SMILES: COc1cc2ncnc(Oc3ccc(NC(=O)C4(C(=O)Nc5ccc(F)cc5)CC4)cc3)c2cc1C(N)=O] | 1-N-[4-(6-carbamoyl-7-methoxyquinazolin-4-yl)oxyphenyl]-1-N'-(4-fluorophenyl)cyclopropane-1,1-dicarboxamide |
| 118 | 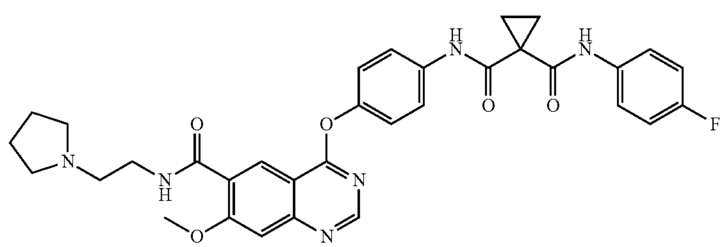 [SMILES: COc1cc2ncnc(Oc3ccc(NC(=O)C4(C(=O)Nc5ccc(F)cc5)CC4)cc3)c2cc1C(=O)NCCN1CCCC1] | 1-N'-(4-fluorophenyl)-1-N-[4-[7-methoxy-6-(2-pyrrolidin-1-ylethylcarbamoyl)quinazolin-4-yl]oxyphenyl]cyclopropane-1,1-dicarboxamide |
| 119 | 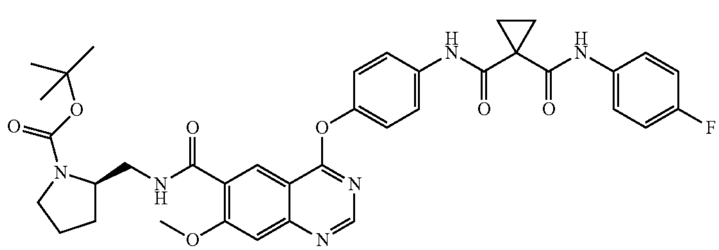 [SMILES: COc1cc2ncnc(Oc3ccc(NC(=O)C4(C(=O)Nc5ccc(F)cc5)CC4)cc3)c2cc1C(=O)NC[C@H]1CCCN1C(=O)OC(C)(C)C] | tert-butyl (2R)-2-[[[4-[4-[1-[(4-fluorophenyl)carbamoyl]cyclopropanecarbonyl]amino]phenoxy]-7-methoxyquinazoline-6-carbonyl]amino]methyl]pyrrolidine-1-carboxylate |
| 120 | 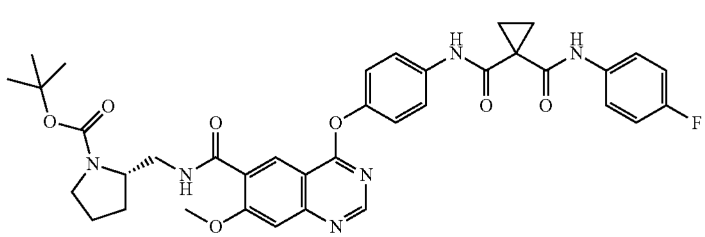 [SMILES: COc1cc2ncnc(Oc3ccc(NC(=O)C4(C(=O)Nc5ccc(F)cc5)CC4)cc3)c2cc1C(=O)NC[C@@H]1CCCN1C(=O)OC(C)(C)C] | tert-butyl (2S)-2-[[[4-[4-[1-[(4-fluorophenyl)carbamoyl]cyclopropanecarbonyl]amino]phenoxy]-7-methoxyquinazoline-6-carbonyl]amino]methyl]pyrrolidine-1-carboxylate |

TABLE 3-continued

Compounds of Formula II

| Comp. | Structure | IUPAC Name |
|---|---|---|
| 121 | 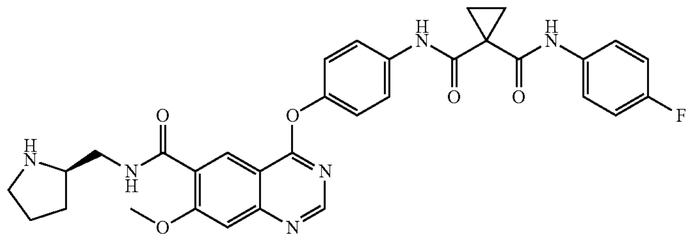 [SMILES: COc1cc2ncnc(Oc3ccc(NC(=O)C4(C(=O)Nc5ccc(F)cc5)CC4)cc3)c2cc1C(=O)NC[C@H]1CCCN1] | 1-N'-(4-fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide |
| 122 | 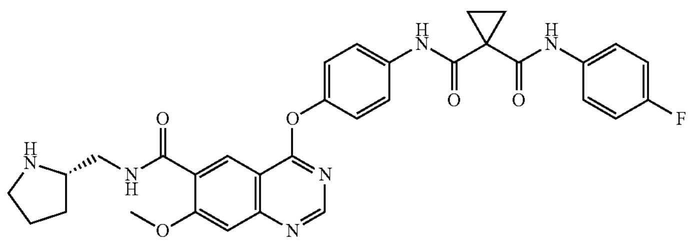 [SMILES: COc1cc2ncnc(Oc3ccc(NC(=O)C4(C(=O)Nc5ccc(F)cc5)CC4)cc3)c2cc1C(=O)NC[C@@H]1CCCN1] | 1-N'-(4-fluorophenyl)-1-N-[4-[7-methoxy-6-[[(2S)-pyrrolidin-2-yl]methylcarbamoyl]quinazolin-4-yl]oxyphenyl]cyclopropane-1,1-dicarboxamide, and |
| 126 | | 1-N'-(4-fluorophenyl)-1-N-[4-[6-(1-methylpyrazol-4-yl)quinazolin-4-yl]oxyphenyl]cyclopropane-1,1-dicarboxamide | or a pharmaceutically acceptable salt thereof.

12. A pharmaceutical composition comprising a compound of claim 1, or a pharmaceutically acceptable salt thereof, and a pharmaceutically acceptable carrier or excipient.

\* \* \* \* \*